US006537948B1

(12) United States Patent
Tohyama et al.

(10) Patent No.: US 6,537,948 B1
(45) Date of Patent: Mar. 25, 2003

(54) URACIL COMPOUNDS AND USE THEREOF

(75) Inventors: Yoshitomo Tohyama, Ashiya (JP); Yuzuru Sanemitsu, Kobe (JP)

(73) Assignee: Sumitomo Chemical Company, Limited, Osaka (JP)

( * ) Notice: Subject to any disclaimer, the term of this patent is extended or adjusted under 35 U.S.C. 154(b) by 60 days.

(21) Appl. No.: 09/774,116

(22) Filed: Jan. 31, 2001

(30) Foreign Application Priority Data

| Feb. 4, 2000 | (JP) | 2000-028123 |
| Feb. 29, 2000 | (JP) | 2000-053521 |
| Sep. 6, 2000 | (JP) | 2000-269730 |

(51) Int. Cl.$^7$ ............... A01N 43/54; C07D 403/00; C07D 211/54; C07D 513/00
(52) U.S. Cl. ............... 504/243; 544/295; 544/296; 544/312; 544/314; 546/243; 548/134; 548/135; 548/356.1; 548/366.1
(58) Field of Search ............... 504/243; 544/295, 544/296, 312, 314; 546/243; 548/134, 135, 356.1, 366.1

(56) References Cited

U.S. PATENT DOCUMENTS

| 4,816,065 A | 3/1989 | Theodoridis ............... 71/94 |
| 4,859,229 A | 8/1989 | Wenger et al. ............... 71/92 |
| 5,981,436 A | 11/1999 | Drewes et al. ............... 504/243 |
| 6,074,989 A | 6/2000 | Andree et al. ............... 504/243 |
| 6,333,296 B1 * | 12/2001 | Pulman et al. ............... 504/243 |

FOREIGN PATENT DOCUMENTS

| DE | 198 53 864 A1 | 1/2000 |
| EP | 0 255 047 | 2/1988 |
| WO | WO 92/11244 | 7/1992 |
| WO | WO 93/11669 | 6/1993 |
| WO | WO 96/07323 | 3/1996 |
| WO | WO 96/08151 | 3/1996 |
| WO | WO 96/16043 | 5/1996 |
| WO | WO 97/01541 | 1/1997 |
| WO | WO 97/01542 | 1/1997 |
| WO | WO 97/05116 | 2/1997 |
| WO | WO 97/33875 | 9/1997 |
| WO | WO 97/33876 | 9/1997 |
| WO | WO 98/27067 | 6/1998 |
| WO | WO 98/27068 | 6/1998 |
| WO | WO 98/41093 | 9/1998 |
| WO | WO 00/02866 | 1/2000 |
| WO | WO 00/32573 | 6/2000 |
| WO | WO 01/34575 A1 | 5/2001 |

* cited by examiner

Primary Examiner—Mukund J. Shah
Assistant Examiner—Tamthom N. Truong
(74) Attorney, Agent, or Firm—Sughrue Mion, PLLC

(57) ABSTRACT

The present invention relates to an uracil compound of the formula [I]:

[I]

[wherein, Q—$R^3$ represents a $R^3$-substituted group of a 5-membered or 6-membered heterocyclic ring having one or two nitrogen selected from the group consisting of moieties represented in the specification (wherein, this heterocyclic ring may be substituted with at least one kind of substituent, Y represents oxygen, sulfur, imino or C1 to C3 alkylimino, $R^1$ represents C1 to C3 alkyl or C1 to C3 haloalkyl, $R^2$ represents C1 to C3 alkyl, $R^3$ represents carboxy C1 to C6 alkyl, C1 to C6 alkoxycarbonyl C1 to C6 alkyl, OR$^7$, SR$^8$, N($R^9$)R$^{10}$ or the like, $X^1$ represents halogen, cyano, thiocarbamoyl or nitro, $X^2$ represents hydrogen or halogen. {wherein, each of R$^7$, R$^8$ and R$^{10}$ independently represents carboxy C1 to C6 alkyl, C1 to C6 alkoxycarbonyl C1 to C6 alkyl, C1 to C6 haloalkoxycarbonyl C1 to C6 alkyl, or the like, and R$^9$ represents hydrogen or C1 to C6 alkyl.}.].

The present compound has an excellent herbicidal activity.

48 Claims, No Drawings

URACIL COMPOUNDS AND USE THEREOF

The present invention relates to uracil compounds and use thereof.

An object of the present invention is to provide compounds having excellent herbicidal activity.

Currently, a lot of herbicides are commercially available and used, however since there are many kinds of weeds to be controlled and generation thereof ranges over a long period, there is requirement a herbicide which have higher herbicidal effect, have a wide range of herbicidal spectrum, and causes no phytotoxicity on crops.

U.S. Pat. No. 4,859,229, WO92/11244, WO97/01541, WO97/05116, WO98/41093 and the like disclose that certain kinds of phenyluracil compounds have herbicidal activity, however, these phenyluracil compounds do not have sufficient abilities as a herbicide.

The present inventors have intensively studied to find a compound having excellent herbicidal activity, and resultantly, found that uracil compounds of the following formula [I] have excellent herbicidal activity, leading to completion of the present invention. Namely, the present invention provides uracil compounds of the formula [I] (hereinafter, referred to as the present compound):

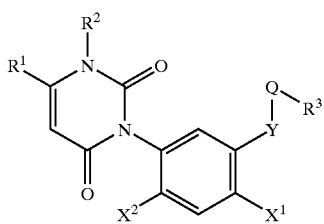

[I]

[wherein, Q-$R^3$ represents a $R^3$-substituted group of a 5-membered or 6-membered heterocyclic ring having one or two nitrogen selected from the group consisting of moieties represented by the following formulae

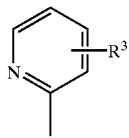

Q-1

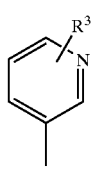

Q-2

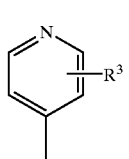

Q-3

-continued

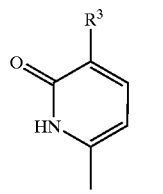

Q-4

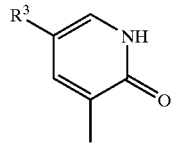

Q-5

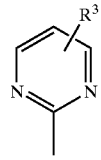

Q-6

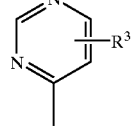

Q-7

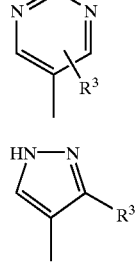

Q-8

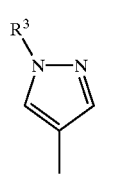

Q-9

Q-10

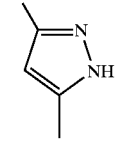

Q-11

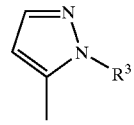

Q-12

Q-13

(wherein, this heterocyclic ring may be substituted with at least one kind of substituent selected from the group consisting of halogen, C1 to C6 alkyl, C1 to C6 haloalkyl, C2 to C6 alkenyl, C2 to C6 haloalkenyl, C2 to C6 alkynyl, C2 to C6 haloalkynyl, C1 to C6 alkoxy C1 to C6 alkyl, C1 to C6 alkoxy, C1 to C6 haloalkoxy, C1 to C6 alkoxycarbonyl C1 to C6 alkoxy, C1 to C6 alkoxycarbonyl C1 to C6 alkyl, cyano, hydroxy, mercapto, oxo and thioxo.), Y represents oxygen, sulfur, imino or C1 to C3 alkylimino, $R^1$ represents C1 to C3 alkyl or C1 to C3 haloalkyl, $R^2$ represents C1 to C3 alkyl, $R^3$ represents carboxy C1 to C6 alkyl, C1 to C6 alkoxycarbonyl C1 to C6 alkyl, C1 to C6 haloalkoxycarbonyl C1 to C6 alkyl, C3 to C6 alkenyloxycarbonyl C1 to C6 alkyl, C3 to C6 haloalkenyloxycarbonyl C1 to C6 alkyl, C3 to C6 alkynyloxycarbonyl C1 to C6 alkyl, C3 to C6 haloalkynyloxycarbonyl C1 to C6 alkyl, $OR^7$, $SR^8$ or $N(R^9)R^{10}$, $X^1$ represents halogen, cyano, thiocarbamoyl or nitro, $X^2$ represents hydrogen or halogen.

{wherein, each of $R^7$, $R^8$ and $R^{10}$ independently represents carboxy C1 to C6 alkyl, C1 to C6 alkoxycarbonyl C1 to C6 alkyl, C1 to C6 haloalkoxycarbonyl C1 to C6 alkyl, C3 to C6 alkenyloxycarbonyl C1 to C6 alkyl, C3 to C6 haloalkenyloxycarbonyl C1 to C6 alkyl, C3 to C6 alkynyloxycarbonyl C1 to C6 alkyl, C3 to C6 haloalkynyloxycarbonyl C1 to C6 alkyl, C3 to C8 cycloalkoxycarbonyl C1 to C6 alkyl, C3 to C8 halocycloalkoxycarbonyl C1 to C6 alkyl, C3 to C8 cycloalkenyloxycarbonyl C1 to C6 alkyl, C3 to C8 halocycloalkenyloxycarbonyl C1 to C6 alkyl, C1 to C6 alkoxycarbonyl C1 to C6 alkoxycarbonyl C1 to C6 alkyl, C1 to C8 alkylidenaminoxycarbonyl C1 to C6 alkyl, phenoxycarbonyl C1 to C6 alkyl which may be substituted, phenyl C1 to C4 alkoxycarbonyl C1 to C6 alkyl which may be substituted, C1 to C6 alkoxyaminocarbonyl C1 to C6 alkyl, (C1 to C6 alkoxy)(C1 to C3 alkyl)aminocarbonyl C1 to C6 alkyl, C1 to C6 alkylaminocarbonyl C1 to C6 alkyl, (C1 to C6 alkyl) C1 to C6 alkylaminocarbonyl C1 to C6 alkyl, phenylaminocarbonyl C1 to C6 alkyl which may be substituted, or phenyl C1 to C4 alkylaminocarbonyl C1 to C6 alkyl which may be substituted, and $R^9$ represents hydrogen or C1 to C6 alkyl.}.], and herbicides containing each of them as an effective ingredient.

In the present invention, as the group represented by Q-$R^3$, for example, there are listed groups of the following formulae:

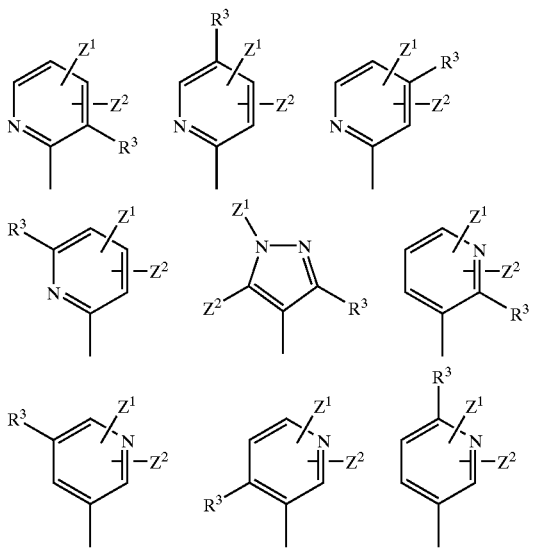

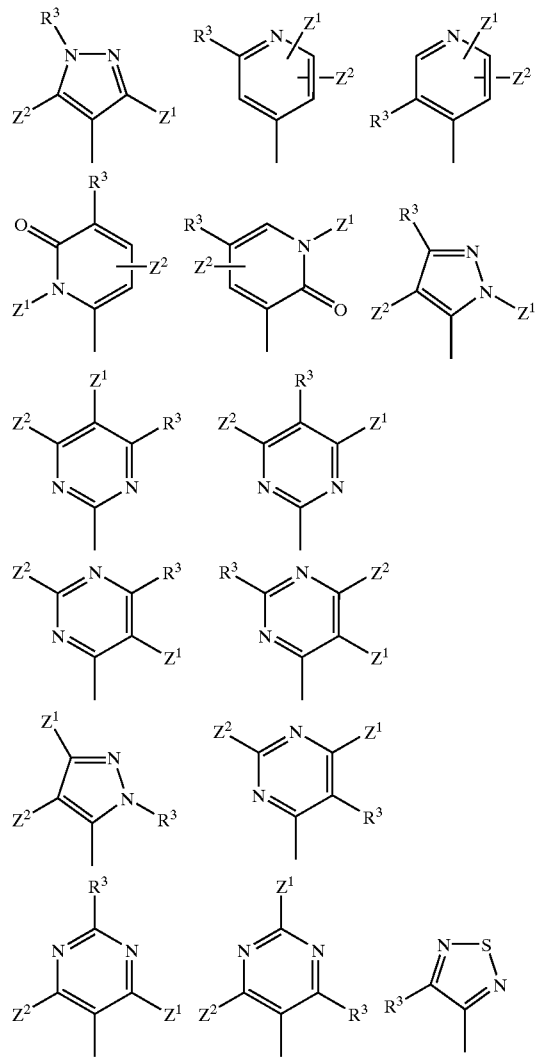

[wherein, $R^3$ is the same as defined above, each of $Z^1$ and $Z^2$ independently represents hydrogen, halogen, C1 to C6 alkyl, C1 to C6 haloalkyl, C2 to C6 alkenyl, C2 to C6 haloalkenyl, C2 to C6 alkynyl, C2 to C6 haloalkynyl, C1 to C6 alkoxy C1 to C6 alkyl, C1 to C6 alkoxy, C1 to C6 haloalkoxy, C1 to C6 alkoxycarbonyl C1 to C6 alkoxy or cyano (wherein, the halogen represented by $Z^1$ or $Z^2$ means fluorine, chlorine, bromine or iodine, and examples of the C1 to C6 alkyl include methyl, ethyl, propyl, isopropyl, butyl, s-butyl, t-butyl and the like, examples of the C1 to C6 haloalkyl include bromomethyl, chloromethyl, fluoromethyl, dichloromethyl, trichloromethyl, difluoromethyl, chlorodifluoromethyl, bromodifluoromethyl, trifluoromethyl, pentafluoroethyl, 2-fluoroethyl, 1,1-difluoroethyl, 2,2,2-trichloroethyl, 3,3,3-trifluoropropyl, 3,3,3-trichloropropyl and the like, examples of the C2 to C6 alkenyl include allyl, 1-methylallyl, 1,1-dimethylallyl, 2-methylallyl, 1-butenyl, 2-butenyl, 3-butenyl and the like, examples of the C2 to C6 haloalkenyl include 1-chloroallyl, 1-bromoallyl, 2-chloroallyl, 3,3-dichloroallyl and the like, examples of the C2 to C6 alkynyl include 2-propynyl, 1-methyl-2-propynyl, 1,1-dimethyl-2-propynyl, 2-butynyl, 3-butynyl, 1-methyl-2-butynyl and the like, examples of the C2 to C6 haloalkynyl include 3-bromo-2-propynyl, 3-iodo-2-propynyl, 1-fluoro-2-propynyl, 1-chloro-2-propynyl, 1-bromo-2-propynyl, 1-chloro-2-butynyl and the like, examples of the C1 to C6 alkoxy C1 to C6 alkyl include methoxymethyl, 2-methoxyethyl, 1-methoxyethyl, 3-methoxypropyl, ethoxymethyl, 2-ethoxyethyl, 3-ethoxypropyl, isopropoxymethyl, 2-isopropoxyethyl and the like, examples of the C1 to C6 alkoxy include methoxy, ethoxy, propoxy, isopropoxy, butyloxy, s-butyloxy, t-butyloxy and the like, examples of the C1 to C6 haloalkoxy include chloromethoxy, bromomethoxy, dichloromethyloxy, trichloromethyloxy, trifluoromethyloxy, 2-fluoroethyloxy, 2,2,2-trichloroethyloxy and the like, examples of the C1 to C6 alkoxycarbonyl C1 to C6 alkoxy include methoxycarbonylmethoxy, ethoxycarbonylmethoxy, propoxycarbonylmethoxy, isopropoxycarbonylmethoxy, 1-methoxycarbonylethoxy, 1-ethoxycarbonylethoxy, 1-propoxycarbonylethoxy, 1-isopropoxycarbonylethoxy, 2-methoxycarbonylethoxy, 2-ethoxycarbonylethoxy, 2-propoxycarbonylethoxy, 2-isopropoxycarbonylethoxy and the like, examples of the C1 to C6 alkoxycarbonyl C1 to C6 alkyl include methoxycarbonylmethyl, ethoxycarbonylmethyl, propoxycarbonylmethyl, isopropoxycarbonylmethyl, t-butoxycarbonylmethyl, amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-t-butoxycarbonylethyl and the like.).].

Examples of the carboxy C1 to C6 alkyl represented by $R^3$ include carboxymethyl, 1-carboxyethyl, 2-carboxyethyl and the like, examples of the C1 to C6 alkoxycarbonyl C1 to C6 alkyl include methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 2-methoxycarbonylethyl, 2-ethoxycarbonylethyl and the like, examples of the C1 to C6 haloalkoxycarbonyl C1 to C6 alkyl include chloromethyloxycarbonylmethyl, 2-fluoroethyloxycarbonylmethyl, 2-chloropropyloxycarbonylmethyl, 1-chloro-2-propyloxycarbonylmethyl, 2,2,2-trifluoroethyloxycarbonylmethyl and the like, examples of the C3 to C6 alkenyloxycarbonyl C1 to C6 alkyl include allyloxycarbonylmethyl, 1-methyl-2-propenyloxycarbonylmethyl, 2-methyl-2-propenyloxycarbonylmethyl, 2-butenyloxycarbonylmethyl, 1-allyloxycarbonylethyl, 1-(1-methyl-2-propenyloxycarbonyl)ethyl, 1-(2-methyl-2-propenyloxycarbonyl)ethyl, 2-allyloxycarbonylethyl, 2-(1-methyl-2-propenyloxycarbonyl)ethyl, 2-(2-methyl-2-propenyloxycarbonyl)ethyl and the like, examples of the C3 to C6 haloalkenyloxycarbonyl C1 to C6 alkyl include 1-chloroallyloxycarbonylmethyl, 1-(1-chloroallyloxycarbonyl)ethyl, 2-chloroallyloxycarbonylmethyl, 1-(2-chloroallyloxycarbonyl)ethyl and the like, examples of the C3 to C6 alkynyloxycarbonyl C1 to C6 alkyl include propargyloxycarbonylmethyl, 1-methyl-2-propynyloxycarbonylmethyl, propynyloxycarbonylmethyl, 1-propargyloxycarbonylethyl, 1-(1-methyl-2-propynyloxycarbonyl)ethyl, 2-propargyloxycarbonylethyl, 2-(1-methyl-2-propynyloxycarbonyl)ethyl and the like, examples of the C3 to C6 haloalkynyloxycarbonyl C1 to C6 alkyl include 1-bromo-2-propynyloxycarbonyl methyl, 1-(1-chloro-2-propynyloxycarbonyl)ethyl and the like, examples of the C1 to C3 alkylimino represented by Y include methylimino, ethylimino and the like, the C1 to C3 alkyl represented by $R^2$ means methyl, ethyl, propyl, isopropyl, and examples of the C1 to C3 haloalkyl include bromomethyl, chloromethyl, fluoromethyl, dichloromethyl, chlorodifluoromethyl, trichloromethyl, difluoromethyl, trifluoromethyl, pentafluoroethyl, 1,1-difluoroethyl, 2,2,2-trifluoroethyl, 3,3,3-trifluoropropyl and the like, the C1 to C3 alkyl represented by $R^2$ means methyl, ethyl, propyl or isopropyl, examples of the carboxy C1 to C6 alkyl represented by $R^7$, $R^8$ or $R^{10}$ include carboxymethyl, 1-carboxyethyl, 2-carboxyethyl and the like, examples of the C1 to C6 alkoxycarbonyl C1 to C6 alkyl include methoxycarbonylmethyl, ethoxycarbonylmethyl, propoxycarbonylmethyl, isopropoxycarbonylmethyl, butoxycarbonylmethyl, isobutoxycarbonylmethyl, s-butoxycarbonylmethyl, t-butoxycarbonylmethyl, amyloxycarbonylmethyl isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-s-butoxycarbonylethyl, 1-t-butoxycarbonylethyl, 2-methoxycarbonylethyl, 2-ethoxycarbonylethyl, and the like, examples of the C1 to C6 haloalkoxycarbonyl C1 to C6 alkyl include chloromethyloxycarbonylmethyl, 2-fluoroethyloxycarbonylmethyl, 2-chloropropyloxycarbonylmethyl, 1-chloro-2-propyloxycarbonylmethyl, 2,2,2-trifluoroethyloxycarbonylmethyl and the like, examples of the C3 to C6 alkenyloxycarbonyl C1 to C6 alkyl include allyloxycarbonylmethyl, 1-methyl-2-propenyloxycarbonylmethyl, 2-methyl-2-propenyloxycarbonylmethyl, 2-butenyloxycarbonylethyl, 1-allyloxycarbonylethyl, 1-(1-methyl-2-propenyloxycarbonyl)ethyl, 1-(2-methyl-2-propenyloxycarbonyl)ethyl, 2-allyloxycarbonylethyl, 2-(1-methyl-2-propenyloxycarbonyl)ethyl, 2-(2-methyl-2-propenyloxycarbonyl)ethyl and the like, examples of the C3 to C6 haloalkenyloxycarbonyl C1 to C6 alkyl include 1-chloro-2-propenyloxycarbonylmethyl, 1-(2-chloro-2-propenyloxycarbonyl)ethyl and the like, examples of the C3 to C6 alkynyloxycarbonyl C1 to C6 alkyl include propargyloxycarbonylmethyl, 1-methyl-2-propynyloxycarbonylmethyl, 1-propargyloxycarbonylethyl, 1-(1-methyl-2-propynyloxycarbonyl)ethyl, 2-propargyloxycarbonylethyl, 2-(1-methyl-2-propynyloxycarbonyl)ethyl and the like, examples of the C3 to C6 haloalkynyloxycarbonyl C1 to C6 alkyl include 1-bromo-2-propynyloxycarbonyl methyl, 1-(1-chloro-2-propynyloxycarbonyl)ethyl and the like, examples of the C3 to C8 cycloalkoxycarbonyl C1 to C6 alkyl include cyclopropyloxycarbonylmethyl, cyclopentyloxycarbonylmethyl, 1-(cyclobutyloxycarbonyl)ethyl and the like, examples of the C3 to C8 halocycloalkoxycarbonyl C1 to C6 alkyl include 2,2-difluorocyclopentyloxycarbonylmethyl, 2-bromocyclopentyloxycarbonylmethyl, 1-(2-chlorocyclobutyloxycarbonyl)ethyl and the like, examples of the C3 to C8 cycloalkenyloxycarbonyl C1 to C6 alkyl include 2-cyclopentenyloxycarbonylmethyl, 1-(2-cyclobutenyloxycarbonyl)ethyl and the like, examples of the C3 to C8 halocycloalkenyloxycarbonyl C1 to C6 alkyl include 4-bromo-2-cyclobutenyloxycarbonylmethyl and 1-(4-bromo-2-cyclopentenyloxycarbonyl)ethyl the like, examples of the C1 to C6 alkoxycarbonyl C1 to C6 alkoxycarbonyl C1 to C6 alkyl include methoxycarbonylmethoxycarbonylmethyl, 2-(methoxycarbonyl)-2-propoxycarbonylmethyl, 1-[1-(ethoxycarbonyl)ethoxycarbonyl]ethyl and the like, examples of the C1 to C8 alkylidenaminoxycarbonyl C1 to C6 alkyl include isoprpylidenaminoxycarbonylmethyl, 2-(isoprpylidenaminoxycarbonyl)ethyl and the like, examples of the phenoxycarbonyl C1 to C6 alkyl which may be substituted include phenoxycarbonylmethyl, 1-phenoxycarbonylethyl and the like, examples of the phenyl C1 to C4 alkoxycarbonyl C1 to C6 alkyl which may be substituted include benzyloxycarbonylmethyl, 1-benzyloxycarbonylethyl and the like, examples of the C1 to C6 alkoxyaminocarbonyl C1 to C6 alkyl include methoxyaminocarbonylmethyl, 1-methoxyaminocarbonylethyl, ethoxyaminocarbonylmethyl, 1-ethoxyaminocarbonylethyl and the like, examples of the (C1 to C6 alkoxy)(C1 to C3 alkyl)aminocarbonyl C1 to C6 alkyl include (methoxy)(methyl)aminocarbonylmethyl, 1-(methoxy)(methyl)aminocarbonylethyl, (ethoxy)(methyl)aminocarbonylmethyl, 1-(ethoxy)(methyl)aminocarbonylethyl and the like, examples of the C1 to C6 alkylaminocarbonyl C1 to C6 alkyl include methylaminocarbonylmethyl, ethylaminocarbonylmethyl, isopropylaminocarbonylmethyl, 1-methylaminocarbonylethyl, 1-isobutylaminocarbonylethyl and the like, examples of the (C1 to C6 alkyl)(C1 to C6 alkyl)aminocarbonyl C1 to C6 alkyl include dimethylaminocarbonylmethyl, 1-dimethylaminocarbonylethyl and the like, examples of the phenylaminocarbonyl C1 to C6 alkyl which may be substituted include phenylaminocarbonylmethyl, 1-phenylaminocarbonylethyl and the like, and examples of the phenyl C1 to C4 alkylaminocarbonyl C1 to C6 alkyl which may be substituted include benzylaminocarbonylmethyl, 1-benzylaminocarbonylethyl and the like, examples of the C1 to C6 alkyl represented by $R^9$ include methyl, ethyl, propyl, isopropyl, butyl and the like, and the halogen represented by $X^1$ and $X^2$ means fluorine, chlorine, bromine or iodine.

In the present compounds, from the standpoint of herbicidal activity, those are preferable wherein Q-$R^3$ is Q-1, Q-2 or Q-6, Y is oxygen or sulfur, more preferably oxygen, $R^1$ is methyl substituted with fluorine (for example, trifluoromethyl, chlorodifluoromethyl, difluoromethyl or the like), or ethyl substituted with fluorine (for example, pentafluoroethyl, 1,1-difluoroethyl or the like), more preferably trifluoromethyl, $R^2$ is methyl or ethyl, more preferably methyl, $R^3$ is C1 to C4 alkoxycarbonyl C1 to C4 alkyl, C1 to C4 alkoxycarbonyl C1 to C4 alkoxy, C3 to C7 cycloalkoxycarbonyl C1 to C4 alkoxy, C1 to C4 alkoxycarbonyl C1 to C4 alkylthio or C1 to C4 alkoxycarbonyl C1 to C4 alkylamino, more preferably C1 to C2 alkoxycarbonyl C1 to C2 alkoxy, $X^1$ is halogen, more preferably chlorine, and/or $X^2$ is halogen, more preferably fluorine.

As the specially prefered compounds, compound wherein Q-$R^3$ is 2-(methoxycarbonyl)methoxy-3-pyridyl, 2-(ethoxycarbonyl)methoxy-3-pyridyl, 4-{1-(methoxycarbonyl)ethoxy}-2-pyrimidyl, $R^1$ is trifluoromethyl, $R^2$ is methyl, $X^1$ is chlorine, $X^2$ is fluorine, and Y is oxygen.

Sometimes, geometrical isomers based on double bond, optical isomers and diastereomers based on asymmetric carbon, may be present in the present compound, and the present compound also includes these isomers and mixtures thereof.

Next, methods for producing the present compounds will be illustrated.

The present compound can be produced, for example, by the following (Production Method 1) to (Production Method 10).

(Production Method 1)

Of the present compounds, the compound [I] wherein $R^3$ is $OR^7$, $SR^8$ or $N(R^9)R^{10}$ can be produced by reacting a compound [III] of the formula [III]

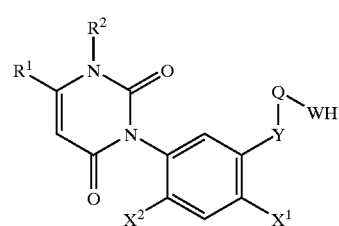

[III]

[wherein, $R^1$, $R^2$, Y, Q, $X^1$ and $X^2$ are the same as defined above, and W represents oxygen, sulfur, imino or, C1 to C3 alkylimino such as methylimino and the like.]
with a compound [IV] of the formula [IV]

 [IV]

[wherein, $R^{11}$ represents carboxy C1 to C6 alkyl, C1 to C6 alkoxycarbonyl C1 to C6 alkyl, C1 to C6 haloalkoxycarbonyl C1 to C6 alkyl, C3 to C6 alkenyloxycarbonyl C1 to C6 alkyl, C3 to C6 alkynyloxycarbonyl C1 to C6 alkyl, phenoxycarbonyl C1 to C6 alkyl which may be substituted, phenyl C1 to C4 alkoxycarbonyl C1 to C6 alkyl which may be substituted, C1 to C6 alkoxyaminocarbonyl C1 to C6 alkyl, (C1 to C6 alkoxy)(C1 to C3 alkyl)aminocarbonyl C1 to C6 alkyl, C1 to C6 alkylaminocarbonyl C1 to C6 alkyl, (C1 to C6 alkyl) C1 to C6 alkylaminocarbonyl C1 to C6 alkyl, phenylaminocarbonyl C1 to C6 alkyl which may be substituted, or phenyl C1 to C4 alkylaminocarbonyl C1 to C6 alkyl which may be substituted, and $R^{12}$ represents a leaving group such as chlorine, bromine, iodine, methanesulfonyloxy, p-toluenesulfonyloxy and the like.]
in the presence of a base.

This reaction is usually conducted in a solvent, and the reaction temperature is usually in a range from 0 to 200° C., and the reaction time is usually in a range from instant to 72 hours.

Regarding the amounts of reagents to be reacted, it is theoretical that the amount of the compound [IV] is 1 mol and the amount of the base is 1 mol based on 1 mol of the compound [III], however, the ratio can be optionally changed depending on reaction conditions.

As the base used, there are listed organic bases such as pyridine, quinoline, benzyldimethylamine, N-methylmorpholine, 1,8-diazabicyclo[5.4.0]undec-7-ene, 1,5-diazabicyclo[4.3.0]non-5-ene, 1,4-diazabicyclo[2.2.2]octane, 4-dimethylaminopyridine, N,N-dimethylaniline, N,N-diethylaniline, triethylamine, tri-n-propylamine, triisopropylamine, tri-n-butylamine, diisopropylethylamine and the like, and inorganic bases such as lithium carbonate, sodium carbonate, potassium carbonate, calcium carbonate, barium carbonate, sodium hydrogen carbonate, potassium hydrogen carbonate, sodium hydride, potassium hydride, lithium hydroxide, sodium hydroxide, potassium hydroxide, and the like.

As the solvent used, there are listed, for example, aliphatic hydrocarbons such as n-hexane, n-heptane, ligroin, cyclohexane, petroleum ether and the like, aromatic hydrocarbons such as benzene, toluene, xylene and the like, aromatic halogenated hydrocarbons such as chlorobenzene, dichlorobenzene, benzotrifluoride and the like, ethers such as diethyl ether, diisopropyl ether, methyl-t-butyl ether, dioxane, tetrahydrofuran, ethylene glycol dimethyl ether, diglyme and the like, ketones such as acetone, 2-butanone, methyl isobutyl ketone and the like, esters such as ethyl formate, ethyl acetate, butyl acetate, diethyl carbonate and the like, nitro compounds such as nitromethane, nitrobenzene and the like, nitriles such as acetonitrile, isobutyronitrile and the like, amides such as N,N-dimethylformamide, N,N-dimethylacetamide, N-methyl-2-pyrrolidone and the like, sulfur compounds such as dimethyl sulfoxide, sulfolane and the like, or mixtures thereof.

After completion of the reaction, an intended present compound can be obtained, for example, by the following operation 1) or 2).

1) The reaction solution is poured into water, this is extracted with an organic solvent, and the organic layer is dried and concentrated.

2) The reaction solution is concentrated as it is, or, filtrated if necessary, and the filtrate is concentrated.

The resulted present compound can also be purified by an operation such as chromatography, re-crystallization and the like.

(Production Method 2)

Of the present compounds, the compound [I] wherein $R^3$ is $OR^7$ can be produced by reacting a compound [V] of the formula [V]

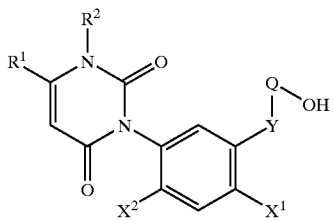

[V]

[wherein, $R^1$, $R^2$, Y, Q, $X^1$ and $X^2$ are the same as defined above.]

with an alcohol compound [VI] of the formula [VI]

$R^7$—OH  [VI]

[wherein, $R^7$ is the same as defined above.]
in the presence of a dehydrating reagent.

This reaction is usually conducted in a solvent, and the reaction temperature is usually in a range from −20 to 150° C., preferably from 0 to 100° C., and the reaction time is usually in a range from instant to 48 hours.

As the dehydrating reagent, there are listed, for example, combinations of triarylphosphine such as triphenylphosphine and the like, and di(lower alkyl)azodicarboxylate such as diethyl azodicarboxylate, diisopropyl azodicarboxylate and the like.

Regarding the amounts of reagents to be reacted, the amount of the alcohol compound [VI] is from 1 to 3 mol, preferably from 1 to 1.5 mol, the amount of the triarylphosphine used as a dehydrating agent is from 1 to 3 mol, preferably from 1 to 1.5 mol, and the amount of a di(lower alkyl)azodicarboxylate is from 1 to 3 mol, preferably from 1 to 1.5 mol, based on 1 mol of the compound [V]. The ratio of these reagents can be optionally changed depending on reaction conditions.

As the solvent used, there are listed, for example, aliphatic hydrocarbons such as n-hexane, n-heptane, ligroin, cyclohexane, petroleum ether and the like, aromatic hydrocarbons such as toluene, xylene and the like, halogenated aromatic hydrocarbons such as chlorobenzene, benzotrifluoride and the like, ethers such as diethyl ether, diisopropyl ether, dioxane, THF, ethylene glycol dimethyl ether, and the like, esters such as ethyl acetate and the like, or mixtures thereof.

After completion of the reaction, an intended present compound can be obtained, for example, by the following operation 1) or 2).

1) The reaction solution is poured into water, this is extracted with an organic solvent, and the organic layer is dried and concentrated, and the residue is subjected to chromatography.

2) The reaction solution is concentrated as it is, and the residue is subjected to chromatography.

The resulted present compound can also be purified by an operation such as re-crystallization and the like, in some cases.

(Production Method 3)

Of the present compounds, some compounds can be produced by using a carboxylic acid compound [VII] of the formula [VII]

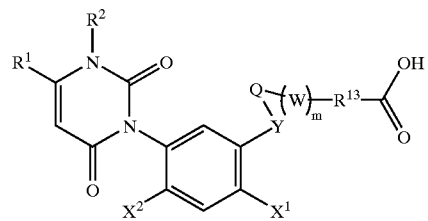

[VII]

[wherein, $R^1$, $R^2$, Y, Q, $X^1$, $X^2$ and W are the same as defined above, $R^{13}$ represents C1 to C6 alkylidene or C2 to C6 alkylene and m represents an integer of 0 or 1.]
and an alcohol compound [VIII] of the formula [VIII]

HO—$R^{14}$  [VIII]

[wherein, $R^{14}$ represents C1 to C6 alkyl, C1 to C6 haloalkyl, C3 to C6 alkenyl, C3 to C6 haloalkenyl, C3 to C6 alkynyl or C3 to C6 haloalkynyl.]
as raw materials.

This reaction is conducted, for example, by reacting the carboxylic acid compound [VII] with a chlorinating agent to give an acid chloride (hereinafter, referred to as <Process 3-1>), then, reacting the acid chloride with the alcohol compound [VIII] in the presence of a base (hereinafter, referred to as <Process 3-2>).

<Process 3-1> is conducted without a solvent or in a solvent, and the reaction temperature is usually in a range from 0 to 150° C. and the reaction time is usually in a range from instant to 24 hours.

Regarding the amounts of reagents to be reacted, it is theoretical that the amount of the chlorinating agent is 1 mol based on 1 mol of the carboxylic acid compound [VII], however, the ratio can be optionally changed depending on reaction conditions.

As the chlorinating agent used, there are listed, for example, thionyl chloride, sulfuryl chloride, phosgene, oxalyl chloride, phosphorus trichloride, phosphorus pentachloride, phosphorus oxychloride and the like.

As the solvent used, there are listed, for example, aliphatic hydrocarbons such as n-hexane, n-heptane, nonane, decane, ligroin, cyclohexane, petroleum ether and the like, aromatic hydrocarbons such as benzene, toluene, xylene, mesitylene and the like, aliphatic halogenated hydrocarbons such as methylene chloride, chloroform, carbon tetrachloride, 1,2-dichloroethane, 1,2,3-trichloropropane and the like, aliphatic halogenated hydrocarbons such as monochlorobenzene, dichlorobenzene, benzotrifluoride and the like, ethers such as diethyl ether, diisopropyl ether, methyl-t-butyl ether, 1,4-dioxane, tetrahydrofuran, ethylene glycol dimethyl ether, diglyme and the like, esters such as ethyl acetate and the like, or mixtures thereof.

After completion of the reaction, for example, the reaction solution is concentrated, and the concentrated residue is used as it is in <Process 3-2>.

<Process 3-2> is conducted without a solvent or in a solvent, and the reaction temperature is usually in a range from −20 to 100° C. and the reaction time is usually in a range from instant to 24 hours.

Regarding the amounts of reagents to be reacted, it is theoretical that the amounts of the alcohol compound [VIII] and the base are 1 mol, respectively, based on 1 mol of the carboxylic acid compound [VII] used in <Process 3-1>, however, the ratio can be optionally changed depending on reaction conditions.

As the base used, there are listed, for example, inorganic bases such as sodium hydrogen carbonate, potassium hydrogen carbonate, lithium carbonate, sodium carbonate, potassium carbonate and the like, nitrogen-containing aromatic compounds such as pyridine, quinoline, 4-dimethylaminopyridine, 2-picoline, 3-picoline, 4-picoline, 2,3-lutidine, 2,4-lutidine, 2,5-lutidine, 2,6-lutidine, 3,4-lutidine, 3,5-lutidine, 3-chloropyridine, 2-ethyl-3-ethylpydirine, 5-ethyl-2-methylpydirine and the like, and tertiary amines such as triethylamine, diisopropylethylamine, tri-n-propylamine, tri-n-butylamine, benzyldimethylamine, N-methylmorpholine, 1,8-diazabicyclo[5.4.0]undec-7-ene, 1,5-diazabicyclo[4.3.0]non-5-ene, 1,4-diazabicyclo[2.2.2]octane and the like.

As the solvent used, there are listed, for example, aliphatic hydrocarbons such as n-hexane, n-heptane, nonane, decane, ligroin, cyclohexane, petroleum ether and the like, aromatic hydrocarbons such as benzene, toluene, xylene, mesitylene and the like, aliphatic halogenated hydrocarbons such as methylene chloride, chloroform, carbon tetrachloride, 1,2-dichloroethane, 1,2,3-trichloropropane and the like, aromatic halogenated hydrocarbons such as monochlorobenzene, dichlorobenzene, benzotrifluoride and the like, ethers such as diethyl ether, diisopropyl ether, methyl-t-butyl ether, 1,4-dioxane, tetrahydrofuran, ethylene glycol dimethyl ether, diglyme and the like, esters such as ethyl acetate and the like, or mixtures thereof.

After completion of the reaction, an intended present compound can be obtained, for example, by the following operation 1) or 2).

1) The reaction solution is poured into water, this is extracted with an organic solvent, and the organic layer is dried and concentrated.

2) The reaction solution is concentrated as it is, or, filtrated if necessary, and the filtrate is concentrated.

The resulted present compound can also be purified by an operation such as chromatography, re-crystallization and the like.

This reaction can also be conducted by reacting the compound [VII] with the compound [VIII] in the presence of a condensing agent with a base or without a base in a solvent. The reaction temperature is usually in a range from 0 to 100° C., and the reaction time is usually in a range from instant to 48 hours.

As the condensing reagent, carbonyldiimidazole, dicyclohexylcarbodiimide, 1-[3-(dimethylamino)propyl]-3-ethylcarbodiimide hydrochloride and the like, are listed.

As the base, organic bases such as triethylamine, diisopropylethylamine and the like, are listed.

Regarding the amounts of reagents to be reacted, the amount of the compound [VIII] is from 1 to 3 mol, the amount of the condensing reagent is from 1 to 3 mol, the amount of the base is from 0.5 to 3 mol, based on 1 mol of the compound [VII]. The ratio of these reagents can be optionally changed depending on reaction conditions.

As the solvent used, dichloromethane, amide such as N,N-dimethylformamide, ethers such as tetrahydrofuran, and the like, or mixtures thereof are listed.

After completion of the reaction, an intended present compound can be obtained, for example, by the reaction solution is poured into water, this is extracted with an organic solvent, and the organic layer is dried and concentrated. The resulted present compound can also be purified by an operation such as chromatography, re-crystallization and the like.

Further, this reaction can also be conducted by a method in which a reaction is conducted in the presence of an acid catalyst, an other known methods, in addition to the above-mentioned methods.

(Production Method 4)

Of the present compounds, the compound [I] wherein $X^1$ is cyano can be produced by reacting a uracil compound [IX] of the formula [IX]

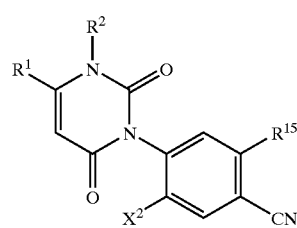

[IX]

[wherein, $R^1$, $R^2$ and $X^2$ are the same as defined above, and $R^{15}$ represents fluorine, chlorine, bromine or iodine.]
with a compound [X] of the formula [X]

[X]

[wherein, Y, Q and $R^3$ are the same as defined above.]
in the presence of a base.

This reaction is usually conducted without a solvent or in a solvent, and the reaction temperature is usually in a range from 0 to 200° C., and the reaction time is usually in a range from instant to 24 hours.

Regarding the amounts of reagents to be reacted, it is theoretical that the amount of the compound [X] is 1 mol and the amount of the base is 1 mol based on 1 mol of the uracil compound [IX], however, the ratio can be optionally changed depending on reaction conditions.

As the base used, there are listed organic bases such as 1,8-diazabicyclo[5.4.0]undec-7-ene, 4-dimethylaminopyridine, N,N-dimethylaniline, N,N-diethylaniline, triethylamine, diisopropylethylamine and the like, and inorganic bases such as lithium carbonate, sodium carbonate, potassium carbonate, calcium carbonate, barium carbonate, sodium hydrogen carbonate, potassium hydrogen carbonate, sodium hydride, potassium hydride, lithium hydroxide, sodium hydroxide, potassium hydroxide, and the like.

As the solvent used, there are listed, for example, aliphatic hydrocarbons such as n-hexane, n-heptane, and the like, aromatic hydrocarbons such as toluene, xylene and the like, aromatic halogenated hydrocarbons such as chlorobenzene, benzotrifluoride and the like, ethers such as diethyl ether, dioxane, tetrahydrofuran, ethylene glycol dimethyl ether, diglyme and the like, ketones such as methyl isobutyl ketone and the like, esters such as ethyl acetate, butyl acetate, and the like, nitriles such as acetonitrile, isobutyronitrile and the like, amides such as N,N-dimethylformamide, N-methyl-2-pyrrolidone and the like, sulfur compounds such as dimethylsulfoxide, sulfolane and the like, or mixtures thereof.

This reaction may sometimes be accelerated by using a catalyst. As the catalyst, copper iodide, copper bromide, copper chloride, copper powder and the like are listed, and the amount of the catalyst to be used in the reaction is from 0.0001 to 1 mol based on 1 mol of the uracil compound [IX], and this ratio can be optionally changed depending on conditions of the reaction.

After completion of the reaction, an intended present compound can be obtained, for example, by the following operation 1) or 2).

1) The reaction solution is poured into water, this is extracted with an organic solvent, and the organic layer is dried and concentrated.

2) The reaction solution is concentrated as it is, or, filtrated if necessary, and the filtrate is concentrated.

The resulted present compound can also be purified by an operation such as chromatography, re-crystallization and the like.

(Production Method 5)

The present compound can be produced by reacting a uracil compound [XI] of the formula [XI]

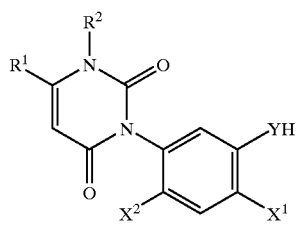

[XI]

[wherein, $R^1$, $R^2$, Y, $X^1$ and $X^2$ are the same as defined above.]

with a compound [XII] of the formula [XII]

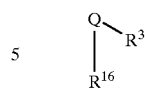

[XII]

[wherein, $R^{16}$ represents a leaving group such as fluorine, chlorine, bromine, iodine, methanesulfonyloxy, p-toluenesulfonyloxy and the like, and $R^3$ is the same as defined above.]

in the presence of a base.

This reaction is usually conducted without a solvent or in a solvent, and the reaction temperature is usually in a range from room temperature to 200° C., and the reaction time is usually in a range from instant to 24 hours.

Regarding the amounts of reagents to be reacted, it is theoretical that the amount of the compound [XII] is 1 mol and the amount of the base is 1 mol based on 1 mol of the compound [XI], however, the ratio can be optionally changed depending on reaction conditions.

As the base used, there are listed organic bases such as N-methylmorpholine, 1,8-diazabicyclo[5.4.0]undec-7-ene, 4-dimethylaminopyridine, N,N-dimethylaniline, N,N-diethylaniline, triethylamine, diisopropylethylamine and the like, and inorganic bases such as lithium carbonate, sodium carbonate, potassium carbonate, calcium carbonate, barium carbonate, sodium hydrogen carbonate, potassium hydrogen carbonate, sodium hydride, potassium hydride, sodium hydroxide, potassium hydroxide, and the like.

As the solvent used, there are listed, for example, aliphatic hydrocarbons such as n-hexane, n-heptane, ligroin, cyclohexane, petroleum ether and the like, aromatic hydrocarbons such as toluene, xylene and the like, aromatic halogenated hydrocarbons such as chlorobenzene, benzotrifluoride and the like, ethers such as diethyl ether, dioxane, tetrahydrofuran, ethylene glycol dimethyl ether, diglyme and the like, ketones such as acetone, 2-butanone, methyl isobutyl ketone and the like, esters such as ethyl acetate, butyl acetate, and the like, nitrites such as acetonitrile, isobutyronitrile and the like, amides such as N,N-dimethylformamide, N,N-dimethylacetamide, N-methyl-2-pyrrolidone and the like, sulfur compounds such as dimethylsulfoxide, sulfolane and the like, or mixtures thereof.

This reaction may sometimes be accelerated by using a catalyst.

The amount of the catalyst to be used in the reaction is preferably from 0.0001 to 1 mol based on 1 mol of the compound [XI], and this ratio can be optionally changed depending on conditions of the reaction.

As the catalyst, there are listed copper compounds such as copper iodide, copper bromine, copper chloride, copper powder and the like, and crown ethers such as 12-crown-4, 15-crown-5, 18-crown-6 and the like.

After completion of the reaction, an intended present compound can be obtained, for example, by the following operation 1) or 2).

1) The reaction solution is poured into water, this is extracted with an organic solvent, and the organic layer is dried and concentrated.

2) The reaction solution is concentrated as it is, or, filtrated if necessary, and the filtrate is concentrated.

The intended compound can also be purified by an operation such as chromatography, re-crystallization and the like.

(Production Method 6)

The present compound can be produced by reacting a uracil compound [XXXI] of the formula [XXXI]

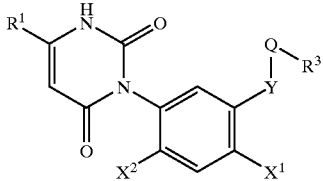

[wherein, $R^1$, $R^3$, Y, Q, $X^1$ and $X^2$ are the same as defined above.]
with a compound [XXXX] of the formula [XXXX]

$$R^{12}-R^2 \quad [XXXX]$$

[wherein, $R^2$ and $R^{12}$ are the same as defined above.]
in the presence of a base.

This reaction is usually conducted without a solvent or in a solvent, and the reaction temperature is usually in a range from −20 to 150° C., and the reaction time is usually in a range from instant to 24 hours.

Regarding the amounts of reagents to be reacted, it is theoretical that the amount of the compound [XXXX] is 1 mol and the amount of the base is 1 mol based on 1 mol of the uracil compound [XXXI], however, the ratio can be optionally changed depending on reaction conditions.

As the base used, there are listed organic bases such as pyridine, quinoline, benzyldimethylamine, N-methylmorpholine, 1,8-diazabicyclo[5.4.0]undec-7-ene, 1,5-diazabicyclo[4.3.0]non-5-ene, 1,4-diazabicyclo[2.2.2]octane, 4-dimethylaminopyridine, N,N-dimethylaniline, N,N-diethylaniline, triethylamine, tri-n-propylamine, triisopropylamine, tri-n-butylamine, diisopropylethylamine and the like, metal alkoxides such as sodium methoxide, sodium ethoxide, potassium t-butoxide and the like, and inorganic bases such as lithium carbonate, sodium carbonate, potassium carbonate, calcium carbonate, barium carbonate, sodium hydrogen carbonate, potassium hydrogen carbonate, sodium hydride, potassium hydride, lithium hydroxide, sodium hydroxide, potassium hydroxide, and the like.

As the solvent used, there are listed, for example, aliphatic hydrocarbons such as n-hexane, n-heptane, ligroin, cyclohexane, petroleum ether and the like, aromatic hydrocarbons such as benzene, toluene, xylene and the like, aromatic halogenated hydrocarbons such as chlorobenzene, dichlorobenzene, benzotrifluoride and the like, ethers such as diethyl ether, diisopropyl ether, methyl-t-butyl ether, dioxane, tetrahydrofuran, ethylene glycol dimethyl ether, diglyme and the like, ketones such as acetone, 2-butanone, methyl isobutyl ketone and the like, esters such as ethyl acetate, butyl acetate, and the like, nitro compounds such as nitromethane, nitrobenzene and the like, nitriles such as acetonitrile, isobutyronitrile and the like, amides such as N,N-dimethylformamide, N,N-dimethylacetamide, N-methyl-2-pyrrolidone and the like, sulfur compounds such as dimethylsulfoxide, sulfolane and the like, alcohols such as methanol, ethanol, ethylene glycol, isopropanol, t-butanol and the like, or mixtures thereof.

After completion of the reaction, an intended present compound can be obtained, for example, by the following operation 1), 2) or 3).

1) The reaction solution is poured into water, this is extracted with an organic solvent, and the organic layer is dried and concentrated.

2) The reaction mixture is poured into water and the precipitate is collected by filtration.

3) A reaction solution is concentrated as it is, or, filtrated if necessary, and the filtrate is concentrated.

The resulted present compound can also be purified by an operation such as chromatography, re-crystallization and the like.

(Production Method 7)

Of the present compounds, the compound [I] wherein Q is a pyrazolediyl group can be produced by a method shown in the following scheme.

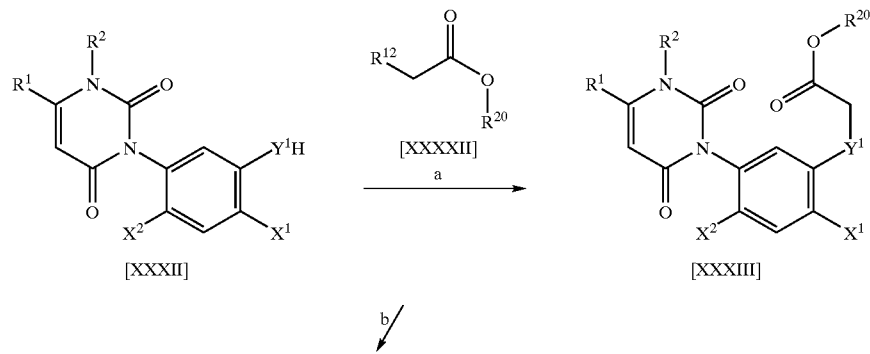

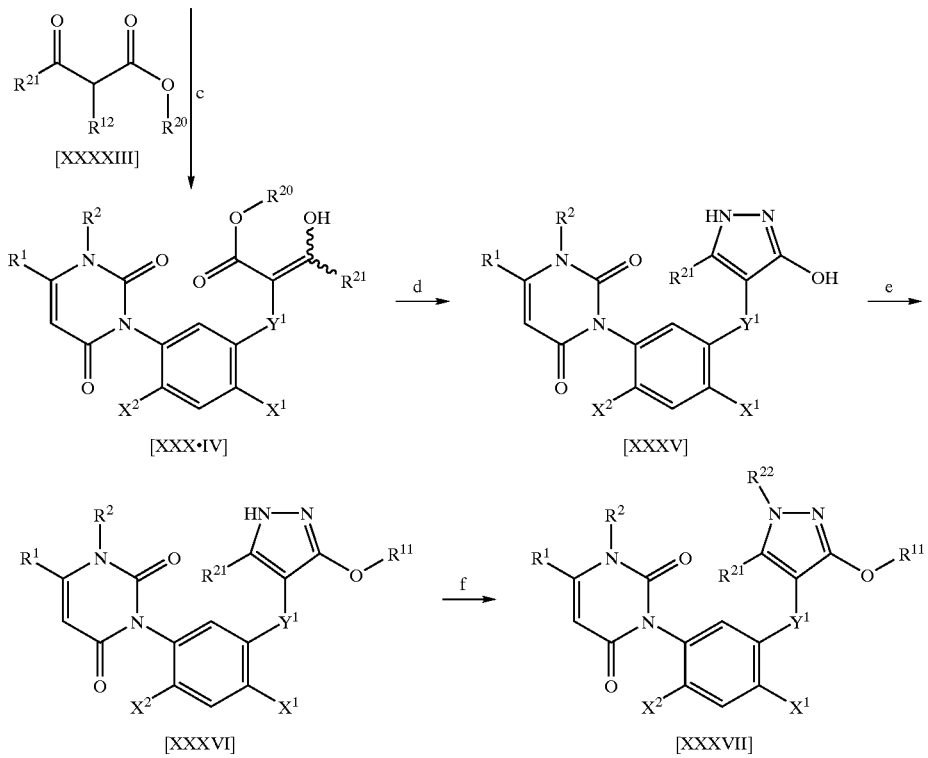

[wherein, $R^1$, $R^2$, $R^{11}$, $R^{12}$, $X^1$ and $X^2$ are the same as defined above. $R^{20}$ represents lower alkyl such as methyl, ethyl and the like, $R^{21}$ represents hydrogen, C1 to C6 alkyl, C2 to C6 alkenyl or C2 to C6 alkynyl, $R^{22}$ represents C1 to C6 alkyl, C2 to C6 alkenyl or C2 to C6 alkynyl, and $Y^1$ represents oxygen, sulfur or alkylimino.].

<Step a>: A process to produce the compound [XXXIII] from the compound [XXXII].

The compound [XXXIII] can be produced by reacting the compound [XXXII] with the compound [XXXXII] in the presence of a base.

This reaction is usually conducted without a solvent or in a solvent, and the reaction temperature is usually in a range from 0 to 150° C., and the reaction time is usually in a range from instant to 24 hours.

Regarding the amounts of reagents to be reacted, it is theoretical that the amount of the compound [XXXXII] is 1 mol and the amount of the base is 1 mol based on 1 mol of the compound [XXXII], however, the ratio can be optionally changed depending on reaction conditions.

As the base used, there are listed organic bases such as pyridine, N-methylmorpholine, 1,8-diazabicyclo[5.4.0]undec-7-ene, 4-dimethylaminopyridine, N,N-dimethylaniline, N,N-diethylaniline, triethylamine, diisopropylethylamine and the like, metal alkoxides such as sodium methoxide, potassium t-butoxide and the like, and inorganic bases such as lithium carbonate, sodium carbonate, potassium carbonate, lithium hydroxide, sodium hydroxide, potassium hydroxide, and the like.

As the solvent used, there are listed, for example, aliphatic hydrocarbons such as n-hexane, n-heptane, ligroin, petroleum ether and the like, aromatic hydrocarbons such as toluene, xylene and the like, aromatic halogenated hydrocarbons such as chlorobenzene, dichlorobenzene, benzotrifluoride and the like, ethers such as diethyl ether, dioxane, tetrahydrofuran, ethylene glycol dimethyl ether, and the like, ketones such as acetone, 2-butanone, methyl isobutyl ketone and the like, esters such as ethyl acetate, and the like, nitriles such as acetonitrile, isobutyronitrile and the like, amides such as N,N-dimethylformamide, N-methyl-2-pyrrolidone and the like, sulfur compounds such as dimethylsulfoxide, sulfolane and the like, alcohols such as methanol, ethanol, t-butanol and the like, or mixtures thereof.

After completion of the reaction, an intended present compound can be obtained, for example, by the following operation 1) or 2).

1) The reaction solution is poured into water, this is extracted with an organic solvent, and the organic layer is dried and concentrated.

2) The reaction solution is concentrated as it is, or, filtrated if necessary, and the filtrate is concentrated.

The intended compound can also be purified by an operation such as chromatography, re-crystallization and the like.

<Step b>: A process to produce the compound [XXXIV] from the compound [XXXIII].

The compound [XXXIV] can be produced by reacting the compound [XXXIII] with a formylating agent in the presence of a base.

This reaction is usually conducted without a solvent or in a solvent, and the reaction temperature is usually in a range from 0 to 100° C., and the reaction time is usually in a range from instant to 24 hours.

Regarding the amounts of reagents to be reacted, it is theoretical that the amount of the formulating agent is 1 mol and the amount of the base is 1 mol based on 1 mol of the compound [XXXIII], however, the ratio can be optionally changed depending on reaction conditions.

As the base used, there are listed metal alkoxides such as sodium methoxide, sodium ethoxide, potassium t-butoxide and the like, and inorganic bases such as sodium hydride, potassium hydride, lithium hydroxide, sodium hydroxide, potassium hydroxide, and the like.

As the solvent used, there are listed, for example, ethers such as diethyl ether, dioxane, tetrahydrofuran, ethylene glycol dimethyl ether, diglyme and the like, ketones such as acetone, 2-butanone, methyl isobutyl ketone and the like, esters such as ethyl acetate, butyl acetate, and the like, or mixtures thereof.

After completion of the reaction, an intended present compound can be obtained, for example, by the following operation 1) or 2).

1) The reaction solution is poured into water, this is extracted with an organic solvent, and the organic layer is dried and concentrated.

2) The reaction solution is concentrated as it is, or, filtrated if necessary, and the filtrate is concentrated.

The intended compound can also be purified by an operation such as chromatography, re-crystallization and the like.

<Step c ($R^{21}$ in not hydrogen(>: A process to produce the compound [XXXIV] from the compound [XXXII].

The compound [XXXIV] can be produced by reacting the compound [XXXII] with the compound [XXXXIII] in the presence of a base.

This reaction is usually conducted without a solvent or in a solvent, and the reaction temperature is usually in a range from 0 to 150° C., and the reaction time is usually in a range from instant to 24 hours.

Regarding the amounts of reagents to be reacted, it is theoretical that the amount of the compound [XXXXIII] is 1 mol and the amount of the base is 1 mol based on 1 mol of the compound [XXXII], however, the ratio can be optionally changed depending on reaction conditions.

As the base used, there are listed organic bases such as pyridine, quinoline, benzyldimethylamine, N-methylmorpholine, 1,8-diazabicyclo[5.4.0]undec-7-ene, 4-dimethylaminopyridine, N, N-dimethylaniline, N,N-diethylaniline, triethylamine, diisopropylethylamine and the like, metal alkoxides such as potassium t-butoxide and the like, and inorganic bases such as lithium carbonate, sodium carbonate, potassium carbonate, sodium hydride, lithium hydroxide, sodium hydroxide, potassium hydroxide and the like.

As the solvent used, there are listed, for example, aliphatic hydrocarbons such as n-hexane, n-heptane, ligroin, petroleum ether and the like, aromatic hydrocarbons such as toluene, xylene and the like, aromatic halogenated hydrocarbons such as chlorobenzene, benzotrifluoride and the like, ethers such as dioxane, tetrahydrofuran, ethylene glycol dimethyl ether, and the like, ketones such as acetone, 2-butanone, methyl isobutyl ketone and the like, esters such as ethyl acetate, butyl acetate, and the like, nitriles such as acetonitrile, isobutyronitrile and the like, amides such as N,N-dimethylformamide, N,N-dimethylacetamide, N-methyl-2-pyrrolidone and the like, sulfur compounds such as dimethylsulfoxide, sulfolane and the like, or mixtures thereof.

After completion of the reaction, an intended present compound can be obtained, for example, by the following operation 1) or 2).

1) The reaction solution is poured into water, this is extracted with an organic solvent, and the organic layer is dried and concentrated.

2) The reaction solution is concentrated as it is, or, filtrated if necessary, and the filtrate is concentrated.

The intended compound can also be purified by an operation such as chromatography, re-crystallization and the like.

<Step d>: A process to produce the compound [XXXV] from the compound [XXXIV].

The compound [XXXV] can be produced, for example, by reacting the compound [XXXIV] with a hydrazine compound in a solvent.

The reaction temperature is in a range from 0 to 200° C., preferably from room temperature to reflux temperature. The reaction time is usually in a range from instant to 24 hours.

Regarding the amounts of reagents to be reacted, it is theoretical the amount of the hydrazine compound is 1 mol based on 1 mol of the compound [XXXIV], however, the ratio can be optionally changed depending on reaction conditions.

As the hydrazine compound used, there are listed hydrazine monohydrate, methyl carbazate and the like.

As the solvent used, there are listed, for example, aliphatic hydrocarbons such as n-hexane, n-heptane, ligroin, petroleum ether and the like, aromatic hydrocarbons such as toluene, xylene and the like, aromatic halogenated hydrocarbons such as chlorobenzene, benzotrifluoride and the like, alcohol such as methanol, ethanol and the like.

The reaction solution after completion of the reaction can be poured into water and the precipitated crystals are collected by filtration, or subjected to usual post treatments such as extraction with an organic solvent, neutralization, concentration and the like, to obtain an intended compound.

The intended compound can also be purified by an operation such as chromatography, re-crystallization and the like.

<Step e>: A process to produce the compound [XXXVI] from the compound [XXXV].

The compound [XXXVI] can be produced by reacting the compound [XXXV] A) with the compound [IV] in the presence of a base, or B) with the alcohol compound [VI] in the presence of a dehydrating agent.

A) This reaction is usually conducted without a solvent or in a solvent, and the reaction temperature is in a range from 0 to 200° C., and the reaction time is usually in a range from instant to 24 hours.

Regarding the amounts of reagents to be reacted, it is theoretical that the amount of the compound [IV] is 1 mol and the amount of the base is 1 mol based on 1 mol of the compound [XXXV], however, the ratio can be optionally changed depending on reaction conditions.

As the base used, there are listed organic bases such as pyridine, benzyldimethylamine, N-methylmorpholine, 1,8-diazabicyclo[5.4.0]undec-7-ene, 4-dimethylaminopyridine, N,N-dimethylaniline, N,N-diethylaniline, triethylamine, diisopropylethylamine and the like, metal alkoxides such as sodium methoxide, potassium t-butoxide and the like, and inorganic bases such as lithium carbonate, sodium carbonate, potassium carbonate, lithium hydroxide, sodium hydroxide, potassium hydroxide and the like.

As the solvent used, there are listed, for example, aliphatic hydrocarbons such as n-hexane, n-heptane, ligroin, cyclohexane, petroleum ether and the like, aromatic hydrocarbons such as benzene, toluene, xylene and the like, aromatic halogenated hydrocarbons such as chlorobenzene, dichlorobenzene, benzotrifluoride and the like, ethers such as diethyl ether, dioxane, tetrahydrofuran, ethylene glycol dimethyl ether, diglyme and the like, ketones such as acetone, 2-butanone, methyl isobutyl ketone and the like, esters such as ethyl acetate, butyl acetate, and the like, nitro compounds such as nitromethane, nitrobenzene and the like, nitriles such as acetonitrile, isobutyronitrile and the like, amides such as N,N-dimethylformamide, N,N-dimethylacetamide, N-methyl-2-pyrrolidone and the like, sulfur compounds such as dimethylsulfoxide, sulfolane and the like, alcohols such as methanol, ethanol, ethylene glycol, isopropanol, t-butanol and the like, or mixtures thereof.

After completion of the reaction, an intended compound can be obtained, for example, by pouring the reaction solution into water, extracting this with an organic solvent, and drying and concentrating the organic layer.

The intended compound can also be purified by an operation such as chromatography, re-crystallization and the like.

B) The reaction is usually conducted in a solvent, and the reaction temperature is usually in a range from −20 to 150° C., preferably from 0 to 100° C., and the reaction time is usually in a range from instant to 48 hours.

As the dehydrating reagent, there are listed, for example, combinations of triarylphosphine such as triphenylphosphine and the like, and di(lower alkyl)azodicarboxylate such as diethyl azodicarboxylate, diisopropyl azodicarboxylate and the like.

Regarding the amounts of reagents to be reacted, the amount of the alcohol compound [VI] is from 1 to 3 mol, preferably from 1 to 1.5 mol, the amount of the triarylphosphine used as a dehydrating agent is from 1 to 3 mol, preferably from 1 to 1.5 mol, and the amount of the di(lower alkyl)azodicarboxylate is from 1 to 3 mol, preferably from 1 to 1.5 mol, based on 1 mol of the compound [XXXV]. The ratio of these reagents can be optionally changed depending on reaction conditions.

As the solvent used, there are listed, for example, aliphatic hydrocarbons such as n-hexane, n-heptane, ligroin, cyclohexane, petroleum ether and the like, aromatic hydrocarbons such as benzene, toluene, xylene and the like, halogenated aromatic hydrocarbons such as chlorobenzene, benzotrifluoride and the like, ethers such as diethyl ether, diisopropyl ether, dioxane, THF, ethylene glycol dimethyl ether, diglyme and the like, esters such as ethyl acetate and the like, or mixtures thereof.

After completion of the reaction, an intended compound can be obtained by subjecting the reaction solution to usual post treatments such as addition of water and then extraction with an organic solvent, concentration and the like.

The intended compound can also be purified by an operation such as chromatography, re-crystallization and the like.

<Step f>: A process to produce the compound [XXXVII] from the compound [XXXVI],

The compound [XXXVII] can be produced by reacting the compound [XXXVI] with a compound [XXXXIV] of the formula [XXXXIV]

$$R^{22}—R^{12}$$  [XXXXIV]

[wherein, $R^{12}$ and $R^{22}$ are the same as defined above.]
in the presence of a base.

This reaction is usually conducted without a solvent or in a solvent, and the reaction temperature is in a range from 0 to 200° C., and the reaction time is usually in a range from instant to 24 hours.

Regarding the amounts of reagents to be reacted, it is theoretical that the amount of the compound [XXXXIV] is 1 mol and the amount of the base is 1 mol based on 1 mol of the compound [XXXVI], however, the ratio can be optionally changed depending on reaction conditions.

As the base used, there are listed organic bases such as pyridine, N-methylmorpholine, 1,8-diazabicyclo[5.4.0]undec-7-ene, 4-dimethylaminopyridine, N,N-dimethylaniline, N,N-diethylaniline, triethylamine, diisopropylethylamine and the like, metal alkoxides such as sodium methoxide, sodium ethoxide, potassium t-butoxide and the like, and inorganic bases such as lithium carbonate, sodium carbonate, potassium carbonate, sodium hydride, potassium hydride, lithium hydroxide, sodium hydroxide, potassium hydroxide and the like.

As the solvent used, there are listed, for example, aliphatic hydrocarbons such as n-hexane, n-heptane, ligroin, cyclohexane, petroleum ether and the like, aromatic hydrocarbons such as toluene, xylene and the like, aromatic halogenated hydrocarbons such as chlorobenzene, benzotrifluoride and the like, ethers such as diethyl ether, dioxane, tetrahydrofuran, ethylene glycol dimethyl ether, diglyme and the like, ketones such as acetone, 2-butanone, methyl isobutyl ketone and the like, esters such as ethyl acetate, and the like, nitriles such as acetonitrile, isobutyronitrile and the like, amides such as N,N-dimethylformamide, N-methyl-2-pyrrolidone and the like, sulfur compounds such as dimethylsulfoxide, sulfolane and the like, alcohols such as methanol, ethanol, ethylene glycol,=t-butanol and the like, or mixtures thereof.

After completion of the reaction, an intended compound can be obtained by by pouring the reaction solution into water and collecting the precipitated crystals by filtration, or by pouring the reaction solution into water, then, subjecting the mixture to usual post treatments such as extraction with an organic solvent, concentration and the like.

The intended compound can also be purified by an operation such as chromatography, re-crystallization and the like.

(Production Method 8)

The present compound can be produced by a method shown in the following scheme.

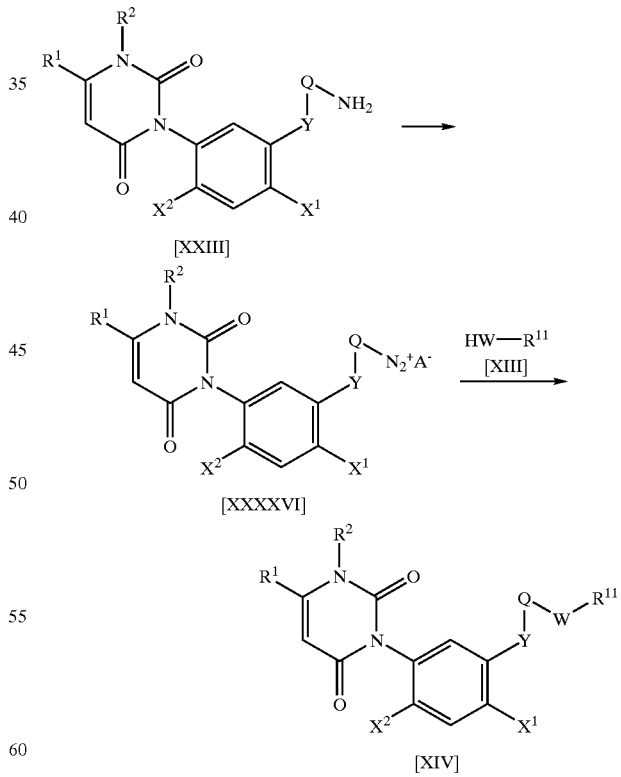

[wherein, $R^1$, $R^2$, $R^{11}$, W, Y, Q, $X^1$ and $X^2$ are the same as defined above, $A^-$ represents counter anion of diazonium ion such as $Cl^-$, $BF_4^-$, $CF_3SO_3^-$ and the like.].

<Step 8-1>: A process to produce the compound [XXXXVI] from the compound [XXIII].

The compound [XXXXVI] can be produced, for example, by reacting the compound [XXIII] with a diazotizing agent and an acid in a solvent.

The reaction temperature is from −30 to 30° C., and the reaction time is usually from an instant to 10 hours.

Regarding the amounts of reagents to be reacted, the amount of the diazotizing agent is from 1 mol to 3 mol, and the amount of the acid is from 1 mol to 6 mol based on 1 mol of the compound [XXIII], however, the ratio can be optionally changed depending on the reaction conditions.

diazotizing agent: nitrites such as sodium nitrite, isoamyl nitrite, t-butyl nitrite and the like acid: inorganic acids such as tetrafluoroboric acid, hydrochloric acid and the like, organic acids such as trifluoromethanesulfonic acid and the like, lewis acid such as boron trifluoride diethyl etherate and the like.

solvent: aliphatic halogenated hydrocarbons such as methylene chloride, chloroform 1,2-dichloroethane, 1,2, 3-trichloropropane and the like, ethers such as diethyl ether, dioxane, tetrahydrofuran, ethylene glycol dimethyl ether and the like, aqueous hydrochloric acid solution, aqueous hydrobromic acid solution, aqueous sulfuric acid solution and the like, or mixtures thereof.

After completion of the reaction, the reaction solution is used in the subsequent reaction as it is, or nonpolar organic solvent such as n-pentane, n-hexane and the like is added to the reaction solution and the precipitate is collected by filtration, for example.

<Step 8-2>: A process to produce the compound [XIV] from the compound [XXXXVI].

The compound [XIV] can be produced, for example, by reacting the diazonium salt compound [XXXXVI] with the compound [XIII] in a solvent.

The reaction temperature is from 0 to 120° C., and the reaction time is usually from an instant to 20 hours.

Regarding the amounts of reagents to be reacted, the amount of the compound [XIII] is from 1 mol to 10 mol based on 1 mol of the compound [XXXXVI], however, the ratio can be optionally changed depending on the reaction conditions.

solvent: aromatic hydrocarbons such as toluene and the like, aliphatic halogenated hydrocarbons such as methylene chloride, chloroform, 1,2-dichloroethane and the like, ethers such as diethyl ether, tetrahydrofuran, ethylene glycol dimethyl ether and the like, or mixtures thereof.

After completion of the reaction, the intended present compound can be obtained, for example, by the following operation 1) or 2).

1) The reaction solution is poured into water, this is extracted with an organic solvent, and the organic layer is dried and concentrated.

2) The reaction solution is concentrated as it is, or, filtrated if necessary, and the filtrate is concentrated.

Further, the resulted present compound can also be purified by a procedure such as chromatography, re-crystallization and the like.

(Production Method 9)

Of the present compounds, the compound [I] wherein $X^1$ is nitro (compound [XVI]) or halogen (compound [XVIII]) can be produced by a method shown in the following scheme.

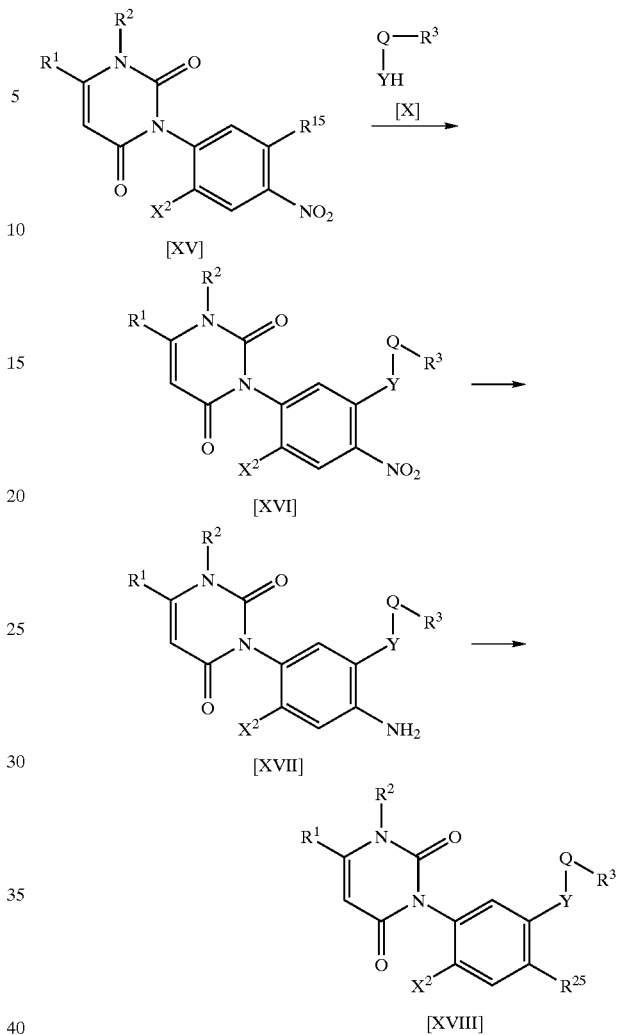

[wherein, $R^1$, $R^2$, $R^3$, $R^{15}$, Q, Y and $X^2$ are the same as defined above, and $R^{25}$ represents fluorine, chlorine, bromine or iodine.].

<Process 9-1>: The compound [XVI] can be produced, for example, by reacting the compound [XV] with the compound [X] in the presence of a base.

This reaction is conducted usually without a solvent or in a solvent, and the reaction temperature is from 0 to 200° C., and the reaction time is usually from an instant to 24 hours.

Regarding the amounts of reagents to be reacted, it is theoretical that the amount of the compound [X] is 1 mol and the amount of the base is 1 mol based on 1 mol of the uracil compound [XV], however,the ratio can be optionally changed depending on the reaction conditions.

The base to be used includes organic bases such as pyridine, quinoline, benzyldimethylamine, N-methylmorpholine, 1,8-diazabicyclo[5.4.0]undec-7-en, 1,5-diazabicyclo[4.3.0]non-5-ene, 1,4-diazabicyclo[2.2.2] octane, 4-dimethylaminopyridine, N,N-dimethylaniline, N,N-diethylaniline, triethylamine, tri-n-propylamine, triisopropylamine, tri-n-butylamine, diisopropylethylamine and the like, metal alkoxides such as sodium methoxide, sodium ethoxide, potassium t-butoxide and the like, and inorganic bases such as lithium carbonate, sodium carbonate, potassium carbonate, calcium carbonate, barium carbonate, sodium hydrogen carbonate, potassium hydrogen carbonate, sodium hydride, potassium hydride, lithium hydroxide, sodium hydroxide, potassium hydroxide and the like.

Examples of the solvent to be used include aliphatic hydrocarbons such as n-hexane, n-heptane, ligroin, cyclohexane, petroleum ether and the like; aromatic hydrocarbons such as benzene, toluene, xylene and the like; aromatic halogenated hydrocarbons such as chlorobenzene, benzotrifluoride and the like; ethers such as diethyl ether, diisopropyl ether, methyl-t-butyl ether, dioxane, tetrahydrofuran, ethylene glycol dimethyl ether, diglyme and the like; ketones such as acetone, 2-butanone, methyl isobutyl ketone and the like; esters such as ethyl acetate, butyl acetate and the like; nitriles such as acetonitrile, isobutyronitrile and the like; amides such as N,N-dimethylformamide, N,N-dimethylacetamide, 1-methyl-2-pyrrolidinone and the like; sulfur compounds such as dimethyl sulfoxide, sulfolane and the like; alcohols such as methanol, ethanol, ethylene glycol, isopropanol, t-butanol and the like; or mixtures thereof.

After completion of the reaction, the intended present compound can be obtained, for example, by the following operation 1), 2) or 3).

1) The reaction solution is poured into water, this is extracted with an organic solvent, and the organic layer is dried and concentrated.

2) The reaction mixture is poured into water and the precipitate is collected by filtration.

3) The reaction solution is concentrated as it is, or, filtrated if necessary, and the filtrate is concentrated.

Further, the resulted present compound can also be purified by a procedure such as chromatography, re-crystallization and the like.

<Process 9-2>: The compound [XVII] can be produced, for example, by reducing the compound [XVI] in a solvent, A) using an iron powder in the presence of an acid, B) with hydrogen in the presence of a catalyst.

A) This reaction is conducted usually in a solvent, and the reaction temperature is usually from 0 to 150° C., preferably from room temperature to the reflux temperature. The reaction time is usually from an instant to 24 hours.

Regarding the amounts of reagents to be used in the reaction, the amount of the iron powder is from 3 mol to excess and the amount of the acid is 1 to 10 mol based on 1 mol of the compound [XVI], however, the ratio can be optionally changed depending on the reaction conditions.

As the acid to be used, acetic acid and the like are listed.

As the solvent to be used, there are listed, for example, water, aceti c acid, ethyl acetate and the like or mixtures thereof.

After completion of the reaction, an intended material can be obtained by a usual post-treatment operation such as by filtrating, then, pouring a reaction solution into water and the deposited crystals are collected by filtration, or, extracting with an organic solvent, neutralization, drying, concentration and the like.

B) This reaction is usually conducted in a solvent, the reaction temperature is usually from −20 to 150° C., preferably from 0 to 50° C. The reaction time is usually from an instant to 48 hours.

This reaction can also be conducted under pressure, and the reaction is preferably conducted under a pressure of 1 to 5 atom.

The amount of the catalyst used in this reaction is from 0.001 to 10% by weight based on the compound [XVI].

As the catalyst to be used in the reaction, anhydrous palladium/carbon, water-containing palladium/carbon, platinum oxide and the like are listed.

The solvent includes carboxylic acids such as formic acid, acetic acid, propionic acid and the like, esters such as ethyl formate, ethyl acetate, butyl acetate and the like, ethers such as 1,4-dioxane, tetrahydrofuran, ethylene glycol dimethyl ether and the like, alcohols such as methanol, ethanol and the like, or mixtures thereof and the like.

After completion of the reaction, an intended material can be obtained by a usual post-treatment operation such as filtrating a reaction solution before concentrating the solution itself, and the like.

The intended material can also be purified by a procedure such as chromatography, re-crystallization and the like.

<Process 9-3>: The compound [XVIII] can be produced from the compound [XVII], for example, A) by i) diazotizing the compound [XVII] in a solvent, then, ii) subsequently reacting it with halogenating agent in a solvent.

B) by reacting the compound [XVII] with a diazotizing agent in a solvent in the presence of halogenating agent. (see, Heterocycles., 38, 1581 (1994) and the like)

A)i) In the diazotization reaction of the first step, the reaction temperature is usually from −20 to 10° C., and the reaction time is usually from an instant to 5 hours.

Regarding the amounts of reagents to be reacted, it is theoretical that the amount of the diazotizing agent is 1 mol based on 1 mol of the compound [XVII], however, the ratio can be optionally changed depending on the reaction conditions.

As the diazotizing agent to be used, nitrites such as sodium nitrite, potassium nitrite, isoamyl nitrite, t-butyl nitrite and the like, are listed.

As the solvent to be used, there are listed, for example, acetonitrile, hydrobromic acid, hydrochloric acid, sulfuric acid, water and the like or mixtures thereof.

The reaction solution after completion of the reaction is used as it is in the following reaction.

ii) In the reaction of the second step, the reaction temperature is usually in a range from 0 to 80° C., and the reaction time is usually in a range from an instant to 48 hours.

Regarding the amounts of reagents to be used in the reaction, halogenating agent is from 1 to 3 mol based on 1 mol of the compound [XVII], and the amounts thereof can be optionally changed depending on the reaction condition.

As the halogenating agent used, potassium iodide, copper (I) bromide (or mixture with copper(II) bromide), copper(I) chloride (or mixture with copper(II) chloride) or a mixture of hydrofluoric acid and boric acid (hereinafter, referred to as hydroborofluoric acid) and the like are listed.

As the solvent to be used, there are listed, for example, acetonitrile, diethyl ether, hydrobromic acid, hydrochloric acid, sulfuric acid, water and the like or mixtures thereof.

After completion of the reaction, an intended present compound can be obtained, for example, by the following treatment; reaction solution is poured into water and if necessary acid such as hydrochloric acid, this is extracted with an organic solvent, and the resulted organic layer is dried and concentrated.

(see, Org. Syn. Coll. Vol. 2, 604 (1943), Vol. 1, 136 (1932))

B) the reaction temperature is usually from −20 to 50° C., preferably from −10° C. to room temperaature, and the reaction time is usually from an instant to 48 hours.

Regarding the amounts of reagents to be reacted, the amount of the the halogenating agent is from 1 mol to 3 mol, the amount of the diazotizing agent is from 1 mol to 3 mol respectively, based on 1 mol of the compound [XVII], however, the ratio can be optionally changed depending on the reaction conditions.

As the halogenating agent used, for example, iodine, copper(I) bromide (or mixture with copper(II) bromide), copper(I) chloride (or mixture with copper(II) chloride) or hydroborofluoric acid and the like are listed.

As the diazotizing agent to be used, nitrites such as isoamyl nitrite, t-butyl nitrite and the like, are listed.

As the solvent to be used, there are listed, for example, acetonitrile, benzene, toluene and the like or mixtures thereof.

After completion of the reaction, an intended present compound can be obtained, for example, by the following treatment; the reaction solution is poured into water, and added if necessary acid such as hydrochloric acid, then, this is extracted with an organic solvent, and the resulted organic layer is dried and concentrated.

Further, the resulted present compound can also be purified by a procedure such as chromatography, re-crystallization and the like.

(Production Method 10)

Of the present compounds, the compound [I] wherein $X^1$ is cyano (compound [10-3]) can be produced by a method shown in the following scheme.

Wherein $R^1$, $R^2$, $R^3$, Q, $X^2$ and Y are the same as defined above, $X^{10}$ is bromine or iodine, and $M^1$ represents metal such as copper, potassium, sodium, and the like.

The compound [10-3] can be produced by reacting the compound [10-1] with the compound [10-2].

This reaction is usually carried out in a solvent. The reaction temperature is usually in a range from 130 to 250° C., preferably 150° C. to reflux temperature and the reaction time is usually from an instant to 24 hours.

The compound [10-2] used in the reaction includes copper cyanide, potassium cyanide, sodium cyanide and the like.

The amount of the compound [10-2] is in a ratio from 1 mole to excess amount, preferably from 1 to 3 mole based on 1 mole of the compound[10-1], however, the ratio can be optionally changed depending on the reaction conditions.

Examples of the solvent to be used include ethers such as diethyl ether, diisopropyl ether, methyl t-butyl ether, dioxane, tetrahydrofuran, ethylene glycol dimethyl ether, diglyme and the like; amides such as N,N-dimethylformamide, N,N-dimethylacetamide, N-methyl-2-pyrrolidone and the like; sulfur compounds such as dimethyl sulfoxide, sulfolane and the like; or mixtures thereof.

After completion of the reaction, an objected compound can be obtained, for example, by subjecting to the ordinary after treatment by the following procedure.

1) The reaction mixture is filtered and concentrated.

2) The reaction mixture is added to water, extracted with an organic solvent, washed with water, dried and concentrated.

Further, the object compound can also be purified by a procedure such as chromatography, re-crystallization and the like.

The compound [IV], alcohol compound [VI], alcohol compound [VIII], compound [X], compound [XIII], compound [XV], compound [XXXX], compound [XXXXII], compound [XXXXIII], compound [XXXXIV] used in the production methods of the present compound are commercially available, or can be produced by known methods.

The compound [IX] is known, for example, from DE4412079 A.

The carboxylic acid compound [VII] can be produced by acidolyzing the present compound [I] wherein the corresponding site is an ester.

The compound [XI] is known, for example, from JP-A Nos. 63-41466, 61-40261 and WO9847904, or can be produced according to methods in these publications.

Some production intermediates used in the production methods of the present compound can be produced, for example, by the following (Intermediate Production Method 1) to (Intermediate Production Method 12).

(Intermediate Production Method 1)

Compound [XII] wherein $R^3$ is $OR^7$, $SR^8$ or $N(R^9)R^{10}$ can be produced by a method shown in the following scheme.

[wherein, $R^{26}$ represents a leaving group such as fluorine, chlorine, bromine, iodine, methanesulfonyloxy, p-toluenesulfonyloxy and the like, $R^{11}$, $R^{16}$, Q and W are the same as defined above.].

The compound [X1-2] can be produced, for example, by reacting the compound [X1-1] with the compound [XIII] in a solvent, in the presence of a base.

This reaction condition, for example, is as follows.

Reaction temperature: from 0 to 180° C.

Reaction time: from an instant to 24 hours

The amount of the compound [XIII]: from 1 mol to 1.5 mol based on 1 mol of the compound [X1-1]

The amount of the base : from 1 mol to 1.5 mol based on 1 mol of the compound [X1-1]

However, the ratio can be optionally changed depending on the reaction conditions.

Base: triethylamine, diisopropylethylamine, potassium carbonate, sodium hydride and the like Solvent: dioxane, tetrahydrofuran, N,N-dimethylformamide, 1-methyl-2-pyrrolidinone and the like After completion of the reaction, the intended compound can be obtained, for example, by the following treatment; the reaction solution is poured into water, this is extracted with an organic solvent, and the organic layer is dried and concentrated. Further, the resulted compound can also be purified by a procedure such as chromatography and the like.

(Intermediate Production Method 2)

Compound [III] wherein W is NH (compound [XXIII]) can be produced by a method shown in the following scheme.

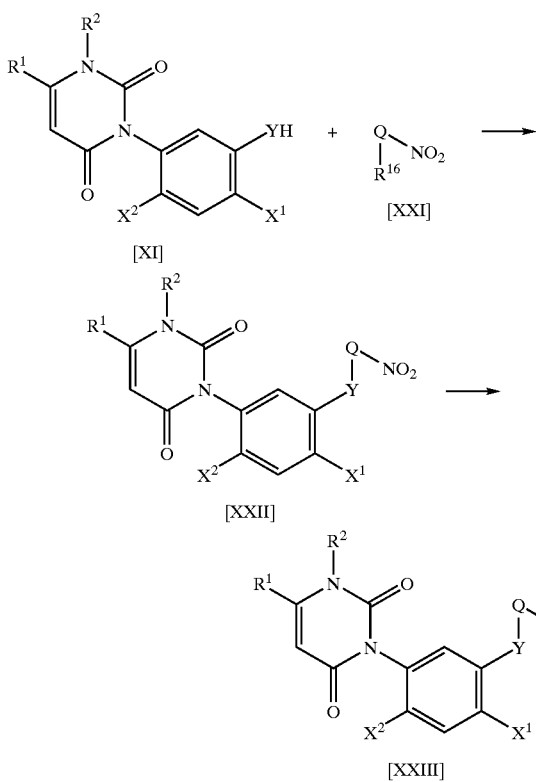

[wherein, $R^1$, $R^2$, $R^{16}$, Y, Q, $X^1$ and $X^2$ have the same meanings as described above.].

<Process A2-1>: A process to produce the compound [XXII] from the compound [XI].

The compound [XXII] can be produced by reacting the compound [XI] with the compound [XXI] in the presence of a base.

This reaction is usually conducted without a solvent or in a solvent, and the reaction temperature is in a range from 0 to 200° C., and the reaction time is usually in a range from instant to 24 hours.

Regarding the amounts of reagents to be reacted, it is theoretical that the amount of the compound [XXI] is 1 mol and the amount of the base is 1 mol based on 1 mol of the compound [XI], however, the ratio can be optionally changed depending on reaction conditions.

Base: triethylamine, diisopropylethylamine, potassium carbonate, sodium hydride, sodium hydroxide and the like Solvent: toluene, dioxane, tetrahydrofuran, N,N-dimethylformamide, 1-methyl-2-pyrrolidinone, dimethylsulfoxide, sulfolane and the like, or mixtures thereof.

This reaction may sometimes be accelerated by addition of a catalyst.

The preferrable amount of the catalyst to be used in the reaction is from 0.0001 to 0.1 mol based on 1 mol of the compound [XI], and this ratio can be optionally changed depending on conditions of the reaction.

As the catalyst, copper compounds such as copper iodide, copper bromide, copper chloride, copper powder and the like, and crown ethers such as 15-crown-5, 18-crown-6 and the like, are listed.

After completion of the reaction, an intended compound can be obtained, for example, by the following treatment; the reaction solution is poured into water, this is extracted with an organic solvent, and the organic layer is dried and concentrated.

An intended compound can also be purified by an operation such as chromatography, re-crystallization and the like.

<Process A2-2>: A process to produce the compound [XXIII] from the compound [XXII].

The compound [XXIII] can be produced, for example, by reducing the compound [XXII] in a solvent, A) using an iron powder in the presence of an acid, B) with hydrogen in the presence of a catalyst.

A) The reaction temperature is usually from 0 to 150° C., preferably from room temperature to the reflux temperature. The reaction time is usually from an instant to 24 hours.

Regarding the amounts of reagents to be used in the reaction, the amount of the iron powder is from 3 mol to excess and the amount of the acid is 1 to 10 mol based on 1 mol of the compound [XXII], however, the ratio can be optionally changed depending on the reaction conditions.

As the acid to be used, acetic acid and the like are listed.

As the solvent to be used, there are listed, for example, water, acetic acid, ethyl acetate and the like or mixtures thereof.

After completion of the reaction, an intended material can be obtained by a usual post-treatment operation such as filtrating, then, pouring a reaction solution into water and collecting the deposited crystals by filtration, or, extracting with an organic solvent, neutralization, drying, concentration and the like.

B) The reaction temperature is usually from −20 to 150° C., preferably from 0 to 50° C. The reaction time is usually from an instant to 48 hours.

This hydrogenation reaction can also be conducted under pressure, and the reaction is preferably conducted under a pressure of 1 to 5 atom.

The amount of the catalyst used in this reaction is from 0.01 to 10% by weight based on the compound [XXII].

As the catalyst to be used in the reaction, palladium/carbon, platinum oxide and the like are listed.

The solvent includes acetic acid, ethyl acetate, methanol, ethanol and the like, or mixtures thereof.

After completion of the reaction, an intended material can be obtained by a usual post-treatment operation such as filtrating a reaction solution before concentrating the solution itself, and the like.

The intended compound can also be purified by an operation such as chromatography, re-crystallization and the like.

(Intermediate Production Method 3)

Compounds [III] wherein W is oxygen (compound [V]) can be produced by a method shown in the following scheme.

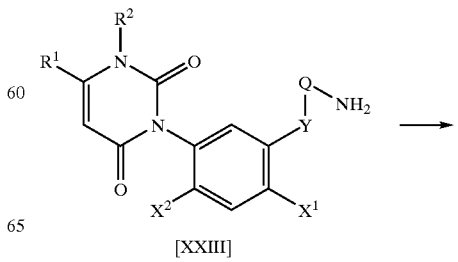

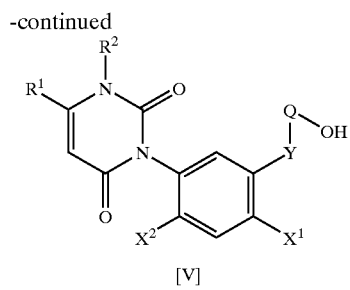

[wherein, $R^1$, $R^2$, Y, Q, $X^1$ and $X^2$ are the same as defined above.].

The compound [V] can be produced by i) reacting the compound [XXIII] with a diazotizing agent in a solvent, in the presence or absence of an acid, then, ii) subsequently, heating the reaction product in an acidic solvent or allowing a copper salt to act on the reaction product in the presence or absence of a copper catalyst.

i) In the reaction of the first step, the reaction temperature is in a range from −20 to 10° C. and the reaction time is usually in a range from instant to 5 hours.

Regarding the amounts of reagents to be reacted, it is theoretical that the amount of the diazotizing agent is 1 mol and the amount of the acid is 1 mol based on 1 mol of the compound [XXIII], however, the ratio can be optionally changed depending on reaction conditions.

As the diazotizing agent used, there are listed, nitrite such as sodium nitrite, potassium nitrite, isoamyl nitrite, t-butyl nitrite and the like.

As the acid used, there are listed, for example, tetrafluoroboric acid, hydrochloric acid, trifluoromethanesulfonic acid, lewis acid such as boron trifluoride diethyl etherate, and the like.

As the solvent used, there are listed, for example, aliphatic halogenated hydrocarbons such as methylene chloride, chloroform, carbon tetrachloride, 1,2-dichloroethane, 1,2,3-trichloropropane and the like, ethers such as diethyl ether, diisopropyl ether, methyl-t-butyl ether, dioxane, tetrahydrofuran, ethylene glycol dimethyl ether, diglyme and the like, acetonitrile, aqueous hydrochloric acid solution, aqueous hydrobromic acid solution, aqueous sulfuric acid solution and the like, or mixtures thereof.

The reaction solution after completion of the reaction is used in the subsequent reaction as it is, for example.

ii) In the reaction in which heating is conducted in an acidic solvent, in the second step, the reaction temperature is in a range from 60° C. to reflux heating temperature, and the reaction time is usually in a range from instant to 24 hours.

As the acidic solvent, there are listed, for example, aqueous hydrochloric acid solution, aqueous hydrobromic acid solution, aqueous sulfuric acid solution and the like.

After completion of the reaction, an intended material can be obtained, for example, by subjecting the reaction solution to usual post-treatments such as filtrating a reaction solution, extraction with an organic solvent, drying, concentration and the like.

(see, Org. Syn. Coll. Vol. 2, 604 (1943), Vol. 1, 136 (1932))

The reaction in which the copper salt is allowed to act in the presence or absence of the copper catalyst, in the second step, is conducted in a solvent, the reaction temperature is in a range from 0° C. to reflux heating temperature, and the reaction time is usually in a range from instant to 24 hours.

Regarding the amounts of reagents to be reacted, the amount of the copper catalyst is from 0.001 to 5 mol and the amount of the copper salt is from 1 to 100 mol based on 1 mol of the compound [XXIII], however, the ratio can be optionally changed depending on reaction conditions.

As the copper catalyst used, copper(I) oxide and the like are listed, and as the copper salt, copper(II) sulfate, copper (II) nitrate and the like are listed.

As the solvent, water, aqueous hydrochloric acid solution, aqueous sulfuric acid solution, acetic acid and the like, or mixtures thereof, for example, are listed.

After completion of the reaction, an intended compound can be obtained, for example, by subjecting the reaction solution to usual post-treatments such as filtrating a reaction solution, neutralization, extraction with an organic solvent, drying, concentration and the like.

The intended compound can also be purified by an operation such as chromatography, re-crystallization and the like.

(Intermediate Production Method 4)

Compound [X] wherein $R^3$ is $OR^7$ or $SR^8$ (compound [XXVI]) can be produced by a method shown in the following scheme.

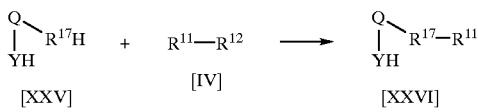

[wherein, $R^{11}$, $R^{12}$, Y and Q are the same as defined above, and $R^{17}$ represents oxygen or sulfur.].

The compound [XXVI] can be produced by reacting the compound [XXV] with the compound [IV] in the presence of a base.

This reaction is usually conducted in a solvent, and the reaction temperature is usually in a range from 0 to 150° C., and the reaction time is usually in a range from instant to 24 hours.

Regarding the amounts of reagents to be reacted, it is theoretical that the amount of the compound [IV] is 1 mol and the amount of the base is 1 mol based on 1 mol of the compound [XXV], however, the ratio can be optionally changed depending on reaction conditions.

As the base used, there are listed organic bases such as pyridine, 4-dimethylaminopyridine, N,N-dimethylaniline, N,N-diethylaniline, triethylamine, diisopropylethylamine and the like, and inorganic bases such as sodium carbonate, potassium carbonate, sodium hydride, sodium hydroxide, potassium hydroxide, and the like.

As the solvent used, there are listed, for example, aromatic hydrocarbons such as toluene, xylene and the like, aromatic halogenated hydrocarbons such as chlorobenzene, benzotrifluoride and the like, ethers such as diethyl ether, dioxane, tetrahydrofuran, ethylene glycol dimethyl ether and the like, ketones such as acetone, 2-butanone, methyl isobutyl ketone and the like, esters such as ethyl acetate and the like, nitriles such as acetonitrile and the like, amides such as N,N-dimethylformamide, N-methyl-2-pyrrolidone and the like, sulfur compounds such as dimethylsulfoxide and the like, alcohols such as methanol, ethanol and the like, or mixtures thereof.

After completion of the reaction, an intended compound can be obtained, for example, by the following operation 1) or 2).

1) The reaction solution is poured into water, this is extracted with an organic solvent, and the organic layer is dried and concentrated.

2) The reaction solution is concentrated as it is, or, filtrated if necessary, and the filtrate is concentrated.

The intended compound can also be purified by an operation such as chromatography, re-crystallization and the like.

(Intermediate Production Method 5)

Compound [X] wherein $R^3$ is $OR^7$, $SR^8$ or $N(R^9)R^{10}$, and Y is oxygen or sulfur (compound [XXX]) can be produced by a method shown in the following scheme.

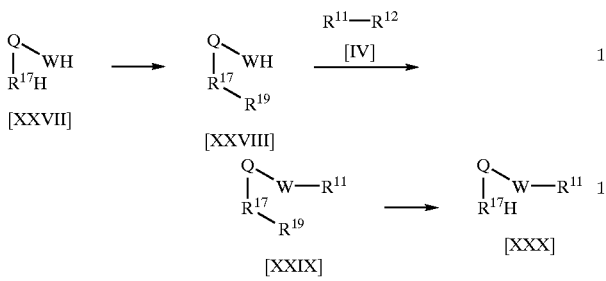

[wherein, $R^{11}$, $R^{12}$, $R^{17}$, W and Q are the same as defined above, and $R^{19}$ represents a protective group such as t-butyldimethylsilyl, t-butyl, benzyl, methyl or the like.].

<Process A5-1>: A process to produce the compound [XXVIII] from the compound [XXVII].

The compound [XXVIII] can be produced by reacting the compound [XXVII] with t-butyldimethylsilyl chloride, isobutene, benzyl chloride, benzyl bromide or the like (see, "Yuki Kagaku Jikken no Tebiki" vol.4, (published by Kagaku Dojin), Protective Groups in Organic Synthesis (published by JOHN WILEY & SONS, INC.)).

<Process A5-2>: A process to produce the compound [XXIX] from the compound [XXVIII].

The compound [XXIX] can be produced by reacting the compound [XXVIII] with the compound [IV] in the presence of a base.

This reaction is usually conducted in a solvent, and the reaction temperature is usually in a range from 0 to 150° C., and the reaction time is usually in a range from instant to 24 hours.

Regarding the amounts of reagents to be reacted, it is theoretical that the amount of the compound [IV] is 1 mol and the amount of the base is 1 mol based on 1 mol of the compound [XXVIII], however, the ratio can be optionally changed depending on reaction conditions.

As the base used, there are listed organic bases such as pyridine, 4-dimethylaminopyridine, N,N-dimethylaniline, N,N-diethylaniline, triethylamine, diisopropylethylamine and the like, and inorganic bases such as sodium carbonate, potassium carbonate, sodium hydride, sodium hydroxide, potassium hydroxide, and the like.

As the solvent used, there are listed, for example, aromatic hydrocarbons such as toluene, xylene and the like, aromatic halogenated hydrocarbons such as chlorobenzene, benzotrifluoride and the like, ethers such as diethyl ether, dioxane, tetrahydrofuran, ethylene glycol dimethyl ether and the like, ketones such as acetone and the like, esters such as ethyl acetate and the like, nitriles such as acetonitrile, isobutyronitrile and the like, amides such as N,N-dimethylformamide, N-methyl-2-pyrrolidone and the like, sulfur compounds such as dimethylsulfoxide and the like, alcohols such as methanol, ethanol and the like, or mixtures thereof.

After completion of the reaction, an intended compound can be obtained, for example, by the following operation 1) or 2).

1) The reaction solution is poured into water, this is extracted with an organic solvent, and the organic layer is dried and concentrated.

2) The reaction solution is concentrated as it is, or, filtrated if necessary, and the filtrate is concentrated.

The intended compound can also be purified by an operation such as chromatography, re-crystallization and the like.

<Process A5-3>: A process to produce the compound [XXX] from the compound [XXIX].

The compound [XXX] can be produced by de-protecting the compound [XXIX], for example, according to a method described in "Yuki Kagaku Jikken no Tebiki" vol. 4, (published by Kagaku Dojin), Protective Groups in Organic Synthesis (published by JOHN WILEY & SONS, INC.).

(Intermediate Production Method 6)

Compound [III] wherein W is oxygen (compound [V]) can be produced by a method shown in the following scheme.

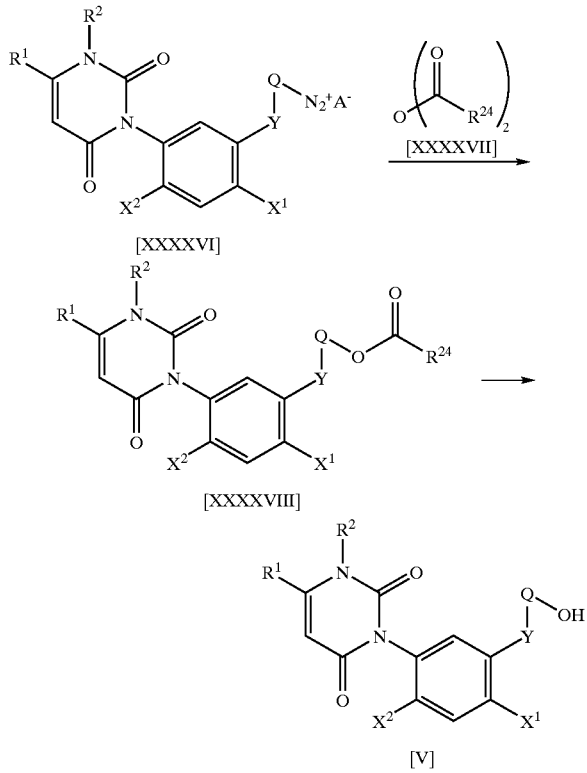

[wherein, $R^1$, $R^2$, $A^-$, Y, Q, $X^1$ and $X^2$ are the same as defined above, $R^{24}$ represents alkyl such as methyl and the like, or haloalkyl such as trifluoromethyl and the like.].

<Step A6-1>: A process to produce the compound [XXXXVIII] from the compound [XXXXVI].

The compound [XXXXVIII] can be produced, for example, by reacting the diazonium salt compound [XXXXVI] with the compound [XXXXVII].

This reaction is usually conducted without a solvent or in a solvent, the reaction temperature is from room temperature to 120° C., preferably from 50 to 90° C., and the reaction time is usually from an instant to 5 hours.

Regarding the amounts of reagents to be reacted, the amount of the compound [XXXXVII] is from 1 mol to excess based on 1 mol of the compound [XXXXVI], however, the ratio can be optionally changed depending on the reaction conditions.

As the solvent used, acetic acid and the like.

After completion of the reaction, the intended compound can be obtained, for example, by the following treatment;

the reaction solution is concentrated as it is, the residue is diluted with water, this is extracted with an organic solvent, and the organic layer is dried and concentrated. Further, the resulted compound can also be purified by a procedure such as chromatography, re-crystallization and the like.

<Step A6-2>: A process to produce the compound [V] from the compound [XXXXVIII].

The compound [V] can be produced, for example, by reacting the compound [XXXXVIII] in the presence of a base in a solvent.

The reaction temperature is from 0 to 100° C., preferably from room temperature to 60° C., and the reaction time is usually from 0.5 to 20 hours.

Regarding the amounts of reagents to be reacted, the amount of the base is from 0.1 mol to 10 mol based on 1 mol of the compound [XXXXVIII], however, the ratio can be optionally changed depending on the reaction conditions.

As the base used, there are listed inorganic bases such as sodium carbonate, potassium carbonate, sodium hydrogen carbonate and the like.

As the solvent used, for example, there are listed, methanol, ethanol, water and the like, or mixtures thereof.

After completion of the reaction, the intended compound can be obtained, for example, by the following treatment; the reaction solution is concentrated as it is, the residue is diluted with water, this is extracted with an organic solvent, and the organic layer is dried and concentrated. Further, the resulted compound can also be purified by a procedure such as chromatography, re-crystallization and the like.

(Intermediate Production Method 7)

Compound [XXXI] can be produced by a method shown in the following scheme.

[wherein, $R^1$, $R^3$, $R^{15}$, Y, Q, $X^1$ and $X^2$ are the same as defined above, and $R^{18}$ represents lower alkyl such as methyl, ethyl and the like, $R^{27}$ represents $C_1$ to $C_6$ alkyl such as methyl, ethyl and the like, or phenyl which may be substituted such as phenyl and the like.].

<Process A7-1>: A process for producing the compound [XXXXXI] from the compound [XXXXX]

The compound [XXXXXI] can be produced, for example, by reacting the compound [XXXXX] with the compound [X] in the presence of a base.

This reaction is usually conducted without a solvent or in a solvent, and the reaction temperature is usually in a range from 0 to 150° C., and the reaction time is usually in a range from instant to 48 hours.

Regarding the amounts of reagents to be reacted, it is theoretical that the amount of the compound [X] is 1 mol and the amount of the base is 1 mol based on 1 mol of the compound [XXXXX], however, the ratio can be optionally changed depending on reaction conditions.

As the base used, there are listed organic bases such as pyridine, N,N-dimethylaniline, N,N-diethylaniline, triethylamine, diisopropylethylamine and the like, metal alkoxides such as sodium methoxide, sodium ethoxide, potassium t-butoxide and the like, and inorganic bases such as potassium carbonate, sodium hydrogen carbonate, sodium hydride, lithium hydroxide, sodium hydroxide and the like.

As the solvent used, there are listed, for example, aromatic hydrocarbons such as toluene, xylene and the like, ethers such as dioxane, tetrahydrofuran, ethylene glycol dimethyl ether and the like, ketones such as acetone, 2-butanone, methyl isobutyl ketone and the like, esters such

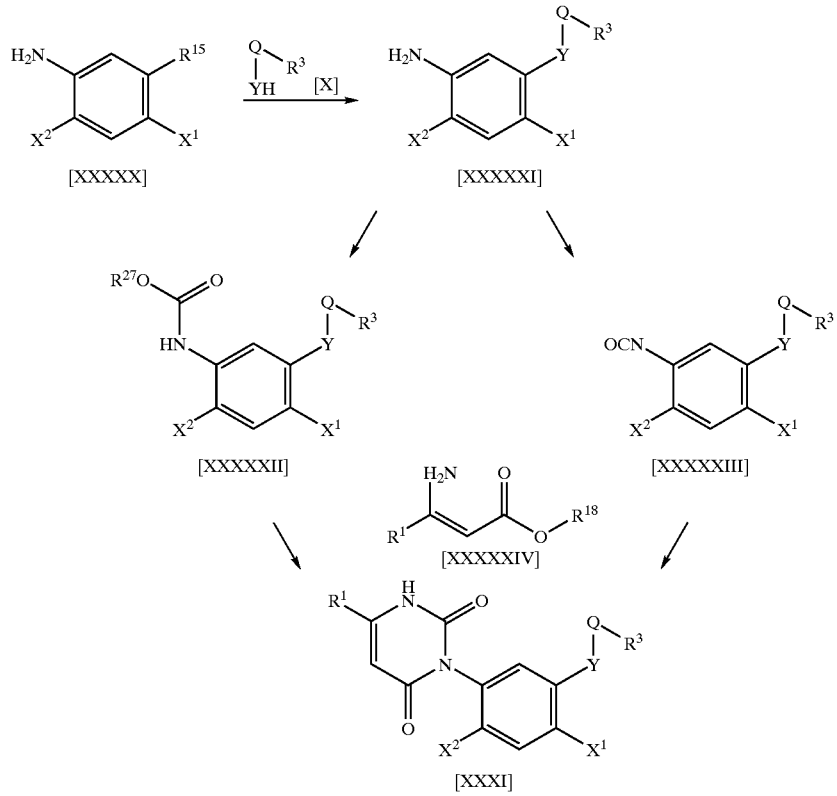

as ethyl acetate, and the like, nitriles such as acetonitrile, isobutyronitrile and the like, amides such as N,N-dimethylformamide, and the like, sulfur compounds such as dimethylsulfoxide and the like, alcohols such as methanol, ethanol and the like, or mixtures thereof.

After completion of the reaction, an intended compound can be obtained, for example, by the following operation 1) or 2).

1) The reaction solution is poured into water, this is extracted with an organic solvent, and the organic layer is dried and concentrated.

2) The reaction solution is concentrated as it is, or, filtrated if necessary, and the filtrate is concentrated.

The resulted present compound can also be purified by an operation such as chromatography, re-crystallization and the like.

<Process A7-2>: A process for producing the compound [XXXXXIII] from the compound [XXXXXI]

The compound [XXXXXIII] can be produced by isocyanating the compound [XXXXXI] in a solvent or without a solvent.

Isocyanating agent: phosgene, trichloromethyl chloroformate, triphosgene, oxalyl chloride and the like.

Amount of isocyanating agent: from 1 mol to excess, preferably from 1.0 to 3 mol based on 1 mol of the compound [XXXXXI].

Solvent: aromatic hydrocarbons such as benzene, toluene and the like, halogenated aromatic hydrocarbons such as chlorobenzene and the like, esters such as ethyl acetate and the like.

Reaction Temperature: from room temperature to reflux temperature.

Reaction Time: from an instant to 48 hours.

This reaction may sometimes be accelerated by adding a catalyst.

The amount of the catalyst used in this reaction is from 0.001 to 300% by weight based on the compound [XXXXXI], and the amounts thereof can be changed optionally depending on the reaction condition.

As the catalyst, charcoal (activated), amines such as triethylamine and the like are listed.

After completion of the reaction, an intended material can be obtained by concentrating a reaction solution itself, and the like. This compound can also be purified by an operation such as re-crystallization and the like.

<Process A7-3>: A process for producing the compound [XXXXXII] from the compound [XXXXXI]

The compound [XXXXXII] can be produced by reacting the compound [XXXXXI] with a compound [a7-1] of the formula [a7-1]

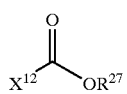

[a7-1]

[wherein, $R^{27}$ is the same as defined above, and $X^{12}$ represents fluorine, chlorine, bromine or iodine.]
in the presence of a base.

This reaction is usually conducted in a solvent, and also can be conducted without a solvent. The reaction temperature is usually from −20 to 200° C. The reaction time is usually from an instant to 48 hours.

The amount of the compound [a7-1] used in the reaction is from 0.5 mol to excess, preferably from 1.0 to 1.2 mol based on 1 mol of the compound [XXXXXI].

The amount of the base used in the reaction is from 0.5 mol to excess, preferably from 1.0 to 1.2 mol based on 1 mol of the compound [XXXXXI].

The base includes inorganic bases such as sodium carbonate, sodium hydroxide and the like, organic bases such as pyridine, 4-dimethylaminopyridine, N,N-dimethylaniline, N,N-diethylaniline, triethylamine, diisopropylethylamine and the like.

The solvent include aliphatic halogenated hydrocarbons such as chloroform and the like, ethers such as tetrahydrofuran, 1,4-dioxane and the like, nitriles such as acetonitrile and the like, esters such as ethyl acetate, water or mixtures thereof, and the like.

After completion of the reaction, an intended material can be obtained by a usual post-treatment operation such as filtrating the reaction solution before concentrating the solution itself, or, pouring the reaction solution into water and collecting the produced crystals by filtration, or, pouring the reaction solution into water and subjecting the mixture to extraction with an organic solvent, drying, concentration and the like. This compound can also be purified by an operation such as re-crystallization, chromatography and the like.

<Process A7-4>: A process for producing the compound [XXXI] from the compound [XXXXXIII]

The compound [XXXI] can be produced by reacting the compound [XXXXXIII] with the compound [XXXXXIV] in a solvent in the presence of a base.

Amount of the compound [XXXXXIV]: 0.5 mol to excess, preferably from 0.8 to 1.2 mol based on 1 mol of the compound [XXXXXIII].

Base: inorganic bases such as sodium hydride and the like, metal alkoxides such as sodium methoxide, sodium ethoxide and the like.

Amount of a base: 0.5 mol to excess, preferably from 0.8 to 1.2 mol based on 1 mol of the compound [XXXXXIII].

Solvent: aromatic hydrocarbons such as benzene, toluene and the like; halogenated aromatic hydrocarbons such as chlorobenzene and the like; amides such as N,N-dimethylformamide and the like; ethers such as tetrahydrofuran and the like; halogenated aliphatic hydrocarbons such as chloroform and the like; sulfur compounds such as dimethyl sulfoxide and the like; and mixtures thereof Reaction temperature: −40° C. to solvent reflux temperature Reaction time: instant to 72 hours After completion of the reaction, an intended material can be obtained by a post-treatment operation such as filtrating a reaction solution before concentrating the solution itself, or, adding an acid to a reaction solution and collecting the produced crystals by filtration, or, adding an acid to a reaction solution, then, subjecting the mixture to extraction with an organic solvent, concentration and the like. As the acid to be added, hydrochloric acid, acetic acid, trifluoroacetic acid, p-toluenesulfonic acid, or aqueous solutions thereof and the like. This compound can also be purified by an operation such as re-crystallization, chromatography and the like.

The resulted compound [XXXI] can also be reacted with the compound [XXXX] according to a method described in (Production Method 6) without conducting the above-mentioned post-treatment, to produce the present compound.

<Process A7-5>: A process for producing the compound [XXXI] from the compound [XXXXXII]

The compound [XXXI] can be produced by reacting the compound [XXXXXII] with the compound [XXXXXIV] in the presence of a base.

This reaction is usually conducted in a solvent, and the reaction temperature is usually from −20 to 200° C., preferably from 0 to 130° C. The reaction time is usually from an instant to 72 hours.

The amount of the compound [XXXXXIV] used in the reaction is from 0.5 mol to excess, preferably from 0.8 to 1.2 mol based on 1 mol of the compound [XXXXXII].

The amount of the base used in the reaction is from 0.5 mol to excess, preferably from 0.8 to 1.2 mol based on the compound [XXXXXII].

The base includes organic bases such as 4-dimethylaminopyridine, diisopropylethylamine and the like, inorganic bases such as sodium carbonate, potassium carbonate, sodium hydride, potassium hydride and the like, metal alkoxides such as sodium methoxide, sodium ethoxide, potassium t-butoxide and the like.

The solvent includes ketones such as acetone, methyl isobutyl ketone and the like; aliphatic hydrocarbons such as hexane, heptane, petroleum ether and the like; aromatic hydrocarbons such as benzene, toluene, ethylbenzene, xylene, mesitylene and the like; ethers such as diethyl ether, diisopropyl ether, 1,4-dioxane, tetrahydrofuran, ethylene glycol dimethyl ether, methyl-t-butyl ether and the like; acid amides such as N,N-dimethylformamide, N,N-dimethylacetamide and the like; tertiary amines such as pyridine, N,N-dimethylaniline, N,N-diethylaniline, triethylamine, diisopropylethylamine and the like; sulfur compounds such as dimethylsulfoxide, sulfolane and the like; or mixtures thereof and the like.

After completion of the reaction, an intended material can be obtained by a usual post-treatment operation such as filtrating the reaction solution before concentrating the solution itself, or, adding an acid to the reaction solution and collecting the produced crystals by filtration, or, adding an acid to the reaction solution, then, subjecting the mixture to extraction with an organic solvent, concentration and the like. As the acid to be added, there are listed hydrochloric acid, acetic acid, trifluoroacetic acid, p-toluenesulfonic acid, or aqueous solutions thereof and the like. This compound can also be purified by an operation such as re-crystallization, chromatography and the like.

The resulted compound [XXXI] can also be reacted with the compound [XXXX] according to the method described in (Production Method 6) without conducting the above-mentioned post-treatment, to produce the present compound.

(Intermediate Production Method 8)

Compound [X] wherein Y is oxygen, Q is a pyridine ring, and $R^3$ is $OR^7$, $SR^8$ or $N(R^9)R^{10}$ (compound [XXXXXX]) can be produced by a method shown in the following scheme.

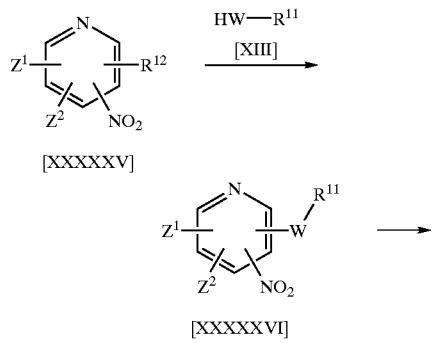

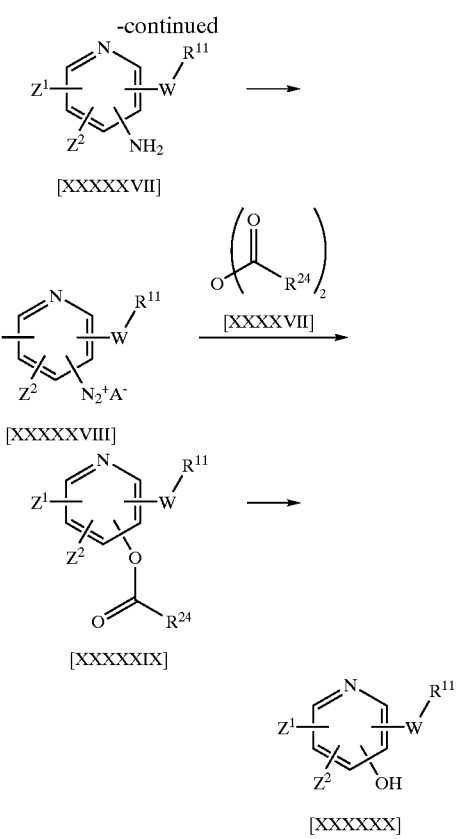

[wherein, $R^{11}$, $R^{12}$, $R^{24}$, $Z^1$, $Z^2$, W and $A^-$ are the same as defined above.].

<Step A8-1>: The compound [XXXXXVI] can be produced, for example, by reacting the compound [XXXXXV] with the compound [XIII] in the presence of a base.

This reaction is conducted usually without a solvent or in a solvent, and the reaction temperature is from 0 to 200° C., and the reaction time is usually from an instant to 48 hours.

Regarding the amounts of reagents to be reacted, it is theoretical that the amount of the compound [XIII] is 1 mol and the amount of the base is 1 mol based on 1 mol of the compound [XXXXXV], however, the ratio can be optionally changed depending on the reaction conditions.

The base to be used includes organic bases such as pyridine, quinoline, 1,8-diazabicyclo[5.4.0]undec-7-en, 4-dimethylaminopyridine, N,N-dimethylaniline, N,N-diethylaniline, triethylamine, diisopropylethylamine and the like, and inorganic bases such as lithium carbonate, potassium carbonate, sodium hydride, potassium hydride, lithium hydroxide, sodium hydroxide and the like.

Examples of the solvent to be used include aromatic hydrocarbons such as toluene, xylene and the like; aromatic halogenated hydrocarbons such as benzotrifluoride and the like; ethers such tetrahydrofuran, ethylene glycol dimethyl ether and the like; ketones such as acetone, 2-butanone, methyl isobutyl ketone and the like; esters such as ethyl acetate, butyl acetate and the like; nitriles such as acetonitrile, isobutyronitrile and the like; amides such as N,N-dimethylformamide, N,N-dimethylacetamide, 1-methyl-2-pyrrolidinone and the like; sulfur compounds such as dimethyl sulfoxide, sulfolane and the like or mixtures thereof.

After completion of the reaction, the intended compound can be obtained, for example, by the following operation 1), 2) or 3).

1) The reaction solution is poured into water, this is extracted with an organic solvent, and the organic layer is dried and concentrated.

2) The reaction mixture is poured into water and the precipitate is collected by filtration.

3) The reaction solution is concentrated as it is, or, filtrated if necessary, and the filtrate is concentrated.

Further, the resulted present compound can also be purified by a procedure such as chromatography, re-crystallization and the like.

<Step A8-2>: The compound [XXXXXVII] can be produced, for example, by reducing the compound [XXXXXVI] in a solvent, A) using an iron powder in the presence of an acid, B) with hydrogen in the presence of a catalyst.

A) This reaction is conducted usually in a solvent, and the reaction temperature is usually from 0 to 100° C., preferably from room temperature to the reflux temperature. The reaction time is usually from an instant to 48 hours.

Regarding the amounts of reagents to be used in the reaction, the amount of the iron powder is from 3 mol to excess and the amount of the acid is 1 to 10 mol based on 1 mol of the compound [XXXXXVI], however, the ratio can be optionally changed depending on the reaction conditions.

As the acid to be used, acetic acid and the like are listed.

As the solvent to be used, there are listed, for example, water, acetic acid, ethyl acetate and the like or mixtures thereof.

After completion of the reaction, an intended material can be obtained by a usual post-treatment operation such as filtrating, then, pouring a reaction solution into water and collecting the deposited crystals by filtration, or, extracting with an organic solvent, neutralization, drying, concentration and the like.

B) This reaction is usually conducted in a solvent. The reaction temperature is usually from −20 to 150° C., preferably from 0 to 50° C. The reaction time is usually from an instant to 48 hours.

This reaction can also be conducted under pressure, and the reaction is preferably conducted under a pressure of 1 to 5 atom.

The amount of the catalyst used in this reaction is from 0.001 to 10% by weight based on the compound [XXXXXVI].

As the catalyst to be used in the reaction, anhydrous palladium/carbon, water-containing palladium/carbon, platinum oxide and the like are listed.

The solvent includes carboxylic acids such as formic acid, acetic acid, propionic acid and the like, esters such as ethyl acetate, butyl acetate and the like, alcohols such as methanol, ethanol and the like, or mixtures thereof and the like.

After completion of the reaction, an intended material can be obtained by a usual post-treatment operation such as filtrating a reaction solution before concentrating the solution itself, and the like.

The intended material can also be purified by a procedure such as chromatography, re-crystallization and the like.

<Step A8-3>: The compound [XXXXXVIII] can be produced, for example, by reacting the compound [XXXXXVII] with a diazotizing agent and an acid in a solvent.

The reaction temperature is from −30 to 30° C., and the reaction time is usually from an instant to 5 hours.

Regarding the amounts of reagents to be reacted, the amount of the diazotizing agent is from 1 mol to 3 mol, and the amount of the acid is from 1 mol to 6 mol based on 1 mol of the compound [XXXXXVII], however, the ratio can be optionally changed depending on the reaction conditions.

As the diazotizing agent used, there are listed, for example, nitrites such as sodium nitrite, isoamyl nitrite, t-butyl nitrite and the like.

As the acid used, there are listed, for example, inorganic acids such as tetrafluoroboric acid, hydrochloric acid and the like, organic acids such as trifluoromethanesulfonic acid and the like, lewis acid such as boron trifluoride diethyl etherate and the like.

As the solvent used, there are listed, for example, aliphatic halogenated hydrocarbons such as methylene chloride, chloroform, 1,2-dichloroethane, 1,2,3-trichloropropane and the like, ethers such as diethyl ether, dioxane, tetrahydrofuran, ethylene glycol dimethyl ether and the like, or mixtures thereof.

After completion of the reaction, the reaction solution is used in the subsequent reaction as it is, or nonpolar organic solvent such as n-pentane, n-hexane and the like is added to the reaction solution and the precipitate is collected by filtration, for example.

<Step A8-4>: The compound [XXXXXIX] can be produced, for example, by reacting the diazonium salt compound [XXXXXVIII] with the compound [XXXXVII].

This reaction is usually conducted without a solvent or in a solvent, the reaction temperature is from room temperature to 120° C., preferably from 50 to 90° C., and the reaction time is usually from an instant to 5 hours.

Regarding the amounts of reagents to be reacted, the amount of the compound [XXXXVII] is from 1 mol to excess based on 1 mol of the compound [XXXXXVIII], however, the ratio can be optionally changed depending on the reaction conditions.

As the solvent used, acetic acid and the like.

After completion of the reaction, the intended compound can be obtained, for example, by the following treatment; the reaction solution is concentrated as it is, the residue is diluted with water, this is extracted with an organic solvent, and the organic layer is dried and concentrated. Further, the resulted compound can also be purified by a procedure such as chromatography, re-crystallization and the like.

<Step A8-5>: The compound [XXXXXX] can be produced, for example, by reacting the compound [XXXXXIX] in the presence of a base in a solvent.

The reaction temperature is from 0 to 100° C., preferably from room temperature to 60° C., and the reaction time is usually from 0.5 to 20 hours.

Regarding the amounts of reagents to be reacted, the amount of the base is from 0.1 mol to 10 mol based on 1 mol of the compound [XXXXXIX], however, the ratio can be optionally changed depending on the reaction conditions.

As the base used, there are listed inorganic bases such as sodium carbonate, potassium carbonate, sodium hydrogen carbonate and the like.

As the solvent used, for example, there are listed, methanol, ethanol, water and the like, or mixtures thereof.

After completion of the reaction, the intended compound can be obtained, for example, by the following treatment; the reaction solution is concentrated as it is, the residue is diluted with water, this is extracted with an organic solvent, and the organic layer is dried and concentrated. Further, the resulted compound can also be purified by a procedure such as chromatography, re-crystallization and the like.

(Intermediate Production Method 9)

Compound [X] wherein Y is oxygen, Q is a pyrimidine ring, and $R^3$ is $OR^7$, $SR^8$ or $N(R^9)R^{10}$ (compound [I9-4]) can be produced by a method shown in the following scheme.

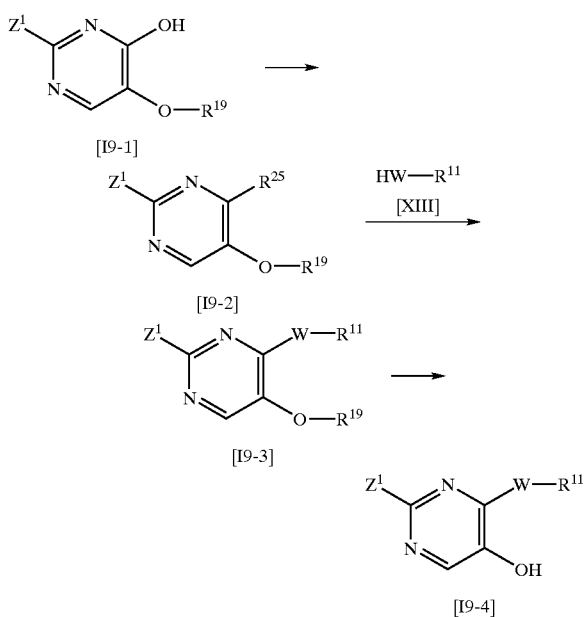

[wherein, $R^{11}$, $R^{19}$, $R^{25}$, W and $Z^1$ are the same as defined above.].

<Step A9-1>: The compound [I9-2] can be produced, for example, by reacting the compound [I9-1] with a halogenating agent, without a solvent or in a solvent.

Reaction temperature: from 50° C. to reflux temperature.

Reaction time: from an instant to 36 hours halogenating agent: phosphorus oxybromide, phosphorus oxychloride and the like The amount of the halogenating agent: from 1 mol to excess based on 1 mol of the compound [I9-1]

However, the ratio can be optionally changed depending on the reaction conditions.

Solvent: toluene, and the like

After completion of the reaction, the intended compound can be obtained, for example, by the following treatment; the reaction solution is concentrated as it is, the residue is diluted with water, this is extracted with an organic solvent, and the organic layer is dried and concentrated. Further, the resulted compound can also be purified by a procedure such as chromatography, re-crystallization and the like.

<Step A9-2>: The compound [I9-3] can be produced, for example, by reacting the compound [I9-2] with the compound [XIII] in a solvent, in the presence of a base.

Reaction temperature: from 0 to 180° C.

Reaction time: from an instant to 24 hours

The amount of the compound [XIII]: from 1 mol to 1.5 mol based on 1 mol of the compound [I9-2]

The amount of the base: from 1 mol to 1.5 mol based on 1 mol of the compound [I9-2]

However, the ratio can be optionally changed depending on the reaction conditions.

Base: triethylamine, diisopropylethylamine, potassium carbonate, sodium hydride and the like Solvent: dioxane, tetrahydrofuran, N,N-dimethylformamide, 1-methyl-2-pyrrolidinone and the like After completion of the reaction, the intended compound can be obtained, for example, by the following treatment; the reaction solution is poured into water, this is extracted with an organic solvent, and the organic layer is dried and concentrated. Further, the resulted compound can also be purified by a procedure such as chromatography and the like.

<Step A9-3>: The compound [I9-4] can be produced by de-protecting the compound [I9-3], for example, according to a method described in "Yuki Kagaku Jikken no Tebiki" vol. 4, (published by Kagaku Dojin), Protective Groups in Organic Synthesis (published by JOHN WILEY & SONS, INC.).

(Intermediate Production Method 10)

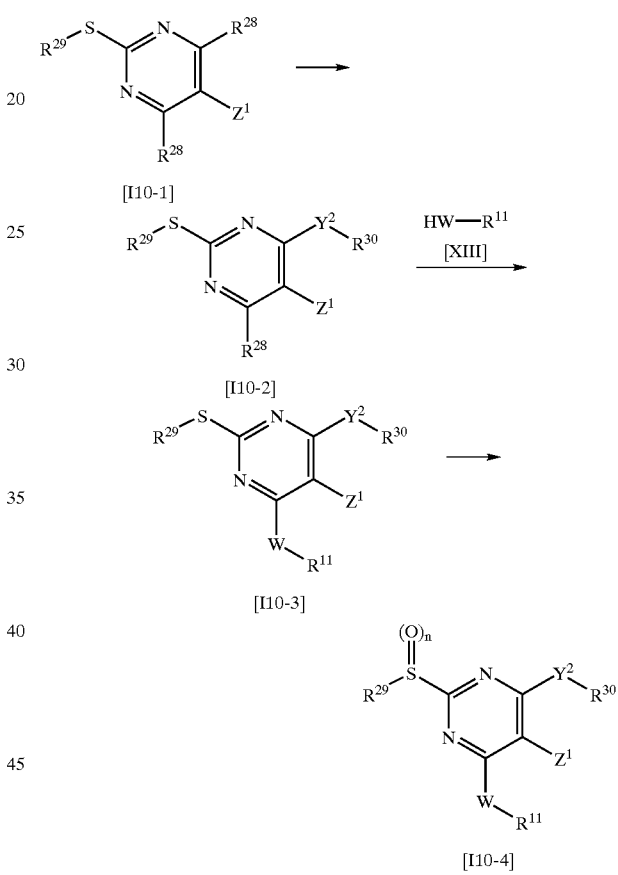

[wherein, $R^{11}$, W and $Z^1$ are the same as defined above, and $R^{28}$ represents chlorine or bromine, $R^{29}$ represents $C_1$ to $C_6$ alkyl such as methyl, ethyl and the like, or phenyl which may be substituted such as phenyl, 4-methylphenyl and the like, $R^{30}$ represents $C_1$ to $C_6$ alkyl such as methyl, ethyl and the like, or $C_1$ to $C_6$ haloalkyl such as trifluoromethyl and the like, $Y^2$ represents oxygen or sulfur, n represents 1 or 2.]

(Intermediate Production Method 11)

Compound [XXXXXI] wherein $X^1$ is nitro, fluorine, chlorine, bromine or ioine (compound [I11-5]) can be produced by a method shown in the following scheme.

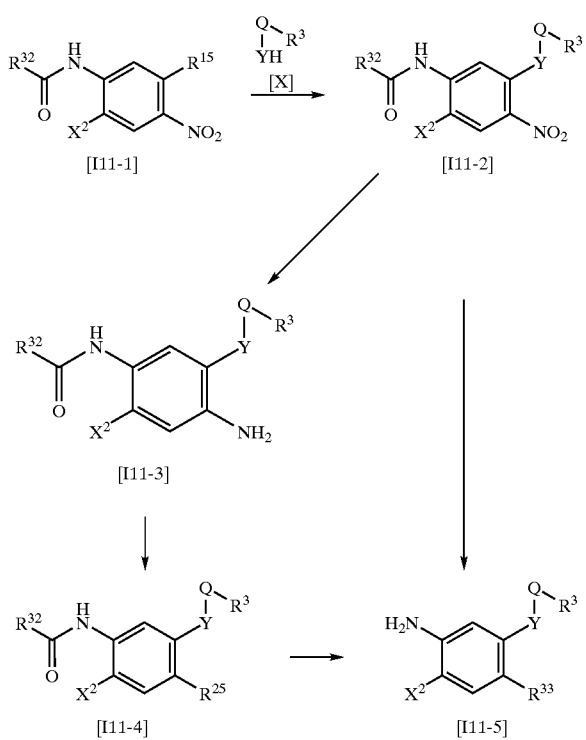

[wherein, $R^3$, $R^{15}$, $R^{25}$, Y, Q and $X^2$ are the same as defined above. $R^{32}$ represents $C_1$ to $C_6$ alkyl which may be substituted such as methyl, ethyl, trifluoromethyl, trichloromethyl and the like, and $R^{33}$ represents nitro, fluorine, chlorine, bromine or iodine.].

(Intermediate Production Method 12)

The compound [XXXI] may be produced by a method described in the following scheme.

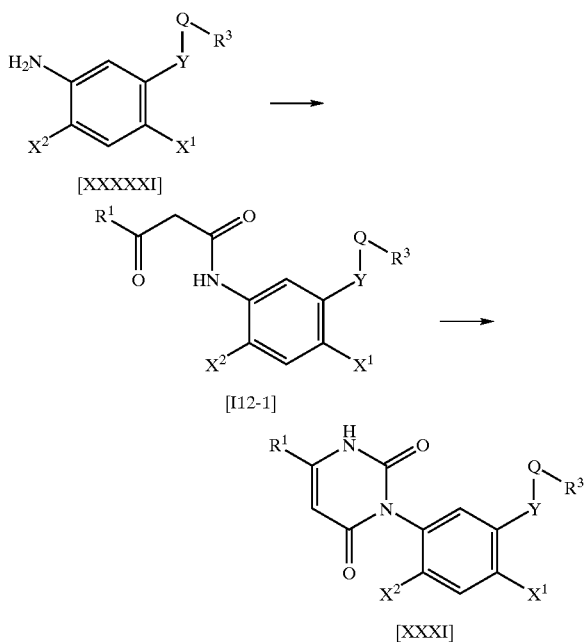

Wherein Q, $R^1$, $R^3$, $X^1$, $X^2$ and Y are the same as defined above.

<Process A12-1>: A process for producing compounds [I12-1] from the compound [XXXXXI].

The compound [I12-1] may be produced by reacting the compound [XXXXXI] with the compound [I12-2] of the formula [I12-2]

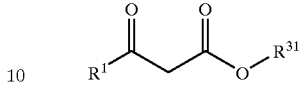

[I12-2]

wherein $R^1$ is the same as defined above, and $R^{31}$ represents $C_1$ to $C_6$ alkyl such as methyl, ethyl and the like.

The reaction may be carried out without a solvent or in a solvent, and the reaction temperature is usually in a range from room temperature to 150° C. or boiling point of the solvent.

The amount of the compound [I12-2] may be 1 to 5 mole based on 1 mole of the compound [XXXXXI].

Examples of the solvent to be used include aliphatic hydrocarbons such as n-hexane, n-heptane, ligroin and the like, aromatic hydrocarbons such as toluene, xylene and the like.

This reaction may be accelerated by using a dealcoholated agent such as molecular sieves 4A and 5A and the like.

After completion of the reaction, an objected compound can be obtained by subjecting to the ordinary after treatment by the following procedure.

1) The reaction mixture is filtered and concentrated.
2) The reaction mixture is poured into water, and the deposited crystals are collected.
3) The reaction mixture is added to acids such as concentrated hydrochloric acid and the like or water, and this is extracted with an organic solvent, and the resulted organic layer is washed with water, dried and concentrated.

Further, the object compound can also be purified by a procedure such as chromatography, re-crystallization and the like.

The compound [I12-1] may be exist as enol isomers and as the hydrate compound [I12-3]

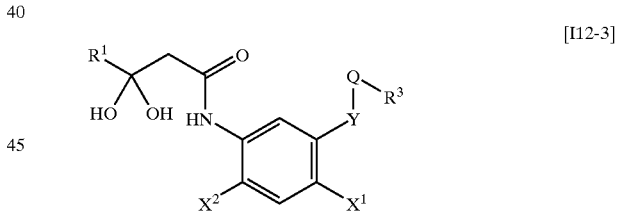

[I12-3]

Wherein Q, $R^1$, $R^3$, $X^1$, $X^2$ and Y are the same as defined above, or the mixtures thereof.

<Process A12-2>: A process for producing the compound [XXXI] from the compound [I12-1].

The compound [XXXI] can be produced, for example, by reacting the compound [I12-1] with cyanate in the presence of an acid.

The reaction may be carried out without a solvent or in a solvent, and the reaction temperature is usually in a range from 55 to 150° C. or boiling point of the solvent, preferably conducted in a range from room temperature to 50° C., at first, then in a range from 55 to 150° C. or boiling point of the solvent.

The cyanate used includes potassium cyanate and sodium cyanate and the like.

The acid used includes acetic acid, and the like.

The amount of the cyanate used in this reaction is in a ratio from 1 to 10 mole, preferably from 1 to 2 mole based on 1 mole of the compound [I12-1].

The amount of the acids used in this reaction is in a ratio from 1 mole to a large excess amount based on 1 mole of the compound [I12-1].

Examples of the solvent to be used include aliphatic hydrocarbons such as n-hexane, n-heptane and the like, aromatic hydrocarbons such as benzene, toluene, xylene and the like.

After completion of the reaction, an objected compound can be obtained, for example, by the following operation 1), 2) or 3).

1) The reaction solution is poured into water, this is extracted with an organic solvent, and the organic layer is dried and concentrated.

2) The reaction mixture is poured into water and the precipitate is collected by filtration.

3) The reaction solution is concentrated as it is, or, filtrated if necessary, and the filtrate is concentrated.

Further, the object compound can also be purified by a procedure such as chromatography, re-crystallization and the like.

The compounds [XXI], [XXV], [XXVII], [XXXXX], [XXXXXIV] [XXXXXV], [I9-1], [I10-1] and [I11-1] are commercially available, or can be produced by known methods.

The present compounds have excellent herbicidal activity and some of them can exhibit excellent selectivity between crops and weeds. In other words, the present compounds have herbicidal activity against various weeds which may cause some trouble in the foliar treatment and soil treatment on upland fields, such as listed below.

Onagraceous Weeds
  large-flowered evening primrose (*Oenothera erythrosepala*), cutleaf evening primrose (*Oenothera laciniata*),
Ranunculaceous Weeds
  roughseeded buttercup (*Ranunculus muricatus*), hairy buttercup (*Ranunculus sardous*)
Polygonaceous Weeds
  wild buckwheat (*Polygonum convolvulus*), pale smartweed (*Polygonum lapathifolium*), pennsylvania smartweed (*Polygonum pensylvanicum*), ladysthumb (*Polygonum persicaria*), curly dock (*Rumex crispus*), broadleaf dock (*Rumex obtusifolius*), Japanese knotweed (*Polygonum cuspidatum*)
Portulacaceous Weeds
  common purslane (*Portulaca oleracea*)
Caryophyllaceous Weeds
  common chickweed (*Stellaria media*), sticky chickweed (*Cerastium glomeratum*)
Chenopodiaceous Weeds
  common lambsquarters (*Chenopodium album*), kochia (*Kochia scoparia*)
Amaranthaceous Weeds
  redroot pigweed (*Amaranthus retroflexus*), smooth pigweed (*Amaranthus hybridus*)
Cruciferous (Brassicaceous) Weeds
  wild radish (*Raphanus raphanistrum*), wild mustard (*Sinapis arvensis*), shepherdpurse (*Capsella bursa-pastoris*), virginia pepperweed (*Lepidium virginicum*)
Leguminous (Fabaceous) Weeds
  hemp sesbania (*Sesbania exaltata*), sicklepod (*Cassia obtusifolia*), Florida beggarweed (*Desmodium tortuosum*), white clover (*Trifolium repens*), common vetch (*Vicia sativa*), black medik (*Medicago lupulina*)
Malvaceous Weeds
  velvetleaf (*Abutilon theophrasti*), prickly sida (*Sida spinosa*)
Violaceous Weeds
  field pansy (*Viola arvensis*), wild pansy (*Viola tricolor*)
Rubiaceous Weeds
  catchweed bedstraw (cleavers) (*Galium aparine*)
Convolvulaceous Weeds
  ivyleaf morningglory (*Ipomoea hederacea*), tall morningglory (*Ipomoea purpurea*), entireleaf morningglory (*Ipomoea hederacea* var. *integriuscula*), pitted morningglory (*Ipomoea lacunosa*), field bindweed (*Convolvulus arvensis*)
Labiate Weeds
  red deadnettle (*Lamium purpureum*), henbit (*Lamium amplexicaule*)
Solanaceous Weeds
  jimsonweed (*Datura stramonium*), black nightshade (*Solanum nigrum*)
Scrophulariaceous Weeds
  birdseye speedwell (*Veronica persica*), corn speedwell (*Veronica arvensis*), ivyleaf speedwell (*Veronica hederaefolia*)
Composite Weeds
  common cocklebur (*Xanthium pensylvanicum*), common sunflower (*Helianthus annuus*), wild camomille (*Matricaria chamomilla*), scentless chamomile (*Matricaria perforata* or *inodora*), corn marigold (*Chrysanthemum segetum*), pineappleweed (*Matricaria matricarioides*), common ragweed (*Ambrosia artemisiufolia*), giant ragweed (*Ambrosia trifida*), horseweed (*Erigeron canadensis*), Japanese mugwort (*Artemisia princeps*), tall goldenrod (*Solidago altissima*), common dandelion (*Taraxacum officinale*)
Boraginaceous Weeds
  forget-me-not (*Myosotis arvensis*)
Asclepiadaceous Weeds
  common milkweed (*Asclepias syriaca*)
Euphorbiaceous Weeds
  sun spurge (*Euphorbia helioscopia*), spotted spurge (*Euphorbia maculata*)
Geraniaceous Weeds
  Carolina geranium (*Geranium carolinianum*)
Oxalidaceous Weeds
  pink woodsorrel (*Oxalis corymbosa*)
Cucurbitaceous Weeds
  burcucumber (*Sicyos angulatus*)
Graminaceous Weeds
  barnyardgrass (*Echinochloa crus-galli*), green foxtail (*Setaria viridis*), giant foxtail (*Setaria faberi*), large crabgrass (*Digitaria sanguinalis*), Southern Crabgrass (*Digitaria ciliaris*), goosegrass (*Eleusine indica*), annual bluegrass (*Poa annua*), blackgrass (*Alopecurus myosuroides*), wild oat (*Avena fatua*), johnsongrass (*Sorghum halepense*), quackgrass (*Agropyron repens*), downy brome (*Bromus tectorum*), bermudagrass (*Cynodon dactylon*), fall panicum (*Panicum dichotomiflorum*), Texas panicum (*Panicum texanum*), shattercane (*Sorghum vulgare*), water foxtail (*Alopecurus geniculatus*)
Commelinaceous Weeds
  common dayflower (*Commelina communis*)
Equisetaceous Weeds
  field horsetail (*Equisetum arvense*)
Cyperaceous Weeds
  rice flatsedge (*Cyperus iria*), purple nutsedge (*Cyperus rotundus*), yellow nutsedge (*Cyperus esculentus*)

Furthermore, some of the present compounds exhibit no significant phytotoxicity on the main crops such as corn (*Zea mays*), wheat (*Triticum aestivum*), barley (*Hordeum vulgare*), rice (*Oryza sativa*), sorghum (*Sorghum bicolor*), soybean (*Glycine max*), cotton (Gossypium spp.), sugar beet (*Beta vulgaris*), peanut (*Arachis hypogaea*), sunflower (*Helianthus annuus*), and canola (*Brassica napus*); horticultural crops such as flowers, ornamental plants, and vegetable crops.

The present compounds can also attain the effective control of various weeds which may cause some trouble in the no-tillage cultivation of soybean (*Glycine max*), corn (*Zea mays*), wheat (*Triticum aestivum*), and other crops. Furthermore, some of the present compounds exhibit no significant phytotoxicity on the crops.

The present compounds also have herbicidal activity against various weeds which may cause some trouble in the flooding treatment on paddy fields, such as listed below.

Graminaceous Weeds
  barnyardgrass (*Echinochloa oryzicola*)
Scrophulariaceous Weeds
  common falsepimpernel (*Lindernia procumbens*)
Lythraceous Weed
  Indian toothcup (*Rotala indica*), red stem (*Ammannia multiflora*)
Elatinaceous Weeds
  waterwort (*Elatine triandra*)
Cyperaceous Weeds
  smallflower umbrella sedge (*Cyperus difformis*), hardstem bulrush (*Scirpus juncoides*), needle spikerush (*Eleocharis acicularis*), water nutgrass (*Cyperus serotinus*), water chestnut (*Eleocharis kuroguwai*)
Pontederiaceous Weeds
  monochoria (*Monochoria vaginalis*)
Alismataceous Weeds
  arrowhead (*Sagittaria pygmaea*), arrowhead (*Sagittaria trifolia*), waterplantain (*Alisma canaliculatum*)
Potamogetonaceous Weeds
  roundleaf pondweed (*Potamogeton distinctus*)
Umbelliferous Weeds
  watercelery sp. (*Oenanthe javanica*)

Furthermore, some of the present compounds exhibit no significant phytotoxicity on transplanted paddy rice.

The present compounds can also attain the control of a wide variety of weeds which are growing or will grow in the other non-cultivated lands in which weed controlling is necessiated such as levee, riverbed, roadside, railroad, green field of park, ground, parking, airport, industrial place (ex. factory, storage equipement), fallow land, vacant lot, and the like, orchards, grasslands, lawns, forests. The present compounds also have herbicidal activity against various aquatic weeds, such as water hyacinth (*Eichhornia crassipes*), which are growing or will grow at the waterside such as rivers, canals, waterways or reservoir.

The present compounds have substantially the same characteristics as those of the herbicidal compounds disclosed in the published specification of International Patent Application, WO95/34659. In the case where crops with tolerance imparted by introducing a herbicide tolerance gene described in the published specification are cultivated, the present compounds can be used at larger rates than those used when ordinary crops without tolerance are cultivated, which makes it possible to control other unfavorable weeds more effectively.

When the present compounds are used as the active ingredients of herbicides, they are usually mixed with solid or liquid carriers or diluents, surfactants, and other auxiliary agents to give emulsifiable concentrates, wettable powders, flowables, granules, concentrated emulsions, water-dispersible granules, or other formulations.

These formulations may contain any of the present compounds as an active ingredient at an amount of 0.001 to 80% by weight, preferably 0.005 to 70% by weight, based on the total weight of the formulation.

The solid carrier may include, fine powders of mineral matters such as kaolin clay, attapulgite clay, bentonite, acid clay, pyrophyllite, talc, diatomaceous earth, and calcite; fine powders of organic substances such as walnut shell powder; fine powders of water-soluble organic substances such as urea; fine powders of inorganic salts such as ammonium sulfate; and fine powders of synthetic hydrated silicon oxide. The liquid carrier may include, aromatic hydrocarbons such as methylnaphthalene, phenylxylylethane, and alkylbenzene (e.g., xylene); alcohols such as isopropanol, ethylene glycol, and 2-ethoxyethanol; esters such as phthalic acid dialkyl esters; ketones such as acetone, cyclohexanone, and isophorone; mineral oils such as machine oil; vegetable oils such as soybean oil and cottonseed oil; dimethyl sulfoxide, N,N-dimethylformamide, acetonitrile, N-methylpyrrolidone, water and the like.

The surfactant used for emulsification, dispersing, or spreading may include surfactants of the anionic type, such as alkylsulfates, alkylsulfonates, alkylarylsulfonates, dialkylsulfosuccinates, and phosphates of polyoxyethylene alkyl aryl ethers; and surfactants of the nonionic type, such as polyoxyethylene alkyl ethers, polyoxyethylene alkyl aryl ethers, polyoxyethylene polyoxypropylene block copolymers, sorbitan fatty acid esters, and polyoxyethylene sorbitan fatty acid esters.

The other auxiliary agent may include lignin sulfonates, alginates, polyvinyl alcohol, gum arabic, CMC (carboxymethylcellulose), and PAP (isopropyl acid phosphate).

The present compounds are usually formulated and then used for soil, foliar, or flooding treatment at pre- or post-emergence of weeds. The soil treatment may include soil surface treatment and soil incorporation. The foliar treatment may include application over the plants and directed application in which a chemical is applied only to weeds so as to keep off the crop plants.

The present compounds may often exhibit the enhancement of herbicidal activity when used in admixture with other herbicides. They can also be used in admixture with insecticides, acaricides, nematocides, fungicides, bactericides, plant growth regulators, fertilizers, and soil conditioners.

Such herbicides are shown below, atrazine, cyanazine, dimethametryn, metribuzin, prometryn, simazine, simetryn, chlorotoluron, diuron, fluometuron, isoproturon, linuron, methabenzthiazuron, propanil, bentazone, bromoxynil, ioxynil, pyridate, butamifos, dithiopyr, ethalfluralin, pendimethalin, thiazopyr, trifluralin, acetochlor, alachlor, butachlor, diethatyl-ethyl, dimethenamid, fluthiamide, mefenacet, metolachlor, pretilachlor, propachlor, cinmethylin, acifluorfen, acifluorfen-sodium, benzfendizone, bifenox, butafenacil, chlomethoxynil, fomesafen, lactofen, oxadiazon, oxadiargyl, oxyfluorfen, carfentrazone-ethyl, fluazolate, flumiclorac-pentyl, flumioxazine, fluthiacet-methyl, isopropazol, sulfentrazone, thidiazimin, azafenidin, pyraflufen-ethyl, cinidon-ethyl, difenzoquat, diquat, paraquat, 2,4-D, 2,4-DB, clopyralid, dicamba, fluroxypyr, MCPA, MCPB, mecoprop, quinclorac, triclopyr, azimsulfuron, bensulfuron-methyl, chlorimuronethyl, chlorsulfuron, cloransulam-methyl, cyclosulfamuron, diclosulam, ethoxysulfuron, flazasulfuron, flucarbazone, flumetsulam, flupyrsulfuron, halosulfuron-methyl, imazosulfuron, indosulfuron, metosulam, metsulfuron-methyl, nicosulfuron, oxasulfuron, primisulfuron-methyl, procarbazone-sodium, prosulfuron, pyrazosulfuron-ethyl, rimsulfuron, sulfometuron-methyl, sulfosulfuron, triasulfuron, tribenuron-methyl, tritosulfuron, thifensulfuron-methyl, triflusulfuron-methyl, pyribenzoxim, bispyribac-sodium, pyriminobac-methyl, pyrithiobac-sodium, imazameth, imazamethabenz-methyl, imazamox, imazapic, imazapyr, imazaquin, imazethapyr, tepraloxydim, alloxydim-sodium, clethodim, clodinafop-propargyl, cyhalofop-butyl, dichlofop-methyl, fenoxaprop-ethyl, fenoxaprop-p-ethyl, fluazifop-buthyl, fluazifop-p-butyl, haloxyfop-methyl, quizalofop-p-ethyl, sethoxydim, tralkoxydim, diflufenican, flurtamone, norflurazone, benzofenap, isoxaflutole, pyrazolate, pyrazoxyfen, sulcotrione, clomazone, mesotrione, isoxachlortole, bialaphos, glufosinate-ammonium, glyphosate, sulfosate, dichlobenil, isoxaben, benthiocarb, butylate, dimepiperate, EPTC, esprocarb, molinate, pyributicarb, triallate, diflufenzopyr, bromobutide, DSMA, MSMA, cafenstrol, daimron, epoprodan, flupoxam, metobenzuron, pentoxazone, piperophos, triaziflam, beflubutamid, benzobicyclon, clomeprop, fentrazamide, flufenacet, florasulam, indanofan, isoxadifen, mesotrione, naploanilide, oxaziclomefone, pethoxyamid, phnothiol, pyridafol The above compounds are described in the catalog of Farm Chemicals Handbook, 1995 (Meister Publishing Company); AG CHEM NEW COMPOUND REVIEW, VOL. 13, 1995, VOL. 15, 1997, VOL. 16, 1998 or, VOL. 17, 1999 (AG CHEM INFORMATION SERVICES) or Josouzai Kenkyu Souran (Hakuyu-sha).

When the present compounds are used as the active ingredients of herbicides, the application amount, although it may vary with the weather conditions, formulation types, application times, application methods, soil conditions, crops to be protected, and weeds to be controlled, is usually in the range of 0.01 to 20,000 g, preferably 1 to 12,000 g, per hectare. In the case of emulsifiable concentrates, wettable powders, flowables, concentrated emulsions, water-dispersible granules, or the like, they are usually applied after diluted in their prescribed amounts with water (if necessary, containing an adjuvant such as a spreading agent) at a ratio of 10 to 1000 liters per hectare. In the case of granules or some types of flowables, they are usually applied as such without any dilution.

The adjuvant which can be used, if necessary, may include, in addition to the surfactants as described above, polyoxyethylene resin acids (esters), lignin sulfonates, abietates, dinaphthylmethanedisulfonates, crop oil concentrates, and vegetable oils such as soybean oil, corn oil, cottonseed oil, and sunflower oil.

The present compounds can also be used as the active ingredients of harvesting aids such as defoliants and desiccants for cotton (Gossipyum spp.), and desiccants for potato (*Solanum tuberosum*). In these cases, the present compounds are usually formulated in the same manner as the case where they are used as the active ingredients of herbicides, and used alone or in admixture with other harvesting aids for foliar treatment before the harvesting of crops.

EXAMPLES

The following production examples, formulation examples and test examples and the like will further illustrate the present invention in detail below, but do not limit the scope of the present invention.

First, production examples and intermediate production examples of the present compounds are shown. The compound numbers of the present compounds are described in the following Tables 1 to 10.

Production Example 1

Production of the Present Compound 1-12

109 mg of 2-chloro-4-fluoro-5-[3-methyl-2,6-dioxo-4-(trifluoromethyl)-1,2,3,6-tetrahydropyrimidin-1-yl]phenol and 70 mg of 2-chloro-5-[1-(methoxycarbonyl)ethoxy] pydimidine were dissolved in 1.0 ml of dimethyl sulfoxide, to this solution were added 10 mg of copper(I) bromide and 12 mg of anhydrous lithium carbonate, and the mixture was stirred for 2 hours at 120° C. The reaction solution was cooled to room temperature, then, this reaction solution was poured into ice water, and extracted with ethyl acetate. The organic layer was washed with saturated saline, dried over anhydrous magnesium sulfate, and concentrated. The residue was subjected to silica gel column chromatography to obtain 10 mg of methyl 2-([2-{2-chloro-4-fluoro-5-[3-methyl-2,6-dioxo-4-(trifluoromethyl)-1,2,3,6-tetrahydropyrimidin-1-yl]phenoxy}pyrimidin-5-yl]oxy) propionate [present compound 1-12].

$^1$H-NMR (CDCl$_3$/300 MHz) δ(ppm): 1.65 (d, 3H, J=7.0 Hz), 3.56 (s, 3H), 3.78 (s, 3H), 4.72 (q, 1H, J=7.0 Hz), 6.36 (s, 1H), 7.21 (d, 1H, J=6.8 Hz), 7.39 (d, 1H, J=8.7 Hz), 8.20 (s, 2H)

Intermediate Production Example 1

Production of 2-chloro-5-[1-(methoxycarbonyl) ethoxy]pyrimidine Used in Production Example 1

A mixture of 0.17 g of 2-chloro-5-hydroxypyrimidine, 0.22 g of methyl 2-bromopropionate, 0.20 g of anhydrous potassium carbonate and 2.6 ml of N,N-dimethylformamide was stirred at 60° C. for 1 hour. The reaction solution was cooled to room temperature, then, poured into water, and extracted with t-butyl methyl ether. The organic layer was dried over anhydrous magnesium sulfate, and concentrated. The residue was subjected to silica gel column chromatography to obtain 0.17 g of 2-chloro-5-[1-(methoxycarbonyl) ethoxy]pyrimidine.

$^1$H-NMR(CDCl$_3$/300 MHz) δ(ppm): 1.68 (d, 3H, J=6.6 Hz),3.79(s, 3H), 4.82 (q, 1H, J=6.7 Hz), 8.27(s, 2H)

Production Example 2

Production of Present Compound 7-125

A mixture of 0.30 g of 3-{2-chloro-4-fluoro-5-[3-methyl-2,6-dioxo-4-(trifluoromethyl)-1,2,3,6-tetrahydropyrimidin-1-yl]phenoxy}-2-(methoxycarbonyl)methoxypyridine [present compound 7-7], 0.06 g of sodium carbonate and 3.0 ml of c-pentanol was stirred for 1.5 hours at 100° C., then 2 hours at 120° C. The reaction solution was cooled to room temperature, then, poured into water, and extracted with ethyl acetate. The organic layer was washed with saturated saline, dried over anhydrous magnesium sulfate, and concentrated. The residue was subjected to silica gel column chromatography to obtain 0.15 g of 3-{2-chloro-4-fluoro-5-[3-methyl-2,6-dioxo-4-(trifluoromethyl)-1,2,3,6-tetrahydropyrimidin-1-yl]phenoxy}-2-(c-pentyloxycarbonyl)methoxypyridine [present compound 7-125].

$^1$H-NMR(CDCl$_3$/300 MHz) δ(ppm): 1.5–1.9 (m, 8H), 3.50 (q, 3H, J=1.1 Hz), 4.7–5.0 (m, 2H), 5.1–5.2 (m, 1H), 6.29 (s, 1H), 6.91 (dd, 1H, J=7.8,4.9 Hz), 6.94 (d, 1H, J=6.5 Hz), 7.30 (dd, 1H, J=7.8, 1.6 Hz), 7.37 (d, 1H, J=8.9 Hz), 7.91 (dd, 1H, J=4.9, 1.6 Hz)

Production Example 3

Production of the Present Compound 1-2

339 mg of 2-chloro-4-fluoro-5-[3-methyl-2,6-dioxo-4-(trifluoromethyl)-1,2,3,6-tetrahydropyrimidin-1-yl]phenol and 217 mg of 2-chloro-4-[1-(methoxycarbonyl)ethoxy]pyrimidine were dissolved in 2 ml of N,N-dimethylformamide, to this solution was added 150 mg of potassium carbonate, and the mixture was stirred for 2 hours at 80° C. The reaction solution was cooled to room temperature, then, this reaction solution was poured into ice water, and extracted with ethyl acetate. The organic layer was washed with saturated saline, dried over anhydrous magnesium sulfate, and concentrated. The residue was subjected to silica gel column chromatography to obtain 256 mg of methyl 2-([2-{2-chloro-4-fluoro-5-[3-methyl-2,6-dioxo-4-(trifluoromethyl)-1,2,3,6-tetrahydropyrimidin-1-yl]phenoxy}pyrimidin-4-yl]oxy)propionate [present compound 1-2].

$^1$H-NMR(CDCl$_3$/300 MHz) δ(ppm): 1.56 (d, 3H, J=7.1 Hz), 3.55 (s, 3H), 3.69 (s, 3H), 5.32 (q, 1H, J=6.3 Hz), 6.35 (s, 1H), 6.59 (d, 1H, J=5.6 Hz), 7.18 (d, 1H, J=6.1 Hz), 7.39 (d, 1H, J=9.1 Hz), 8.28 (d, 1H, J=5.7 Hz)

Production Example 4

Production of the Present Compound 3-2

156 mg of 2-chloro-4-fluoro-5-[3-methyl-2,6-dioxo-4-(trifluoromethyl)-1,2,3,6-tetrahydropyrimidin-1-yl]phenol and 100 mg of 4-chloro-2-[1-(methoxycarbonyl)ethoxy]pydimidine were dissolved in 1 ml of N,N-dimethylformamide, to this solution was added 75 mg of potassium carbonate, and the mixture was stirred for 2 hours at room temperature. The reaction solution was poured into ice water, and extracted with ethyl acetate. The organic layer was washed with saturated saline, dried over anhydrous magnesium sulfate, and concentrated. The residue was subjected to silica gel column chromatography to obtain 69 mg of methyl 2-([4-{2-chloro-4-fluoro-5-[3-methyl-2,6-dioxo-4-(trifluoromethyl)-1,2,3,6-tetrahydropyrimidin-1-yl]phenoxy}pyrimidin-2-yl]oxy)propionate [present compound 3-2].

$^1$H-NMR(CDCl$_3$/300 MHz) δ(ppm): 1.56 (d, 3H, J=7.1 Hz), 3.55(s, 3H), 3.65 (s, 3H), 5.0–5.3 (m, 1H), 6.35 (s, 1H), 6.63 (d, 1H, J=5.8 Hz), 7.20 (d, 1H, J=6.4 Hz), 7.39 (d, 1H, J=8.6 Hz), 8.38 (d, 1H, J=5.8 Hz)

Intermediate Production Example 2

Production of 2-chloro-4-[-(methoxycarbonyl)ethoxy]pyrimidine and 4-chloro-2-[1-(methoxycarbonyl)ethoxy]pyrimidine used in Production Examples 3 and 4

A mixture of 3.12 g of methyl lactate and 10 ml of acetonitrile was added to a mixture of 1.2 g of sodium hydride and 40 ml of acetonitrile dropwise under ice cooling, and the mixture was stirred for 30 minutes. To this was added a mixture of 4.47 g of 2,4-dichloropyrimidine and 10 ml of acetonitrile dropwise at the same temperature, and the mixture was stirred at 60° C. for 2 hours. This reaction solution was cooled to room temperature, then, poured into water, and extracted with ethyl acetate. The organic layer was washed with saturated saline, dried over anhydrous magnesium sulfate, and concentrated. The residue was subjected to silica gel column chromatography to obtain 2.5 g of 2-chloro-4-[1-(methoxycarbonyl)ethoxy]pyrimidine and 0.25 g of 4-chloro-2-[1-(methoxycarbonyl)ethoxy]pyrimidine. 2-Chloro-4-[1-(methoxycarbonyl)ethoxy]pyrimidine $^1$H-NMR(CDCl$_3$/250 MHz) δ(ppm): 3.51 (q, 3H, J=1.2 Hz), 5.04 (s, 2H), 6.31 (s, 1H), 6.87 (d, 1H, J=5.9 Hz), 6.9–7.1 (m, 4H), 7.3–7.5 (m, 5H), 7.84 (d, 1H, J=8.6 Hz) 4-Chloro-2-[1-(methoxycarbonyl)ethoxy]pyrimidine.

$^1$H-NMR(CDCl$_3$/250 MHz) δ(ppm): 1.67 (d, 3H, J=7.0 Hz), 3.75 (s, 3H), 5.33 (q, 1H, J=7.0 Hz), 7.03 (d, 1H, J=5.3 Hz), 8.38 (d, 1H, J=5.3 Hz)

Production Example 5

Production of the Present Compound 7-7

First Step 2.08 g of potassium carbonate was added to a solution of 3.0 g of 3-hydroxy-2-(methoxycarbonyl)methoxypyridine and 2.95 g of N-(2,5-difluoro-4-nitrophenyl)acetamide in 40 ml of N,N-dimethylformamide. The mixture was stirred for 2 hours at temperature from 60 to 70° C. Then, the mixture was cooled to room temperature, poured into water, extracted with ethyl acetate. The organic layer was washed with saturated saline, dried over magnesium sulfate, and concentrated to obtain crude crystal. The crude was washed with diisopropyl ether to obtain 3.67 g of N-[2-fluoro-5-{2-(methoxycarbonyl)methoxy-3-pyridyloxy}-4-nitrophenyl]acetamide.

$^1$H-NMR(CDCl$_3$/250 MHz) δ(ppm): 2.21 (s, 3H), 3.72 (s, 3H), 4.90 (s, 2H), 6.96 (dd, 1H, J=7.8,5.0 Hz), 7.35 (dd, 1H, J=7.8,1.6 Hz), 7.5–7.6 (b, 1H), 7.90 (d, 1H, J=10.6 Hz), 7.97 (dd, 1H, J=5.0,1.6 Hz), 8.15 (d, 1H, J=6.8 Hz)

The following compounds are similarly prepared:
N-[2-fluoro-5-{2-(ethoxycarbonyl)methoxy-3-pyridyloxy}-4-nitrophenyl]acetamide
N-(2-fluoro-5-[2-{1-(methoxycarbonyl)ethoxy}-3-pyridyloxy]-4-nitrophenyl)acetamide
N-(2-fluoro-5-[2-{1-(ethoxycarbonyl)ethoxy}-3-pyridyloxy]-4-nitrophenyl)acetamide Second Step To a mixture of 3.6 g of an iron powder, 10 ml of acetic acid and 1 ml of water was added a solution of 3.67 g of N-[2-fluoro-5-{2-(methoxycarbonyl)methoxy-3-pyridyloxy}-4-nitrophenyl]acetamide in 12 ml of acetic acid and 2 ml of ethyl acetate, dropwise while maintaining the temperature of the reaction solution at 45° C. or lower. After completion of the addition, the mixture was stirred for 1 hour at 40° C., then, the reaction mixture was filtrated through Celite, and concentrated. The residue was diluted with saturated aqueous sodium bicarbonate solution, and extracted with ethyl acetate. The organic layer was washed with saturated aqueous sodium bicarbonate solution, dried over anhydrous magnesium sulfate, and concentrated. Then, the resulted residue was washed with diisopropyl ether to obtain 3.09 g of N-[4-amino-2-fluoro-5-{2-(methoxycarbonyl)methoxy-3-pyridyl oxy}phenyl]acetamide.

$^1$H-NMR(CDCl$_3$/250 MHz) δ(ppm): 2.15 (s, 3H), 3.77 (s, 3H), 3.9–4.1 (b, 2H), 5.03 (s, 2H), 6.56 (d, 1H, J=11.8 Hz), 6.84 (dd, 1H, J=7.9,5.0 Hz), 7.0–7.2 (b, 1H), 7.14 (dd, 1H, J=7.9,1.5 Hz), 7.80 (dd, 1H, J=5.0,1.5 Hz), 7.84 (d, 1H, J=7.6 Hz)

The following compounds are similarly prepared:
N-[4-amino-2-fluoro-5-{2-(ethoxycarbonyl)methoxy-3-pyridyloxy}phenyl]acetamide.

N-(4-amino-2-fluoro-5-[2-{1-(methoxycarbonyl)ethoxy}-3-pyridyloxy]phenyl)acetamide.

N-(4-amino-2-fluoro-5-[2-{1-(ethoxycarbonyl)ethoxy}-3-pyridyloxy]phenyl)acetamide.

Third Step

A solution of 2.01 g of isoamyl nitrite in 1 ml of acetonitrile was added to a mixture of 2.0 g of N-[4-amino-2-fluoro-5-{2-(methoxycarbonyl)methoxy-3-pyridyloxy}phenyl]acetamide, 1.13 g of copper(I) chloride, 2.31 g of copper(II) chloride and 20 ml of acetonitrile dropwise at room temperature, and the mixture was stirred for 1 hour. This reaction solution was poured into 2% hydrochloric acid, and extracted with ethyl acetate. The organic layer was washed with saturated saline, dried over anhydrous magnesium sulfate, and concentrated. The residue was subjected to silica gel column chromatography to obtain 1.04 g of N-[4-chloro-2-fluoro-5-{2-(methoxycarbonyl)methoxy-3-pyridyloxy}phenyl]acetamide.

$^1$H-NMR(CDCl$_3$/250 MHz) δ(ppm): 2.18 (s, 3H), 3.75 (s, 3H), 4.98 (s, 2H), 6.87 (dd, 1H, J=7.8,4.9 Hz), 7.08 (dd, 1H, J=7.8,1.4 Hz), 7.23 (d, 1H, J=10.3 Hz), 7.3–7.4 (b, 1H), 7.86 (dd, 1H, J=4.9,1.4 Hz) 8.07 (d, 1H, J=7.3 Hz), The following compounds are similarly prepared:

N-[4-chloro-2-fluoro-5-{2-(ethoxycarbonyl)methoxy-3-pyridyloxy}phenyl]acetamide

N-(4-chloro-2-fluoro-5-[2-{1-(methoxycarbonyl)ethoxy}-3-pyridyloxy]phenyl)acetamide N-(4-chloro-2-fluoro-5-[2-{1-(ethoxycarbonyl)ethoxy}-3-pyridyloxy]phenyl)acetamide Fourth Step A mixture of 20 ml of boron trifluoride methanol complex methanol solution and 1.04 g of N-[4-chloro-2-fluoro-5-{2-(methoxycarbonyl)methoxy-3-pyridyloxy}phenyl]acetamide was stirred for 3 hours at temperature from 60 to 70° C. Thereafter, the reaction solution was concentrated, the residue was diluted with saturated aqueous sodium bicarbonate solution, and extracted with ethyl acetate. The organic layer was washed with saturated saline, dried over magnesium sulfate, and concentrated, and the resulted residue was purified by column chromatography concentrated to obtain 0.87 g of 4-chloro-2-fluoro-5-{2-(methoxycarbonyl)methoxy-3-pyridyloxy}aniline.

$^1$H-NMR(CDCl$_3$/250 MHz) δ(ppm): 3.77 (s, 3H), 3.7–3.9 (b, 2H), 5.00 (s, 2H), 6.49 (d, 1H, J=8.2 Hz), 6.88 (dd, 1H, J=7.9,5.0 Hz), 7.08 (d, 1H, J=10.3 Hz), 7.10 (dd, 1H, J=7.9,1.6 Hz), 7.87 (dd, 1H, J=5.0,1.6 Hz)

The following compounds are similarly prepared:

4-chloro-2-fluoro-5-{2-(ethoxycarbonyl)methoxy-3-pyridyloxy}aniline 4-chloro-2-fluoro-5-[2-{1-(methoxycarbonyl)ethoxy}-3-pyridyloxy]aniline 4-chloro-2-fluoro-5-[2-{1-(ethoxycarbonyl)ethoxy}-3-pyridyloxy]aniline Fifth Step A mixture of 0.50 g of 4-chloro-2-fluoro-5-{2-(methoxycarbonyl)methoxy-3-pyridyloxy}aniline, 0.28 g of ethyl trifluoroacetoacetate and 10 ml of toluene was subjected to azeotropic reaction with removing ethanol by passing through molecular sieves 5A for 3 hours. After cooling, the reaction solution was concentrated to obtain 0.71 g of N-[4-chloro-2-fluoro-5-{2-(methoxycarbonyl)methoxy-3-pyridyloxy}phenyl]trifluoroacetoacetamide.

melting point: 158.8° C.

Sixth Step

To a mixture of 0.71 g of N-[4-chloro-2-fluoro-5-{2-(methoxycarbonyl)methoxy-3-pyridyloxy}phenyl]trifluoroacetoacetamide and 2 ml of acetic acid, 0.33 g of potassium cyanate was added, and the mixture was stirred at 50° C. for 1 hour, then, at 110° C. for 1.5 hours. After cooling, water was added to the reaction mixture and the mixture was extracted with ethyl acetate. The organic layer was washed with saturated aqueous sodium bicarbonate solution, and saturated saline, dried over anhydrous magnesium sulfate, and concentrated under reduced pressure. The residue was subjected to silica gel column chromatography to obtain 0.30 g of 3-{2-chloro-4-fluoro-5-[2,6-dioxo-4-(trifluoromethyl)-1,2,3,6-tetrahydropyrimidin-1-yl]phenoxy}-2-(methoxycarbonyl)methoxypyridine.

$^1$H-NMR (CDCl$_3$/250 MHz) δ(ppm): 3.70 (s, 3H), 4.93 (s, 2/2H), 4.94 (s, 2/2H), 6.19(s, 1H), 6.9–7.0 (m, 2H), 7.3–7.4 (m, 1H), 7.38 (d, 1H, J=8.9 Hz), 7.93 (dd, 1H, J=4.9,1.6 Hz).

melting point: 75.3° C.

Seventh Step

To a mixture of 0.10 g of 3-{2-chloro-4-fluoro-5-[2,6-dioxo-4-(trifluoromethyl)-1,2,3,6-tetrahydropyrimidin-1-yl]phenoxy}-2-(methoxycarbonyl)methoxypyridine, 1 ml of acetonitrile and 31 mg of potassium carbonate, 32 mg of methyl iodide was added to the mixture, and the mixture was stirred at room temperature for 1.5 hours. 64 mg of methyl iodide was added to the mixture, and the mixture was stirred at 50° C. for 1 hour. The mixture was filterated, and the filterate was concentrated under reduced pressure. The residue was subjected to silica gel column chromatography to obtain 97 mg of 3-{2-chloro-4-fluoro-5-[3-methyl-2,6-dioxo-4-(trifluoromethyl)-1,2,3,6-tetrahydropyrimidin-1-yl]phenoxy}-2-(methoxycarbonyl)methoxypyridine [present compound 7-7].

Production Example 6

Production of the Present Compound 3-12

338 mg of 2-chloro-4-fluoro-5-[3-methyl-2,6-dioxo-4-(trifluoromethyl)-1,2,3,6-tetrahydropyrimidin-1-yl]phenol and 216 mg of 4-chloro-6-[1-(methoxycarbonyl)ethoxy]pyrimidine were dissolved in 2 ml of N,N-dimethylformamide, to this solution was added 150 mg of potassium carbonate, and the mixture was stirred for 2 hours at 60° C. The reaction solution was cooled to room temperature, then, this reaction solution was poured into ice water, and extracted with ethyl acetate. The organic layer was washed with saturated saline, dried over anhydrous magnesium sulfate, and concentrated. The residue was subjected to silica gel column chromatography to obtain 101 mg of methyl 2-([4-{2-chloro-4-fluoro-5-[3-methyl-2,6-dioxo-4-(trifluoromethyl)-1,2,3,6-tetrahydropyrimidin-1-yl]phenoxy}pyrimidin-6-yl]oxy)propionate [present compound 3-12].

$^1$H-NMR(CDCl$_3$/300 MHz) δ(ppm): 1.62 (d, 3H, J=7.0 Hz), 3.56 (s, 3H), 3.75 (s, 3H), 5.41 (q, 1 Hz, J=7.0 H), 6.36 (s, 1H), 6.37 (s, 1H), 7.17 (d, 1H, J=6.5 Hz), 7.40 (d, 1H, J=9.1 Hz), 8.34 (s, 1H)

Production Example 7

Production of the Present Compound 5-17

To a solution of 0.21 g of 4-{2-chloro-4-fluoro-5-[3-methyl-2,6-dioxo-4-(trifluoromethyl)-1,2,3,6-tetrahydropyrimidin-1-yl]phenoxy}-3-hydroxy-5-methylpyrazole in 1.0 ml of N,N-dimethylformamide were added 0.10 g of methyl bromoacetate and 0.20 g of potassium carbonate, and the mixture was stirred for 3 hours at room temperature. Dilute hydrochloric acid was poured into this reaction solution, and extracted with ethyl acetate. The organic layer was washed with saturated saline, dried over anhydrous magnesium sulfate. This solution was subjected to silica gel column chromatography to obtain 0.06 g of 3-(methoxycarbonyl)methoxy-4-{2-chloro-4-fluoro-5-[3-methyl-2,6-dioxo-4-(trifluoromethyl)-1,2,3,6-tetrahydropyrimidin-1-yl]phenoxy}-5-methylpyrazole [present compound 5-17].

$^1$H-NMR(CDCl$_3$/300 MHz) δ(ppm): 2.16 (s, 3H), 3.51 (s, 3H), 3.69 (s, 3H), 4.77 (s, 2H), 6.30 (s, 1H), 7.12 (d, 1H, J=6.5 Hz), 7.31 (d, 1H, J=9.0 Hz)

Production Example 8

Production of R Optical Isomer of the Present Compound 5-12

To a solution of 0.13 g of 4-{2-chloro-4-fluoro-5-[3-methyl-2,6-dioxo-4-(trifluoromethyl)-1,2,3,6-tetrahydropyrimidin-1-yl]phenoxy}-3-hydroxy-5-methylpyrazole in 2.0 ml of ethyl acetate were added 0.10 g of (S)-(–)-methyl lactate, 0.26 g of triphenylphosphine and 0.5 ml of a 40% solution of diisopropyl azodicarboxylate in toluene, and the mixture was stirred for 3 hours at room temperature. 6 ml of n-hexane was poured into this reaction solution, and the precipitated insoluble substance was filtrated off. This solution was subjected to silica gel column chromatography to obtain 0.09 g of (R)-3-{1-(methoxycarbonyl)ethoxy}-4-{2-chloro-4-fluoro-5-[3-methyl-2,6-dioxo-4-(trifluoromethyl)-1,2,3,6-tetrahydropyrimidin -1-yl]phenoxy}-5-methylpyrazole [R optical isomer of present compound 5-12, hereinafter, represented as 5-12-R].

$^1$H-NMR(CDCl$_3$/300 MHz) δ(ppm): 1.51 (m, 3H), 2.15 (s, 3H), 3.48 (s, 3/2H), 3.52 (s, 3/2H), 3.67 (s, 3H), 5.05 (m, 1H), 6.30 (s, 1/2H), 6.31 (s, 1/2H), 7.13 (d, 1/2H, J=6.5 Hz), 7.18 (d, 1/2H, J=6.6 Hz), 7.31 (d, 1H, J=8.7 Hz) [α]$_D$ +16.40° (c0.5 methanol)

Production Example 9

Production of S Optical Isomer of the Present Compound 5-12

To a solution of 0.13 g of 4-{2-chloro-4-fluoro-5-[3-methyl-2,6-dioxo-4-(trifluoromethyl)-1,2,3,6-tetrahydropyrimidin-1-yl]phenoxy}-3-hydroxy-5-methylpyrazole in 2.0 ml of ethyl acetate were added 0.10 g of (R)-(+)-methyl lactate, 0.26 g of triphenylphosphine and 0.5 ml of a 40% solution of diisopropyl azodicarboxylate in toluene, and the mixture was stirred for 3 hours at room temperature. 6 ml of n-hexane was poured into this reaction solution, and the precipitated insoluble substance was filtrated off. This solution was subjected to silica gel column chromatography to obtain 0.08 g of (S)-3-{1-(methoxycarbonyl)ethoxy}-4-{2-chloro-4-fluoro-5-[3-methyl-2,6-dioxo-4-(trifluoromethyl)-1,2,3,6-tetrahydropyrimidin-1-yl]phenoxy}-5-methylpyrazole [S optical isomer of present compound 5-12, hereinafter, represented as 5-12-S].

$^1$H-NMR(CDCl$_3$/300 MHz) δ(ppm): 1.51 (m, 3H), 2.15 (s, 3H), 3.49 (s, 3/2H), 3.52 (s, 3/2H), 3.67 (s, 3H), 5.05 (m, 1H), 6.30 (s, 1/2H), 6.31 (s, 1/2H), 7.13 (d, 1/2H, J=6.8 Hz), 7.18 (d, 1/2H, J=6.5 Hz), 7.31 (d, 1H, J=8.8 Hz) [α]$_D$ –16.0° (c0.5 methanol)

Intermediate Production Example 3

Production of 4-{2-chloro-4-fluoro-5-[3-methyl-2,6-dioxo-4-(trifluoromethyl)-1,2,3,6-tetrahydropyrimidin-1-yl]phenoxy}-3-hydroxy-5-methylpyrazole used in Production Examples 7 to 9
First Step 10.0 g of 2-chloro-4-fluoro-5-[3-methyl-2,6-dioxo-4-(trifluoromethyl)-1,2,3,6-tetrahydropyrimidin-1-yl]phenol was dissolved in 30 ml of N,N-dimethylformamide, to this was added 5.0 ml of triethylamine, then 5.0 g of methyl 2-chloroacetoacetate was added to the resulted mixture at room temperature with stirring. Then, stirring was continued for 10 minutes at room temperature and for 1 hour at 60° C. 2.0 ml of triethylamine and 2.0 g of methyl 2-chloroacetoacetate were added to this solution, then, the mixture was further stirred for 1 hour at 60° C. The reaction solution was stirred overnight at room temperature, then, the reaction solution was poured into ice water and dilute hydrochloric acid, and extracted with ethyl acetate. The organic layer was washed with saturated saline, dried over anhydrous magnesium sulfate, and concentrated. The residue was subjected to silica gel column chromatography to obtain 7.86 g methyl 2-{2-chloro-4-fluoro-5-[3-methyl-2,6-dioxo-4-(trifluoromethyl)-1,2,3,6-tetrahydropyrimidin-1-yl] phenoxy}-3-oxobutyrate.

$^1$H-NMR(CDCl$_3$/300 MHz) δ(ppm): 2.01 (s, 3/2H ), 2.47 (s, 3/2H), 3.55 (s, 3H), 3.75 (s, 3/2H), 3.81 (s, 3/2H ), 4.99 (s, 1/2H), 6.34 (s, 1/2H), 6.35 (s, 1/2H), 6.65 (d, 1/2H, J=6.4 Hz), 6.83 (m, 1/2H), 7.35(m,1H)
Second Step 3.09 g of methyl 2-{2-chloro-4-fluoro-5-[3-methyl-2,6-dioxo-4-(trifluoromethyl)-1,2,3,6-tetrahydropyrimidin-1-yl] phenoxy}-3-oxobutyrate and 1.23 g of methyl carbazate were suspended in 30 ml of toluene, and the mixture was heated under reflux for 5 hours. The solution was cooled to room temperature, then, the reaction solution was poured into ice water and dilute hydrochloric acid, and extracted with ethyl acetate. The organic layer was washed with saturated saline, dried over anhydrous magnesium sulfate, and concentrated. The residue was washed with a mixed solvent of n-hexane:ethyl acetate (3:1) to obtain 2.94 g of 4-{2-chloro-4-fluoro-5-[3-methyl-2,6-dioxo-4-(trifluoromethyl)-1,2,3,6-tetrahydropyrimidin-1-yl] phenoxy}-3-hydroxy-5-methylpyrazole.

$^1$H-NMR(CDCl$_3$+CD$_3$OD/250 MHz) δ(ppm): 2.08 (s, 3H), 3.51 (s, 3H), 6.32 (s, 1H), 6.81 (d, 1H, J=6.5 Hz), 7.32 (d, 1H, J=8.8 Hz).

Production Example 10

Production of the Present Compound 6-2

0.40 g of 2-chloro-4-fluoro-5-[3-methyl-2,6-dioxo-4-(trifluoromethyl)-1,2,3,6-tetrahydropyrimidin-1-yl]phenyl mercaptan was dissolved in 6 ml of acetonitrile, to this solution was added 0.31 g of potassium carbonate, and the mixture was stirred for 30 minutes, then, 0.29 g of 2-chloro-4-[1-(methoxycarbonyl)ethoxy]pyrimidine was added and the mixture was stirred for 3 hours. This reaction solution was poured into ice water, and extracted with ethyl acetate. The organic layer was washed with saturated saline, dried over anhydrous magnesium sulfate, and concentrated. The residue was subjected to silica gel column chromatography to obtain 0.46 g of methyl 2-([2-{2-chloro-4-fluoro-5-[3-methyl-2,6-dioxo-4-(trifluoromethyl)-1,2,3,6-tetrahydropyrimidin-1-yl]phenylthio}pyrimidin-4-yl] oxy}propionate [present compound 6-2].

$^1$H-NMR(CDCl$_3$/300 MHz) δ(ppm): 1.49 (d, 3H, J=7.1 Hz), 3.56 (d, 3H, J=1.1 Hz), 3.67 (d, 3H, J=1.3 Hz), 5.23 (m, 1H), 6.36 (s, 1H), 6.52 (d, 1H, J=5.7 Hz), 7.46 (d, 1H, J=9.2 Hz), 7.62 (m, 1H), 8.26 (d, 1H, J=5.7 Hz)

melting point: 60.2° C.

Intermediate Production Example 4

Production of 2-chloro-4-fluoro-5-[3-methyl-2,6-dioxo-4-(trifluoromethyl)-1,2,3,6-tetrahydropyrimidin-1-yl]phenyl mercaptan used in Production Example 10

1.65 g of 2-chloro-4-fluoro-5-[3-methyl-2,6-dioxo-4-(trifluoromethyl)-1,2,3,6-tetrahydropyrimidin-1-yl]

benzenesulfonyl chloride was dissolved in 16 ml of acetic acid, to this was added 4.4 g of zinc, then, they were reacted while heating under reflux. After completion of the reaction, the reaction solution was cooled, then, this was poured into ice water, extracted with ethyl acetate, and filtrated. The filtrate was separated, then, the organic layer was washed with saturated saline, dried over anhydrous magnesium sulfate, and concentrated to obtain 1.35 g of 2-chloro-4-fluoro-5-[3-methyl-2,6-dioxo-4-(trifluoromethyl)-1,2,3,6-tetrahydropyrimidin-1-yl]phenyl mercaptan.

$^1$H-NMR(CDCl$_3$/300 MHz) δ(ppm): 3.55 (m, 3H), 3.86 (s, 1H), 6.36 (s, 1H), 7.27 (d, 1H, J=6.4 Hz), 7.33 (d, 1H, J=9.1 Hz).

melting point: 132.5° C.

Production Example 11

Production of the Present Compound 2-2

200 mg of 2-{2-chloro-4-fluoro-5-[3-methyl-2,6-dioxo-4-(trifluoromethyl)-1,2,3,6-tetrahydropyrimidin-1-yl]phenoxy}-3-hydroxypyridine and 80 mg of methyl 2-bromopropionate were dissolved in acetonitrile, to this was added 66 mg of potassium carbonate, and the mixture was stirred for 2 hours at 60° C. This reaction solution was poured into ice water, and extracted with ethyl acetate. The organic layer was washed with saturated saline, dried over anhydrous magnesium sulfate, and concentrated. The residue was subjected to silica gel column chromatography to obtain 77 mg of 2-{2-chloro-4-fluoro-5-[3-methyl-2,6-dioxo-4-(trifluoromethyl)-1,2,3,6-tetrahydropyrimidin-1-yl]phenoxy}-3-{1-(methoxycarbonyl)ethoxy}pyridine [present compound 2-2].

$^1$H-NMR(CDCl$_3$/250 MHz) δ(ppm): 1.67 (d, 3H, J=6.8 Hz), 3.55 (m, 3H), 3.76 (s, 3H), 4.94 (q, 1H, J=6.9 Hz), 6.35 (s, 1H), 6.95 (m, 1H), 7.20 (d, 1H, J=6.8 Hz), 7.28 (m, 1H), 7.39 (d, 1H, J=9.0 Hz), 7.75 (m, 1H)

Production Example 12

Production of the Present Compound 2-7

60 mg of 2-{2-chloro-4-fluoro-5-[3-methyl-2,6-dioxo-4-(trifluoromethyl)-1,2,3,6-tetrahydropyrimidin-1-yl]phenoxy}-3-hydroxypyridine and 20 mg of methyl bromoacetate were dissolved in 2 ml of acetonitrile, to this was added 20 mg of potassium carbonate, and the mixture was stirred for 2 hours at 60° C. This reaction solution was poured into ice water, and extracted with ethyl acetate. The organic layer was washed with saturated saline, dried over anhydrous magnesium sulfate, and concentrated. The residue was subjected to silica gel column chromatography to obtain 60 mg of 2-{2-chloro-4-fluoro-5-[3-methyl-2,6-dioxo-4-(trifluoromethyl)-1,2,3,6-tetrahydropyrimidin-1-yl]phenoxy}-3-(methoxycarbonyl)methoxypyridine [present compound 2-7].

$^1$H-NMR(CDCl$_3$/300 MHz) δ(ppm): 3.55 (s, 3H), 3.80 (s, 3H), 4.81 (s, 2H), 6.35 (s, 1H), 6.97 (m, 1H), 7.21 (d, 1H, J=6.8 Hz), 7.27 (m, 1H), 7.39 (d, 1H, J=9.1 Hz), 7.75 (d, 1H, J=4.1 Hz)

Intermediate Production Example 5

Production of 2-{2-chloro-4-fluoro-5-[3-methyl-2,6-dioxo-4-(trifluoromethyl)-1,2,3,6-tetrahydropyrimidin-1-yl]phenoxy}-3-hydroxypyridine Used in Production Examples 11 and 12

First Step 11.8 g of 2chloro-4-fluoro-5-[3-methyl-2,6-dioxo-4-(trifluoromethyl)-1,2,3,6-tetrahydropyrimidin-1-yl]phenol and 5.2 g of 2-chloro-3-nitropyridine were dissolved in 10 ml of toluene, to this were added 2.3 g of potassium hydroxide and 56 mg of 18-crown-6, and the mixture was stirred for 3 hours at 90° C. The reaction solution was cooled to room temperature, then the solvent was distilled off, and the residue was poured into ice water, and the precipitated crystals were collected by filtration to obtain 11.5 g of 2-{2-chloro-4-fluoro-5-[3-methyl-2,6-dioxo-4-(trifluoromethyl)-1,2,3,6-tetrahydropyrimidin-1-yl]phenoxy}-3-nitropyridine.

$^1$H-NMR(CDCl$_3$/250 MHz) δ(ppm): 3.56 (m, 3H), 6.36 (s, 1H), 7.4–7.2(m, 2H), 7.41 (d, 1H, J=8.9 Hz), 8.3 (m, 1H), 8.4 (m, 1H)

Second Step

To a mixture of 3.8 g of an iron powder, 50 ml of acetic acid and 5 ml of water was added a solution of 3.8 g of 2-{2-chloro-4-fluoro-5-[3-methyl-2,6-dioxo-4-(trifluoromethyl)-1,2,3,6-tetrahydropyrimidin-1-yl]phenoxy}-3-nitropyridine in 5.0 ml of acetic acid dropwise while maintaining the temperature of the reaction solution at 35° C. or lower. After completion of the addition, the mixture was stirred for 2 hours, then, the reaction solution was filtrated through Celite, and diluted with ethyl acetate. The mixture was neutralized with saturated aqueous sodium bicarbonate solution, the organic layer was washed with saturated saline, dried over anhydrous magnesium sulfate, and concentrated, then, the resulted residue was subjected to silica gel chromatography to obtain 3.4 g of 3-amino-2-{2-chloro-4-fluoro-5-[3-methyl-2,6-dioxo-4-(trifluoromethyl)-1,2,3,6-tetrahydropyrimidin-1-yl]phenoxy}pyridine.

$^1$H-NMR(CDCl$_3$/300 MHz) δ(ppm): 3.53 (s, 3H), 4.00 (s, 2H), 6.34 (s, 1H), 6.82 (m, 1H), 6.99 (m, 1H), 7.29 (d, 1H, J=6.7 Hz), 7.35 (d, 1H, J=9.0 Hz), 7.47 (m, 1H)

Third Step 0.76 ml of boron trifluoride diethyl etherate was added to a mixture of 3.4 g of 3-amino-2-{2-chloro-4-fluoro-5-[3-methyl-2,6-dioxo-4-(trifluoromethyl)-1,2,3,6-tetrahydropyrimidin-1-yl]phenoxy}pyridine, 3 ml of 1,2-dimethoxyethane and 1 ml of methylene chloride dropwise at −5° C., the mixture was stirred for 5 minutes, then, 0.44 ml of t-butyl nitrite was added to the mixture dropwise, and the mixture was stirred for 30 minutes at the same temperature. n-pentane was poured into the mixture, and 2.0 g of the precipitated crystals were collected by filtration.

Subsequently, 200 mg of the above-mentioned crystals were dissolved into 1 ml of acetic anhydride, and the mixture was stirred for 2 hours at 70° C. After removal of the solvent, the resulted residue was subjected to silica gel chromatography to obtain 89 mg of 3-acetoxy-2-{2-chloro-4-fluoro-5-[3-methyl-2,6-dioxo-4-(trifluoromethyl)-1,2,3,6-tetrahydropyrimidin-1-yl]phenoxy}pyridine.

$^1$H-NMR(CDCl$_3$/300 MHz) δ(ppm): 2.43 (s, 3H), 3.55 (s, 3H), 6.35 (s, 1H), 7.05 (m, 1H), 7.21 (d, 1H, J=6.9 Hz), 7.39 (d, 1H, J=8.8 Hz), 7.47 (m, 1H), 7.97 (m, 1H)

Fourth Step

A mixture of 100 mg of 3-acetoxy-2-{2-chloro-4-fluoro-5-[3-methyl-2,6-dioxo-4-(trifluoromethyl)-1,2,3,6-tetrahydropyrimidin-1-yl]phenoxy}pyridine, 15 mg of potassium carbonate and 1 ml of methanol was stirred for 3 hours at room temperature. The reaction solution was poured into ice water, then, to this was poured acetic acid. The precipitated crystals were collected by filtration to obtain 65 mg of 2-{2-chloro-4-fluoro-5-[3-methyl-2,6-dioxo-4-(trifluoromethyl)-1,2,3,6-tetrahydropyrimidin-1-yl]phenoxy}-3-hydroxypyridine

Production Example 13

Production of the Present Compound 7-7

First Step 0.4 g of sodium hydride was added to a mixture of 1.59 g of 2-chloro-3-nitropyridine, 0.95 g of methyl glycolate and 10 ml of 1,4-dioxane at 10° C. The mixture was stirred at room temperature for 2 hours, then, the reaction solution was poured into ice water, and extracted with ethyl acetate. The organic layer was dried over anhydrous magnesium sulfate, and concentrated. The residue was subjected to silica gel column chromatography to obtain 1.5 g of 2-(methoxycarbonyl)methoxy-3-nitropyridine.

melting point: 61.5° C.

Second Step

A mixture of 0.3 g of 2-(methoxycarbonyl)methoxy-3-nitropyridine, 20 mg of platinum oxide and 1.4 ml of ethanol was stirred for 3 hours at room temperature under hydrogen atmosphere. The reaction system was purged with nitrogen, then, the reaction solution was filtrated through Celite, and the filtrate was concentrated. The residue was subjected to silica gel column chromatography to obtain 0.22 g of 3-amino-2-(methoxycarbonyl)methoxypyridine.

$^1$H-NMR(CDCl$_3$/250 MHz) δ(ppm): 3.77 (s, 3H), 3.85 (bs, 2H), 4.95 (s, 2H), 6.75 (dd, 1H, J=7.5,5.0 Hz), 6.91 (dd, 1H, J=7.5,1.6 Hz), 7.50 (dd, 1H, J=5.0,1.6 Hz)

Third Step 1.6 g of boron trifluoride diethyl etherate was added to a mixture of 1.0 g of 3-amino-2-(methoxycarbonyl)methoxypyridine, 3 ml of 1,2-dimethoxyethane and 1 ml of dichloromethane dropwise at −10° C. The mixture was stirred for 10 minutes at the same temperature, then, to the reaction solution was added a solution of 0.68 g of t-butyl nitrite in 1 ml of 1,2-dimethoxyethane dropwise at −5° C. or lower. The mixture was stirred for 30 minutes at the same temperature, then, into the mixture was poured n-pentane. The lower layer of two separated layers was dissolved in 5 ml of acetic anhydride, and the mixture was stirred for 1 hour at 80° C. The solvent was distilled off, then, the resulted residue was subjected to silica gel chromatography to obtain 0.45 g of 3-acetoxy-2-(methoxycarbonyl)methoxypyridine.

$^1$H-NMR(CDCl$_3$/250 MHz) δ(ppm): 2.33 (s, 3H), 3.75 (s, 3H), 4.92 (s, 2H), 6.93 (dd, 1H, J=7.7, 5.0 Hz), 7.38 (dd, 1H, J=7.7, 1.6 Hz), 7.97 (dd, 1H, J=5.0,1.6 Hz)

Fourth Step

A mixture of 0.1 g of 3-acetoxy-2-(methoxycarbonyl)methoxypyridine, 31 mg of potassium carbonate and 1 ml of methanol was stirred for 3 hours at room temperature. The reaction solution was poured into water, and extracted with ethyl acetate. The organic layer was dried over anhydrous magnesium sulfate, and concentrated. The residue was subjected to silica gel column chromatography to obtain 73 mg of 3-hydroxy-2-(methoxycarbonyl)methoxypyridine.

$^1$H-NMR(CDCl$_3$/250 MHz) δ(ppm): 3.78 (s, 3H), 4.98 (s, 2H), 6.84 (dd, 1H, J=7.7,5.0 Hz), 7.17 (dd, 1H, J=7.7,1.3 Hz), 7.63 (dd, 1H, J=5.0,1.3 Hz)

Fifth Step

To a mixture of 0.29 g of 3-hydroxy-2-(methoxycarbonyl)methoxypyridine, 0.23 g of 2,5-difluoro-4-[3-methyl-2,6-dioxo-4-(trifluoromethyl)-1,2,3,6-tetrahydropyrimidin-1-yl]nitrobenzene and 3.2 ml of N,N-dimethylformamide was added 0.11 g of potassium carbonate, and the mixture was stirred for 2 hours at 70° C. 0.12 g of 2,5-difluoro-4-[3-methyl-2,6-dioxo-4-(trifluoromethyl)-1,2,3,6-tetrahydropyrimidin-1-yl]nitrobenzene and 0.05 g of potassium carbonate were additionally added, and the mixture was stirred for 1 hour at 70° C. The solution was cooled to room temperature, poured into ice water, and extracted with ethyl acetate. The organic layer was washed with saturated saline, dried over anhydrous magnesium sulfate, and concentrated. The residue was subjected to silica gel column chromatography to obtain 0.39 g of 3-{4-fluoro-5-[3-methyl-2,6-dioxo-4-(trifluoromethyl)-1,2,3,6-tetrahydropyrimidin-1-yl]-2-nitrophenoxy}-2-(methoxycarbonyl)methoxypyridine [present compound 9-45].

$^1$H-NMR(CDCl$_3$/250 MHz) δ(ppm): 3.51 (q, 3H, J=1.1 Hz), 3.68 (s, 3H), 4.86 (d, 1H), 4.98 (d, 1H), 6.29 (s, 1H), 6.99 (dd, 1H, J=7.8, 4.9 Hz), 7.11 (d, 1H, J=6.0 Hz), 7.51 (dd, 1H, J=7.8, 1.6 Hz), 7.87 (d, 1H, J=8.6 Hz), 7.99 (dd, 1H, J=4.9, 1.6 Hz)

Sixth Step

To a mixture of 0.3 g of an iron powder, 3 ml of acetic acid and 0.3 ml of water was added a solution of 0.30 g of 3-{4-fluoro-5-[3-methyl-2,6-dioxo-4-(trifluoromethyl)-1,2,3,6-tetrahydropyrimidin-1-yl]-2-nitrophenoxy}-2-(methoxycarbonyl)methoxypyridine [present compound 9-45] in 2 ml of acetic acid dropwise while maintaining the temperature of the reaction solution at 35° C. or lower. After completion of the addition, the mixture was stirred for 2 hours, then, the reaction solution was filtrated through Celite, and diluted with ethyl acetate. The mixture was neutralized with saturated aqueous sodium bicarbonate solution, the organic layer was washed with saturated saline, dried over anhydrous magnesium sulfate, and concentrated, then, the resulted residue was subjected to silica gel column chromatography to obtain 0.24 g of 3-{2-amino-4-fluoro-5-[3-methyl-2,6-dioxo-4-(trifluoromethyl)-1,2,3,6-tetrahydropyrimidin-1-yl]phenoxy}-2-(methoxycarbonyl)methoxypyridine.

$^1$H-NMR(CDCl$_3$/250 MHz) δ(ppm): 3.52 (s, 3H), 3.74 (s, 3H), 4.29 (bs, 2H), 5.00 (s, 2H), 6.30 (s, 1H), 6.61 (d, 1H, J=11.3 Hz), 6.76 (d, 1H, J=6.8 Hz), 6.86 (dd, 1H, J=7.8, 5.0 Hz), 7.22 (dd, 1H, J=7.8, 1.1 Hz), 7.82 (dd, 1H, J=5.0, 1.1 Hz)

Seventh Step 88 mg of isoamyl nitrite was added to a mixture of 0.24 g of 3-{2-amino-4-fluoro-5-[3-methyl-2,6-dioxo-4-(trifluoromethyl)-1,2,3,6-tetrahydropyrimidin-1-yl]phenoxy}-2-(methoxycarbonyl)methoxypyridine, 99 mg of copper(I) chloride, 0.20 g of copper(II) chloride and 2.5 ml of acetonitrile dropwise at room temperature, and the mixture was stirred for 1 hour. This reaction solution was poured into 2% hydrochloric acid, and extracted with ethyl acetate. The organic layer was washed with saturated saline, dried over anhydrous magnesium sulfate, and concentrated. The residue was subjected to silica gel column chromatography to obtain 0.21 g of 3-{2-chloro-4-fluoro-5-[3-methyl-2,6-dioxo-4-(trifluoromethyl)-1,2,3,6-tetrahydropyrimidin-1-yl]phenoxy}-2-(methoxycarbonyl)methoxypyridine [present compound 7-7].

melting point: 52.2° C. $^1$H-NMR(CDCl$_3$/300 MHz) δ(ppm): 3.50 (q, 3H, J=1.0 Hz), 3.70 (s, 3H), 4.90 (d, 1H, J=15.8 Hz), 4.97 (d, 1H, J=15.8 Hz), 6.29 (s, 1H), 6.9–7.0 (m, 2H), 7.32 (dd, 1H, J=7.7, 1.9 Hz), 7.37 (d, 1H, J=8.7 Hz), 7.92 (dd, 1H, J=4.9, 1.9 Hz)

Production Example 14

Production of the Present Compound 4-85

First Step 68 mg of sodium hydride was added to a mixture of 0.4 g of 5-benzyloxy-4-chloro-2-methylpyrimidine, 0.17 g of methyl glycolate and 3.4 ml of tetrahydrofuran at 0° C. The mixture was stirred at room temperature for 1 hour, then, the reaction solution was stirred for 30 minutes at 90° C. 18 mg of methyl glycolate was additionally added to this, and the mixture was stirred for 30 minutes at 90° C. The reaction solution was cooled to room temperature, then, poured into ice water, and extracted with ethyl acetate. The organic layer was washed with dilute hydrochloric acid and saturated saline, dried over anhydrous magnesium sulfate, and concentrated. The residue was subjected to silica gel column chromatography to obtain 0.21 g of 5-benzyloxy-4-(methoxycarbonyl)methoxy-2-methylpyrimidine.

$^1$H-NMR(CDCl$_3$/300 MHz) δ(ppm): 2.49 (s, 3H), 3.78 (s, 3H), 5.01 (s, 2H), 5.17 (s, 2H), 7.2–7.5 (m, 5H), 7.99 (s, 1H)

Second Step

A mixture of 0.21 g of 5-benzyloxy-4-(methoxycarbonyl)methoxy-2-methylpyrimidine, 16 mg of 10% palladium/carbon and 1.5 ml of ethyl acetate was stirred for 3 hours at room temperature under hydrogen atmosphere. The reaction system was purged with nitrogen, then, the reaction solution was filtrated through Celite, and the filtrate was concentrated to obtain 0.15 g of 5-hydroxy-4-(methoxycarbonyl)methoxy-2-methylpyrimidine.

$^1$H-NMR(CDCl$_3$/300 MHz) δ(ppm): 2.51 (s, 3H), 3.81 (s, 3H), 5.00 (s, 2H), 8.10 (s, 1H)

Third Step

To a mixture of 0.15 g of 5-hydroxy-4-(methoxycarbonyl)methoxy-2-methylpyrimidine, 0.16 g of 2,5-difluoro-4-[3-methyl-2,6-dioxo-4-(trifluoromethyl)-1,2,3,6-tetrahydropyrimidin-1-yl]nitrobenzene and 2 ml of N,N-dimethylformamide was added 74 mg of potassium carbonate, and the mixture was stirred for 1 hour at 70° C. The reaction solution was cooled to room temperature, then, poured into ice water, and extracted with ethyl acetate. The organic layer was washed with saturated saline, dried over anhydrous magnesium sulfate, and concentrated. The residue was subjected to silica gel column chromatography to obtain 0.20 g of 5-{4-fluoro-5-[3-methyl-2,6-dioxo-4-(trifluoromethyl)-1,2,3,6-tetrahydropyrimidin-1-yl]-2-nitrophenoxy}-4-(methoxycarbonyl)methoxy-2-methylpyrimidine.

melting point: 149.5° C.

Fourth Step

A mixture of 0.19 g of 5-{4-fluoro-5-[3-methyl-2,6-dioxo-4-(trifluoromethyl)-1,2,3,6-tetrahydropyrimidin-1-yl]-2-nitrophenoxy}-4-(methoxycarbonyl)methoxy-2-methylpyrimidine, 5 mg of platinum oxide, 2 ml of ethanol and 2 ml of ethyl acetate was stirred for 1.5 hours at room temperature under hydrogen atmosphere. The reaction system was purged with nitrogen, then, the reaction solution was filtrated through Celite, and the filtrate was concentrated to obtain 0.17 g of 5-{2-amino-4-fluoro-5-[3-methyl-2,6-dioxo-4-(trifluoromethyl)-1,2,3,6-tetrahydropyrimidin-1-yl]phenoxy}-4-(methoxycarbonyl)methoxy-2-methylpyrimidine.

$^1$H-NMR(CDCl$_3$/300 MHz) δ(ppm): 2.55 (s, 3H), 3.51 (s, 3H), 3.75 (s, 3H), 4.9–5.1 (m, 2H), 6.30 (s, 1H), 6.67 (d, 1H, J=6.3 Hz), 6.83 (bs, 1H), 7.15 (d, 1H, J=11.0 Hz), 7.42 (bs, 1H), 8.18 (s, 1H)

Fifth Step 60 mg of isoamyl nitrite was added to a mixture of 0.17 g of 5-{2-amino-4-fluoro-5-[3-methyl-2,6-dioxo-4-(trifluoromethyl)-1,2,3,6-tetrahydropyrimidin-1-yl]phenoxy}-4-(methoxycarbonyl)methoxy-2-methylpyrimidine, 67 mg of copper(I) chloride, 137 mg of copper(II) chloride and 2 ml of acetonitrile dropwise at room temperature, and the mixture was stirred for 1 hour. This reaction solution was poured into 2% hydrochloric acid, and extracted with ethyl acetate. The organic layer was washed with saturated saline, dried over anhydrous magnesium sulfate, and concentrated. The residue was subjected to silica gel column chromatography to obtain 20 mg of 5-{2-chloro-4-fluoro-5-[3-methyl-2,6-dioxo-4-(trifluoromethyl)-1,2,3,6-tetrahydropyrimidin-1-yl]phenoxy}-4-(methoxycarbonyl)methoxy-2-methylpyrimidine [present compound 4-85].

$^1$H-NMR(CDCl$_3$/300 MHz) δ(ppm): 2.57 (s, 3H), 3.51 (q, 3H, J=1.1 Hz), 3.71 (s, 3H), 4.90 (d, 1H, J=15.7 Hz), 5.00 (d, 1H, J=15.7 Hz), 6.29 (s, 1H), 6.89 (d, 1H, J=6.4 Hz), 7.37 (d, 1H, J=9.0 Hz), 8.26 (s, 1H)

Production Example 15

Production of the Present Compound 4-76

First Step

Sodium hydride is added to a mixture of 5-benzyloxy-4-chloro-2-methylpyrimidine, methyl lactate and tetrahydrofuran at 0° C. The mixture is stirred at room temperature for 1 hour, then, stirred at 90° C. for 30 minutes. The reaction solution was cooled to room temperature and poured into ice water, and extracted with ethyl acetate. The organic layer is washed with dilute hydrochloric acid and saturated saline, dried over anhydrous magnesium sulfate, and concentrated. The residue is subjected to silica gel column chromatography to obtain 5-benzyloxy-4-{1-(methoxycarbonyl)ethoxy}-2-methylpyrimidine Second Step A mixture of 5-benzyloxy-4-{1-(methoxycarbonyl)ethoxy)}-2-methylpyrimidine, 10% palladium/carbon and ethyl acetate is stirred for 3 hours at room temperature under hydrogen atmosphere. The reaction system is purged with nitrogen, then, the reaction solution is filtrated through Celite, and the filtrate is concentrated to obtain 5-hydroxy-4-{1-(methoxycarbonyl)ethoxy}-2-methylpyrimidine.

Third Step

To a mixture of 5-hydroxy-4-{1-(methoxycarbonyl)ethoxy}-2-methylpyrimidine, 2,5-difluoro-4-[3-methyl-2,6-dioxo-4-(trifluoromethyl)-1,2,3,6-tetrahydropyrimidin-1-yl]nitrobenzene and N,N-dimethylformamide is added potassium carbonate, and the mixture is stirred for 1 hour at 70° C. The reaction solution is cooled to room temperature, then, poured into ice water, and extracted with ethyl acetate. The organic layer is washed with saturated saline, dried over anhydrous magnesium sulfate, and concentrated. The residue is subjected to silica gel column chromatography to obtain 5-{4-fluoro-5-[3-methyl-2,6-dioxo-4-(trifluoromethyl)-1,2,3,6-tetrahydropyrimidin-1-yl]-2-nitrophenoxy}-4-{1-(methoxycarbonyl)ethoxy}-2-methylpyrimidine.

Fourth Step

A mixture of 5-{4-fluoro-5-[3-methyl-2,6-dioxo-4-(trifluoromethyl)-1,2,3,6-tetrahydropyrimidin-1-yl]-2-nitrophenoxy}-4-{1-(methoxycarbonyl)ethoxy}-2-methylpyrimidine, platinum oxide, ethanol and ethyl acetate is stirred for 1.5 hours at room temperature under hydrogen atmosphere. The reaction system is purged with nitrogen, then, the reaction solution is filtrated through Celite, and the filtrate is concentrated to obtain 5-{2-amino-4-fluoro-5-[3-methyl-2,6-dioxo-4-(trifluoromethyl)-1,2,3,6-tetrahydropyrimidin-1-yl]phenoxy}-4-{1-(methoxycarbonyl)ethoxy}-2-methylpyrimidine.

Fifth Step

Isoamyl nitrite is added to a mixture of 5-{2-amino-4-fluoro-5-[3-methyl-2,6-dioxo-4-(trifluoromethyl)-1,2,3,6-tetrahydropyrimidin-1-yl]phenoxy}-4-{1-(methoxycarbonyl)ethoxy}-2-methylpyrimidine, copper(I) chloride, copper(II) chloride and acetonitrile dropwise at room temperature, and the mixture is stirred for 1 hour. This reaction solution is poured into 2% hydrochloric acid, and extracted with ethylacetate. The organic layer is washed with saturated saline, dried over anhydrous magnesium sulfate, and concentrated. The residue is subjected to silica gel column chromatography to obtain 5-{2-chloro-4-fluoro-5-[3-methyl-2,6-dioxo-4-(trifluoromethyl)-1,2,3,6-tetrahydropyrimidin-1-yl]phenoxy}-4-{1-(methoxycarbonyl)ethoxy}-2-methylpyrimidine [present compound4-76].

Production Example 16

Production of the Present Compound 7-2
First Step 0.8 g of sodium hydride was added to a mixture of 3.17 g of 2-chloro-3-nitropyridine, 2.19 g of methyl lactate and 20 ml of 1,4-dioxane at 10° C. The mixture was stirred at room temperature for 1.5 hours, then, poured into ice water, and extracted with ethyl acetate. The organic layer was dried over anhydrous magnesium sulfate, and concentrated. The residue was subjected to silica gel column chromatography to obtain 3.3 g of 2-{1-(methoxycarbonyl)ethoxy}-3-nitropyridine.

$^1$H-NMR(CDCl$_3$/300 MHz) δ(ppm): 1.70 (d, 3H, J=7.0 Hz), 3.74 (s, 3H), 5.46 (q, 1H, J=7.0 Hz), 7.07 (dd, 1H, J=7.8,5.0 Hz), 8.2–8.4 (m, 2H)
Second Step A mixture of 1.7 g of 2-{1-(methoxycarbonyl)ethoxy}-3-nitropyridine, 102 mg of platinum oxide and 7.5 ml of ethanol was stirred for 3.5 hours at room temperature under hydrogen atmosphere. The reaction system was purged with nitrogen, then, the reaction solution was filtrated through Celite, and the filtrate was concentrated. The residue was subjected to silica gel column chromatography to obtain 1.16 g of 3-amino-2-{1-(methoxycarbonyl)ethoxy}pyridine.

$^1$H-NMR(CDCl$_3$/300 MHz) δ(ppm): 1.63 (d, 3H, J=6.8 Hz), 3.74 (s, 3H), 3.84 (bs, 2H), 5.38 (d, 1H, J=6.8 Hz), 6.72 (dd, 1H, J=7.7,5.0 Hz), 6.90 (dd, 1H, J=7.7,1.4 Hz), 7.48 (dd, 1H, J=5.0,1.4 Hz)
Third Step 1.5 ml of boron trifluoride diethyl etherate was added to a mixture of 1.1 g of 3-amino-2-{1-(methoxycarbonyl)ethoxy}pyridine, 3 ml of 1,2-dimethoxyethane and 1 ml of dichloromethane dropwise at −10° C. After mixing for 10 minutes at the same temperature, a solution of 0.80 ml of t-butyl nitrite in 1 ml of 1,2-dimethoxyethane was added to the reaction solution dropwise at −5° C. or lower. After mixing for 30 minutes at the same temperature, n-pentane was poured into the mixture. The lower layer of two separated layers was dissolved in 5 ml of acetic anhydride, and the mixture was stirred for 1 hour at 70° C. The solvent was distilled off, then, the resulted residue was subjected to silica gel chromatography to obtain 0.34 g of 3-acetoxy-2-{1-(methoxycarbonyl)ethoxy}pyridine.

$^1$H-NMR(CDCl$_3$/300 MHz) δ(ppm): 1.60 (d, 1H, J=7.0 Hz), 2.33 (s, 3H), 3.73 (s, 3H), 5.34 (q, 1H, J=7.0 Hz), 6.91 (dd, 1H, J=7.6, 5.0 Hz), 7.36 (dd, 1H, J=7.6, 1.5 Hz), 7.97 (dd, 1H, J=5.0,1.5 Hz)
Fourth Step A mixture of 0.34 g of 3-acetoxy-2-{1-(methoxycarbonyl)ethoxy}pyridine, 0.11 g of potassium carbonate and 2 ml methanol was stirred for 1 hour at room temperature. The reaction solution was poured into water, and extracted with ethyl acetate. The organic layer was dried over anhydrous magnesium sulfate, and concentrated. The residue was subjected to silica gel column chromatography to obtain 190 mg of 3-hydroxy-2-{1-(methoxycarbonyl)ethoxy}pyridine.

$^1$H-NMR(CDCl$_3$/300 MHz) δ(ppm): 1.64 (d, 1H, J=7.0 Hz), 3.75 (s, 3H), 5.45 (q, 1H, J=7.0 Hz), 6.0–6.2 (bs, 1H), 6.83 (dd, 1H, J=7.7,5.0 Hz), 7.15 (dd, 1H, J=7.7,1.5 Hz), 7.63 (dd, 1H, J=5.0,1.5 Hz)
Fifth Step To a mixture of 0.18 g of 3-hydroxy-2-{1-(methoxycarbonyl)ethoxy}pyridine, 0.19 g of 2,5-difluoro-4-[3-methyl-2,6-dioxo-4-(trifluoromethyl)-1,2,3,6-tetrahydropyrimidin-1-yl]nitrobenzene and 2.0 ml of N,N-dimethylformamide was added 91 mg of potassium carbonate, and the mixture was stirred for 3 hours at 70° C. The reaction solution was cooled to room temperature, then, poured into ice water, and extracted with ethyl acetate. The organic layer was washed with saturated saline, dried over anhydrous magnesium sulfate, and concentrated. The residue was subjected to silica gel column chromatography to obtain 0.21 g of 3-{4-fluoro-5-[3-methyl-2,6-dioxo-4-(trifluoromethyl)-1,2,3,6-tetrahydropyrimidin-1-yl]-2-nitrophenoxy}-2-{1-(methoxycarbonyl)ethoxy}pyridine [present compound 9-42] (as a mixture of two diastereomerical isomers).

$^1$H-NMR(CDCl$_3$/300 MHz) δ(ppm): 1.45 (d, 3/2H, J=7.1 Hz), 1.46 (d, 3/2H, J=7.1 Hz), 3.49 (S, 3/2H), 3.51 (s, 3/2H), 3.66 (s, 3H), 5.29 (q, 1/2H, J=7.1 Hz), 5.31 (q, 1/2H, J=7.1 Hz), 6.28 (s, 1/2H), 6.30 (s, 1/2H), 6.9–7.0 (m, 1H), 7.10 (d, 1/2H, J=6.1 Hz), 7.17 (d, 1/2H, J=6.1 Hz), 7.4–7.6 (m, 1H), 7.8–7.9 (m, 1H), 7.9–8.0 (m, 1H),
Sixth Step To a mixture of 0.21 g of an iron powder, 3 ml of acetic acid and 0.3 ml of water was added a solution of 3-{4-fluoro-5-[3-methyl-2,6-dioxo-4-(trifluoromethyl)-1,2,3,6-tetrahydropyrimidin-1-yl]-2-nitrophenoxy}-2-{1-(methoxycarbonyl)ethoxy}pyridine [present compound 9-42] in 1.2 ml of acetic acid dropwise while maintaining the temperature of the reaction solution at 35° C. or lower. After completion of the addition, the mixture was stirred for 1 hour, then, the reaction solution was filtrated through Celite, and diluted with ethyl acetate. The mixture was neutralized with saturated aqueous sodium bicarbonate solution, the organic layer was washed with saturated saline, dried over anhydrous magnesium sulfate, and concentrated, then, the resulted residue was subjected to silica gel chromatography to obtain 0.16 g of 3-{2-amino-4-fluoro-5-[3-methyl-2,6-dioxo-4-(trifluoromethyl)1,2,3,6-tetrahydropyrimidin-1-yl]phenoxy}-2-{1-(methoxycarbonyl)ethoxy}pyridine (as a mixture of two diastereomerical isomers).

$^1$H-NMR(CDCl$_3$/300 MHz) δ(ppm): 1.61 (d, 3H, J=7.1 Hz), 3.52 (s, 3H), 3.72 (s, 3H), 4.28 (bs, 2H), 5.40 (q, 1/2H, J=7.1 Hz), 5.41 (q, 1/2H, J=7.1 Hz), 6.30 (s, 1H), 6.62 (d, 1H, J=10.9 Hz), 6.7–6.8 (m, 1H), 6.8–6.9 (m, 1H), 7.2–7.3 (m, 1H), 7.7–7.9 (m, 1H)
Seventh Step 18 mg of Isoamyl nitrite was added to a mixture of 0.16 g of 3-{2-amino-4-fluoro-5-[3-methyl-2,6-dioxo-4-(trifluoromethyl)-1,2,3,6-tetrahydropyrimidin-1-yl]phenoxy}-2-{1-(methoxycarbonyl)ethoxy}pyridine, 63 mg of copper(I) chloride, 129 mg of copper(II) chloride and 1.5 ml acetonitrile dropwise at 0° C. and the mixture was stirred for 10 minutes, then at room temperature for 1 hour. This reaction solution was poured into a mixture of 1N hydrochloric acid and ice, and extracted with ethyl acetate. The organic layer was washed with saturated saline, dried over anhydrous magnesium sulfate, and concentrated. The residue was subjected to silica gel column chromatography to obtain 0.12 g of 3-{2-chloro-4-fluoro-5-[3-methyl-2,6-dioxo-4-(trifluoromethyl)-1,2,3,6-tetrahydropyrimidin-1-yl]phenoxy}-2-{1-(methoxycarbonyl) ethoxy} pyridine (as a mixture of two diastereomerical isomers) [present compound 7-2].

$^1$H-NMR(CDCl$_3$/300 MHz) δ(ppm): 1.51 (d, 3/2H, J=7.0 Hz), 1.52 (d, 3/2H, J=7.0 Hz), 3.50 (S,3H), 3.67 (s, 3H), 5.29 (q,1/2H, J=7.0 Hz), 5.30 (q, 1/2H, J=7.0 Hz), 6.28 (s, 1/2H), 6.29 (s, 1/2H), 6.8–7.0 (m, 2H), 7.3–7.4 (m, 2H), 7.8–7.9 (m, 1H)

Production Example 17

Production of the Present Compound 4-7

First Step

To a mixture of 0.297 g of sodium hydride and N,N-dimethylformamide, 0.668 g of methyl glycolate was added and stirred at room temperature for 1 hour. Then 5-benzyloxy-4-chloropyrimidine (yielded as follows: A mixture of 1.5 g of 5-benzyloxy-4-pyrimidinone and 30 ml of phosphoryl chloride was stirred for 30 minutes at reflux temperature, then the mixture was cooled to room temperature, and concentrated. Ice-water was added to the residue, extracted with ether and concentrated.) was added to the mixture, and stirred for 3 hours at room temperature. The mixture was poured into saturated ammonium chloride solution, and extracted with ethyl acetate. The organic layer was washed with saturated ammonium chloride solution and saturated saline, dried over anhydrous magnesium sulfate, and concentrated. The residue was subjected to silica gel column chromatography to obtain 0.934 g of 5-benzyloxy-4-(methoxycarbonyl)methoxypyrimidine.

melting point: 78.7° C.

Second Step

A mixture of 0.9 g of 5-benzyloxy-4-(methoxycarbonyl)methoxypyrimidine, 10% palladium/carbon and ethyl acetate was stirred for 3 hours at room temperature under hydrogen atmosphere. The reaction system was purged with nitrogen, then, the reaction solution was filtrated through Celite, and the filtrate was concentrated to obtain 0.574 g of 5-hydroxy-4-(methoxycarbonyl)methoxypyrimidine.

melting point: 105.0° C.

Third Step

To a mixture of 42 mg of Sodium hydride and N,N-dimethylformamide, 0.184 g of 5-hydroxy-4-(methoxycarbonyl)methoxypyrimidine was added and stirred at room temperature for 1 hour. Then 0.35 g of 2,5-difluoro-4-[3-methyl-2,6-dioxo-4-(trifluoromethyl)-1,2,3,6-tetrahydropyrimidin-1-yl]nitrobenzene was added to the mixture, and stirred for 2 hours at room temperature, then for 1 hour at 50° C. The mixture was poured into saturated ammonium chloride solution, and extracted with ethyl acetate. The organic layer was washed with saturated ammonium chloride solution and saturated saline, dried over anhydrous magnesium sulfate, and concentrated. The residue was subjected to silica gel column chromatography to obtain 0.448 g of 5-{4-fluoro-5-[3-methyl-2,6-dioxo-4-(trifluoromethyl)-1,2,3,6-tetrahydropyrimidin-1-yl]-2-nitrophenoxy}-4-(methoxycarbonyl)methoxypyrimidine.

melting point: 55.7° C.

Fourth Step

To a mixture of 0.4 g of an iron powder, 2 ml of acetic acid and 0.2 ml of water was added a solution of 0.393 g of 5-{4-fluoro-5-[3-methyl-2,6-dioxo-4-(trifluoromethyl)-1,2,3,6-tetrahydropyrimidin-1-yl]-2-nitrophenoxy}-4-(methoxycarbonyl)methoxypyrimidine in 1 ml of acetic acid and 2 ml of ethyl acetate dropwise. After completion of the addition, the mixture was stirred for 1 hour at room temperature, for 2 hours at 30–40° C. Water was added to the mixture, then, the mixture was filtrated through Celite, and extracted with ethyl acetate. The organic layer was washed with saturated aqueous sodium bicarbonate solution, and saturated saline, dried over anhydrous magnesium sulfate, and concentrated. Then, the resulted residue was subjected to silica gel chromatography to obtain 0.315 g of 5-{2-amino-4-fluoro-5-[3-methyl-2,6-dioxo-4-(trifluoromethyl)-1,2,3,6-tetrahydropyrimidin-1-yl]phenoxy}-4-(methoxycarbonyl)methoxypyrimidine.

melting point: 71.2° C.

Fifth Step

A solution of 0.228 g of isoamyl nitrite in acetonitrile was added to a mixture of 0.315 g of 5-{2-amino-4-fluoro-5-[3-methyl-2,6-dioxo-4-(trifluoromethyl)-1,2,3,6-tetrahydropyrimidin-1-yl]phenoxy}-4-(methoxycarbonyl)methoxypyrimidine, 0.129 g of copper(I) chloride, 0.262 g of copper(II) chloride and acetonitrile dropwise at room temperature, and the mixture was stirred for 3 hours. The mixture was concentrated, diluted with ethyl acetate, filtrated through Celite. To the filtrate, water was added, then, extracted with ethyl acetate. The organic layer was washed with 1% hydrochloric acid, and saturated saline, dried over anhydrous magnesium sulfate, and concentrated. The residue was subjected to silica gel column chromatography to obtain 5-{2-chloro-4-fluoro-5-[3-methyl-2,6-dioxo-4-(trifluoromethyl)-1,2,3,6-tetrahydropyrimidin-1-yl]phenoxy}-4-(methoxycarbonyl)methoxypyrimidine [present compound 4-7].

melting point: 52.5° C.

Production Example 18

Production of the Present Compound 4-2

First Step

Sodium hydride is added to a mixture of 5-benzyloxy-4-chloropyrimidine, methyl lactate and tetrahydrofuran at 0° C. The mixture is stirred at room temperature for 1 hour, then, stirred for 30 minutes at 90° C. The reaction solution is cooled to room temperature, then, poured into ice water, and extracted with ethyl acetate. The organic layer is washed with dilute hydrochloric acid and saturated saline, dried over anhydrous magnesium sulfate, and concentrated. The residue is subjected to silica gel column chromatography to obtain 5-benzyloxy-4-{1-(methoxycarbonyl)ethoxy}pyrimidine.

Second Step

A mixture of 5-benzyloxy-4-{1-(methoxycarbonyl)ethoxy}pyrimidine, 10% palladium/carbon and ethyl acetate is stirred for 3 hours at room temperature under hydrogen atmosphere. The reaction system is purged with nitrogen, then, the reaction solution is filtrated through Celite, and the filtrate is concentrated to obtain 5-hydroxy-4-{1-(methoxycarbonyl)ethoxy}pyrimidine.

Third Step

To a mixture of 5-hydroxy-4-{1-(methoxycarbonyl)ethoxy}pyrimidine, 2,5-difluoro-4-[3-methyl-2,6-dioxo-4-(trifluoromethyl)-1,2,3,6-tetrahydropyrimidin-1-yl] nitrobenzene and N,N-dimethylformamide is added potassium carbonate, and the mixture is stirred for 1 hour at 70° C. The reaction solution is cooled to room temperature, then, poured into ice water, and extracted with ethyl acetate. The organic layer is washed with saturated saline, dried over anhydrous magnesium sulfate, and concentrated. The residue is subjected to silica gel column chromatography to obtain 5-{4-fluoro-5-[3-methyl-2,6-dioxo-4-(trifluoromethyl)-1,2,3,6-tetrahydropyrimidin-1-yl]-2-nitrophenoxy}-4-{1-(methoxycarbonyl)ethoxy}pyrimidine.

Fourth Step

A mixture of 5-{4-fluoro-5-[3-methyl-2,6-dioxo-4-(trifluoromethyl)-1,2,3,6-tetrahydropyrimidin-1-yl]-2-nitrophenoxy}-4-{1-(methoxycarbonyl)ethoxy}pyrimidine, platinum oxide, ethanol and ethyl acetate is stirred for 1.5 hours at room temperature under hydrogen atmosphere. The reaction system is purged with nitrogen, then, the reaction solution is filtrated through Celite, and the filtrate is concentrated to obtain 5-{2-amino-4-fluoro-5-[3-methyl-2,6-dioxo-4-{1-(trifluoromethyl)-1,2,3,6-tetrahydropyrimidin-1-yl]phenoxy}-4-(methoxycarbonyl)ethoxy}pyrimidine.

Fifth Step

Isoamyl nitrite is added to a mixture of 5-{2-amino-4-fluoro-5-[3-methyl-2,6-dioxo-4-(trifluoromethyl)-1,2,3,6-tetrahydropyrimidin-1-yl]phenoxy}-4-{1-(methoxycarbonyl)ethoxy}pyrimidine, copper(I) chloride, copper(II) chloride and acetonitrile dropwise at room temperature, and the mixture is stirred for 1 hour. This reaction solution is poured into 2% hydrochloric acid, and extracted with ethyl acetate. The organic layer is washed with saturated saline, dried over anhydrous magnesium sulfate, and concentrated. The residue is subjected to silica gel column chromatography to obtain 5-{2-chloro-4-fluoro-5-[3-methyl-2,6-dioxo-4-(trifluoromethyl)-1,2,3,6-tetrahydropyrimidin-1-yl]phenoxy}-4-{1-(methoxycarbonyl)ethoxy}pyrimidine [present compound 4-2].

Production Example 19

Production of the Present Compound 7-42

First Step

To a mixture of 0.385 g of sodium hydride and dimethyl sulfoxide, a solution of 1.04 g of benzyl alcohol in dimethyl sulfoxide was added at room temperature. Then the mixture was stirred for 30 minutes at 50° C., and cooled to room temperature. A solution of 1.7 g of 4-bromo-3-methoxymethoxypyridine (produced by the method described in Tetrahedron, 12745–12774, (1998)) in dimethyl sulfoxide was added to the mixture, and the mixture was stirred for 2 hours at 50–60° C. The mixture was poured into water, and extracted with ethyl acetate. The organic layer was washed with water, then saturated saline, dried over anhydrous magnesium sulfate, and concentrated. The residue was subjected to silica gel column chromatography to obtain 4-benzyloxy-3-methoxymethoxypyridine.

melting point: 71.2° C.

Second Step

A mixture of 0.7 g of 4-benzyloxy-3-methoxymethoxypyridine and 1N hydrochloric acid was stirred for 2 hours at 60° C. The mixture was poured into saturated aqueous sodium bicarbonate solution, extracted with ethyl acetate. The organic layer is washed with saturated saline, dried over anhydrous magnesium sulfate, concentrated to obtain 0.547 g of 4-benzyloxy-3-hydroxypyridine.

melting point: 173.0° C.

Third Step

To a mixture of 57 mg of sodium hydride and N,N-dimethylformamide, 0.286 g of 4-benzyloxy-3-hydroxypyridine was added and stirred at room temperature for 30 minutes. Then 0.5 g of 2,5-difluoro-4-[3-methyl-2,6-dioxo-4-(trifluoromethyl)-1,2,3,6-tetrahydropyrimidin-1-yl]nitrobenzene was added to the mixture, and stirred for 1 hour at room temperature, then for 1 hour at 50–60° C. The mixture was poured into saturated ammonium chloride solution, and extracted with ethyl acetate. The organic layer was washed with saturated ammonium chloride solution and saturated saline, dried over anhydrous magnesium sulfate, and concentrated. The residue was subjected to silica gel column chromatography to obtain 0.548 g of 4-benzyloxy-3-{4-fluoro-5-[3-methyl-2,6-dioxo-4-(trifluoromethyl)-1,2,3,6-tetrahydropyrimidin-1-yl]-2-nitrophenoxy}pyridine.

$n_D^{23.7}$: 1.5497

Fourth Step

To a mixture of 0.55 g of an iron powder, 3 ml of acetic acid and 0.3 ml of water was added a solution of 0.548 g of 4-benzyloxy-3-{4-fluoro-5-[3-methyl-2,6-dioxo-4-(trifluoromethyl)-1,2,3,6-tetrahydropyrimidin-1-yl]-2-nitrophenoxy}pyridine in 0.5 ml of acetic acid and 3 ml of ethyl acetate dropwise. After completion of the addition, the mixture was stirred for 3 hour at 40–50° C. The mixture was poured into water, then, the mixture was filtrated through Celite, and extracted with ethyl acetate. The organic layer was washed with saturated aqueous sodium bicarbonate solution, and saturated saline, dried over anhydrous magnesium sulfate, and concentrated to obtain 0.438 g of 3-{2-amino-4-fluoro-5-[3-methyl-2,6-dioxo-4-(trifluoromethyl)-1,2,3,6-tetrahydropyrimidin-1-yl]phenoxy}-4-benzyloxypyridine.

melting point: 69.3° C.

Fifth Step

A solution of 0.307 g of isoamyl nitrite in acetonitrile was added to a mixture of 0.438 g of 3-{2-amino-4-fluoro-5-[3-methyl-2,6-dioxo-4-(trifluoromethyl)-1,2,3,6-tetrahydropyrimidin-1-yl]phenoxy}-4-benzyloxypyridine, 0.173 g of copper(I) chloride, 0.352 g of copper(II) chloride and acetonitrile dropwise at room temperature, and the mixture was stirred for 1 hour. On the next day, the mixture was concentrated, diluted with water and ethyl acetate, filtrated through Celite. The filtrate was extracted with ethyl acetate. The organic layer was washed with 1% hydrochloric acid, and saturated saline, dried over anhydrous magnesium sulfate, and concentrated. The residue was subjected to silica gel column chromatography to obtain 0.362 g of 4-benzyloxy-3-{2-chloro-4-fluoro-5-[3-methyl-2,6-dioxo-4-(trifluoromethyl)-1,2,3,6-tetrahydropyrimidin-1-yl]phenoxy}pyridine.

melting point: 55.0° C.

Sixth Step

A mixture of 0.356 g of 4-benzyloxy-3-{2-chloro-4-fluoro-5-[3-methyl-2,6-dioxo-4-(trifluoromethyl)-1,2,3,6-tetrahydropyrimidin-1-yl]phenoxy}pyridine, 10% palladium/carbon and ethyl acetate was stirred for 8 hours at room temperature under hydrogen atmosphere. The reaction system was purged with nitrogen, then, the reaction solution was filtrated through Celite, and the filtrate was concentrated to obtain 0.32 g of 3-{2-chloro-4-fluoro-5-[3-methyl-2,6-dioxo-4-(trifluoromethyl)-1,2,3,6-tetrahydropyrimidin-1-yl]phenoxy}-4-hydroxypyridine.

melting point: 196.1° C.

Seventh Step

To a mixture of 30 mg of sodium hydride and N,N-dimethylformamide, 0.31 g of 3-{2-chloro-4-fluoro-5-[3-methyl-2,6-dioxo-4-(trifluoromethyl)-1,2,3,6-tetrahydropyrimidin-1-yl]phenoxy}-4-hydroxypyridine was added and stirred at room temperature for 1 hour. Then 0.114 g of methyl bromoacetate was added to the mixture, and stirred for 8 hours at room temperature. The mixture was poured into saturated ammonium chloride solution, and extracted with ethyl acetate. The organic layer was washed with saturated ammonium chloride solution and saturated saline, dried over anhydrous magnesium sulfate, and concentrated. The residue was subjected to silica gel column chromatography to obtain 27 mg of 3-{2-chloro-4-fluoro-5-[3-methyl-2,6-dioxo-4-(trifluoromethyl)-1,2,3,6-tetrahydropyrimidin-1-yl]phenoxy}-4-(methoxycarbonyl)methoxypyridine [present compound 7-42].

$^1$H-NMR(CDCl$_3$/250 MHz) δ(ppm): 3.51 (q, 3H, J=1.2 Hz), 3.74 (s, 3H), 4.71 (s, 2H), 6.29 (s, 1H), 6.7–6.8 (m, 2H), 7.37 (d, 1H, J=8.8 Hz), 8.35 (d, 1H, J=5.5 Hz), 8.37 (s, 1H)

Production Example 20

Production of the Present Compound 2-45

First Step 2.0 g of sodium hydride was added to a mixture of 9.65 g of 2,6-dichloro-3-nitropyridine, 4.95 g of methyl glycolate and 100 ml of tetrahydrofuran at 0° C. The mixture was stirred at 0° C. for 4 hours. The reaction solution was poured into ice water, and extracted with ethyl acetate. The organic layer was washed with saturated saline, dried over anhydrous magnesium sulfate, and concentrated. The residue was subjected to silica gel column chromatography to obtain 10.86 g of 6-chloro-2-(methoxycarbonyl)methoxy-3-nitropyridine.

$^1$H-NMR(CDCl$_3$/300 MHz) δ(ppm): 3.80 (s, 3H), 5.09 (s, 2H), 7.11 (d, 1H, J=8.4 Hz), 8.34 (d, 1H, J=8.4 Hz), Second Step A mixture of 1.0 g of 6-chloro-2-(methoxycarbonyl)methoxy-3-nitropyridine, 1.37 g of 2-chloro-4-fluoro-5-[3-methyl-2,6-dioxo-4-(trifluoromethyl)-1,2,3,6-tetrahydropyrimidin-1-yl]phenol, 0.67 g of potassium carbonate and 5 ml of N,N-dimethylformamide was stirred for 1 hour at room temperature, then at 50° C. for 30 minutes. The resulted residue was added to ice water, extracted with ethyl acetate, and organic layer was washed with saturated saline, dried over anhydrous magnesium sulfate, and concentrated. The residue was subjected to silica gel column chromatography to obtain 2.25 g of 6-{2-chloro-4-fluoro-5-[3-methyl-2,6-dioxo-4-(trifluoromethyl)-1,2,3,6-tetrahydropyrimidin-1-yl]phenoxy}-2-(methoxycarbonyl)methoxy-3-nitropyridine.

$^1$H-NMR(CDCl$_3$/250 MHz) δ(ppm): 3.56 (s, 3H), 3.64 (s, 3H), 4.81 (s, 2H), 6.36 (s, 1H), 6.75 (d, 1H, J=8.6 Hz), 7.14 (d, 1H, J=6.6 Hz), 7.41 (d, 1H, J=8.9 Hz), 8.52 (d, 1H, J=8.6 Hz), Third Step A mixture of 2.25 g of 6-{2-chloro-4-fluoro-5-[3-methyl-2,6-dioxo-4-(trifluoromethyl)-1,2,3,6-tetrahydropyrimidin-1-yl]phenoxy}-2-(methoxycarbonyl)methoxy-3-nitropyridine, 0.3 g of 10% palladium/carbon and 40 ml of ethyl acetate was stirred for 3 hours at room temperature under hydrogen atmosphere. The reaction system was purged with nitrogen, then, the reaction solution was filtrated through Celite, and the filtrate was concentrated. The residue was subjected to silica gel column chromatography to obtain 1.38 g of 3-amino-6-{2-chloro-4-fluoro-5-[3-methyl-2,6-dioxo-4-(trifluoromethyl)-1,2,3,6-tetrahydropyrimidin-1-yl]phenoxy}-2-(methoxycarbonyl)methoxypyridine.

$^1$H-NMR(CDCl$_3$/250 MHz) δ(ppm): 3.54 (s, 3H), 3.6–3.7 (b, 2H), 3.67 (s, 3H), 4.76 (s, 2H), 6.33 (s, 1H), 6.47 (d, 1H, J=8.1 Hz), 7.0–7.1 (m, 2H), 7.35 (d, 1H, J=8.9 Hz)

Fourth Step 0.72 g of boron trifluoride diethyl ether complex was added to a mixture of 1.28 g of 3-amino-6-{2-chloro-4-fluoro-5-[3-methyl-2,6-dioxo-4-(trifluoromethyl)-1,2,3,6-tetrahydropyrimidin-1-yl]phenoxy}-2-(methoxycarbonyl)methoxypyridine, 3 ml of 1,2-dimethoxyethane and 1 ml of dichloromethane dropwise at −7° C. The mixture was stirred for 10 minutes at the same temperature, then, to the reaction solution was added 0.31 g of t-butyl nitrite dropwise at −5° C. or lower. The mixture was stirred for 1 hour at the same temperature, then, into the mixture was poured n-pentane. The solvent was removed by decantation. 7 ml of ethanol, and 1.2 g of zinc (dust) was added to the residue, and it was stirred at reflux temperature for 1.5 hour. The reaction solution was filtrated through Celite, and the solvent was distilled off, then, the resulted residue was subjected to silica gel chromatography to obtain 0.73 g of 2-{2-chloro-4-fluoro-5-[3-methyl-2,6-dioxo-4-(trifluoromethyl)-1,2,3,6-tetrahydropyrimidin-1-yl]phenoxy}-6-(methoxycarbonyl)methoxypyridine [present compound 2-45].

$^1$H-NMR(CDCl$_3$/300 MHz) δ(ppm): 3.55 (s, 3H), 3.66 (s, 3H), 4.67 (s, 2H), 6.34 (s, 1H), 6.5–6.6 (m, 1H), 7.1–7.2 (m, 1H), 7.3–7.4 (m, 1H), 7.6–7.7 (m, 1H)

Production Example 21

Production of the Present Compound 7-95

First Step

Sodium hydride is added to a mixture of 2,6-dichloro-3-nitropyridine, methyl glycolate and 1,4-dioxane at 10° C. The mixture is stirred at room temperature for 2 hours, then, poured into ice water, and extracted with ethyl acetate. The organic layer is dried over anhydrous magnesium sulfate, and concentrated. The residue is subjected to silica gel column chromatography to obtain 6-chloro-2-(methoxycarbonyl)methoxy-3-nitropyridine.

Second Step

A mixture of 6-chloro-2-(methoxycarbonyl)methoxy-3-nitropyridine, platinum oxide and ethanol is stirred for 3 hours at room temperature under hydrogen atmosphere. The reaction system is purged with nitrogen, then, the reaction solution is filtrated through Celite, and the filtrate is concentrated. The residue is subjected to silica gel column chromatography to obtain 3-amino-6-chloro-2-(methoxycarbonyl)methoxypyridine.

Third Step

A boron trifluoride diethyl etherate is added to a mixture of 3-amino-6-chloro-2-(methoxycarbonyl)methoxypyridine, 1,2-dimethoxyethane and dichloromethane dropwise at −10° C. After mixing for 10 minutes at the same temperature, a solution of t-butyl nitrite in 1,2-dimethoxyethane is added to the reaction solution dropwise at −5° C. or lower. After mixing for 30 minutes at the same temperature, n-pentane is poured into the mixture. The lower layer of two separated layers is dissolved in acetic anhydride, and the mixture is stirred for 1 hour at 80° C. The solvent is distilled off, then, the resulted residue is subjected to silica gel chromatography to obtain 3-acetoxy-6-chloro-2-(methoxycarbonyl)methoxypyridine.

Fourth Step

A mixture of 3-acetoxy-6-chloro-2-(methoxycarbonyl)methoxypyridine, potassium carbonate and methanol is stirred for 3 hours at room temperature. The reaction solution is poured into water, and extracted with ethyl acetate. The organic layer is dried over anhydrous magnesium sulfate, and concentrated. The residue is subjected to silica gel column chromatography to obtain 6-chloro-3-hydroxy-2-(methoxycarbonyl)methoxypyridine.

Fifth Step

To a mixture of 6-chloro-3-hydroxy-2-(methoxycarbonyl)methoxypyridine, 2,5-difluoro-4-[3-methyl-2,6-dioxo-4-(trifluoromethyl)-1,2,3,6-tetrahydropyrimidin-1-yl] nitrobenzene and N,N-dimethylformamide is added potassium carbonate, and the mixture is stirred for 2 hours at 70° C. The reaction solution is cooled to room temperature, then, poured into ice water, and extracted with ethyl acetate. The organic layer is washed with saturated saline, dried over anhydrous magnesium sulfate, and concentrated. The residue is subjected to silica gel column chromatography to obtain 3-{4-fluoro-5-[3-methyl-2,6-dioxo-4-(trifluoromethyl)-1,2,3,6-tetrahydropyrimidin-1-yl]-2-nitrophenoxy}-6-chloro-2-(methoxycarbonyl)methoxypyridine.

Sixth Step

To a mixture of an iron powder, acetic acid and water is added a solution of 3-{4-fluoro-5-[3-methyl-2,6-dioxo-4-(trifluoromethyl)--1,2,3,6-tetrahydropyrimidin-1-yl]-2-nitrophenoxy}-6-chloro-2-(methoxycarbonyl)methoxypyridine in acetic acid dropwise while maintaining the temperature of the reaction solution at 35° C. or lower. After completion of the addition, the mixture is stirred for 2 hours, then, the reaction solution is filtrated through Celite, and diluted with ethyl acetate. The mixture is neutralized with saturated aqueous sodium bicarbonate solution, the organic layer is washed with saturated saline, dried over anhydrous magnesium sulfate, and concentrated, then, the resulted residue is subjected to silica gel chromatography to obtain 3-{2-amino-4-fluoro-5-[3-methyl-2,6-dioxo-4-(trifluoromethyl)-1,2,3,6-tetrahydropyrimidin-1-yl]phenoxy}-6-chloro-2-(methoxycarbonyl)methoxypyridine.

Seventh Step

Isoamyl nitrite is added to a mixture of 3-{2-amino-4-fluoro-5-[3-methyl-2,6-dioxo-4-(trifluoromethyl)-1,2,3,6-tetrahydropyrimidin-1-yl]phenoxy}-6-chloro-2-(methoxycarbonyl)methoxypyridine, copper(I) chloride, copper(II) chloride and acetonitrile dropwise at room temperature, and the mixture is stirred for 1 hour. This reaction solution is poured into 2% hydrochloric acid, and extracted with ethyl acetate. The organic layer is washed with saturated saline, dried over anhydrous magnesium sulfate, and concentrated. The residue is subjected to silica gel column chromatography to obtain 3-{2-chloro-4-fluoro-5-[3-methyl-2,6-dioxo-4-(trifluoromethyl)-1,2,3,6-tetrahydropyrimidin-1-yl]phenoxy}-6-chloro-2-(methoxycarbonyl)methoxypyridine [present compound 7-95].

Production Example 22

Production of the Present Compound 7-109

First Step

Sodium hydride is added to a mixture of 2-chloro-6-methoxy-3-nitropyridine, methyl glycolate and 1,4-dioxane at 10° C. The mixture is stirred at room temperature for 2 hours, then, poured into ice water, and extracted with ethyl acetate. The organic layer is dried over anhydrous magnesium sulfate, and concentrated. The residue is subjected to silica gel column chromatography to obtain 6-methoxy-2-(methoxycarbonyl)methoxy-3-nitropyridine.

Second Step

A mixture of 6-methoxy-2-(methoxycarbonyl)methoxy-3-nitropyridine, platinum oxide and ethanol is stirred for 3 hours at room temperature under hydrogen atmosphere. The reaction system is purged with nitrogen, then, the reaction solution is filtrated through Celite, and the filtrate is concentrated. The residue is subjected to silica gel column chromatography to obtain 3-amino-6-methoxy-2-(methoxycarbonyl)methoxypyridine.

Third Step

A boron trifluoride diethyl etherate is added to a mixture of 3-amino-6-methoxy-2-(methoxycarbonyl)methoxypyridine, 1,2-dimethoxyethane and dichloromethane dropwise at −10° C. After mixing for 10 minutes at the same temperature, a solution of t-butyl nitrite in 1,2-dimethoxyethane is added to the reaction solution dropwise at −5° C. or lower. After mixing for 30 minutes at the same temperature, n-pentane is poured into the mixture. The lower layer of two separated layers is dissolved in acetic anhydride, and the mixture is stirred for 1 hour at 80° C. The solvent is distilled off, then, the resulted residue is subjected to silica gel chromatography to obtain 3-acetoxy-6-methoxy-2-(methoxycarbonyl)methoxypyridine.

Fourth Step

A mixture of 3-acetoxy-6-methoxy-2-(methoxycarbonyl)methoxypyridine, potassium carbonate and methanol is stirred for 3 hours at room temperature. The reaction solution is poured into water, and extracted with ethyl acetate. The organic layer is dried over anhydrous magnesium sulfate, and concentrated. The residue is subjected to silica gel column chromatography to obtain 3-hydroxy-6-methoxy-2-(methoxycarbonyl)methoxypyridine.

Fifth Step

To a mixture of 3-hydroxy-6-methoxy-2-(methoxycarbonyl)methoxypyridine, 2,5-difluoro-4-[3-methyl-2,6-dioxo-4-(trifluoromethyl)-1,2,3,6-tetrahydropyrimidin-1-yl]nitrobenzene and N,N-dimethylformamide is added potassium carbonate, and the mixture is stirred for 2 hours at 70° C. The reaction solution is cooled to room temperature, then, poured into ice water, and extracted with ethyl acetate. The organic layer is washed with saturated saline, dried over anhydrous magnesium sulfate, and concentrated. The residue is subjected to silica gel column chromatography to obtain 3-{4-fluoro-5-[3-methyl-2,6-dioxo-4-(trifluoromethyl)-1,2,3,6-tetrahydropyrimidin-1-yl]-2-nitrophenoxy}-6-methoxy-2-(methoxycarbonyl)methoxypyridine.

Sixth Step

To a mixture of an iron powder, acetic acid and water is added a solution of 3-{4-fluoro-5-[3-methyl-2,6-dioxo-4-(trifluoromethyl)-1,2,3,6-tetrahydropyrimidin-1-yl]-2-nitrophenoxy}-6-methoxy-2-(methoxycarbonyl)methoxypyridine in acetic acid dropwise while maintaining the temperature of the reaction solution at 35° C. or lower. After completion of the addition, the mixture is stirred for 2 hours, then, the reaction solution is filtrated through Celite, and diluted with ethyl acetate. The mixture is neutralized with saturated aqueous sodium bicarbonate solution, the organic layer is washed with saturated saline, dried over anhydrous magnesium sulfate, and concentrated, then, the resulted residue is subjected to silica gel chromatography to obtain 3-{2-amino-4-fluoro-5-[3-methyl-2,6-dioxo-4-(trifluoromethyl)-1,2,3,6-tetrahydropyrimidin-1-yl]phenoxy}-6-methoxy-2-(methoxycarbonyl)methoxypyridine.

Seventh Step

Isoamyl nitrite is added to a mixture of 3-{2-amino-4-fluoro-5-[3-methyl-2,6-dioxo-4-(trifluoromethyl)-1,2,3,6-tetrahydropyrimidin-1-yl]phenoxy}-6-methoxy-2-(methoxycarbonyl)methoxypyridine, copper(I) chloride, copper(II) chloride and acetonitrile dropwise at room temperature,and the mixture is stirred for 1 hour. This reaction solution is poured into 2% hydrochloric acid, and extracted with ethyl acetate. The organic layer is washed with saturated saline, dried over anhydrous magnesium sulfate, and concentrated. The residue is subjected to silica gel column chromatography to obtain 3-{2-chloro-4-fluoro-5-[3-methyl-2,6-dioxo-4-(trifluoromethyl)-1,2,3,6-tetrahydropyrimidin-1-yl]phenoxy}-6-methoxy-2-(methoxycarbonyl)methoxypyridine [present compound 7-109].

Production Example 23

Production of Present Compound 7-8

A mixture of 0.60 g of 3-{2-chloro-4-fluoro-5-[3-methyl-2,6-dioxo-4-(trifluoromethyl)-1,2,3,6-tetrahydropyrimidin-1-yl]phenoxy}-2-(methoxycarbonyl)methoxypyridine [present compound 7-7], 0.13 g of sodium carbonate and 7.0 ml of ethanol was heated under reflux for 2 hours. It was cooled to room temperature, then, the solvent was distilled off under reduced pressure, and the resulted residue was subjected to silica gel chromatography to obtain 0.55 g of 3-{2-chloro-4-fluoro-5-[3-methyl-2,6-dioxo-4-(trifluoromethyl)-1,2,3,6-tetrahydropyrimidin-1-yl]phenoxy}-2-(ethoxycarbonyl)methoxypyridine [present compound 7-8].

$^1$ H-NMR(CDCl$_3$/250 MHz) δ(ppm): 1.25(t, 3H, J=7.1 Hz), 3.50 (q, 3H, J=1.2 Hz), 4.16 (q, 2H, J=7.1 Hz), 4.88 (d, 1H, J=15.9 Hz), 4.96 (d, 1H, J=15.9 Hz), 6.29 (s, 1H), 6.9–7.0 (m, 2H), 7.3–7.4 (m, 2H), 7.9–8.0 (m, 1H)

Production Example 24

Production of Present Compound 7-48

A mixture of 0.60 g of 3-{2-chloro-4-fluoro-5-[3-methyl-2,6-dioxo-4-(trifluoromethyl)-1,2,3,6-tetrahydropyrimidin-1-yl]phenoxy}-2-(methoxycarbonyl)methoxypyridine [present compound 7-7], 0.13 g of sodium carbonate and 7.0 ml of n-propanol was refluxed for 2 hours. It was cooled to room temperature, then, the solvent was distilled off under reduced pressure, and the resulted residue was subjected to silica gel chromatography to obtain 0.62 g of 3-{2-chloro-4-fluoro-5-[3-methyl-2,6-dioxo-4-(trifluoromethyl)-1,2,3,6-tetrahydropyrimidin-1-yl]phenoxy}-2-(n-propoxycarbonyl)methoxypyridine [present compound 7-48].

$^1$H-NMR(CDCl$_3$/300 MHz) δ(ppm): 0.89 (t, 3H, J=7.3 Hz), 1.63 (qt, 2H, J=7.3, 6.5 Hz), 3.50 (q, 3H, J=0.8 Hz), 4.06 (t, 2H, J=6.5 Hz), 4.89 (d, 1H, J=16.0 Hz), 4.97 (d, 1H, J=16.0 Hz), 6.28 (s, 1H), 6.91 (dd, 1H, J=7.8, 5.0 Hz), 6.93 (d, 1H, J=6.5 Hz), 7.31 (dd, 1H, J=7.8, 1.6 Hz), 7.36 (d, 1H, J=8.9 Hz), 7.91 (dd, 1H, J=5.0, 1.6 Hz)

Production Example 25

Production of Present Compound 7-50

A mixture of 0.30 g of 3-{2-chloro-4-fluoro-5-[3-methyl-2,6-dioxo-4-(trifluoromethyl)-1,2,3,6-tetrahydropyrimidin-1-yl]phenoxy}-2-(methoxycarbonyl)methoxypyridine [present compound 7-7], 0.06 g of sodium carbonate and 3.0 ml of n-pentanol was stirred for 1.5 hours at 100° C. The reaction solution was cooled to room temperature, then, poured into water, and extracted with ethyl acetate. The organic layer was washed with saturated saline, dried over anhydrous magnesium sulfate, and concentrated. The residue was subjected to silica gel column chromatography to obtain 0.07 g of 3-{2-chloro-4-fluoro-5-[3-methyl-2,6-dioxo-4-(trifluoromethyl)-1,2,3,6-tetrahydropyrimidin-1-yl]phenoxy}-2-(n-pentyloxycarbonyl)methoxypyridine [present compound 7-50].

$^1$H-NMR(CDCl$_3$/300 MHz) δ(ppm): 0.88 (t, 3H, J=6.6 Hz), 1.2–1.4 (m, 4H), 1.5–1.7 (m, 2H), 3.50 (q, 3H, J=1.0 Hz), 4.0–4.2 (m, 2H), 4.8–5.1 (m, 2H), 6.29 (s, 1H), 6.9–7.0 (m, 2H), 7.28 (dd, 1H, J=7.9, 1.4 Hz), 7.37 (d, 1H, J=9.0 Hz), 7.91 (dd, 1H, J=4.9, 1.4 Hz)

Intermediate Production Example 7

Production of 3-amino-2-(methoxycarbonyl)methoxypyridine Used in Production Example 13, Third Process A mixture of 55.9 g of 2-(methoxycarbonyl)methoxy-3-nitropyridine, 8.64 g of 10% palladium/carbon and 600 ml of ethyl acetate was stirred for 2 hours at room temperature under hydrogen atmosphere. The reaction system was purged with nitrogen, then, the reaction solution was filtrated through Celite, and the filtrate was concentrated. The residue was subjected to silica gel column chromatography to obtain 46.76 g of 3-amino-2-(methoxycarbonyl)methoxypyridine. Intermediate Production Example 8

Production of 3-acetoxy-2-(methoxycarbonyl)methoxypyridine Used in Production Example 13, Fourth Process 0.41 g of trifluoromethanesulfonic acid was added to a mixture of 0.5 g of 3-amino-2-(methoxycarbonyl)methoxypyridine, 1.5 ml of 1,2-dimethoxyethane and 0.5 ml of dichloromethane dropwise at −5° C. The mixture was stirred for 10 minutes at the same temperature, then, a solution of 0.34 g of t-butyl nitrite in 0.5 ml of 1,2-dimethoxyethane was added to the reaction solution dropwise at −5° C. or lower. The mixture was stirred for 1 hour at the same temperature, then, n-pentane was poured into the mixture. The lower layer of two separated layers was dissolved in 1.5 ml of acetic anhydride, and the mixture was stirred for 30 minutes at 60° C. The reaction solution was cooled to room temperature, then, poured into water, and extracted with t-butyl methyl ether. The organic layer was washed with saturated aqueous sodium hydrogen carbonate solution and saturated saline, then, dried over anhydrous magnesium sulfate, and concentrated. The residue was subjected to silica gel chromatography to obtain 0.30 g of 3-acetoxy-2-(methoxycarbonyl)methoxypyridine.

Production Example 26

Production of the Present Compound 7-17
First Step 1.26 g of sodium hydride was added to a mixture of 5.0 g of 2-chloro-5-nitropyridine, 3.13 g of methyl glycolate and 50 ml of tetrahydrofuran at 0° C. The mixture was stirred at 0° C. for 15 minutes, then at room temperature for 1 hour. The reaction solution was poured into ice water, and extracted with ethyl acetate. The organic layer was dried over anhydrous magnesium sulfate, and concentrated. The residue was subjected to silica gel column chromatography to obtain 5.18 g of 2-(methoxycarbonyl)methoxy-5-nitropyridine.

$^1$H-NMR(CDCl$_3$/300 MHz) δ(ppm): 3.79 (s, 3H), 5.01 (s, 2H), 6.99 (d, 1H, J=9.1 Hz), 8.41 (dd, 1H, J=9.1,2.8 Hz), 9.03 (d, 1H, J=2.8 Hz)
Second Step A mixture of 5.18 g of 2-(methoxycarbonyl)methoxy-5-nitropyridine, 0.8 g of 10% palladium/carbon and 50 ml of ethyl acetate was stirred for 3 hours at room temperature under hydrogen atmosphere. The reaction system was purged with nitrogen, then, the reaction solution was filtrated through Celite, and the filtrate was concentrated. The residue was subjected to silica gel column chromatography to obtain 4.45 g of 5-amino-2-(methoxycarbonyl)methoxypyridine.

$^1$H-NMR(CDCl$_3$/250 MHz) δ(ppm): 3.3–3.5 (bs, 2H), 3.76 (s, 3H), 4.82 (s, 2H), 6.72 (d, 1H, J=8.6 Hz), 7.04 (dd, 1H, J=8.6,2.9 Hz), 7.58 (dd, 1H, J=2.9 Hz)
Third Step 1.46 ml of trifluoromethanesulfonic acid was added to a mixture of 3.0 g of 5-amino-2-(methoxycarbonyl)methoxypyridine, 9 ml of 1,2-dimethoxyethane and 3 ml of dichloromethane dropwise at −10° C. The mixture was stirred for 10 minutes at the same temperature, then, to the reaction solution was added a solution of 2.35 ml of t-butyl nitrite in 1 ml of 1,2-dimethoxyethane dropwise at −10° C. or lower. 1,2-dimethoxyethane was added to the mixture, and it was stirred for 20 minutes at the same temperature, then, into the mixture was poured n-pentane. The precipitated solid was washed with n-pentane, then it was dissolved in 18 ml of acetic anhydride, and the mixture was stirred for 2 hour at 80° C. The mixture was poured into ice-water, and extracted with t-butyl methyl ether. The organic layer was concentrated, then diluted with t-butyl methyl ether. The dilute was washed with saturated aqueous sodium bicarbonate solution, then saturated saline, dried over anhydrous magnesium sulfate, and concentrated. The residue is subjected to silica gel column chromatography to obtain 1.4 g of 5-acetoxy-2-(methoxycarbonyl)methoxypyridine.

$^1$H-NMR(CDCl$_3$/300 MHz) δ(ppm): 2.30 (s, 3H), 3.77 (s, 3H), 4.89 (s, 2H), 6.88 (d, 1H, J=8.8 Hz), 7.40 (dd, 1H, J=8.8,2.8 Hz), 7.89 (dd, 1H, J=2.8 Hz)

Fourth Step

A mixture of 1.4 g of 5-acetoxy-2-(methoxycarbonyl)methoxypyridine, 0.47 g of potassium carbonate and 10 ml of methanol was stirred for 4.5 hours at room temperature. The solvent was distilled off under reduced pressure, and to the resulted residue was added water, then neutralized with hydrochloric acid. The mixture was extracted with ethyl acetate, and organic layer was washed with saturated saline, dried over anhydrous magnesium sulfate, and concentrated. The residue was subjected to silica gel column chromatography to obtain 1.0 g of 5-hydroxy-2-(methoxycarbonyl)methoxypyridine.

$^1$H-NMR(CDCl$_3$/300 MHz) δ(ppm): 3.78 (s, 3H), 4.84 (s, 2H), 5.92 (bs, 1H), 6.72 (d, 1H, J=8.9 Hz), 7.12 (dd, 1H, J=8.9,2.9 Hz), 7.62 (d, 1H, J=2.9 Hz)

Fifth Step

To a mixture of 0.5 g of 5-hydroxy-2-(methoxycarbonyl)methoxypyridine, 0.80 g of 2,5-difluoro-4-[3-methyl-2,6-dioxo-4-(trifluoromethyl)-1,2,3,6-tetrahydropyrimidin-1-yl]nitrobenzene and 5 ml of N,N-dimethylformamide was added 0.35 g of potassium carbonate, and the mixture was stirred for 1.5 hours at 50° C. The solution was cooled to room temperature, poured into a mixture of water, hydrochloric acid and saline, and extracted with ethyl acetate. The organic layer was washed with saturated saline, dried over anhydrous magnesium sulfate, and concentrated. The residue was subjected to silica gel column chromatography to obtain 0.93 g of 5-{4-fluoro-5-[3-methyl-2,6-dioxo-4-(trifluoromethyl)-1,2,3,6-tetrahydropyrimidin-1-yl]-2-nitrophenoxy}-2-(methoxycarbonyl)methoxypyridine.

$^1$H-NMR(CDCl$_3$/300 MHz) δ(ppm): 3.54 (q, 3H, J=1.2 Hz), 3.79 (s, 3H), 4.89 (s, 2H), 6.34 (s, 1H), 6.8–7.0 (m, 2H), 7.42 (dd, 1H, J=9.2,2,9 Hz), 7.88 (d, 1H, J=8.5 Hz), 7.96 (d, 1H, J=2.9 Hz)

Sixth Step

To a mixed solution of 1.2 g of an iron powder, 5 ml of acetic acid and 0.5 ml of water was added a solution of 0.93 g of 5-{4-fluoro-5-[3-methyl-2,6-dioxo-4-(trifluoromethyl)-1,2,3,6-tetrahydropyrimidin-1-yl]-2-nitrophenoxy}-2-(methoxycarbonyl)methoxypyridine in 4 ml of acetic acid dropwise while maintaining the temperature of the reaction solution at 35° C. or lower. After completion of the addition, the mixture was stirred for 2 hours, then, filtrated through Celite, and concentrated. The residue was diluted with water, and extracted with ethyl acetate. The organic layer was mixture was washed with saturated aqueous sodium bicarbonate solution, then saturated saline, dried over anhydrous magnesium sulfate, and concentrated. Then, the resulted residue was subjected to silica gel chromatography to obtain 0.83 g of 5-{2-amino-4-fluoro-5-[3-methyl-2,6-dioxo-4-(trifluoromethyl)-1,2,3,6-tetrahydropyrimidin-1-yl]phenoxy}-2-(methoxycarbonyl)methoxypyridine.

$^1$H-NMR(CDCl$_3$/250 MHz) δ(ppm): 3.52 (q, 3H, J=1.2 Hz), 3.78 (s, 3H), 4.16 (bs, 2H), 4.87 (s, 2H), 6.31 (s, 1H), 6.57 (d, 1H, J=6.8 Hz), 6.64 (d, 1H, J=10.8 Hz), 6.85 (dd, 1H, J=8.9,0.5 Hz), 7.35 (dd, 1H, J=8.9,3.1 Hz), 7.90 (dd, 1H, J=3.1,0.5 Hz)

Seventh Step 0.3 g of isoamyl nitrite was added to a mixture of 0.83 g of 5-{2-amino-4-fluoro-5-[3-methyl-2,6-dioxo-4-(trifluoromethyl)-1,2,3,6-tetrahydropyrimidin-1-yl]phenoxy}-2-(methoxycarbonyl)methoxypyridine, 0.34 g of copper(I) chloride, 0.69 g of copper(II) chloride and 3 ml of acetonitrile dropwise at room temperature, and the mixture was stirred for 1 hour. 0.3 g of isoamyl nitrite was added to the mixture, and stirred for 20 minutes. This reaction solution was poured into 2% hydrochloric acid, and extracted with ethyl acetate. The organic layer was washed with saturated saline, dried over anhydrous magnesium sulfate, and concentrated. The residue was subjected to silica gel column chromatography to obtain 0.52 g of 5-{2-chloro-4-fluoro-5-[3-methyl-2,6-dioxo-4-(trifluoromethyl)-1,2,3,6-tetrahydropyrimidin-1-yl]phenoxy}-2-(methoxycarbonyl)methoxypyridine [present compound 7-17].

$^1$H-NMR(CDCl$_3$/250 MHz) δ(ppm): 3.53 (q, 3H, J=1.3 Hz), 3.78 (s, 3H), 4.88 (s, 2H), 6.33 (s, 1H), 6.76 (d, 1H, J=6.5 Hz), 6.88 (d, 1H, J=8.9 Hz), 7.3–7.4 (m, 1H), 7.39 (d, 1H, J=8.9 Hz), 7.8–7.9 (m, 1H)

Production Example 27

Production of the Present Compound 7-12

First Step

A mixture of 0.08 g of 5-{2-chloro-4-fluoro-5-[3-methyl-2,6-dioxo-4-(trifluoromethyl)-1,2,3,6-tetrahydropyrimidin-1-yl]phenoxy}-2-(methoxycarbonyl)methoxypyridine [present compound 7-17] and 1 ml of 48% hydrobromic acid was stirred at reflux temperature for 3 hours. The mixture was neutralized with saturated aqueous sodium bicarbonate solution, and extracted with ethyl acetate. The organic layer was dried over anhydrous magnesium sulfate, and concentrated to obtain 0.06 g of 5-{2-chloro-4-fluoro-5-[3-methyl-2,6-dioxo-4-(trifluoromethyl)-1,2,3,6-tetrahydropyrimidin-1-yl]phenoxy}-2-pyridone.

$^1$H-NMR(CDCl$_3$/300 MHz) δ(ppm): 3.51 (s, 3H), 6.31 (s, 1H), 6.58 (d, 1H, J=9.8 Hz), 6.79 (d, 1H, J=6.5 Hz), 7.24 (d, 1H, J=3.0 Hz), 7.3–7.4 (m, 2H)

Second Step

To a mixture of 60 mg of 5-{2-chloro-4-fluoro-5-[3-methyl-2,6-dioxo-4-(trifluoromethyl)-1,2,3,6-tetrahydropyrimidin-1-yl]phenoxy}-2-pyridone, 1.0 ml of tetrahydrofuran, 25 mg of methyl lactate, and 64 mg of triphenylphosphine, 123 mg of a 40% solution of diisopropyl azodicarboxylate in toluene, and the mixture was stirred for 2 hours at room temperature. The reaction solution was poured into water, and extracted with ethyl acetate. The organic layer was washed with saturated saline, dried over anhydrous magnesium sulfate, and concentrated. The residue was subjected to silica gel column chromatography to obtain 20 mg of 5-{2-chloro-4-fluoro-5-[3-methyl-2,6-dioxo-4-(trifluoromethyl)-1,2,3,6-tetrahydropyrimidin-1-yl]phenoxy}-2-{1-(methoxycarbonyl)ethoxy}pyridine [present compound 7-12].

$^1$H-NMR(CDCl$_3$/300 MHz) δ(ppm): 1.60 (d, 3H, J=7.0 Hz), 3.53 (s, 3H), 3.75 (s, 3H), 5.28 (q, 1H, J=7.0 Hz), 6.32 (s, 1/2H), 6.33 (s, 1/2H), 6.7–6.8 (m, 1H), 6.84 (d, 1H, J=9.1 Hz), 7.3–7.4 (m, 1H), 7.38 (d, 1H, J=8.8 Hz), 7.8–7.9 (m, 1H)

Production Example 28

Production of the Present Compound 1-45

First Step 0.4 g of sodium hydride was added to a mixture of 1.59 g of 4-chloro-6-methoxy-2-methylthiopyrimidine, 0.98 g of methyl glycolate and 10 ml of N,N-dimethylformamide at 0° C. The mixture was stirred at room temperature for 5 hours, then, the reaction solution was poured into water, and extracted with ethyl acetate. The organic layer was washed with saturated saline, dried over anhydrous magnesium sulfate, and concentrated. The residue was subjected to silica gel column chromatography to obtain 1.22 g of 6-methoxy-4-(methoxycarbonyl)methoxy-2-methylthiopyrimidine.

$^1$H-NMR(CDCl$_3$/250 MHz) δ(ppm): 2.48 (s, 3H), 3.77 (s, 3H), 3.93 (s, 3H), 4.88 (s, 2H), 5.87 (s, 1H)

Second Step 2.59 g of 3-chloroperoxybenzoic acid was added to a solution of 1.22 g of 6-methoxy-4-(methoxycarbonyl) methoxy-2-methylthiopyrimidine in 10 ml of chloroform at 0° C. The mixture was stirred at room temperature for 3 hours, then 30 ml of saturated aqueous sodium thiosulfate solution was added to the mixture. The mixture was poured into saturated aqueous sodium bicarbonate solution, extracted with chloroform, the organic layer was washed with saturated saline, dried over anhydrous magnesium sulfate, and concentrated, then, the resulted residue was subjected to silica gel chromatography to obtain 1.32 g of 6-methoxy-4-(methoxycarbonyl)methoxy-2-methylsulfonylpyrimidine.

$^1$H-NMR(CDCl$_3$/300 MHz) δ(ppm): 3.26 (s, 3H), 3.78 (s, 3H), 4.06 (s, 3H), 4.97 (s, 2H), 6.34 (s, 1H)

Third Step

To a mixture of 400 mg of 2-chloro-4-fluoro-5-[3-methyl-2,6-dioxo-4-(trifluoromethyl)-1,2,3,6-tetrahydropyrimidin-1-yl]phenol, 359 mg of 6-methoxy-4-(methoxycarbonyl)methoxy-2-methylsulfonylpyrimidine and 3 ml of N,N-dimethylformamide, 196 mg of potassium carbonate was added, and the mixture was stirred for 1 hour at 80° C. The reaction solution was cooled to room temperature, then, this reaction solution was poured into water, and extracted with ethyl acetate. The organic layer was washed with saturated saline, dried over anhydrous magnesium sulfate, and concentrated. The residue was subjected to silica gel column chromatography to obtain 620 mg of 2-{2-chloro-4-fluoro-5-[3-methyl-2,6-dioxo-4-(trifluoromethyl)-1,2,3,6-tetrahydropyrimidin-1-yl]phenoxy}-6-methoxy-4-(methoxycarbonyl)methoxypyrimidine [present compound 1-45].

$^1$H-NMR(CDCl$_3$/300 MHz) δ(ppm): 3.55 (s, 3H), 3.71 (s, 3H), 3.87 (s, 3H), 4.78 (s, 2H), 5.95 (s, 1H), 6.34 (s, 1H), 7.1–7.2 (m,1H), 7.37 (d, 1H, J=9.1 Hz)

melting point: 60.3° C.

Production Example 29

Production of the Present Compound 1-42

First Step 3.86 g of 28% sodium methoxide methanol solution was added dropwise over 20 minutes to a solution of 3.9 g of 4,6-dichloro-2-methylthiopyrimidine in 20 ml of N,N-dimethylformamide at 0° C. Then the mixture was stirred at room temperature for 7 hours. 20 g of ice was added to the mixture, then white precipitate was collected by suction filtration, and the solid was washed with water. The solid was dissolved in ethyl acetate, washed with saturated saline, dried over anhydrous magnesium sulfate, and concentrated to obtain 3.18 g of 4-chloro-6-methoxy-2-methylthiopyrimidine.

$^1$H-NMR(CDCl$_3$/300 MHz) δ(ppm): 2.55 (s, 3H), 3.98 (s, 3H), 6.41 (s, 1H)

Second Step 0.4 g of sodium hydride was added to a mixture of 1.59 g of 4-chloro-6-methoxy-2-methylthiopyrimidine, 1.13 g of methyl lactate and 10 ml of N,N-dimethylformamide at 0° C. The mixture was stirred at room temperature for 5 hours, then, the reaction solution was poured into water, and extracted with ethyl acetate. The organic layer was washed with saturated saline, dried over anhydrous magnesium sulfate, and concentrated. The residue was subjected to silica gel column chromatography to obtain 1.5 g of 6-methoxy-4-{1-(methoxycarbonyl)ethoxy}-2-methylthiopyrimidine.

$^1$H-NMR(CDCl$_3$/250 MHz) δ(ppm): 1.58 (d, 3H, J=7.0 Hz), 2.46 (s, 3H), 3.73 (s, 3H), 3.92 (s, 3H), 5.33 (q, 1H, J=7.0 Hz), 5.83 (s, 1H)

Third Step 2.81 g of 3-chloroperoxybenzoic acid was added to a solution of 1.40 g of 6-methoxy-4-{1-(methoxycarbonyl)ethoxy}-2-methylthiopyrimidine in 13 ml of chloroform at 0° C. The mixture was stirred at room temperature for 3 hours, then 30 ml of saturated aqueous sodium thiosulfate solution was added to the mixture. The mixture was poured into saturated aqueous sodium bicarbonate solution, extracted with chloroform, the organic layer was washed with saturated saline, dried over anhydrous magnesium sulfate, and concentrated, then, the resulted residue was subjected to silica gel chromatography to obtain 1.62 g of 6-methoxy-4-{1-(methoxycarbonyl)ethoxy}-2-methylsulfonylpyrimidine.

$^1$H-NMR(CDCl$_3$/250 MHz) δ(ppm): 1.63 (d, 3H, J=7.0 Hz), 3.25 (s, 3H), 3.75 (s, 3H), 4.06 (s, 3H), 5.36 (q, 1H, J=7.0 Hz), 6.30 (s, 1H)

Fourth step

To a mixture of 400 mg of 2-chloro-4-fluoro-5-[3-methyl-2,6-dioxo-4-(trifluoromethyl)-1,2,3,6-tetrahydropyrimidin-1-yl]phenol, 377 mg of 6-methoxy-4-{1-(methoxycarbonyl)ethoxy}-2-methylsulfonylpyrimidine and 3 ml of N,N-dimethylformamide, 196 mg of potassium carbonate was added, and the mixture was stirred for 1 hour at 80° C. The reaction solution was cooled to room temperature, then, this reaction solution was poured into water, and extracted with ethyl acetate. The organic layer was washed with saturated saline, dried over anhydrous magnesium sulfate, and concentrated. The residue was subjected to silica gel column chromatography to obtain 630 mg of 2-{2-chloro-4-fluoro-5-[3-methyl-2,6-dioxo-4-(trifluoromethyl)-1,2,3,6-tetrahydropyrimidin-1-yl]phenoxy}-6-methoxy-4-{1-(methoxycarbonyl)ethoxy}pyrimidine [present compound 1-42].

$^1$H-NMR(CDCl$_3$/300 MHz) δ(ppm): 1.52 (d, 3H, J=6.8 Hz), 3.55 (s, 3H), 3.67 (s, 3H), 3.87 (s, 3H), 5.2–5.3 (m, 1H), 5.91 (s, 1H), 6.35 (s, 1H), 7.16 (d, 1H, J=6.7 Hz), 7.37 (d, 1H, J=9.1 Hz) melting point: 71.2° C.

Production Example 30

Production of Present Compound 7-82

A mixture of 0.60 g of 3-{2-chloro-4-fluoro-5-[3-methyl-2,6-dioxo-4-(trifluoromethyl)-1,2,3,6-tetrahydropyrimidin-1-yl]phenoxy}-2-(methoxycarbonyl)methoxypyridine [present compound 7-7], 0.13 g of sodium carbonate, 0.39 g of benzyl alcohol and 2.4 ml of toluene was heated at 90° C. for 2 hours, then under reflux for 2 hours. It was cooled to room temperature, then, the solvent was distilled off under reduced pressure, and the resulted residue was subjected to silica gel chromatography to obtain 0.24 g of 3-{2-chloro-4-fluoro-5-[3-methyl-2,6-dioxo-4-(trifluoromethyl)-1,2,3,6-tetrahydropyrimidin-1-yl]phenoxy}-2-(benzyloxycarbonyl)methoxypyridine [present compound 7-82].

$^1$H-NMR(CDCl$_3$/300 MHz) δ(ppm): 3.47 (s, 3H), 5.15 (s, 2H), 6.25 (s, 1H), 6.8–7.0 (m, 2H), 7.2–7.4 (m, 7H), 7.89 (dd, 1H, J=4.9,1.3 Hz)

Production Example 31

Production of Present Compound 7-6

A mixture of 0.24 g of 3-{2-chloro-4-fluoro-5-[3-methyl-2,6-dioxo-4-(trifluoromethyl)-1,2,3,6-tetrahydropyrimidin-1-yl]phenoxy}-2-(benzyloxycarbonyl)methoxypyridine [present compound 7-82], 10 mg of 10% palladium/carbon and 1 ml of ethyl acetate was stirred for 1.5 hours at room temperature under hydrogen atmosphere. There action system was purged with nitrogen, then, the reaction solution was filtrated through Celite, and the filtrate was concentrated. The residue was subjected to silica gel column chromatography to obtain 0.16 g of 3-{2-chloro-4-fluoro-5-[3-methyl-2,6-dioxo-4-(trifluoromethyl)-1,2,3,6-tetrahydropyrimidin-1-yl]phenoxy}-2-carboxymethoxypyridine [present compound 7-6].

$^1$H-NMR(CDCl$_3$/300 MHz) δ(ppm): 3.50 (s, 3H), 4.92 (s, 2H), 6.32 (s, 1H), 6.80 (d, 1H, J=6.4 Hz), 6.95 (dd, 1H, J=7.7,4.9 Hz), 7.35 (dd, 1H, J=7.7,1.2 Hz), 7.37 (d, 1H, J=6.0 Hz), 7.93 (dd, 1H, J=4.9,1.2 Hz)

Production Example 32

Production of Present Compound 7-84

0.13 g of 1-[3-(dimethylamino)propyl]-3-ethylcarbodiimide hydrochloride was added to a mixture of 0.30 g of 3-{2-chloro-4-fluoro-5-[3-methyl-2,6-dioxo-4-(trifluoromethyl)-1,2,3,6-tetrahydropyrimidin-1-yl]phenoxy}-2-carboxymethoxypyridine [present compound 7-6], 56 mg of O-methylhydroxylamine hydrochloride, 68 mg of triethylamine and 2 ml of N,N-dimethylformamide at room temperature, and stirred for 2 hours. Then the mixture was poured into water and extracted with ethyl acetate. The organic layer was dried over anhydrous magnesium sulfate, and concentrated. The residue was subjected to silica gel column chromatography to obtain 90 mg of 3-{2-chloro-4-fluoro-5-[3-methyl-2,6-dioxo-4-(trifluoromethyl)-1,2,3,6-tetrahydropyrimidin-1-yl]phenoxy}-2-[(methoxyaminocarbonyl)methoxy]pyridine [present compound 7-84].

$^1$H-NMR(CDCl$_3$/300 MHz) δ(ppm): 3.52 (s, 3H), 3.74 (s, 3H), 4.87 (s, 2H), 6.32 (s, 1H), 6.71 (d, 1H, J=6.0 Hz), 6.99 (dd, 1H, J=7.6,5.0 Hz), 7.38 (dd, 1H, J=7.6,1.7 Hz), 7.44 (d, 1H, J=8.7 Hz), 8.00 (dd, 1H, J=5.0,1.7 Hz), 8.7–9.0 (bs, 1H)

Production Example 33

Production of Present Compound 7-119

0.13 g of 1-[3-(dimethylamino)propyl]-3-ethylcarbodiimide hydrochloride was added to a mixture of 0.30 g of 3-{2-chloro-4-fluoro-5-[3-methyl-2,6-dioxo-4-(trifluoromethyl)-1,2,3,6-tetrahydropyrimidin-1-yl]phenoxy}-2-carboxymethoxypyridine [present compound 7-6], 60 mg of methyl glycolate and 2 ml of N,N-dimethylformamide at room temperature, and stirred for 1.5 hours. Then the mixture was poured into water and extracted with ethyl acetate. The organic layer was dried over anhydrous magnesium sulfate, and concentrated. The residue was subjected to silica gel column chromatography to obtain 0.18 g of 3-{2-chloro-4-fluoro-5-[3-methyl-2,6-dioxo-4-(trifluoromethyl)-1,2,3,6-tetrahydropyrimidin-1-yl]phenoxy}-2-[(methoxycarbonyl)methoxycarbonylmethoxy]pyridine [present compound 7-119].

$^1$H-NMR(CDCl$_3$/300 MHz) δ(ppm): 3.50 (s, 3H), 3.74 (s, 3H), 4.65 (s, 2H), 5.01 (d, 1H, J=16.2 Hz), 5.09 (d, 1H, J=16.2 Hz), 6.28 (s, 1H), 6.88 (d, 1H, J=6.7 Hz), 6.93 (dd, 1H, J=7.8,4.9 Hz), 7.32 (dd, 1H, J=7.8,1.4 Hz), 7.37 (d, 1H, J=9.0 Hz), 7.93 (dd, 1H, J=4.9,1.4 Hz)

Production Example 34

Production of Present Compound 7-118

0.13 g of 1-[3-(dimethylamino)propyl]-3-ethylcarbodiimide hydrochloride was added to a mixture of 0.30 g of 3-{2-chloro-4-fluoro-5-[3-methyl-2,6-dioxo-4-(trifluoromethyl)-1,2,3,6-tetrahydropyrimidin-1-yl]phenoxy}-2-carboxymethoxypyridine [present compound 7-6], 49 mg of acetone oxime and 2 ml of N,N-dimethylformamide at room temperature, and stirred for 2 hours. Then the mixture was poured into water and extracted with ethyl acetate. The organic layer was dried over anhydrous magnesium sulfate, and concentrated. The residue was subjected to silica gel column chromatography to obtain 0.16 g of 3-{2-chloro-4-fluoro-5-[3-methyl-2,6-dioxo-4-(trifluoromethyl)-1,2,3,6-tetrahydropyrimidin-1-yl]phenoxy}-2-isopropylidenaminoxycarbonylmethoxypyridine [present compound 7-118].

$^1$H-NMR(CDCl$_3$/300 MHz) δ(ppm): 1.94 (s, 3H), 2.01 (s, 3H), 3.49 (s, 3H), 5.0–5.2 (m, 2H), 6.27 (s, 1H), 6.92 (dd, 1H, J=7.8,4.9 Hz), 6.98 (d, 1H, J=6.5 Hz), 7.3–7.4 (m, 2H), 7.92 (d, 1H, J=4.9 Hz)

Production Example 35

Production of the Present Compound 9-7

A solution of 0.5 g of 3-{2-amino-4-fluoro-5-[3-methyl-2,6-dioxo-4-(trifluoromethyl)-1,2,3,6-tetrahydropyrimidin-1-yl]phenoxy}-2-(methoxycarbonyl)methoxypyridine in 1.5 ml of acetonitrile was added to a mixture of 0.22 g of copper(I) bromide, 0.05 g of copper(II) bromide and 1 ml of acetonitrile at 0° C. A solution of 0.18 g of t-butyl nitrite in 1 ml of acetonitrile was added to the mixture dropwise over 30 minutes, then stirred at room temperature for 1 night. This reaction solution was poured into hydrochloric acid, and extracted with ethyl acetate. The organic layer was washed with saturated saline, dried over anhydrous magnesium sulfate, and concentrated. The residue was subjected to silica gel column chromatography to obtain 0.28 g of 3-{2-bromo-4-fluoro-5-[3-methyl-2,6-dioxo-4-(trifluoromethyl)-1,2,3,6-tetrahydropyrimidin-1-yl]phenoxy}-2-(methoxycarbonyl)methoxypyridine [present compound 9-7].

$^1$H-NMR(CDCl$_3$/300 MHz) δ(ppm): 3.50 (q, 3H, J=1.2 Hz), 3.70 (s, 3H), 4.8–5.0 (m, 2H), 6.29 (s, 1H), 6.88 (d, 1H, J=6.4 Hz), 6.93 (dd, 1H, J=7.8, 5.0 Hz), 7.32 (d, 1H, J=7.8 Hz), 7.53 (d, 1H, J=8.5 Hz), 7.92 (d, 1H, J=5.0 Hz)

Production Example 36

Production of the Present Compound 9-27

A mixture of 0.23 g of 3-{2-bromo-4-fluoro-5-[3-methyl-2,6-dioxo-4-(trifluoromethyl)-1,2,3,6-tetrahydropyrimidin-1-yl]phenoxy}-2-(methoxycarbonyl)methoxypyridine [present compound 9-7], 75 mg of copper cyanide and 2 ml of N-methyl-2-pyrrolidone was stirred at 160° C. for 2 hours. There action mixture was cooled to room temperature, water was added to the mixture and the resultant was extracted with ethyl acetate. The organic layer was dried over anhydrous magnesium sulfate, and concentrated. The residue was subjected to silica gel column chromatography to obtain 0.16 g of 3-{2-cyano-4-fluoro-5-[3-methyl-2,6-dioxo-4-(trifluoromethyl)-1,2,3,6-tetrahydropyrimidin-1-yl]phenoxy}-2-(methoxycarbonyl)methoxypyridine [present compound 9-27].

melting point: 173.1° C.

$^1$H-NMR(CDCl$_3$/300 MHz) δ(ppm): 3.49 (s, 3H), 3.67(s, 3H), 4.8–5.0 (m, 2H), 6.28 (s, 1H), 6.96 (d, 1H, J=5.7 Hz), 7.00 (dd, 1H, J=7.8,5.0 Hz), 7.50 (d, 1H, J=8.4 Hz), 7.54 (d, 1H, J=7.8 Hz), 8.01 (d, 1H, J=5.0 Hz)

Production Example 37

Production of the Present Compound 2-42

First Step 2.0 g of sodium hydride was added to a mixture of 9.65 g of 2,6-dichloro-3-nitropyridine, 5.41 g of benzyl alcohol and 30 ml of tetrahydrofuran 0° C. The mixture was stirred at 0° C. for 1.5 hours, then at room temperature for 1.5 hours. The reaction solution was poured into ice water, and extracted with ethyl acetate. The organic layer was washed with saturated saline, dried over anhydrous magnesium sulfate, and concentrated. The residue was subjected to silica gel column chromatography to obtain 10.93 g of 6-chloro-2-benzyloxy-3-nitropyridine.

$^1$H-NMR(CDCl$_3$/250 Hz) δ(ppm): 5.18 (s, 2H), 7.05 (d, 1H, J=8.3 Hz), 7.3–7.6(m, 5H), 8.28 (d, 1H, J=8.3 Hz)

Second Step

A mixture of 5.29 g of 6-chloro-2-benzyloxy-3-nitropyridine, 6.77 g of 2-chloro-4-fluoro-5-[3-methyl-2,6-dioxo-4-(trifluoromethyl)-1,2,3,6-tetrahydropyrimidin-1-yl]phenol, 3.32 g of potassium carbonate and 30 ml of N,N-dimethylformamide was stirred for 30 minutes at room temperature, then at 50° C. for 2.5 hours. The resulted residue was added to ice water, extracted with ethyl acetate, and organic layer was washed with saturated saline, dried over anhydrous magnesium sulfate, and concentrated. The residue was recrystallized from ethyl acetate and hexane to obtain 9.11 g of 6-{2-chloro-4-fluoro-5-[3-methyl-2,6-dioxo-4-(trifluoromethyl)-1,2,3,6-tetrahydropyrimidin-1-yl]phenoxy}-2-benzyloxy-3-nitropyridine.

$^1$H-NMR(CDCl$_3$/300 MHz) δ(ppm): 3.56(s, 3H), 5.29 (s, 2H), 6.37 (s, 1H), 6.68 (d, 1H, J=8.6 Hz), 7.1–7.4 (m, 6H), 7.37 (d, 1H, J=8.8 Hz), 8.47 (d, 1H, J=8.6 Hz)

Third Step

To a mixed solution of 3.0 g of an iron powder, 15 ml of acetic acid and 1.5 ml of water was added a solution of 3.0 g of 6-{2-chloro-4-fluoro-5-[3-methyl-2,6-dioxo-4-(trifluoromethyl)-1,2,3,6-tetrahydropyrimidin-1-yl]phenoxy}-2-benzyloxy-3-nitropyridine in 10 ml of acetic acid and 10 ml of ethyl acetate dropwise while maintaining the temperature of the reaction solution at 35° C. or lower. After completion of the addition, the mixture was stirred over night, then, the reaction solution was filtrated through Celite, and the solvent was removed at reduced pressure. The residue was diluted with saturated aqueous sodium bicarbonate solution, extracted with ethyl acetate. The organic layer was washed with saturated saline, dried over anhydrous magnesium sulfate, and concentrated. The resulted residue was subjected to silica gel chromatography to obtain 2.55 g of 3-amino-6-{2-chloro-4-fluoro-5-[3-methyl-2,6-dioxo-4-(trifluoromethyl)-1,2,3,6-tetrahydropyrimidin-1-yl]phenoxy}-2-benzyloxypyridine $^1$H-NMR(CDCl$_3$/300 MHz) δ(ppm): 3.51 (s, 3H), 3.60 (bs, 2H), 5.1–5.3 (m, 2H), 6.33 (s, 1H), 6.42 (d, 1H, J=7.9 Hz), 6.99 (d, 1H, J=8.2 Hz), 7.08 (d, 1H, J=6.7 Hz), 7.2–7.4 (m, 6H)

Fourth Step 1.38 g of boron trifluoride diethyl ether complex was added to a mixture of 2.55 g of 3-amino-6-{2-chloro-4-fluoro-5-[3-methyl-2,6-dioxo-4-(trifluoromethyl)-1,2,3,6-tetrahydropyrimidin-1-yl]phenoxy}-2-benzyloxypyridine, 6 ml of 1,2-dimethoxyethane and 2 ml of dichloromethane dropwise at –5° C. The mixture was stirred for 15 minutes at the same temperature, then, to the reaction solution was added 0.59 g of t-butyl nitrite dropwise at –5° C. The mixture was stirred for 1 hour at the same temperature, then, into the mixture was poured n-pentane. The solvent was removed by decantation. 15 ml of ethanol, and 2.3 g of zinc (dust) was added to the residue, and it was stirred at reflux temperature for 1.5 hour. The reaction solution was filtrated through Celite, and the solvent was distilled off, then, the resulted residue was subjected to silica gel chromatography to obtain 0.75 g of 2-{2-chloro-4-fluoro-5-[3-methyl-2,6-dioxo-4-(trifluoromethyl)-1,2,3,6-tetrahydropyrimidin-1-yl]phenoxy}-6-benzyloxypyridine.

$^1$H-NMR(CDCl$_3$/300 MHz) δ(ppm): 3.52 (s, 3H), 5.0–5.2 (m, 2H), 6.34 (s, 1H), 6.5–6.6 (m, 2H), 7.1–7.4 (m, 6H), 7.34 (d, 1H, J=9.1 Hz), 7.5–7.7 (m, 1H)

Fifth Step

A mixture of 0.90 g of 2-{2-chloro-4-fluoro-5-[3-methyl-2,6-dioxo-4-(trifluoromethyl)-1,2,3,6-tetrahydropyrimidin-1-yl]phenoxy}-6-benzyloxypyridine, 0.1 g of 10% palladium/carbon and 5 ml of ethyl acetate was stirred for 3 hours at room temperature under hydrogen atmosphere. The reaction system was purged with nitrogen, then, the reaction solution was filtrated through Celite, and the filtrate was concentrated. The residue was subjected to silica gel column chromatography to obtain 0.60 g of 6-{2-chloro-4-fluoro-5-[3-methyl-2,6-dioxo-4-(trifluoromethyl)-1,2,3,6-tetrahydropyrimidin-1-yl]phenoxy}-2-pyridone. $^1$H-NMR (CDCl$_3$/250 MHz) δ(ppm): 3.54 (s, 3H), 6.11 (d, 1H, J=7.9 Hz), 6.33 (s, 1H), 6.44 (d, 1H, J=7.8 Hz), 7.09 (d, 1H, J=6.7 Hz), 7.37 (d, 1H, J=8.9 Hz), 7.55 (dd, 1H, J=7.9,7.8 Hz)

Sixth Step

To a mixture of 50 mg of 6-{2-chloro-4-fluoro-5-[3-methyl-2,6-dioxo-4-(trifluoromethyl)-1,2,3,6-tetrahydropyrimidin-1-yl]phenoxy}-2-pyridone, 21 mg of methyl 2-bromopropionate and 1 ml of N,N-dimethylformamide was added 21 mg of potassium carbonate, and the mixture was stirred for 1 hour at 50° C. The solution was cooled to room temperature, poured into water, and extracted with ethyl acetate. The organic layer was washed with saturated saline, dried over anhydrous magnesium sulfate, and concentrated. The residue was subjected to silica gel column chromatography to obtain 72 mg of 2-{2-chloro-4-fluoro-5-[3-methyl-2,6-dioxo-4-(trifluoromethyl)-1,2,3,6-tetrahydropyrimidin-1-yl]phenoxy}-6-{1-(methoxycarbonyl)ethoxy}pyridine [present compound 2-42].

$^1$H-NMR(CDCl$_3$/300 MHz) δ(ppm): 1.48 (d, 3H, J=6.9 Hz), 3.55 (s, 3H), 3.60 (s, 3/2H), 3.61 (s, 3/2H), 5.10 (q, 1H, J=6.9 Hz), 5.12 (q, 1H, J=6.9 Hz), 6.34 (s, 1H), 6.55 (d, 1H, J=8.0 Hz), 6.56 (dd, 1H, J=7.9, 2.9 Hz), 7.14 (dd, 1H, J=6.9, 2.9 Hz), 7.37 (d, 1H, J=9.0 Hz), 7.62 (dd, 1H, J=7.9,6.9 Hz)

Production Example 38

Production of the Present Compound 1-67

To a mixture of 400 mg of 2-chloro-4-fluoro-5-[3-methyl-2,6-dioxo-4-(trifluoromethyl)-1,2,3,6-tetrahydropyrimidin-1-yl]aniline, 360 mg of 6-methoxy-4-(methoxycarbonyl)methoxy-2-methylsulfonylpyrimidine and 2 ml of N,N-dimethylformamide, 196 mg of potassium carbonate was added, and the mixture was stirred for 5 hours at 80° C. The reaction solution was cooled to room temperature, then, this reaction solution was poured into water, and extracted with ethyl acetate. The organic layer was washed with saturated saline, dried over anhydrous magnesium sulfate, and concentrated. The residue was subjected to silica gel column chromatography to obtain 98 mg of 2-{2-chloro-4-fluoro-5-[3-methyl-2,6-dioxo-4-(trifluoromethyl)-1,2,3,6-tetrahydropyrimidin-1-yl]phenylamino}-6-methoxy-4-(methoxycarbonyl)methoxypyrimidine [present compound 1-67].

$^1$H-NMR(CDCl$_3$/250 MHz) δ(ppm): 3.57 (s, 3H), 3.65 (s, 3H), 3.91 (s, 3H), 4.7–4.9 (m, 2H), 5.75 (s, 1H), 6.38 (s, 1H), 7.32 (d, 1H, J=8.8 Hz), 7.37 (bs, 1H), 8.37(d, 1H, J=7.3 Hz)

melting point: 155.6° C.

Production Example 39

Production of the Present Compound 2-52

A mixture of 1 g of 3-amino-2-{2-chloro-4-fluoro-5-[3-methyl-2,6-dioxo-4-(trifluoromethyl)-1,2,3,6-tetrahydropyrimidin-1-yl]phenoxy}pyridine and 1.16 g of methyl 2-bromopropionate was stirred for 30 minutes at 60° C., then for 4hours at 80° C. The mixture was subjected to silica gel column chromatography to obtain 0.4 g of 2-{2-chloro-4-fluoro-5-[3-methyl-2,6-dioxo-4-(trifluoromethyl)-1,2,3,6-tetrahydropyrimidin-1-yl]phenoxy}-3-{1-(methoxycarbonyl)ethylamino}pyridine[present compound 2-52].

melting point: 66.4° C.

Production Example 40

Production of the present compound 7-8
First Step 11 g of sodium hydride was added to a mixture of 39.63 g of 2-chloro-3-nitropyridine, 31.23 g of ethyl glycolate, 250 ml of tetrahydrofuran and 20 ml of N,N-dimethylformamide at 0° C. The mixture was stirred at room temperature for 5 hours, then, the reaction solution was poured into ice water, and extracted with ethyl acetate. The organic layer was dried over anhydrous magnesium sulfate, and concentrated. The residue was subjected to silica gel column chromatography to obtain 48.3 g of 2-(ethoxycarbonyl)methoxy-3-nitropyridine.

$^1$H-NMR(CDCl$_3$/300 MHz) δ(ppm): 1.26 (t, 3H, J=7.1 Hz), 4.23 (q, 2H, J=7.1 Hz), 5.06 (s, 2H), 7.0–7.2 (m, 1H), 8.3–8.4 (m, 2H)
Second Step A mixture of 48.3 g of 2-(ethoxycarbonyl)methoxy-3-nitropyridine, 7.8 g of 10% palladium/carbon and 540 ml of ethyl acetate was stirred for 3 hours at room temperature under hydrogen atmosphere. The reaction system was purged with nitrogen, then, the reaction solution was filtrated through Celite, and the filtrate was concentrated. The residue was subjected to silica gel column chromatography to obtain 37.1 g of 3-amino-2-(ethoxycarbonyl)methoxypyridine. $^1$H-NMR(CDCl$_3$/300 MHz) δ(ppm): 1.27 (t, 3H, J=7.1 Hz), 3.8–3.9 (b, 2H), 4.24 (q, 2H, J=7.1 Hz), 4.93 (s, 2H), 6.7–6.8 (m, 1H), 6.8–7.0 (m, 1H), 7.4–7.6(m, 1H)
Third Step 9.18 g of trifluoromethanesulfonic acid was added to a mixture of 12 g of 3-amino-2-(ethoxycarbonyl)methoxypyridine, 36 ml of 1,2-dimethoxyethane and 12 ml of dichloromethane dropwise at −5° C. The mixture was stirred for 10 minutes at the same temperature, then, to the reaction solution was added a solution of 7.57 g of t-butyl nitrite in 3 ml of 1,2-dimethoxyethane dropwise at −5° C. or lower. The mixture was stirred for 30 minutes at the same temperature, then, into the mixture was poured n-pentane. The lower layer of two separated layers was dissolved in 12 ml of acetic anhydride, and the mixture was stirred for 2.5 hours at 50° C. The reaction solution was poured into ice water, and extracted with t-butyl methyl ether. The organic layer was washed with saturated aqueous sodium bicarbonate solution, then, saturated saline, dried over anhydrous magnesium sulfate, and concentrated. The resulted residue was subjected to silica gel chromatography to obtain 4.2 g of 3-acetoxy-2-(ethoxycarbonyl)methoxypyridine.

$^1$H-NMR(CDCl$_3$/300 MHz) δ(ppm): 1.26 (t, 3H, J=7.1 Hz), 2.34 (s, 3H), 4.22 (q, 2H, J=7.1 Hz), 4.90 (s, 2H), 6.94 (dd, 1H, J=7.8, 5.0 Hz), 7.38 (dd, 1H, J=7.8, 1.5 Hz), 7.97 (dd, 1H, J=5.0,1.5 Hz)
Fourth Step A mixture of 13.8 g of 3-acetoxy-2-(ethoxycarbonyl)methoxypyridine, 4.38 g of potassium carbonate and 60 ml of ethanol was stirred for over night at room temperature. The reaction solution was poured into a mixture of water, sodium chloride and hydrochloric acid, and extracted with ethyl acetate. The organic layer was washed with saturated saline, dried over anhydrous magnesium sulfate, and concentrated. The residue was subjected to silica gel column chromatography to obtain 10.45 g of 3-hydroxy-2-(ethoxycarbonyl)methoxypyridine.

$^1$H-NMR(CDCl$_3$/250 MHz) δ(ppm): 1.28 (t, 3H, J=7.1 Hz), 4.25 (q, 2H, J=7.1 Hz), 4.97 (s, 2H), 5.93 (s, 1H), 6.86 (dd, 1H, J=7.7, 4.9 Hz), 7.17 (dd, 1H, J=7.7,1.6 Hz), 7.65 (dd, 1H, J=4.9,1.6 Hz)
Fifth Step To a mixture of 10.45 g of 3-hydroxy-2-(ethoxycarbonyl)methoxypyridine, 16.92 g of 2,5-difluoro-4-[3-methyl-2,6-dioxo-4-(trifluoromethyl)-1,2,3,6-tetrahydropyrimidin-1-yl]nitrobenzene and 100 ml of N,N-dimethylformamide was added 7.32 g of potassium carbonate, and the mixture was stirred for 2 hours at 70° C. The solution was cooled to room temperature, poured into a mixture of ice water, sodium chloride and hydrochloric acid, and extracted with ethyl acetate. The organic layer was washed with saturated saline, dried over anhydrous magnesium sulfate, and concentrated. The residue was subjected to silica gel column chromatography to obtain 17.28 g of 3-{4-fluoro-5-[3-methyl-2,6-dioxo-4-(trifluoromethyl)-1,2,3,6-tetrahydropyrimidin-1-yl]-2-nitrophenoxy}-2-(ethoxycarbonyl)methoxypyridine [present compound 9-46].

$^1$H-NMR(CDCl$_3$/300 MHz) δ(ppm): 1.25 (t, 3H, J=7.3 Hz), 3.50 (s, 3H), 4.12 (q, 2H, J=7.3 Hz), 4.85 (d, 1H, J=15.9 Hz), 4.95 (d, 1H, J=15.9H), 6.28 (s, 1H), 6.98 (dd, 1H, J=7.8, 5.0 Hz), 7.13 (d, 1H, J=6.1 Hz), 7.50 (dd, 1H, J=7.8, 1.4 Hz), 7.87 (d, 1H, J=8.6 Hz), 7.99 (dd, 1H, J=5.0, 1.4 Hz)
Sixth Step To a mixture of 17 g of an iron powder, 30 ml of acetic acid and 3 ml of water was added a solution of 17.28 g of 3-{4-fluoro-5-[3-methyl-2,6-dioxo-4-(trifluoromethyl)-1,2,3,6-tetrahydropyrimidin-1-yl]-2-nitrophenoxy}-2-(ethoxycarbonyl)methoxypyridine [present compound 9-46] in 20 ml of acetic acid dropwise while maintaining the temperature of the reaction solution at 35° C. or lower. After completion of the addition, the mixture was stirred for 1 hour at room temperature, for 3 hours at 40° C., then, the reaction solution was filtrated through Celite, and diluted with ethyl acetate. The mixture was neutralized with saturated aqueous sodium bicarbonate solution, the organic layer was washed with saturated saline, dried over anhydrous magnesium sulfate, and concentrated. Then, the resulted residue was subjected to silica gel column chromatography to obtain 15.46 g of 3-{2-amino-4-fluoro-5-[3-methyl-2,6-dioxo-4-(trifluoromethyl)-1,2,3,6-tetrahydropyrimidin-1-yl]phenoxy}-2-(ethoxycarbonyl)methoxypyridine.

$^1$H-NMR(CDCl$_3$/250 MHz) δ(ppm): 1.27 (t, 3H, J=7.1 Hz), 3.52 (q, 3H, J=1.2 Hz), 4.21 (q, 2H, J=7.1 Hz), 4.27 (bs, 2H), 4.9–5.1 (m, 2H), 6.31 (s, 1H), 6.63 (d, 1H, J=10.9 Hz), 6.79 (d, 1H, J=6.9 Hz), 6.86 (dd, 1H, J=7.8, 4.9 Hz), 7.23 (dd, 1H, J=7.8, 1.5 Hz), 7.83 (dd, 1H, J=4.9,1.5 Hz)

Seventh Step

A solution of 10.99 g of isoamyl nitrite in 10 ml of acetonitrile was added to a mixture of 15.46 g of 3-{2-amino-4-fluoro-5-[3-methyl-2,6-dioxo-4-(trifluoromethyl)-1,2,3,6-tetrahydropyrimidin-1-yl]phenoxy}-2-(ethoxycarbonyl)methoxypyridine, 6.19 g of copper(I) chloride, 12.61 g of copper(II) chloride and 120 ml of acetonitrile dropwise at room temperature, and the mixture was stirred for 3 hours. This reaction solution was poured into a mixture of ice and hydrochloric acid, and extracted with ethyl acetate. The organic layer was washed with saturated saline, dried over anhydrous magnesium sulfate, and concentrated. The residue was subjected to silica gel column chromatography to obtain 13.16 g of 3-{2-chloro-4-fluoro-5-[3-methyl-2,6-dioxo-4-(trifluoromethyl)-1,2,3,6-tetrahydropyrimidin-1-yl]phenoxy)-2-(ethoxycarbonyl)methoxypyridine [present compound 7-8].

Intermediate Production Example 9

Production of 3-{2-chloro-4-fluoro-5-[2,6-dioxo-4-(trifluoromethyl)-1,2,3,6-tetrahydropyrimidin-1-yl]phenoxy}-2-(methoxycarbonyl)methoxypyridine First Step Into a solution of 227 mg of triphosgene in 8 ml of ethyl acetate, a solution of 155 mg of triethylamine and 250 mg of 4-chloro-2-fluoro-5-{2-(methoxycarbonyl)methoxy-3-pyridyloxy}aniline in 8 ml of ethyl acetate was added at 0° C. The mixture was stirred for 30 minutes at the same temperature, then for 2 hours at reflux temperature. The reaction solution was filterated while it was hot, and the solvent was distilled off under reduced pressure to obtain 266 mg of 4-chloro-2-fluoro-5-{2-(methoxycarbonyl)methoxy-3-pyridyloxy}phenyl isocyanate.

melting point: 113.8° C.

$^1$H-NMR(CDCl$_3$/300 MHz) δ(ppm): 3.76 (s, 3H), 4.96 (s, 2H), 6.69 (d, 1H, J=7.1 Hz), 6.93 (dd, 1H, J=7.8, 5.0 Hz), 7.2–7.3 (m, 2H), 7.94 (dd, 1H, J=5.0,1.4 Hz)

The following are similarly prepared:
4-chloro-2-fluoro-5-{2-(ethoxycarbonyl)methoxy-3-pyridyloxy}phenyl isocyanate.
4-chloro-2-fluoro-5-[2-{1-(methoxycarbonyl}ethoxy}-3-pyridyloxy]phenyl isocyanate.
4-chloro-2-fluoro-5-[2-{1-(ethoxycarbonyl)ethoxy}-3-pyridyloxy]phenyl isocyanate.

Second Step

To a mixture of 1 ml of N,N-dimethylformamide and 26 mg of sodium hydride, a solution of 126 mg of ethyl 3-amino-4,4,4-trifluorocrotonate in 1 ml of N,N-dimethylformamide was added and the mixture was stirred at 0° C. Thereafter, to the reaction mixture was added a mixture of 266 mg of 4-chloro-2-fluoro-5-{2-(methoxycarbonyl)methoxy-3-pyridyloxy}phenyl isocyanate and 1 ml of N,N-dimethylformamide at the same temperature, and the mixture was stirred over night at room temperature. The reaction solution was poured into a mixture of hydrochloric acid and ice water, and to obtain 3-{2-chloro-4-fluoro-5-[2,6-dioxo-4-(trifluoromethyl)-1,2,3,6-tetrahydropyrimidin-1-yl]phenoxy}-2-(methoxycarbonyl)methoxypyridine.

Production Example 41

Production of the Present Compound 10-2

First Step

To a mixture of 24 g of sodium hydride and 500 ml of tetrahydrofuran, 65 g of benzyl alcohol was added dropwise at room temperature. The mixture was stirred until the evolution of hydrogen stopped, cooled to –50° C., then, 100 g of 3,4-dichloro-1,2,5-thiadiazole was added to the mixture. The mixture was stirred over night at room temperature, and for 3 hours at reflux temperature. The mixture was concentrated, then poured into dilute hydrochloric acid, extracted with t-butyl methyl ether. The organic layer was washed with water, then, saturated saline, dried over anhydrous magnesium sulfate, and concentrated. The residue was subjected to silica gel column chromatography to obtain 33 g of 4-benzyloxy-3-chloro-1,2,5-thiadiazole (purity: 72%).

$^1$H-NMR(CDCl$_3$/300 MHz) δ(ppm): 5.43 (s, 2H), 7.2–7.5 (m, 5H)

Second Step

To a solution of 0.60 g of 2-chloro-4-fluoro-5-[3-methyl-2,6-dioxo-4-(trifluoromethyl)-1,2,3,6-tetrahydropyrimidin-1-yl]phenol and 0.50 g of 4-benzyloxy-3-chloro-1,2,5-thiadiazole in 8 ml of dimethyl sulfoxide, 0.25 g of potassium carbonate was added, and stirred for 30 minutes at 50° C., and for 3 hours at 100° C. The reaction solution was poured into dilute hydrochloric acid, and extracted with ethyl acetate. The organic layer was washed with water, then, saturated saline, dried over anhydrous magnesium sulfate, and concentrated. The residue was subjected to silica gel column chromatography to obtain 0.27 g of 4-benzyloxy-3-{2-chloro-4-fluoro-5-[3-methyl-2,6-dioxo-4-(trifluoromethyl)-1,2,3,6-tetrahydropyrimidin-1-yl]phenoxy}-1,2,5-thiadiazole (purity: 44%)

Third Step

A solution of 2.5 g of crude product of 4-benzyloxy-3-{2-chloro-4-fluoro-5-[3-methyl-2,6-dioxo-4-(trifluoromethyl)-1,2,3,6-tetrahydropyrimidin-1-yl]phenoxy}-1,2,5-thiadiazole in 20 ml of trifluoroacetic acid was stirred over night at room temperature. The solution was concentrated, and the residue was subjected to silica gel column chromatography to obtain 0.50 g of 3-{2-chloro-4-fluoro-5-[3-methyl-2,6-dioxo-4-(trifluoromethyl)-1,2,3,6-tetrahydropyrimidin-1-yl]phenoxy}-4-hydroxy-1,2,5-thiadiazole.

$^1$H-NMR(CDCl$_3$/300 MHz) δ(ppm):3.56 (s, 3H), 6.38 (s, 1H), 7.3–7.5 (m, 2H)

Fourth Step 200 mg of 3-{2-chloro-4-fluoro-5-[3-methyl-2,6-dioxo-4-(trifluoromethyl)-1,2,3,6-tetrahydropyrimidin-1-yl]phenoxy}-4-hydroxy-1,2,5-thiadiazole and 150 mg of methyl 2-bromopropionate were dissolved in 10 ml of N,N-dimethylformamide, to this was added 100 mg of potassium carbonate, and the mixture was stirred for 3 hours at room temperature. This reaction solution was poured into dilute hydrochloric acid, and extracted with ethyl acetate. The organic layer was washed with water, then, saturated saline, dried over anhydrous magnesium sulfate, and concentrated. The residue was subjected to silica gel column chromatography to obtain 0.17 g of 3-{2-chloro-4-fluoro-5-[3-methyl-2,6-dioxo-4-(trifluoromethyl)-1,2,3,6-tetrahydropyrimidin-1-yl]phenoxy}-4-[1-(methoxycarbonyl)ethoxyl]-1,2,5-thiadiazole [present compound 10-2].

$^1$H-NMR(CDCl$_3$/300 MHz) δ(ppm): 1.70 (d, 3H, J=6.9 Hz), 3.55 (s, 3H), 3.79 (s, 3H), 5.31 (q, 1H, J=6.9 Hz), 6.36 (s, 1H), 7.3–7.5 (m, 2H)

Production Example 42

Production of the Present Compound 10-7

200 mg of 3-{2-chloro-4-fluoro-5-[3-methyl-2,6-dioxo-4-(trifluoromethyl)-1,2,3,6-tetrahydropyrimidin-1-yl]phenoxy}-4-hydroxy-1,2,5-thiadiazole and 150 mg of methyl bromoacetate were dissolved in 10 ml of N,N-dimethylformamide, to this was added 100 mg of potassium carbonate, and the mixture was stirred for 3 hours at room temperature. This reaction solution was poured into dilute hydrochloric acid, and extracted with ethyl acetate. The organic layer was washed with water, then, saturated saline, dried over anhydrous magnesium sulfate, and concentrated. Then, the resulted residue was washed with hexane to obtain 0.18 g of 3-{2-chloro-4-fluoro-5-[3-methyl-2,6-dioxo-4-(trifluoromethyl)-1,2,3,6-tetrahydropyrimidin-1-yl]phenoxy}-4-(methoxycarbonyl)methoxy-1,2,5-thiadiazole [present compound 10-7].

$^1$H-NMR(CDCl$_3$/300 MHz) δ(ppm): 3.56 (s, 3H), 3.81 (s, 3H), 5.01 (s, 2H), 6.36 (s, 1H), 7.3–7.5 (m, 2H)

Production Example 43

Production of the Present Compound 3-52

First Step

To a mixture of 0.098 g of sodium hydride and N,N-dimethylformamide, 0.829 g of 2-chloro-4-fluoro-5-[3-methyl-2,6-dioxo-4-(trifluoromethyl)-1,2,3,6-tetrahydropyrimidin-1-yl]phenol was added and stirred at room temperature for 2 hours. Then 5-benzyloxy-4-chloropyrimidine (yielded as follows: A mixture of 0.495 g of 5-benzyloxy-4-pyrimidinone and 10 ml of phosphoryl chloride was stirred for 30 minutes at reflux temperature, then the mixture was cooled to room temperature, and concentrated. Ice water was added to the residue, extracted with ether and concentrated.) was added to the mixture, and stirred for 1 hour at room temperature, and for 1 hour at 60–70° C. The mixture was poured into saturated ammonium chloride solution, and extracted with ethyl acetate. The organic layer was washed with saturated ammonium chloride solution, water, 20% aqueous potassium carbonate solution, water, dilute hydrochloric acid and saturated saline, dried over anhydrous magnesium sulfate, and concentrated. The residue was subjected to silica gel column chromatography to obtain 0.959 g of 5-benzyloxy-4-{2-chloro-4-fluoro-5-[3-methyl-2,6-dioxo-4-(trifluoromethyl)-1,2,3,6-tetrahydropyrimidin-1-yl]phenoxy}pyrimidine.

melting point: 58.6° C.

Second Step

A mixture of 0.959 g of 5-benzyloxy-4-{2-chloro-4-fluoro-5-[3-methyl-2,6-dioxo-4-(trifluoromethyl)-1,2,3,6-tetrahydropyrimidin-1-yl]phenoxy}pyrimidine, 10% palladium/carbon and ethyl acetate was stirred for 8 hours at room temperature under hydrogen atmosphere. The reaction system was purged with nitrogen, then, the reaction solution was filtrated through Celite, and the filtrate was concentrated to obtain 0.824 g of 4-{2-chloro-4-fluoro-5-[3-methyl-2,6-dioxo-4-(trifluoromethyl)-1,2,3,6-tetrahydropyrimidin-1-yl]phenoxy}-5-hydroxypyrimidine.

melting point: 190.7° C.

Third Step

To a mixture of 32 mg of Sodium hydride and N,N-dimethylformamide, 0.35 g of 4-{2-chloro-4-fluoro-5-[3-methyl-2,6-dioxo-4-(trifluoromethyl)-1,2,3,6-tetrahydropyrimidin-1-yl]phenoxy}-5-hydroxypyrimidine was added and stirred at room temperature for 1 hour. Then 0.135 g of methyl2-bromopropionate was added to the mixture, and stirred for 2 hours at room temperature, then for 1 hour at 50° C. The mixture was poured into saturated ammonium chloride solution, and extracted with ethyl acetate. The organic layer was washed with saturated ammonium chloride solution and saturated saline, dried over anhydrous magnesium sulfate, and concentrated. The residue was subjected to silica gel column chromatography to obtain 0.319 g of 4-{2-chloro-4-fluoro-5-[3-methyl-2,6-dioxo-4-(trifluoromethyl)-1,2,3,6-tetrahydropyrimidin-1-yl]phenoxy}-5-{1-(methoxycarbonyl)ethoxy}pyrimidine [present compound 3-52].

$^1$H-NMR(CDCl$_3$/300 MHz) δ(ppm): 1.71 (d, 3H, J=6.8 Hz), 3.57 (d, 3H, J=0.9 Hz), 3.78 (s, 3H), 5.01 (q, 1H, J=6.8 Hz), 6.37 (s, 1H), 7.24 (d, 1H, J=6.7 Hz), 7.42 (d, 1H, J=8.7 Hz), 8.32 (s, 1H), 8.40 (s, 1H)

Production Example 44

Production of the Present Compound 3-57

To a mixture of 32 mg of Sodium hydride and N,N-dimethylformamide, 0.35 g of 4-{2-chloro-4-fluoro-5-[3-methyl-2,6-dioxo-4-(trifluoromethyl)-1,2,3,6-tetrahydropyrimidin-1-yl]phenoxy}-5-hydroxypyrimidine was added and stirred at room temperature for 1 hour. Then 0.124 g of methyl bromoacetate was added to the mixture, and stirred for 2 hours at room temperature, then for 1 hour at 50° C. The mixture was poured into saturated ammonium chloride solution, and extracted with ethyl acetate. The organic layer was washed with saturated ammonium chloride solution and saturated saline, dried over anhydrous magnesium sulfate, and concentrated. The residue was subjected to silica gel column chromatography to obtain 0.328 g of 4-{2-chloro-4-fluoro-5-[3-methyl-2,6-dioxo-4-(trifluoromethyl)-1,2,3,6-tetrahydropyrimidin-1-yl]phenoxy}-5-(methoxycarbonyl)methoxypyrimidine [present compound 3-57].

melting point: 62.5° C.

Production Example 45

Production of the Present Compound 1-7

First Step 2.6 g of 2-chloro-4-fluoro-5-[3-methyl-2,6-dioxo-4-(trifluoromethyl)-1,2,3,6-tetrahydropyrimidin-1-yl]phenol and 1.7 g of 4-benzyloxy-2-chloropyrimidine were dissolved in 20 ml of N,N-dimethylformamide, to this solution was added 1.07 g of potassium carbonate, and the mixture was stirred for 2 hours at 80° C. The reaction solution was cooled to room temperature, then, this reaction solution was poured into ice water, and extracted with ethyl acetate. The organic layer was washed with 10% aqueous sodium hydroxide solution, dried over anhydrous magnesium sulfate, and concentrated to obtain 1.6 g of 4-benzyloxy-2-{2-chloro-4-fluoro-5-[3-methyl-2,6-dioxo-4-(trifluoromethyl)-1,2,3,6-tetrahydropyrimidin-1-yl]phenoxy}pyrimidine.

Second Step

A solution of 1 g of 4-benzyloxy-2-{2-chloro-4-fluoro-5-[3-methyl-2,6-dioxo-4-(trifluoromethyl)-1,2,3,6-tetrahydropyrimidin-1-yl]phenoxy}pyrimidine in trifluoroacetic acid was stirred for 2 hours at 70° C. This reaction solution was cooled to room temperature, then, poured into water, and filterated to obtain 0.3 g of 2-{2-chloro-4-fluoro-5-[3-methyl-2,6-dioxo-4-(trifluoromethyl)-1,2,3,6-tetrahydropyrimidin-1-yl]phenoxy}-4-hydroxy-pyrimidine.

Third Step 30 mg of sodium hydride was added to a mixture of 0.3 g of 2-{2-chloro-4-fluoro-5-[3-methyl-2,6-dioxo-4-

(trifluoromethyl)-1,2,3,6-tetrahydropyrimidin-1-yl]phenoxy}-4-hydroxy-pyrimidine, 127 mg of methyl bromoacetate and N,N-dimethylformamide at 0° C., then, the mixture was stirred at room temperature. The solution was poured into a mixture of ice water, and extracted with ethyl acetate. The organic layer was dried over anhydrous magnesium sulfate, and concentrated. The residue was subjected to silica gel column chromatography to obtain 0.2 g of 2-{2-chloro-4-fluoro-5-[3-methyl-2,6-dioxo-4-(trifluoromethyl)-1,2,3,6-tetrahydropyrimidin-1-yl]phenoxy}-4-(methoxycarbonyl)methoxypyrimidine [present compound 1-7].

$^1$H-NMR(CDCl$_3$/300 MHz) δ(ppm): 3.56 (d, 3H, J=1.1 Hz), 3.73 (s, 3H), 4.85 (s, 2H), 6.35 (s, 1H), 6.63 (d, 1H, J=5.6 Hz), 7.18 (d, 1H, J=6.9 Hz), 7.38 (d, 1H, J=9.1 Hz), 8.30 (d, 1H, J=5.7 Hz)

Next, some of present compounds are exemplified in Tables 1 to 10 together with compound numbers, but do not limit the scope of the present compound.

TABLE 1

Compound of the formula [I-1]:

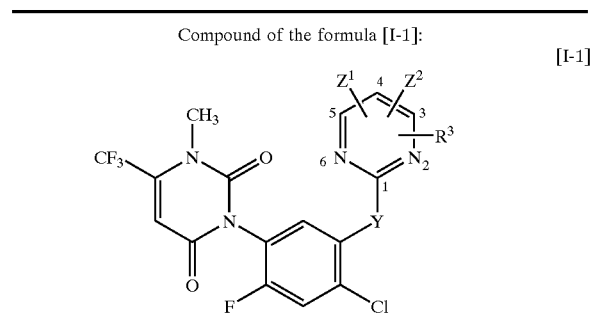

| Compound No. | Y | $Z^1$ | $Z^2$ | $R^3$ |
|---|---|---|---|---|
| 1-1 | O | H | H | 3-OCH(CH$_3$)CO$_2$H |
| 1-2 | O | H | H | 3-OCH(CH$_3$)CO$_2$CH$_3$ |
| 1-3 | O | H | H | 3-OCH(CH$_3$)CO$_2$CH$_2$CH$_3$ |
| 1-4 | O | H | H | 3-OCH(CH$_3$)CO$_2$CH(CH$_3$)$_2$ |
| 1-5 | O | H | H | 3-OCH(CH$_3$)CO$_2$CH$_2$CH=CH$_2$ |
| 1-6 | O | H | H | 3-OCH$_2$CO$_2$H |
| 1-7 | O | H | H | 3-OCH$_2$CO$_2$CH$_3$ |
| 1-8 | O | H | H | 3-OCH$_2$CO$_2$CH$_2$CH$_3$ |
| 1-9 | O | H | H | 3-OCH$_2$CO$_2$CH(CH$_3$)$_2$ |
| 1-10 | O | H | H | 3-OCH$_2$CO$_2$CH$_2$CH=CH$_2$ |
| 1-11 | O | H | H | 4-OCH(CH$_3$)CO$_2$H |
| 1-12 | O | H | H | 4-OCH(CH$_3$)CO$_2$CH$_3$ |
| 1-13 | O | H | H | 4-OCH(CH$_3$)CO$_2$CH$_2$CH$_3$ |
| 1-14 | O | H | H | 4-OCH(CH$_3$)CO$_2$CH(CH$_3$)$_2$ |
| 1-15 | O | H | H | 4-OCH(CH$_3$)CO$_2$CH$_2$CH=CH$_2$ |
| 1-16 | O | H | H | 4-OCH$_2$CO$_2$H |
| 1-17 | O | H | H | 4-OCH$_2$CO$_2$CH$_3$ |
| 1-18 | O | H | H | 4-OCH$_2$CO$_2$CH$_2$CH$_3$ |
| 1-19 | O | H | H | 4-OCH$_2$CO$_2$CH(CH$_3$)$_2$ |
| 1-20 | O | H | H | 4-OCH$_2$CO$_2$CH$_2$CH=CH$_2$ |
| 1-21 | O | H | H | 3-SCH(CH$_3$)CO$_2$H |
| 1-22 | O | H | H | 3-SCH(CH$_3$)CO$_2$CH$_3$ |
| 1-23 | O | H | H | 3-SCH(CH$_3$)CO$_2$CH$_2$CH$_3$ |
| 1-24 | O | H | H | 3-SCH(CH$_3$)CO$_2$CH(CH$_3$)$_2$ |
| 1-25 | O | H | H | 3-SCH(CH$_3$)CO$_2$CH$_2$CH=CH$_2$ |
| 1-26 | O | H | H | 3-SCH$_2$CO$_2$H |
| 1-27 | O | H | H | 3-SCH$_2$CO$_2$CH$_3$ |
| 1-28 | O | H | H | 3-SCH$_2$CO$_2$CH$_2$CH$_3$ |
| 1-29 | O | H | H | 3-SCH$_2$CO$_2$CH(CH$_3$)$_2$ |
| 1-30 | O | H | H | 3-SCH$_2$CO$_2$CH$_2$CH=CH$_2$ |
| 1-31 | O | H | H | 4-SCH(CH$_3$)CO$_2$H |
| 1-32 | O | H | H | 4-SCH(CH$_3$)CO$_2$CH$_3$ |
| 1-33 | O | H | H | 4-SCH(CH$_3$)CO$_2$CH$_2$CH$_3$ |
| 1-34 | O | H | H | 4-SCH(CH$_3$)CO$_2$CH(CH$_3$)$_2$ |
| 1-35 | O | H | H | 4-SCH(CH$_3$)CO$_2$CH$_2$CH=CH$_2$ |
| 1-36 | O | H | H | 4-SCH$_2$CO$_2$H |
| 1-37 | O | H | H | 4-SCH$_2$CO$_2$CH$_3$ |
| 1-38 | O | H | H | 4-SCH$_2$CO$_2$CH$_2$CH$_3$ |
| 1-39 | O | H | H | 4-SCH$_2$CO$_2$CH(CH$_3$)$_2$ |
| 1-40 | O | H | H | 4-SCH$_2$CO$_2$CH$_2$CH=CH$_2$ |
| 1-41 | O | 5-OCH$_3$ | H | 3-OCH(CH$_3$)CO$_2$H |
| 1-42 | O | 5-OCH$_3$ | H | 3-OCH(CH$_3$)CO$_2$CH$_3$ |
| 1-43 | O | 5-OCH$_3$ | H | 3-OCH(CH$_3$)CO$_2$CH$_2$CH$_3$ |
| 1-44 | O | 5-OCH$_3$ | H | 3-OCH$_2$CO$_2$H |
| 1-45 | O | 5-OCH$_3$ | H | 3-OCH$_2$CO$_2$CH$_3$ |
| 1-46 | O | 5-OCH$_3$ | H | 3-OCH$_2$CO$_2$CH$_2$CH$_3$ |
| 1-47 | O | H | H | 4-NHCH$_2$CO$_2$H |
| 1-48 | O | H | H | 4-NHCH$_2$CO$_2$CH$_2$CH$_3$ |
| 1-49 | O | H | H | 4-NHCH$_2$CO$_2$CH(CH$_3$)$_2$ |
| 1-50 | O | H | H | 4-NHCH$_2$CO$_2$CH$_2$CH=CH$_2$ |
| 1-51 | O | H | H | 3-NHCH(CH$_3$)CO$_2$H |
| 1-52 | O | H | H | 3-NHCH(CH$_3$)CO$_2$CH$_3$ |
| 1-53 | O | H | H | 3-NHCH(CH$_3$)CO$_2$CH$_2$CH$_3$ |
| 1-54 | O | H | H | 3-NHCH(CH$_3$)CO$_2$CH(CH$_3$)$_2$ |
| 1-55 | O | H | H | 3-NHCH(CH$_3$)CO$_2$CH$_2$CH=CH$_2$ |
| 1-56 | O | H | H | 3-NHCH$_2$CO$_2$H |
| 1-57 | O | H | H | 3-NHCH$_2$CO$_2$CH$_3$ |
| 1-58 | O | H | H | 3-NHCH$_2$CO$_2$CH$_2$CH$_3$ |
| 1-59 | O | H | H | 3-NHCH$_2$CO$_2$CH(CH$_3$)$_2$ |
| 1-60 | O | H | H | 3-NHCH$_2$CO$_2$CH$_2$CH=CH$_2$ |
| 1-61 | O | H | H | 4-NHCH(CH$_3$)CO$_2$H |
| 1-62 | O | H | H | 4-NHCH(CH$_3$)CO$_2$CH$_3$ |
| 1-63 | O | H | H | 4-NHCH(CH$_3$)CO$_2$CH$_2$CH$_3$ |
| 1-64 | O | H | H | 4-NHCH(CH$_3$)CO$_2$CH(CH$_3$)$_2$ |
| 1-65 | O | H | H | 4-NHCH(CH$_3$)CO$_2$CH$_2$CH=CH$_2$ |
| 1-66 | O | H | H | 4-NHCH$_2$CO$_2$H |
| 1-67 | NH | 5-OCH$_3$ | H | 3-OCH$_2$CO$_2$CH$_3$ |

TABLE 2

Compound of the formula [I-2]:

| Compound No. | $Z^1$ | $Z^2$ | $R^3$ |
|---|---|---|---|
| 2-1 | H | H | 2-OCH(CH$_3$)CO$_2$H |
| 2-2 | H | H | 2-OCH(CH$_3$)CO$_2$CH$_3$ |
| 2-3 | H | H | 2-OCH(CH$_3$)CO$_2$CH$_2$CH$_3$ |
| 2-4 | H | H | 2-OCH(CH$_3$)CO$_2$CH(CH$_3$)$_2$ |
| 2-5 | H | H | 2-OCH(CH$_3$)CO$_2$CH$_2$CH=CH$_2$ |
| 2-6 | H | H | 2-OCH$_2$CO$_2$H |
| 2-7 | H | H | 2-OCH$_2$CO$_2$CH$_3$ |

TABLE 2-continued

Compound of the formula [I-2]: [I-2]

| Compound No. | $Z^1$ | $Z^2$ | $R^3$ |
|---|---|---|---|
| 2-8 | H | H | 2-OCH$_2$CO$_2$CH$_2$CH$_3$ |
| 2-9 | H | H | 2-OCH$_2$CO$_2$CH(CH$_3$)$_2$ |
| 2-10 | H | H | 2-OCH$_2$CO$_2$CH$_2$CH=CH$_2$ |
| 2-11 | H | H | 4-OCH(CH$_3$)CO$_2$H |
| 2-12 | H | H | 4-OCH(CH$_3$)CO$_2$CH$_3$ |
| 2-13 | H | H | 4-OCH(CH$_3$)CO$_2$CH$_2$CH$_3$ |
| 2-14 | H | H | 4-OCH(CH$_3$)CO$_2$CH(CH$_3$)$_2$ |
| 2-15 | H | H | 4-OCH(CH$_3$)CO$_2$CH$_2$CH=CH$_2$ |
| 2-16 | H | H | 4-OCH$_2$CO$_2$H |
| 2-17 | H | H | 4-OCH$_2$CO$_2$CH$_3$ |
| 2-18 | H | H | 4-OCH$_2$CO$_2$CH$_2$CH$_3$ |
| 2-19 | H | H | 4-OCH$_2$CO$_2$CH(CH$_3$)$_2$ |
| 2-20 | H | H | 4-OCH$_2$CO$_2$CH$_2$CH=CH$_2$ |
| 2-21 | H | H | 2-SCH(CH$_3$)CO$_2$H |
| 2-22 | H | H | 2-SCH(CH$_3$)CO$_2$CH$_3$ |
| 2-23 | H | H | 2-SCH(CH$_3$)CO$_2$CH$_2$CH$_3$ |
| 2-24 | H | H | 2-SCH(CH$_3$)CO$_2$CH(CH$_3$)$_2$ |
| 2-25 | H | H | 2-SCH(CH$_3$)CO$_2$CH$_2$CH=CH$_2$ |
| 2-26 | H | H | 2-SCH$_2$CO$_2$H |
| 2-27 | H | H | 2-SCH$_2$CO$_2$CH$_3$ |
| 2-28 | H | H | 2-SCH$_2$CO$_2$CH$_2$CH$_3$ |
| 2-29 | H | H | 2-SCH$_2$CO$_2$CH(CH$_3$)$_2$ |
| 2-30 | H | H | 2-SCH$_2$CO$_2$CH$_2$CH=CH$_2$ |
| 2-31 | H | H | 4-SCH(CH$_3$)CO$_2$H |
| 2-32 | H | H | 4-SCH(CH$_3$)CO$_2$CH$_3$ |
| 2-33 | H | H | 4-SCH(CH$_3$)CO$_2$CH$_2$CH$_3$ |
| 2-34 | H | H | 4-SCH(CH$_3$)CO$_2$CH(CH$_3$)$_2$ |
| 2-35 | H | H | 4-SCH(CH$_3$)CO$_2$CH$_2$CH=CH$_2$ |
| 2-36 | H | H | 4-SCH$_2$CO$_2$H |
| 2-37 | H | H | 4-SCH$_2$CO$_2$CH$_3$ |
| 2-38 | H | H | 4-SCH$_2$CO$_2$CH$_2$CH$_3$ |
| 2-39 | H | H | 4-SCH$_2$CO$_2$CH(CH$_3$)$_2$ |
| 2-40 | H | H | 4-SCH$_2$CO$_2$CH$_2$CH=CH$_2$ |
| 2-41 | H | H | 5-OCH(CH$_3$)CO$_2$H |
| 2-42 | H | H | 5-OCH(CH$_3$)CO$_2$CH$_3$ |
| 2-43 | H | H | 5-OCH(CH$_3$)CO$_2$CH$_2$CH$_3$ |
| 2-44 | H | H | 5-OCH$_2$CO$_2$H |
| 2-45 | H | H | 5-OCH$_2$CO$_2$CH$_3$ |
| 2-46 | H | H | 5-OCH$_2$CO$_2$CH$_2$CH$_3$ |
| 2-47 | 5-OCH$_3$ | H | 2-OCH$_2$CO$_2$C(CH$_3$)$_3$ |
| 2-48 | 5-OCH$_3$ | H | 2-OCH$_2$CO$_2$CH$_2$C$_6$H$_5$ |
| 2-49 | 5-OCH$_3$ | H | 2-OCH$_2$CO$_2$C$_6$H$_5$ |
| 2-50 | 5-OCH$_3$ | H | 2-OCH$_2$CONHOCH$_3$ |
| 2-51 | H | H | 2-NHCH(CH$_3$)CO$_2$H |
| 2-52 | H | H | 2-NHCH(CH$_3$)CO$_2$CH$_3$ |
| 2-53 | H | H | 2-NHCH(CH$_3$)CO$_2$CH$_2$CH$_3$ |
| 2-54 | H | H | 2-NHCH(CH$_3$)CO$_2$CH(CH$_3$)$_2$ |
| 2-55 | H | H | 2-NHCH(CH$_3$)CO$_2$CH$_2$CH=CH$_2$ |
| 2-56 | H | H | 2-NHCH$_2$CO$_2$H |
| 2-57 | H | H | 2-NHCH$_2$CO$_2$CH$_3$ |
| 2-58 | H | H | 2-NHCH$_2$CO$_2$CH$_2$CH$_3$ |
| 2-59 | H | H | 2-NHCH$_2$CO$_2$CH(CH$_3$)$_2$ |
| 2-60 | H | H | 2-NHCH$_2$CO$_2$CH$_2$CH=CH$_2$ |
| 2-61 | H | H | 4-NHCH(CH$_3$)CO$_2$H |
| 2-62 | H | H | 4-NHCH(CH$_3$)CO$_2$CH$_3$ |
| 2-63 | H | H | 4-NHCH(CH$_3$)CO$_2$CH$_2$CH$_3$ |
| 2-64 | H | H | 4-NHCH(CH$_3$)CO$_2$CH(CH$_3$)$_2$ |
| 2-65 | H | H | 4-NHCH(CH$_3$)CO$_2$CH$_2$CH=CH$_2$ |
| 2-66 | H | H | 4-NHCH$_2$CO$_2$H |
| 2-67 | H | H | 4-NHCH$_2$CO$_2$CH$_3$ |
| 2-68 | H | H | 4-NHCH$_2$CO$_2$CH$_2$CH$_3$ |
| 2-69 | H | H | 4-NHCH$_2$CO$_2$CH(CH$_3$)$_2$ |
| 2-70 | H | H | 4-NHCH$_2$CO$_2$CH$_2$CH=CH$_2$ |
| 2-71 | 5-OCH$_3$ | H | 2-OCH(CH$_3$)CONHOCH$_3$ |
| 2-72 | 5-OCH$_3$ | H | 2-OCH$_2$CO$_2$H |
| 2-73 | 5-OCH$_3$ | H | 2-OCH$_2$CO$_2$CH$_3$ |
| 2-74 | 5-OCH$_3$ | H | 2-OCH$_2$CO$_2$CH$_2$CH$_3$ |
| 2-75 | H | H | 2-OCH(CH$_3$)CO$_2$C(CH$_3$)$_3$ |
| 2-76 | H | H | 2-OCH(CH$_3$)CO$_2$CH$_2$C$_6$H$_5$ |
| 2-77 | H | H | 2-OCH(CH$_3$)CO$_2$C$_6$H$_5$ |
| 2-78 | H | H | 2-OCH(CH$_3$)CONHOCH$_3$ |
| 2-79 | H | H | 2-OCH(CH$_3$)CONHOCH$_2$CH$_3$ |
| 2-80 | H | H | 2-OCH(CH$_3$)CON(CH$_3$)OCH$_3$ |
| 2-81 | H | H | 2-OCH$_2$CO$_2$C(CH$_3$)$_3$ |
| 2-82 | H | H | 2-OCH$_2$CO$_2$CH$_2$C$_6$H$_5$ |
| 2-83 | H | H | 2-OCH$_2$CO$_2$C$_6$H$_5$ |
| 2-84 | H | H | 2-OCH$_2$CONHOCH$_3$ |
| 2-85 | H | H | 2-OCH$_2$CONHOCH$_2$CH$_3$ |
| 2-86 | H | H | 2-OCH$_2$CON(CH$_3$)OCH$_3$ |
| 2-87 | 5-Cl | H | 2-OCH(CH$_3$)CO$_2$H |
| 2-88 | 5-Cl | H | 2-OCH(CH$_3$)CO$_2$CH$_3$ |
| 2-89 | 5-Cl | H | 2-OCH(CH$_3$)CO$_2$CH$_2$CH$_3$ |
| 2-90 | 5-Cl | H | 2-OCH(CH$_3$)CO$_2$C(CH$_3$)$_3$ |
| 2-91 | 5-Cl | H | 2-OCH(CH$_3$)CO$_2$CH$_2$C$_6$H$_5$ |
| 2-92 | 5-Cl | H | 2-OCH(CH$_3$)CO$_2$C$_6$H$_5$ |
| 2-93 | 5-Cl | H | 2-OCH(CH$_3$)CONHOCH$_3$ |
| 2-94 | 5-Cl | H | 2-OCH$_2$CO$_2$H |
| 2-95 | 5-Cl | H | 2-OCH$_2$CO$_2$CH$_3$ |
| 2-96 | 5-Cl | H | 2-OCH$_2$CO$_2$CH$_2$CH$_3$ |
| 2-97 | 5-Cl | H | 2-OCH$_2$CO$_2$C(CH$_3$)$_3$ |
| 2-98 | 5-Cl | H | 2-OCH$_2$CO$_2$CH$_2$C$_6$H$_5$ |
| 2-99 | 5-Cl | H | 2-OCH$_2$CO$_2$C$_6$H$_5$ |
| 2-100 | 5-Cl | H | 2-OCH$_2$CONHOCH$_3$ |
| 2-101 | 5-OCH$_3$ | H | 2-OCH(CH$_3$)CO$_2$H |
| 2-102 | 5-OCH$_3$ | H | 2-OCH(CH$_3$)CO$_2$CH$_3$ |
| 2-103 | 5-OCH$_3$ | H | 2-OCH(CH$_3$) CO$_2$CH$_2$CH$_3$ |
| 2-104 | 5-OCH$_3$ | H | 2-OCH(CH$_3$)CO$_2$C(CH$_3$)$_3$ |
| 2-105 | 5-OCH$_3$ | H | 2-OCH(CH$_3$)CO$_2$CH$_2$C$_6$H$_5$ |
| 2-106 | 5-OCH$_3$ | H | 2-OCH(CH$_3$)CO$_2$C$_6$H$_5$ |

TABLE 3

Compound of the formula [I-3]

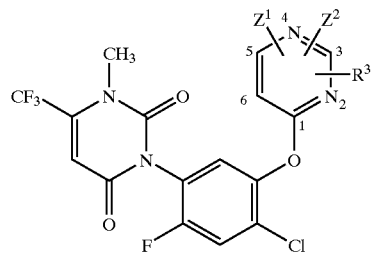

[I-3]

| Compound No. | $Z^1$ | $Z^2$ | $R^3$ |
|---|---|---|---|
| 3-1 | H | H | 3-OCH(CH$_3$)CO$_2$H |
| 3-2 | H | H | 3-OCH(CH$_3$)CO$_2$CH$_3$ |
| 3-3 | H | H | 3-OCH(CH$_3$)CO$_2$CH$_2$CH$_3$ |
| 3-4 | H | H | 3-OCH(CH$_3$)CO$_2$CH(CH$_3$)$_2$ |
| 3-5 | H | H | 3-OCH(CH$_3$)CO$_2$CH$_2$CH=CH$_2$ |
| 3-6 | H | H | 3-OCH$_2$CO$_2$H |
| 3-7 | H | H | 3-OCH$_2$CO$_2$CH$_3$ |
| 3-8 | H | H | 3-OCH$_2$CO$_2$CH$_2$CH$_3$ |
| 3-9 | H | H | 3-OCH$_2$CO$_2$CH(CH$_3$)$_2$ |
| 3-10 | H | H | 3-OCH$_2$CO$_2$CH$_2$CH=CH$_2$ |
| 3-11 | H | H | 5-OCH(CH$_3$)CO$_2$H |
| 3-12 | H | H | 5-OCH(CH$_3$)CO$_2$CH$_3$ |
| 3-13 | H | H | 5-OCH(CH$_3$)CO$_2$CH$_2$CH$_3$ |
| 3-14 | H | H | 5-OCH(CH$_3$)CO$_2$CH(CH$_3$)$_2$ |
| 3-15 | H | H | 5-OCH(CH$_3$)CO$_2$CH$_2$CH=CH$_2$ |
| 3-16 | H | H | 5-OCH$_2$CO$_2$H |
| 3-17 | H | H | 5-OCH$_2$CO$_2$CH$_3$ |
| 3-18 | H | H | 5-OCH$_2$CO$_2$CH$_2$CH$_3$ |
| 3-19 | H | H | 5-OCH$_2$CO$_2$CH(CH$_3$)$_2$ |
| 3-20 | H | H | 5-OCH$_2$CO$_2$CH$_2$CH=CH$_2$ |
| 3-21 | H | H | 3-SCH(CH$_3$)CO$_2$H |
| 3-22 | H | H | 3-SCH(CH$_3$)CO$_2$CH$_3$ |
| 3-23 | H | H | 3-SCH(CH$_3$)CO$_2$CH$_2$CH$_3$ |
| 3-24 | H | H | 3-SCH(CH$_3$)CO$_2$CH(CH$_3$)$_2$ |
| 3-25 | H | H | 3-SCH(CH$_3$)CO$_2$CH$_2$CH=CH$_2$ |
| 3-26 | H | H | 3-SCH$_2$CO$_2$H |
| 3-27 | H | H | 3-SCH$_2$CO$_2$CH$_3$ |
| 3-28 | H | H | 3-SCH$_2$CO$_2$CH$_2$CH$_3$ |
| 3-29 | H | H | 3-SCH$_2$CO$_2$CH(CH$_3$)$_2$ |
| 3-30 | H | H | 3-SCH$_2$CO$_2$CH$_2$CH=CH$_2$ |
| 3-31 | H | H | 5-SCH(CH$_3$)CO$_2$H |
| 3-32 | H | H | 5-SCH(CH$_3$)CO$_2$CH$_3$ |
| 3-33 | H | H | 5-SCH(CH$_3$)CO$_2$CH$_2$CH$_3$ |
| 3-34 | H | H | 5-SCH(CH$_3$)CO$_2$CH(CH$_3$)$_2$ |
| 3-35 | H | H | 5-SCH(CH$_3$)CO$_2$CH$_2$CH=CH$_2$ |
| 3-36 | H | H | 5-SCH$_2$CO$_2$H |
| 3-37 | H | H | 5-SCH$_2$CO$_2$CH$_3$ |
| 3-38 | H | H | 5-SCH$_2$CO$_2$CH$_2$CH$_3$ |
| 3-39 | H | H | 5-SCH$_2$CO$_2$CH(CH$_3$)$_2$ |
| 3-40 | H | H | 5-SCH$_2$CO$_2$CH$_2$CH=CH$_2$ |
| 3-41 | H | H | 6-NHCH(CH$_3$)CO$_2$H |
| 3-42 | H | H | 6-NHCH(CH$_3$)CO$_2$CH$_3$ |
| 3-43 | H | H | 6-NHCH(CH$_3$)CO$_2$CH$_2$CH$_3$ |
| 3-44 | H | H | 6-NHCH(CH$_3$)CO$_2$CH(CH$_3$)$_2$ |
| 3-45 | H | H | 6-NHCH(CH$_3$)CO$_2$CH$_2$CH=CH$_2$ |
| 3-46 | H | H | 6-NHCH$_2$CO$_2$H |
| 3-47 | H | H | 6-NHCH$_2$CO$_2$CH$_3$ |
| 3-48 | H | H | 6-NHCH$_2$CO$_2$CH$_2$CH$_3$ |
| 3-49 | H | H | 6-NHCH$_2$CO$_2$CH(CH$_3$)$_2$ |
| 3-50 | H | H | 6-NHCH$_2$CO$_2$CH$_2$CH=CH$_2$ |
| 3-51 | H | H | 6-OCH(CH$_3$)CO$_2$H |
| 3-52 | H | H | 6-OCH(CH$_3$)CO$_2$CH$_3$ |
| 3-53 | H | H | 6-OCH(CH$_3$)CO$_2$CH$_2$CH$_3$ |
| 3-54 | H | H | 6-OCH(CH$_3$)CO$_2$CH(CH$_3$)$_2$ |
| 3-55 | H | H | 6-OCH(CH$_3$)CO$_2$CH$_2$CH=CH$_2$ |
| 3-56 | H | H | 6-OCH$_2$CO$_2$H |
| 3-57 | H | H | 6-OCH$_2$CO$_2$CH$_3$ |
| 3-58 | H | H | 6-OCH$_2$CO$_2$CH$_2$CH$_3$ |
| 3-59 | H | H | 6-OCH$_2$CO$_2$CH(CH$_3$)$_2$ |
| 3-60 | H | H | 6-OCH$_2$CO$_2$CH$_2$CH=CH$_2$ |
| 3-61 | H | H | 6-SCH(CH$_3$)CO$_2$H |

TABLE 3-continued

Compound of the formula [I-3]

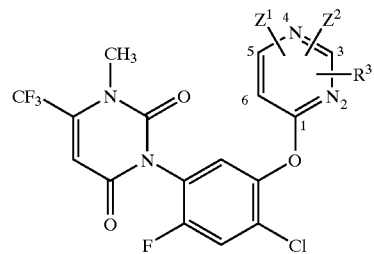

[I-3]

| Compound No. | $Z^1$ | $Z^2$ | $R^3$ |
|---|---|---|---|
| 3-62 | H | H | 6-SCH(CH$_3$)CO$_2$CH$_3$ |
| 3-63 | H | H | 6-SCH(CH$_3$)CO$_2$CH$_2$CH$_3$ |
| 3-64 | H | H | 6-SCH(CH$_3$)CO$_2$CH(CH$_3$)$_2$ |
| 3-65 | H | H | 6-SCH(CH$_3$)CO$_2$CH$_2$CH=CH$_2$ |
| 3-66 | H | H | 6-SCH$_2$CO$_2$H |
| 3-67 | H | H | 6-SCH$_2$CO$_2$CH$_3$ |
| 3-68 | H | H | 6-SCH$_2$CO$_2$CH$_2$CH$_3$ |
| 3-69 | H | H | 6-SCH$_2$CO$_2$CH(CH$_3$)$_2$ |
| 3-70 | H | H | 6-SCH$_2$CO$_2$CH$_2$CH=CH$_2$ |
| 3-71 | H | H | 5-NHCH$_2$CO$_2$H |
| 3-72 | H | H | 5-NHCH$_2$CO$_2$CH$_3$ |
| 3-73 | H | H | 5-NHCH$_2$CO$_2$CH$_2$CH$_3$ |
| 3-74 | H | H | 5-NHCH$_2$CO$_2$CH(CH$_3$)$_2$ |
| 3-75 | H | H | 5-NHCH$_2$CO$_2$CH$_2$CH=CH$_2$ |
| 3-76 | H | H | 3-NHCH(CH$_3$)CO$_2$H |
| 3-77 | H | H | 3-NHCH(CH$_3$)CO$_2$CH$_3$ |
| 3-78 | H | H | 3-NHCH(CH$_3$)CO$_2$CH$_2$CH$_3$ |
| 3-79 | H | H | 3-NHCH(CH$_3$)CO$_2$CH(CH$_3$)$_2$ |
| 3-80 | H | H | 3-NHCH(CH$_3$)CO$_2$CH$_2$CH=CH$_2$ |
| 3-81 | H | H | 3-NHCH$_2$CO$_2$H |
| 3-82 | H | H | 3-NHCH$_2$CO$_2$CH$_3$ |
| 3-83 | H | H | 3-NHCH$_2$CO$_2$CH$_2$CH$_3$ |
| 3-84 | H | H | 3-NHCH$_2$CO$_2$CH(CH$_3$)$_2$ |
| 3-85 | H | H | 3-NHCH$_2$CO$_2$CH$_2$CH=CH$_2$ |
| 3-86 | H | H | 5-NHCH(CH$_3$)CO$_2$H |
| 3-87 | H | H | 5-NHCH(CH$_3$)CO$_2$CH$_3$ |
| 3-88 | H | H | 5-NHCH(CH$_3$)CO$_2$CH$_2$CH$_3$ |
| 3-89 | H | H | 5-NHCH(CH$_3$)CO$_2$CH(CH$_3$)$_2$ |
| 3-90 | H | H | 5-NHCH(CH$_3$)CO$_2$CH$_2$CH=CH$_2$ |

TABLE 4

Compound of the formula [I-4]:

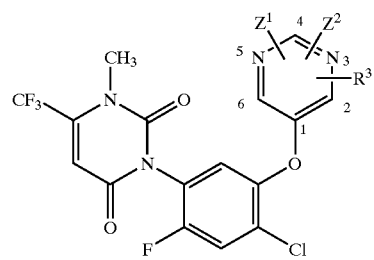

[I-4]

| Compound No. | $Z^1$ | $Z^2$ | $R^3$ |
|---|---|---|---|
| 4-1 | H | H | 2-OCH(CH$_3$)CO$_2$H |
| 4-2 | H | H | 2-OCH(CH$_3$)CO$_2$CH$_3$ |
| 4-3 | H | H | 2-OCH(CH$_3$)CO$_2$CH$_2$CH$_3$ |
| 4-4 | H | H | 2-OCH(CH$_3$)CO$_2$CH(CH$_3$)$_2$ |
| 4-5 | H | H | 2-OCH(CH$_3$)CO$_2$CH$_2$CH=CH$_2$ |
| 4-6 | H | H | 2-OCH$_2$CO$_2$H |
| 4-7 | H | H | 2-OCH$_2$CO$_2$CH$_3$ |
| 4-8 | H | H | 2-OCH$_2$CO$_2$CH$_2$CH$_3$ |
| 4-9 | H | H | 2-OCH$_2$CO$_2$CH(CH$_3$)$_2$ |

TABLE 4-continued

Compound of the formula [I-4]: [I-4]

| Compound No. | $Z^1$ | $Z^2$ | $R^3$ |
|---|---|---|---|
| 4-10 | H | H | 2-OCH$_2$CO$_2$CH$_2$CH=CH$_2$ |
| 4-11 | H | H | 4-OCH(CH$_3$)CO$_2$H |
| 4-12 | H | H | 4-OCH(CH$_3$)CO$_2$CH$_3$ |
| 4-13 | H | H | 4-OCH(CH$_3$)CO$_2$CH$_2$CH$_3$ |
| 4-14 | H | H | 4-OCH(CH$_3$)CO$_2$CH(CH$_3$)$_2$ |
| 4-15 | H | H | 4-OCH(CH$_3$)CO$_2$CH$_2$CH=CH$_2$ |
| 4-16 | H | H | 4-OCH$_2$CO$_2$H |
| 4-17 | H | H | 4-OCH$_2$CO$_2$CH$_3$ |
| 4-18 | H | H | 4-OCH$_2$CO$_2$CH$_2$CH$_3$ |
| 4-19 | H | H | 4-OCH$_2$CO$_2$CH(CH$_3$)$_2$ |
| 4-20 | H | H | 4-OCH$_2$CO$_2$CH$_2$CH=CH$_2$ |
| 4-21 | H | H | 2-SCH(CH$_3$)CO$_2$H |
| 4-22 | H | H | 2-SCH(CH$_3$)CO$_2$CH$_3$ |
| 4-23 | H | H | 2-SCH(CH$_3$)CO$_2$CH$_2$CH$_3$ |
| 4-24 | H | H | 2-SCH(CH$_3$)CO$_2$CH(CH$_3$)$_2$ |
| 4-25 | H | H | 2-SCH(CH$_3$)CO$_2$CH$_2$CH=CH$_2$ |
| 4-26 | H | H | 2-SCH$_2$CO$_2$H |
| 4-27 | H | H | 2-SCH$_2$CO$_2$CH$_3$ |
| 4-28 | H | H | 2-SCH$_2$CO$_2$CH$_2$CH$_3$ |
| 4-29 | H | H | 2-SCH$_2$CO$_2$CH(CH$_3$)$_2$ |
| 4-30 | H | H | 2-SCH$_2$CO$_2$CH$_2$CH=CH$_2$ |
| 4-31 | H | H | 4-SCH(CH$_3$)CO$_2$H |
| 4-32 | H | H | 4-SCH(CH$_3$)CO$_2$CH$_3$ |
| 4-33 | H | H | 4-SCH(CH$_3$)CO$_2$CH$_2$CH$_3$ |
| 4-34 | H | H | 4-SCH(CH$_3$)CO$_2$CH(CH$_3$)$_2$ |
| 4-35 | H | H | 4-SCH(CH$_3$)CO$_2$CH$_2$CH=CH$_2$ |
| 4-36 | H | H | 4-SCH$_2$CO$_2$H |
| 4-37 | H | H | 4-SCH$_2$CO$_2$CH$_3$ |
| 4-38 | H | H | 4-SCH$_2$CO$_2$CH$_2$CH$_3$ |
| 4-39 | H | H | 4-SCH$_2$CO$_2$CH(CH$_3$)$_2$ |
| 4-40 | H | H | 4-SCH$_2$CO$_2$CH$_2$CH=CH$_2$ |
| 4-41 | 4-CH$_3$ | H | 2-SCH(CH$_3$)CO$_2$C$_6$H$_5$ |
| 4-42 | 4-CH$_3$ | H | 2-SCH(CH$_3$)CONHOCH$_3$ |
| 4-43 | 4-CH$_3$ | H | 2-SCH$_2$CO$_2$H |
| 4-44 | 4-CH$_3$ | H | 2-SCH$_2$CO$_2$CH$_3$ |
| 4-45 | 4-CH$_3$ | H | 2-SCH$_2$CO$_2$CH$_2$CH$_3$ |
| 4-46 | 4-CH$_3$ | H | 2-SCH$_2$CO$_2$CH(CH$_3$)$_2$ |
| 4-47 | 4-CH$_3$ | H | 2-SCH$_2$CO$_2$C(CH$_3$)$_3$ |
| 4-48 | 4-CH$_3$ | H | 2-SCH$_2$CO$_2$CH$_2$C$_6$H$_5$ |
| 4-49 | 4-CH$_3$ | H | 2-SCH$_2$CO$_2$C$_6$H$_5$ |
| 4-50 | 4-CH$_3$ | H | 2-SCH$_2$CONHOCH$_3$ |
| 4-51 | H | H | 2-NHCH(CH$_3$)CO$_2$H |
| 4-52 | H | H | 2-NHCH(CH$_3$)CO$_2$CH$_3$ |
| 4-53 | H | H | 2-NHCH(CH$_3$)CO$_2$CH$_2$CH$_3$ |
| 4-54 | H | H | 2-NHCH(CH$_3$)CO$_2$CH(CH$_3$)$_2$ |
| 4-55 | H | H | 2-NHCH(CH$_3$)CO$_2$CH$_2$CH=CH$_2$ |
| 4-56 | H | H | 2-NHCH$_2$CO$_2$H |
| 4-57 | H | H | 2-NHCH$_2$CO$_2$CH$_3$ |
| 4-58 | H | H | 2-NHCH$_2$CO$_2$CH$_2$CH$_3$ |
| 4-59 | H | H | 2-NHCH$_2$CO$_2$CH(CH$_3$)$_2$ |
| 4-60 | H | H | 2-NHCH$_2$CO$_2$CH$_2$CH=CH$_2$ |
| 4-61 | H | H | 4-NHCH(CH$_3$)CO$_2$H |
| 4-62 | H | H | 4-NHCH(CH$_3$)CO$_2$CH$_3$ |
| 4-63 | H | H | 4-NHCH(CH$_3$)CO$_2$CH$_2$CH$_3$ |
| 4-64 | H | H | 4-NHCH(CH$_3$)CO$_2$CH(CH$_3$)$_2$ |
| 4-65 | H | H | 4-NHCH(CH$_3$)CO$_2$CH$_2$CH=CH$_2$ |
| 4-66 | H | H | 4-NHCH$_2$CO$_2$H |
| 4-67 | H | H | 4-NHCH$_2$CO$_2$CH$_3$ |
| 4-68 | H | H | 4-NHCH$_2$CO$_2$CH$_2$CH$_3$ |
| 4-69 | H | H | 4-NHCH$_2$CO$_2$CH(CH$_3$)$_2$ |
| 4-70 | H | H | 4-NHCH$_2$CO$_2$CH$_2$CH=CH$_2$ |
| 4-71 | 4-CH$_3$ | H | 2-SCH(CH$_3$)CO$_2$CH$_2$CH$_3$ |
| 4-72 | 4-CH$_3$ | H | 2-SCH(CH$_3$)CO$_2$CH(CH$_3$)$_2$ |
| 4-73 | 4-CH$_3$ | H | 2-SCH(CH$_3$)CO$_2$C(CH$_3$)$_3$ |
| 4-74 | 4-CH$_3$ | H | 2-SCH(CH$_3$)CO$_2$CH$_2$C$_6$H$_5$ |
| 4-75 | 4-CH$_3$ | H | 2-OCH(CH$_3$)CO$_2$H |
| 4-76 | 4-CH$_3$ | H | 2-OCH(CH$_3$)CO$_2$CH$_3$ |
| 4-77 | 4-CH$_3$ | H | 2-OCH(CH$_3$)CO$_2$CH$_2$CH$_3$ |
| 4-78 | 4-CH$_3$ | H | 2-OCH(CH$_3$)CO$_2$CH(CH$_3$)$_2$ |
| 4-79 | 4-CH$_3$ | H | 2-OCH(CH$_3$)CO$_2$CH$_2$CH=CH$_2$ |
| 4-80 | 4-CH$_3$ | H | 2-OCH(CH$_3$)CO$_2$C(CH$_3$)$_3$ |
| 4-81 | 4-CH$_3$ | H | 2-OCH(CH$_3$)CO$_2$CH$_2$C$_6$H$_5$ |
| 4-82 | 4-CH$_3$ | H | 2-OCH(CH$_3$)CO$_2$C$_6$H$_5$ |
| 4-83 | 4-CH$_3$ | H | 2-OCH(CH$_3$)CONHOCH$_3$ |
| 4-84 | 4-CH$_3$ | H | 2-OCH$_2$CO$_2$H |
| 4-85 | 4-CH$_3$ | H | 2-OCH$_2$CO$_2$CH$_3$ |
| 4-86 | 4-CH$_3$ | H | 2-OCH$_2$CO$_2$CH$_2$CH$_3$ |
| 4-87 | 4-CH$_3$ | H | 2-OCH$_2$CO$_2$CH(CH$_3$)$_2$ |
| 4-88 | 4-CH$_3$ | H | 2-OCH$_2$CO$_2$CH$_2$CH=CH$_2$ |
| 4-89 | 4-CH$_3$ | H | 2-OCH$_2$CO$_2$C(CH$_3$)$_3$ |
| 4-90 | 4-CH$_3$ | H | 2-OCH$_2$CO$_2$CH$_2$C$_6$H$_5$ |
| 4-91 | 4-CH$_3$ | H | 2-OCH$_2$CO$_2$C$_6$H$_5$ |
| 4-92 | 4-CH$_3$ | H | 2-OCH$_2$CONHOCH$_3$ |
| 4-93 | 4-CH$_3$ | | 2-SCH(CH$_3$)CO$_2$H |
| 4-94 | 4-CH$_3$ | H | 2-SCH(CH$_3$)CO$_2$CH$_3$ |

TABLE 5

Compound of the formula [I-5]: [I-5]

| Compound No. | $Z^1$ | $Z^2$ | $R^3$ |
|---|---|---|---|
| 5-1 | H | H | 2-OCH(CH$_3$)CO$_2$H |
| 5-2 | H | H | 2-OCH(CH$_3$)CO$_2$CH$_3$ |
| 5-3 | H | H | 2-OCH(CH$_3$)CO$_2$CH$_2$CH$_3$ |
| 5-4 | H | H | 2-OCH(CH$_3$)CO$_2$CH(CH$_3$)$_2$ |
| 5-5 | H | H | 2-OCH(CH$_3$)CO$_2$CH$_2$CH=CH$_2$ |
| 5-6 | H | H | 2-OCH$_2$CO$_2$H |
| 5-7 | H | H | 2-OCH$_2$CO$_2$CH$_3$ |
| 5-8 | H | H | 2-OCH$_2$CO$_2$CH$_2$CH$_3$ |
| 5-9 | H | H | 2-OCH$_2$CO$_2$CH(CH$_3$)$_2$ |
| 5-10 | H | H | 2-OCH$_2$CO$_2$CH$_2$CH=CH$_2$ |
| 5-11 | 5-CH$_3$ | H | 2-OCH(CH$_3$)CO$_2$H |
| 5-12 | 5-CH$_3$ | H | 2-OCH(CH$_3$)CO$_2$CH$_3$ |
| 5-13 | 5-CH$_3$ | H | 2-OCH(CH$_3$)CO$_2$CH$_2$CH$_3$ |
| 5-14 | 5-CH$_3$ | H | 2-OCH(CH$_3$)CO$_2$CH(CH$_3$)$_2$ |

TABLE 5-continued

Compound of the formula [I-5]:

[I-5]

| Compound No. | $Z^1$ | $Z^2$ | $R^3$ |
|---|---|---|---|
| 5-15 | 5-CH₃ | H | 2-OCH(CH₃)CO₂CH₂CH=CH₂ |
| 5-16 | 5-CH₃ | H | 2-OCH₂CO₂H |
| 5-17 | 5-CH₃ | H | 2-OCH₂CO₂CH₃ |
| 5-18 | 5-CH₃ | H | 2-OCH₂CO₂CH₂CH₃ |
| 5-19 | 5-CH₃ | H | 2-OCH₂CO₂CH(CH₃)₂ |
| 5-20 | 5-CH₃ | H | 2-OCH₂CO₂CH₂CH=CH₂ |
| 5-21 | 4-CH₃ | H | 2-OCH(CH₃)CO₂H |
| 5-22 | 4-CH₃ | H | 2-OCH(CH₃)CO₂CH₃ |
| 5-23 | 4-CH₃ | H | 2-OCH(CH₃)CO₂CH₂CH₃ |
| 5-24 | 4-CH₃ | H | 2-OCH(CH₃)CO₂CH(CH₃)₂ |
| 5-25 | 4-CH₃ | H | 2-OCH(CH₃)CO₂CH₂CH=CH₂ |
| 5-26 | 4-CH₃ | H | 2-OCH₂CO₂H |
| 5-27 | 4-CH₃ | H | 2-OCH₂CO₂CH₃ |
| 5-28 | 4-CH₃ | H | 2-OCH₂CO₂CH₂CH₃ |
| 5-29 | 4-CH₃ | H | 2-OCH₂CO₂CH(CH₃)₂ |
| 5-30 | 4-CH₃ | H | 2-OCH₂CO₂CH₂CH=CH₂ |
| 5-31 | 4-CH₃ | 5-CH₃ | 2-OCH(CH₃)CO₂H |
| 5-32 | 4-CH₃ | 5-CH₃ | 2-OCH(CH₃)CO₂CH₃ |
| 5-33 | 4-CH₃ | 5-CH₃ | 2-OCH(CH₃)CO₂CH₂CH₃ |
| 5-34 | 4-CH₃ | 5-CH₃ | 2-OCH(CH₃)CO₂CH(CH₃)₂ |
| 5-35 | 4-CH₃ | 5-CH₃ | 2-OCH(CH₃)CO₂CH₂CH=CH₂ |
| 5-36 | 4-CH₃ | 5-CH₃ | 2-OCH₂CO₂H |
| 5-37 | 4-CH₃ | 5-CH₃ | 2-OCH₂CO₂CH₃ |
| 5-38 | 4-CH₃ | 5-CH₃ | 2-OCH₂CO₂CH₂CH₃ |
| 5-39 | 4-CH₃ | 5-CH₃ | 2-OCH₂CO₂CH(CH₃)₂ |
| 5-40 | 4-CH₃ | 5-CH₃ | 2-OCH₂CO₂CH₂CH=CH₂ |
| 5-41 | H | H | 2-SCH(CH₃)CO₂H |
| 5-42 | H | H | 2-SCH(CH₃)CO₂CH₃ |
| 5-43 | H | H | 2-SCH(CH₃)CO₂CH₂CH₃ |
| 5-44 | H | H | 2-SCH(CH₃)CO₂CH(CH₃)₂ |
| 5-45 | H | H | 2-SCH(CH₃)CO₂CH₂CH=CH₂ |
| 5-46 | H | H | 2-SCH₂CO₂H |
| 5-47 | H | H | 2-SCH₂CO₂CH₃ |
| 5-48 | H | H | 2-SCH₂CO₂CH₂CH₃ |
| 5-49 | H | H | 2-SCH₂CO₂CH(CH₃)₂ |
| 5-50 | H | H | 2-SCH₂CO₂CH₂CH=CH₂ |
| 5-51 | 5-CH₃ | H | 2-SCH(CH₃)CO₂H |
| 5-52 | 5-CH₃ | H | 2-SCH(CH₃)CO₂CH₃ |
| 5-53 | 5-CH₃ | H | 2-SCH(CH₃)CO₂CH₂CH₃ |
| 5-54 | 5-CH₃ | H | 2-SCH(CH₃)CO₂CH(CH₃)₂ |
| 5-55 | 5-CH₃ | H | 2-SCH(CH₃)CO₂CH₂CH=CH₂ |
| 5-56 | 5-CH₃ | H | 2-SCH₂CO₂H |
| 5-57 | 5-CH₃ | H | 2-SCH₂CO₂CH₃ |
| 5-58 | 5-CH₃ | H | 2-SCH₂CO₂CH₂CH₃ |
| 5-59 | 5-CH₃ | H | 2-SCH₂CO₂CH(CH₃)₂ |
| 5-60 | 5-CH₃ | H | 2-SCH₂CO₂CH₂CH=CH₂ |
| 5-61 | 4-CH₃ | H | 2-SCH(CH₃)CO₂H |
| 5-62 | 4-CH₃ | H | 2-SCH(CH₃)CO₂CH₃ |
| 5-63 | 4-CH₃ | H | 2-SCH(CH₃)CO₂CH₂CH₃ |
| 5-64 | 4-CH₃ | H | 2-SCH(CH₃)CO₂CH(CH₃)₂ |
| 5-65 | 4-CH₃ | H | 2-SCH(CH₃)CO₂CH₂CH=CH₂ |
| 5-66 | 4-CH₃ | H | 2-SCH₂CO₂H |
| 5-67 | 4-CH₃ | H | 2-SCH₂CO₂CH₃ |
| 5-68 | 4-CH₃ | H | 2-SCH₂CO₂CH₂CH₃ |
| 5-69 | 4-CH₃ | H | 2-SCH₂CO₂CH(CH₃)₂ |
| 5-70 | 4-CH₃ | H | 2-SCH₂CO₂CH₂CH=CH₂ |
| 5-71 | 4-CH₃ | 5-CH₃ | 2-SCH₂CO₂H |
| 5-72 | 4-CH₃ | 5-CH₃ | 2-SCH₂CO₂CH₃ |
| 5-73 | 4-CH₃ | 5-CH₃ | 2-SCH₂CO₂CH₂CH₃ |
| 5-74 | 4-CH₃ | 5-CH₃ | 2-SCH₂CO₂CH(CH₃)₂ |

TABLE 5-continued

Compound of the formula [I-5]:

[I-5]

| Compound No. | $Z^1$ | $Z^2$ | $R^3$ |
|---|---|---|---|
| 5-75 | 4-CH₃ | 5-CH₃ | 2-SCH₂CO₂CH₂CH=CH₂ |

TABLE 6

Compound of the formula [I-6]:

[I-6]:

| Compound No. | $Z^1$ | $Z^2$ | $R^3$ |
|---|---|---|---|
| 6-1 | H | H | 3-OCH(CH₃)CO₂H |
| 6-2 | H | H | 3-OCH(CH₃)CO₂CH₃ |
| 6-3 | H | H | 3-OCH(CH₃)CO₂CH₂CH₃ |
| 6-4 | H | H | 3-OCH(CH₃)CO₂CH(CH₃)₂ |
| 6-5 | H | H | 3-OCH(CH₃)CO₂CH₂CH=CH₂ |
| 6-6 | H | H | 3-OCH₂CO₂H |
| 6-7 | H | H | 3-OCH₂CO₂CH₃ |
| 6-8 | H | H | 3-OCH₂CO₂CH₂CH₃ |
| 6-9 | H | H | 3-OCH₂CO₂CH(CH₃)₂ |
| 6-10 | H | H | 3-OCH₂CO₂CH₂CH=CH₂ |
| 6-11 | H | H | 4-OCH(CH₃)CO₂H |
| 6-12 | H | H | 4-OCH(CH₃)CO₂CH₃ |
| 6-13 | H | H | 4-OCH(CH₃)CO₂CH₂CH₃ |
| 6-14 | H | H | 4-OCH(CH₃)CO₂CH(CH₃)₂ |
| 6-15 | H | H | 4-OCH(CH₃)CO₂CH₂CH=CH₂ |
| 6-16 | H | H | 4-OCH₂CO₂H |
| 6-17 | H | H | 4-OCH₂CO₂CH₃ |
| 6-18 | H | H | 4-OCH₂CO₂CH₂CH₃ |
| 6-19 | H | H | 4-OCH₂CO₂CH(CH₃)₂ |
| 6-20 | H | H | 4-OCH₂CO₂CH₂CH=CH₂ |
| 6-21 | H | H | 3-SCH(CH₃)CO₂H |
| 6-22 | H | H | 3-SCH(CH₃)CO₂CH₃ |
| 6-23 | H | H | 3-SCH(CH₃)CO₂CH₂CH₃ |
| 6-24 | H | H | 3-SCH(CH₃)CO₂CH(CH₃)₂ |
| 6-25 | H | H | 3-SCH(CH₃)CO₂CH₂CH=CH₂ |
| 6-26 | H | H | 3-SCH₂CO₂H |
| 6-27 | H | H | 3-SCH₂CO₂CH₃ |
| 6-28 | H | H | 3-SCH₂CO₂CH₂CH₃ |
| 6-29 | H | H | 3-SCH₂CO₂CH(CH₃)₂ |
| 6-30 | H | H | 3-SCH₂CO₂CH₂CH=CH₂ |
| 6-31 | H | H | 4-SCH(CH₃)CO₂H |
| 6-32 | H | H | 4-SCH(CH₃)CO₂CH₃ |
| 6-33 | H | H | 4-SCH(CH₃)CO₂CH₂CH₃ |
| 6-34 | H | H | 4-SCH(CH₃)CO₂CH(CH₃)₂ |
| 6-35 | H | H | 4-SCH(CH₃)CO₂CH₂CH=CH₂ |
| 6-36 | H | H | 4-SCH₂CO₂H |
| 6-37 | H | H | 4-SCH₂CO₂CH₃ |

TABLE 6-continued

Compound of the formula [I-6]: [I-6]

| Compound No. | $Z^1$ | $Z^2$ | $R^3$ |
|---|---|---|---|
| 6-38 | H | H | 4-SCH$_2$CO$_2$CH$_2$CH$_3$ |
| 6-39 | H | H | 4-SCH$_2$CO$_2$CH(CH$_3$)$_2$ |
| 6-40 | H | H | 4-SCH$_2$CO$_2$CH$_2$CH=CH$_2$ |
| 6-41 | H | H | 4-NHCH(CH$_3$)CO$_2$H |
| 6-42 | H | H | 4-NHCH(CH$_3$)CO$_2$CH$_3$ |
| 6-43 | H | H | 4-NHCH(CH$_3$)CO$_2$CH$_2$CH$_3$ |
| 6-44 | H | H | 4-NHCH(CH$_3$)CO$_2$CH(CH$_3$)$_2$ |
| 6-45 | H | H | 4-NHCH(CH$_3$)CO$_2$CH$_2$CH=CH$_2$ |
| 6-46 | H | H | 4-NHCH$_2$CO$_2$H |
| 6-47 | H | H | 4-NHCH$_2$CO$_2$CH$_3$ |
| 6-48 | H | H | 4-NHCH$_2$CO$_2$CH$_2$CH$_3$ |
| 6-49 | H | H | 4-NHCH$_2$CO$_2$CH(CH$_3$)$_2$ |
| 6-50 | H | H | 4-NHCH$_2$CO$_2$CH$_2$CH=CH$_2$ |
| 6-51 | H | H | 3-NHCH(CH$_3$)CO$_2$H |
| 6-52 | H | H | 3-NHCH(CH$_3$)CO$_2$CH$_3$ |
| 6-53 | H | H | 3-NHCH(CH$_3$)CO$_2$CH$_2$CH$_3$ |
| 6-54 | H | H | 3-NHCH(CH$_3$)CO$_2$CH(CH$_3$)$_2$ |
| 6-55 | H | H | 3-NHCH(CH$_3$)CO$_2$CH$_2$CH=CH$_2$ |
| 6-56 | H | H | 3-NHCH$_2$CO$_2$H |
| 6-57 | H | H | 3-NHCH$_2$CO$_2$CH$_3$ |
| 6-58 | H | H | 3-NHCH$_2$CO$_2$CH$_2$CH$_3$ |
| 6-59 | H | H | 3-NHCH$_2$CO$_2$CH(CH$_3$)$_2$ |
| 6-60 | H | H | 3-NHCH$_2$CO$_2$CH$_2$CH=CH$_2$ |

TABLE 7

Compound of the formula [I-7]: [I-7]

| Compound No. | $Z^1$ | $Z^2$ | $R^3$ |
|---|---|---|---|
| 7-1 | H | H | 2-OCH(CH$_3$)CO$_2$H |
| 7-2 | H | H | 2-OCH(CH$_3$)CO$_2$CH$_3$ |
| 7-3 | H | H | 2-OCH(CH$_3$)CO$_2$CH$_2$CH$_3$ |
| 7-4 | H | H | 2-OCH(CH$_3$)CO$_2$CH(CH$_3$)$_2$ |
| 7-5 | H | H | 2-OCH(CH$_3$)CO$_2$CH$_2$CH=CH$_2$ |
| 7-6 | H | H | 2-OCH$_2$CO$_2$H |
| 7-7 | H | H | 2-OCH$_2$CO$_2$CH$_3$ |
| 7-8 | H | H | 2-OCH$_2$CO$_2$CH$_2$CH$_3$ |
| 7-9 | H | H | 2-OCH$_2$CO$_2$CH(CH$_3$)$_2$ |
| 7-10 | H | H | 2-OCH$_2$CO$_2$CH$_2$CH=CH$_2$ |
| 7-11 | H | H | 4-OCH(CH$_3$)CO$_2$H |
| 7-12 | H | H | 4-OCH(CH$_3$)CO$_2$CH$_3$ |
| 7-13 | H | H | 4-OCH(CH$_3$)CO$_2$CH$_2$CH$_3$ |
| 7-14 | H | H | 4-OCH(CH$_3$)CO$_2$CH(CH$_3$)$_2$ |
| 7-15 | H | H | 4-OCH(CH$_3$)CO$_2$CH$_2$CH=CH$_2$ |

TABLE 7-continued

Compound of the formula [I-7]: [I-7]

| Compound No. | $Z^1$ | $Z^2$ | $R^3$ |
|---|---|---|---|
| 7-16 | H | H | 4-OCH$_2$CO$_2$H |
| 7-17 | H | H | 4-OCH$_2$CO$_2$CH$_3$ |
| 7-18 | H | H | 4-OCH$_2$CO$_2$CH$_2$CH$_3$ |
| 7-19 | H | H | 4-OCH$_2$CO$_2$CH(CH$_3$)$_2$ |
| 7-20 | H | H | 4-OCH$_2$CO$_2$CH$_2$CH=CH$_2$ |
| 7-21 | H | H | 2-SCH(CH$_3$)CO$_2$H |
| 7-22 | H | H | 2-SCH(CH$_3$)CO$_2$CH$_3$ |
| 7-23 | H | H | 2-SCH(CH$_3$)CO$_2$CH$_2$CH$_3$ |
| 7-24 | H | H | 2-SCH(CH$_3$)CO$_2$CH(CH$_3$)$_2$ |
| 7-25 | H | H | 2-SCH(CH$_3$)CO$_2$CH$_2$CH=CH$_2$ |
| 7-26 | H | H | 2-SCH$_2$CO$_2$H |
| 7-27 | H | H | 2-SCH$_2$CO$_2$CH$_3$ |
| 7-28 | H | H | 2-SCH$_2$CO$_2$CH$_2$CH$_3$ |
| 7-29 | H | H | 2-SCH$_2$CO$_2$CH(CH$_3$)$_2$ |
| 7-30 | H | H | 2-SCH$_2$CO$_2$CH$_2$CH=CH$_2$ |
| 7-31 | H | H | 4-SCH(CH$_3$)CO$_2$H |
| 7-32 | H | H | 4-SCH(CH$_3$)CO$_2$CH$_3$ |
| 7-33 | H | H | 4-SCH(CH$_3$)CO$_2$CH$_2$CH$_3$ |
| 7-34 | H | H | 4-SCH(CH$_3$)CO$_2$CH(CH$_3$)$_2$ |
| 7-35 | H | H | 4-SCH(CH$_3$)CO$_2$CH$_2$CH=CH$_2$ |
| 7-36 | H | H | 4-SCH$_2$CO$_2$H |
| 7-37 | H | H | 4-SCH$_2$CO$_2$CH$_3$ |
| 7-38 | H | H | 4-SCH$_2$CO$_2$CH$_2$CH$_3$ |
| 7-39 | H | H | 4-SCH$_2$CO$_2$CH(CH$_3$)$_2$ |
| 7-40 | H | H | 4-SCH$_2$CO$_2$CH$_2$CH=CH$_2$ |
| 7-41 | H | H | 6-OCH$_2$CO$_2$H |
| 7-42 | H | H | 6-OCH$_2$CO$_2$CH$_3$ |
| 7-43 | H | H | 6-OCH$_2$CO$_2$CH$_2$CH$_3$ |
| 7-44 | H | H | 6-OCH$_2$CO$_2$C(CH$_3$)$_3$ |
| 7-45 | H | H | 6-OCH$_2$CO$_2$CH$_2$C$_6$H$_5$ |
| 7-46 | H | H | 6-OCH$_2$CO$_2$C$_6$H$_5$ |
| 7-47 | H | H | 6-OCH$_2$CONHOCH$_3$ |
| 7-48 | H | H | 2-OCH$_2$CO$_2$CH$_2$CH$_2$CH$_3$ |
| 7-49 | H | H | 2-OCH$_2$CO$_2$CH$_2$CH$_2$CH$_2$CH$_3$ |
| 7-50 | H | H | 2-OCH$_2$CO$_2$CH$_2$CH$_2$CH$_2$CH$_2$CH$_3$ |
| 7-51 | H | H | 2-NHCH(CH$_3$)CO$_2$H |
| 7-52 | H | H | 2-NHCH(CH$_3$)CO$_2$CH$_3$ |
| 7-53 | H | H | 2-NHCH(CH$_3$)CO$_2$CH$_2$CH$_3$ |
| 7-54 | H | H | 2-NHCH(CH$_3$)CO$_2$CH(CH$_3$)$_2$ |
| 7-55 | H | H | 2-NHCH(CH$_3$)CO$_2$CH$_2$CH=CH$_2$ |
| 7-56 | H | H | 2-NHCH$_2$CO$_2$H |
| 7-57 | H | H | 2-NHCH$_2$CO$_2$CH$_3$ |
| 7-58 | H | H | 2-NHCH$_2$CO$_2$CH$_2$CH$_3$ |
| 7-59 | H | H | 2-NHCH$_2$CO$_2$CH(CH$_3$)$_2$ |
| 7-60 | H | H | 2-NHCH$_2$CO$_2$CH$_2$CH=CH$_2$ |
| 7-61 | H | H | 4-NHCH(CH$_3$)CO$_2$H |
| 7-62 | H | H | 4-NHCH(CH$_3$)CO$_2$CH$_3$ |
| 7-63 | H | H | 4-NHCH(CH$_3$)CO$_2$CH$_2$CH$_3$ |
| 7-64 | H | H | 4-NHCH(CH$_3$)CO$_2$CH(CH$_3$)$_2$ |
| 7-65 | H | H | 4-NHCH(CH$_3$)CO$_2$CH$_2$CH=CH$_2$ |
| 7-66 | H | H | 4-NHCH$_2$CO$_2$H |
| 7-67 | H | H | 4-NHCH$_2$CO$_2$CH$_3$ |
| 7-68 | H | H | 4-NHCH$_2$CO$_2$CH$_2$CH$_3$ |
| 7-69 | H | H | 4-NHCH$_2$CO$_2$CH(CH$_3$)$_2$ |
| 7-70 | H | H | 4-NHCH$_2$CO$_2$CH$_2$CH=CH$_2$ |
| 7-71 | H | H | 6-OCH(CH$_3$)CO$_2$C(CH$_3$)$_3$ |
| 7-72 | H | H | 6-OCH(CH$_3$)CO$_2$CH$_2$C$_6$H$_5$ |
| 7-73 | H | H | 6-OCH(CH$_3$)CO$_2$C$_6$H$_5$ |
| 7-74 | H | H | 6-OCH(CH$_3$)CONHOCH$_3$ |
| 7-75 | H | H | 2-OCH(CH$_3$)CO$_2$C(CH$_3$)$_3$ |
| 7-76 | H | H | 2-OCH(CH$_3$)CO$_2$CH$_2$C$_6$H$_5$ |

TABLE 7-continued

Compound of the formula [I-7]:

[I-7]

| Compound No. | $Z^1$ | $Z^2$ | $R^3$ |
|---|---|---|---|
| 7-77 | H | H | 2-OCH(CH$_3$)CO$_2$C$_6$H$_5$ |
| 7-78 | H | H | 2-OCH(CH$_3$)CONHOCH$_3$ |
| 7-79 | H | H | 2-OCH(CH$_3$)CONHOCH$_2$CH$_3$ |
| 7-80 | H | H | 2-OCH(CH$_3$)CON(CH$_3$)OCH$_3$ |
| 7-81 | H | H | 2-OCH$_2$CO$_2$C(CH$_3$)$_3$ |
| 7-82 | H | H | 2-OCH$_2$CO$_2$CH$_2$C$_6$H$_5$ |
| 7-83 | H | H | 2-OCH$_2$CO$_2$C$_6$H$_5$ |
| 7-84 | H | H | 2-OCH$_2$CONHOCH$_3$ |
| 7-85 | H | H | 2-OCH$_2$CONHOCH$_2$CH$_3$ |
| 7-86 | H | H | 2-OCH$_2$CON(CH$_3$)OCH$_3$ |
| 7-87 | 4-Cl | H | 2-OCH(CH$_3$)CO$_2$H |
| 7-88 | 4-Cl | H | 2-OCH(CH$_3$)CO$_2$CH$_3$ |
| 7-89 | 4-Cl | H | 2-OCH(CH$_3$)CO$_2$CH$_2$CH$_3$ |
| 7-90 | 4-Cl | H | 2-OCH(CH$_3$)CO$_2$C(CH$_3$)$_3$ |
| 7-91 | 4-Cl | H | 2-OCH(CH$_3$)CO$_2$CH$_2$C$_6$H$_5$ |
| 7-92 | 4-Cl | H | 2-OCH(CH$_3$)CO$_2$C$_6$H$_5$ |
| 7-93 | 4-Cl | H | 2-OCH(CH$_3$)CONHOCH$_3$ |
| 7-94 | 4-Cl | H | 2-OCH$_2$CO$_2$H |
| 7-95 | 4-Cl | H | 2-OCH$_2$CO$_2$CH$_3$ |
| 7-96 | 4-Cl | H | 2-OCH$_2$CO$_2$CH$_2$CH$_3$ |
| 7-97 | 4-Cl | H | 2-OCH$_2$CO$_2$C(CH$_3$)$_3$ |
| 7-98 | 4-Cl | H | 2-OCH$_2$CO$_2$CH$_2$C$_6$H$_5$ |
| 7-99 | 4-Cl | H | 2-OCH$_2$CO$_2$C$_6$H$_5$ |
| 7-100 | 4-Cl | H | 2-OCH$_2$CONHOCH$_3$ |
| 7-101 | 4-OCH$_3$ | H | 2-OCH(CH$_3$)CO$_2$H |
| 7-102 | 4-OCH$_3$ | H | 2-OCH(CH$_3$)CO$_2$CH$_3$ |
| 7-103 | 4-OCH$_3$ | H | 2-OCH(CH$_3$)CO$_2$CH$_2$CH$_3$ |
| 7-104 | 4-OCH$_3$ | H | 2-OCH(CH$_3$)CO$_2$C(CH$_3$)$_3$ |
| 7-105 | 4-OCH$_3$ | H | 2-OCH(CH$_3$)CO$_2$CH$_2$C$_6$H$_5$ |
| 7-106 | 4-OCH$_3$ | H | 2-OCH(CH$_3$)CO$_2$C$_6$H$_5$ |
| 7-107 | 4-OCH$_3$ | H | 2-OCH(CH$_3$)CONHOCH$_3$ |
| 7-108 | 4-OCH$_3$ | H | 2-OCH$_2$CO$_2$H |
| 7-109 | 4-OCH$_3$ | H | 2-OCH$_2$CO$_2$CH$_3$ |
| 7-110 | 4-OCH$_3$ | H | 2-OCH$_2$CO$_2$CH$_2$CH$_3$ |
| 7-111 | 4-OCH$_3$ | H | 2-OCH$_2$CO$_2$C(CH$_3$)$_3$ |
| 7-112 | 4-OCH$_3$ | H | 2-OCH$_2$CO$_2$CH$_2$C$_6$H$_5$ |
| 7-113 | 4-OCH$_3$ | H | 2-OCH$_2$CO$_2$C$_6$H$_5$ |
| 7-114 | 4-OCH$_3$ | H | 2-OCH$_2$CONHOCH$_3$ |
| 7-115 | H | H | 6-OCH(CH$_3$)CO$_2$H |
| 7-116 | H | H | 6-OCH(CH$_3$)CO$_2$CH$_3$ |
| 7-117 | H | H | 6-OCH(CH$_3$)CO$_2$CH$_2$CH$_3$ |
| 7-118 | H | H | 2-OCH$_2$COON=C(CH$_3$)$_2$ |
| 7-119 | H | H | 2-OCH$_2$CO$_2$CH$_2$CO$_2$CH$_3$ |
| 7-120 | H | H | 2-OCH$_2$CO$_2$CH(CH$_3$)CO$_2$CH$_2$CH$_3$ |
| 7-121 | H | H | 2-OCH$_2$CO$_2$C(CH$_3$)$_2$CO$_2$CH$_3$ |
| 7-122 | H | H | 2-OCH(CH$_3$)CO$_2$CH$_2$CO$_2$CH$_3$ |
| 7-123 | H | H | 2-OCH(CH$_3$)CO$_2$CH(CH$_3$)CO$_2$CH$_2$CH$_3$ |
| 7-124 | H | H | 2-OCH(CH$_3$)CO$_2$C(CH$_3$)$_2$CO$_2$CH$_3$ |
| 7-125 | H | H | 2-OCH$_2$CO$_2$c-C$_5$H$_9$ |

TABLE 8

Compound of the formula [I-8]:

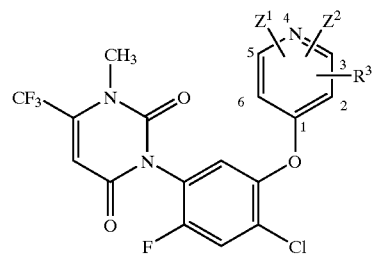

[I-8]

| Compound No. | $Z^1$ | $Z^2$ | $R^3$ |
|---|---|---|---|
| 8-1 | H | H | 2-OCH(CH$_3$)CO$_2$H |
| 8-2 | H | H | 2-OCH(CH$_3$)CO$_2$CH$_3$ |
| 8-3 | H | H | 2-OCH(CH$_3$)CO$_2$CH$_2$CH$_3$ |
| 8-4 | H | H | 2-OCH(CH$_3$)CO$_2$CH(CH$_3$)$_2$ |
| 8-5 | H | H | 2-OCH(CH$_3$)CO$_2$CH$_2$CH=CH$_2$ |
| 8-6 | H | H | 2-OCH$_2$CO$_2$H |
| 8-7 | H | H | 2-OCH$_2$CO$_2$CH$_3$ |
| 8-8 | H | H | 2-OCH$_2$CO$_2$CH$_2$CH$_3$ |
| 8-9 | H | H | 2-OCH$_2$CO$_2$CH(CH$_3$)$_2$ |
| 8-10 | H | H | 2-OCH$_2$CO$_2$CH$_2$CH=CH$_2$ |
| 8-11 | H | H | 2-SCH(CH$_3$)CO$_2$H |
| 8-12 | H | H | 2-SCH(CH$_3$)CO$_2$CH$_3$ |
| 8-13 | H | H | 2-SCH(CH$_3$)CO$_2$CH$_2$CH$_3$ |
| 8-14 | H | H | 2-SCH(CH$_3$)CO$_2$CH(CH$_3$)$_2$ |
| 8-15 | H | H | 2-SCH(CH$_3$)CO$_2$CH$_2$CH=CH$_2$ |
| 8-16 | H | H | 2-SCH$_2$CO$_2$H |
| 8-17 | H | H | 2-SCH$_2$CO$_2$CH$_3$ |
| 8-18 | H | H | 2-SCH$_2$CO$_2$CH$_2$CH$_3$ |
| 8-19 | H | H | 2-SCH$_2$CO$_2$CH(CH$_3$)$_2$ |
| 8-20 | H | H | 2-SCH$_2$CO$_2$CH$_2$CH=CH$_2$ |
| 8-21 | H | H | 2-OCH$_2$CO$_2$CH$_2$C$_6$H$_5$ |
| 8-22 | H | H | 2-OCH$_2$CO$_2$C$_6$H$_5$ |
| 8-23 | H | H | 2-OCH$_2$CONHOCH$_3$ |
| 8-24 | H | H | 2-OCH$_2$CONHOCH$_2$CH$_3$ |
| 8-25 | H | H | 2-OCH$_2$CON(CH$_3$)OCH$_3$ |
| 8-26 | H | H | 2-NHCH(CH$_3$)CO$_2$H |
| 8-27 | H | H | 2-NHCH(CH$_3$)CO$_2$CH$_3$ |
| 8-28 | H | H | 2-NHCH(CH$_3$)CO$_2$CH$_2$CH$_3$ |
| 8-29 | H | H | 2-NHCH(CH$_3$)CO$_2$CH(CH$_3$)$_2$ |
| 8-30 | H | H | 2-NHCH(CH$_3$)CO$_2$CH$_2$CH=CH$_2$ |
| 8-31 | H | H | 2-NHCH$_2$CO$_2$H |
| 8-32 | H | H | 2-NHCH$_2$CO$_2$CH$_3$ |
| 8-33 | H | H | 2-NHCH$_2$CO$_2$CH$_2$CH$_3$ |
| 8-34 | H | H | 2-NHCH$_2$CO$_2$CH(CH$_3$)$_2$ |
| 8-35 | H | H | 2-NHCH$_2$CO$_2$CH$_2$CH=CH$_2$ |
| 8-36 | H | H | 2-OCH$_2$CON(CH$_3$)OCH$_3$ |
| 8-37 | H | H | 2-OCH$_2$CO$_2$C(CH$_3$)$_3$ |
| 8-38 | H | H | 2-OCH(CH$_3$)CO$_2$C(CH$_3$)$_3$ |
| 8-39 | H | H | 2-OCH(CH$_3$)CO$_2$CH$_2$C$_6$H$_5$ |
| 8-40 | H | H | 2-OCH(CH$_3$)CO$_2$C$_6$H$_5$ |
| 8-41 | H | H | 2-OCH(CH$_3$)CONHOCH$_3$ |
| 8-42 | H | H | 2-OCH(CH$_3$)CONHOCH$_2$CH$_3$ |

TABLE 9

Compound of the formula [I-9]:

[I-9]

| Compound No. | $X^1$ | Y | $R^3$ |
|---|---|---|---|
| 9-1 | Br | O | 2-OCH(CH$_3$)CO$_2$H |

TABLE 9-continued

Compound of the formula [I-9]:

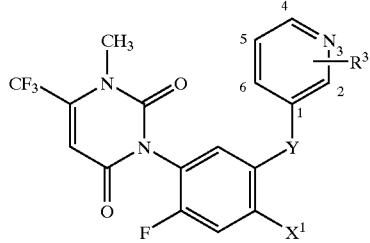

[I-9]

| Compound No. | X¹ | Y | R³ |
|---|---|---|---|
| 9-2 | Br | O | 2-OCH(CH₃)CO₂CH₃ |
| 9-3 | Br | O | 2-OCH(CH₃)CO₂CH₂CH₃ |
| 9-4 | Br | O | 2-OCH(CH₃)CO₂CH(CH₃)₂ |
| 9-5 | Br | O | 2-OCH(CH₃)CO₂CH₂CH=CH₂ |
| 9-6 | Br | O | 2-OCH₂CO₂H |
| 9-7 | Br | O | 2-OCH₂CO₂CH₃ |
| 9-8 | Br | O | 2-OCH₂CO₂CH₂CH₃ |
| 9-9 | Br | O | 2-OCH₂CO₂CH(CH₃)₂ |
| 9-10 | Br | O | 2-OCH₂CO₂CH₂CH=CH₂ |
| 9-11 | Br | O | 2-SCH(CH₃)CO₂H |
| 9-12 | Br | O | 2-SCH(CH₃)CO₂CH₃ |
| 9-13 | Br | O | 2-SCH(CH₃)CO₂CH₂CH₃ |
| 9-14 | Br | O | 2-SCH(CH₃)CO₂CH(CH₃)₂ |
| 9-15 | Br | O | 2-SCH(CH₃)CO₂CH₂CH=CH₂ |
| 9-16 | Br | O | 2-SCH₂CO₂H |
| 9-17 | Br | O | 2-SCH₂CO₂CH₃ |
| 9-18 | Br | O | 2-SCH₂CO₂CH₂CH₃ |
| 9-19 | Br | O | 2-SCH₂CO₂CH(CH₃)₂ |
| 9-20 | Br | O | 2-SCH₂CO₂CH₂CH=CH₂ |
| 9-21 | CN | O | 2-OCH(CH₃)CO₂H |
| 9-22 | CN | O | 2-OCH(CH₃)CO₂CH₃ |
| 9-23 | CN | O | 2-OCH(CH₃)CO₂CH₂CH₃ |
| 9-24 | CN | O | 2-OCH(CH₃)CO₂CH(CH₃)₂ |
| 9-25 | CN | O | 2-OCH(CH₃)CO₂CH₂CH=CH₂ |
| 9-26 | CN | O | 2-OCH₂CO₂H |
| 9-27 | CN | O | 2-OCH₂CO₂CH₃ |
| 9-28 | CN | O | 2-OCH₂CO₂CH₂CH₃ |
| 9-29 | CN | O | 2-OCH₂CO₂CH(CH₃)₂ |
| 9-30 | CN | O | 2-OCH₂CO₂CH₂CH=CH₂ |
| 9-31 | CN | O | 2-SCH(CH₃)CO₂H |
| 9-32 | CN | O | 2-SCH(CH₃)CO₂CH₃ |
| 9-33 | CN | O | 2-SCH(CH₃)CO₂CH₂CH₃ |
| 9-34 | CN | O | 2-SCH(CH₃)CO₂CH(CH₃)₂ |
| 9-35 | CN | O | 2-SCH(CH₃)CO₂CH₂CH=CH₂ |
| 9-36 | CN | O | 2-SCH₂CO₂H |
| 9-37 | CN | O | 2-SCH₂CO₂CH₃ |
| 9-38 | CN | O | 2-SCH₂CO₂CH₂CH₃ |
| 9-39 | CN | O | 2-SCH₂CO₂CH(CH₃)₂ |
| 9-40 | CN | O | 2-SCH₂CO₂CH₂CH=CH₂ |
| 9-41 | NO₂ | O | 2-OCH(CH₃)CO₂H |
| 9-42 | NO₂ | O | 2-OCH(CH₃)CO₂CH₃ |
| 9-43 | NO₂ | O | 2-OCH(CH₃)CO₂CH₂CH₃ |
| 9-44 | NO₂ | O | 2-OCH₂CO₂H |
| 9-45 | NO₂ | O | 2-OCH₂CO₂CH₃ |
| 9-46 | NO₂ | O | 2-OCH₂CO₂CH₂CH₃ |
| 9-47 | CN | S | 2-OCH(CH₃)CO₂CH₃ |
| 9-48 | CN | S | 2-OCH(CH₃)CO₂CH₂CH₃ |
| 9-49 | CN | S | 2-OCH₂CO₂CH₃ |
| 9-50 | CN | S | 2-OCH₂CO₂CH₂CH₃ |

TABLE 10

Compound of the formula [I-10]:

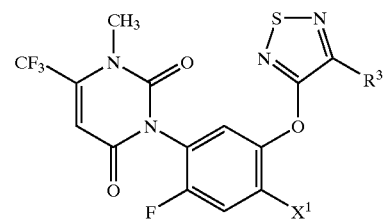

[I-10]

| Compound No. | X¹ | R³ |
|---|---|---|
| 10-1 | Cl | OCH(CH₃)CO₂H |
| 10-2 | Cl | OCH(CH₃)CO₂CH₃ |
| 10-3 | Cl | OCH(CH₃)CO₂CH₂CH₃ |
| 10-4 | Cl | OCH(CH₃)CO₂CH(CH₃)₂ |
| 10-5 | Cl | OCH(CH₃)CO₂CH₂CH=CH₂ |
| 10-6 | Cl | OCH₂CO₂H |
| 10-7 | Cl | OCH₂CO₂CH₃ |
| 10-8 | Cl | OCH₂CO₂CH₂CH₃ |
| 10-9 | Cl | OCH₂CO₂CH(CH₃)₂ |
| 10-10 | Cl | OCH₂CO₂CH₂CH=CH₂ |
| 10-11 | Br | OCH(CH₃)CO₂H |
| 10-12 | Br | OCH(CH₃)CO₂CH₃ |
| 10-13 | Br | OCH(CH₃)CO₂CH₂CH₃ |
| 10-14 | Br | OCH₂CO₂H |
| 10-15 | Br | OCH₂CO₂CH₃ |
| 10-16 | Br | OCH₂CO₂CH₂CH₃ |
| 10-17 | NO₂ | OCH(CH₃)CO₂H |
| 10-18 | NO₂ | OCH(CH₃)CO₂CH₃ |
| 10-19 | NO₂ | OCH(CH₃)CO₂CH₂CH₃ |
| 10-20 | NO₂ | OCH₂CO₂H |
| 10-21 | NO₂ | OCH₂CO₂CH₃ |
| 10-22 | NO₂ | OCH₂CO₂CH₂CH₃ |

Next, the formulation examples of the present compounds are explained. In the examples, the present compounds are shown as Compound No. in Tables 1 to 10, and "part(s)" shows "part(s) by weight".

Formulation Example 1

Fifty (50) parts of each of the present compounds 1-1 to 1-67, 2-1 to 2-106, 3-1 to 3-90, 4-1 to 4-94, 5-1 to 5-75, 6-1 to 6-60, 7-1 to 7-125, 8-1 to 8-42, 9-1 to 9-50, and 10-1 to 10-22, 3 parts of calcium ligninsulfonate, 2 parts of sodium laurylsulfate, and 45 parts of synthetic hydrated silicon dioxide are well pulverized and mixed, to obtain each of the wettable powders.

Formulation Example 2

Ten (10) parts of each of the present compounds 1-1 to 1-67, 2-1 to 2-106, 3-1 to 3-90, 4-1 to 4-94, 5-1 to 5-75, 6-1 to 6-60, 7-1 to 7-125, 8-1 to 8-42, 9-1 to 9-50, and 10-1 to 10-22, 14 parts of polyoxyethylenestyryl phenyl ether, 6 parts of calcium dodecylbenzenesulfonate, 35 parts of xylene, and 35 parts of cyclohexanone are mixed to obtain each of the emulsifiable concentrates.

Formulation Example 3

Two (2) parts of each of the present compounds 1-1 to 1-67, 2-1 to 2-106, 3-1 to 3-90, 4-1 to 4-94, 5-1 to 5-75, 6-1 to 6-60, 7-1 to 7-125, 8-1 to 8-42, 9-1 to 9-50, and 10-1 to 10-22, 2 parts of synthetic hydrated silica, 2 parts of calcium ligninsulfonate, 30 parts of bentonite, and 64 parts of kaolin clay are well pulverized and mixed, and after adding water and well kneading, that is granulated and dried to obtain each of the granules.

Formulation Example 4

Twenty-five (25) parts of each of the present compounds 1-1 to 1-67, 2-1 to 2-106, 3-1 to 3-90, 4-1 to 4-94, 5-1 to 5-75, 6-1 to 6-60, 7-1 to 7-125, 8-1 to 8-42, 9-1 to 9-50, and 10-1 to 10-22, 50 parts of a 10% aqueous solution of polyvinyl alcohol, and 25 parts of water are mixed, are wet pulverized until the average particle diameter is 5 μm or less, to obtain each of the flowables.

Formulation Example 5

Five(5) parts of each of the present compounds 1-1 to 1-67, 2-1 to 2-106, 3-1 to 3-90, 4-1 to 4-94, 5-1 to 5-75, 6-1 to 6-60, 7-1 to 7-125, 8-1 to 8-42, 9-1 to 9-50, and 10-1 to 10-22 is added into 40 parts of 10% aqueous solution of polyvinyl alcohol, and the mixture is emulsified and dispersed until the average diameter is 10μm or less by homogenizer. Next, 55 parts of water is added to the resultant mixture to obtain each of the concentrated emulsion.

Test Example 1

Test for Foliar Treatment of Field

A cylindrical plastic pot having a diameter of 10 cm and a depth of 10 cm was filled with soil and then seeded with ivyleaf morningglory (*Ipomoea hederacea*) and velvetleaf (*Abutilon theophrasti*). These test plants were grown in a greenhouse for 10 days. Then, each of compounds 1-2, 1-42, 1-45, 1-48, 2-2, 2-7, 2-42, 2-45, 3-2, 3-12, 4-7, 4-85, 5-12-R, 5-12-S, 5-17, 6-2, 7-2, 7-6, 7-8, 7-12, 7-48, 7-50, 7-84, 7-118, 7-119, 7-125, 9-7, 9-27 and 9-45 was formulated into an emulsifiable concentrate according to Formulation Example 2 and then diluted to the prescribed amount with water containing a spreading agent and the dilution was uniformly sprayed over the foliage of the test plants with a sprayer at a rate of 1000 liters per hectare. After the application, the test plants were grown in the greenhouse for 16 days, and the herbicidal activity was determined. As a result, the growth of Ivyleaf morningglory and velvetleaf were completely controlled when compounds 1-2, 1-42, 1-45, 1-48, 2-2, 2-7, 2-42, 2-45, 3-2, 3-12, 4-7, 4-85, 5-12-R, 5-12-S, 5-17, 6-2, 7-2, 7-6, 7-8, 7-12, 7-48, 7-50, 7-84, 7-118, 7-119, 7-125, 9-7, 9-27 and 9-45 were applied at the dosage of 125 g/ha, respectively.

Test Example 2

Test for Soil Surface Treatment of Field

A cylindrical plastic pot having a diameter of 10 cm and a depth of 10 cm was filled with soil and then seeded with ivyleaf morningglory (*Ipomoea hederacea*) and velvetleaf (*Abutilon theophrasti*). Then, each of the compounds 1-2, 1-42, 1-48, 2-2, 2-7, 2-42, 2-45, 3-2, 3-12, 4-7, 4-85, 5-12-R, 5-12-S, 5-17, 6-2, 7-2, 7-6, 7-8, 7-12, 7-48, 7-50, 7-84, 7-118, 7-119, 7-125, 9-7, 9-27 and 9-45 was formulated into an emulsifiable concentrate according to Formulation Example 2 and then diluted to the prescribed amount with water, and the dilution was uniformly sprayed over the surface of the soil with a sprayer at a rate of 1000 liters per hectare. After the application, the test plants were grown in the greenhouse for 19 days, and the herbicidal activity was examined. The growth of ivyleaf morningglory And velvetleaf were completely controlled when compounds 1-2, 1-42, 1-48, 2-2, 2-7, 2-42, 2-45, 3-2, 3-12, 4-7, 4-85, 5-12-R, 5-12-S, 5-17, 6-2, 7-2, 7-6, 7-8, 7-12, 7-48, 7-50, 7-84, 7-118, 7-119, 7-125, 9-7, 9-27 and 9-45 were applied at the dosage of 500 g/ha, respectively.

Test Example 3

Test for Foliar Treatment of Field

A plastic pot having longer side of 27 cm, shorter side of 20 cm and depth of 7.5 cm was filled with soil and then seeded with ivyleaf morningglory (*Ipomoea hederacea*) and common cocklebur (*Xanthium pensylvanicum*). These test plants were grown in a greenhouse for 10 days. Then, therein, transplanted were common lambsquarters (*Chenopodium album*), redroot pigweed and giant foxtail (*Setaria faberi*) which had been seeded and grown for 14 days in a green house in advance. The test plants were further grown in the greenhouse for 8 days. After then, present compound 1-12 was formulated into an emulsifiable concentrate according to Formulation Example 2 and then diluted to the prescribed amount with water containing a spreading agent and the dilution was uniformly sprayed over the foliage of the test plants with a sprayer at a rate of 1000 liters per hectare. After the application, the test plants were grown in the greenhouse for 25 days, and the herbicidal activity was examined. As a result, the growth of ivyleaf morningglory, common cocklebur, common lambsquarters, redroot pigweed and giant foxtail were completely controlled when compound 1-12 were applied at the dosage of 16 g/ha.

Test Example 4

Test for Soil Surface Treatment of Field

A plastic pot having longer side of 32 cm, shorter side of 22 cm and depth of 8 cm was filled with soil and then seeded with hemp sesbania (*Sesbania exaltata*), black nightshade (*Solanum nigrum*), velvetleaf (*Abutilon theophrasti*), pale smartweed (*Polygonum lapathifolium*), common lambsquarters (*Chenopodium album*) and giant foxtail (*Setaria faberi*). Then, the present compound 1-12 was formulated into an emulsifiable concentrate according to Formulation Example 2 and then diluted to the prescribed amount with water, and the dilution was uniformly sprayed over the surface of the soil with a sprayer at a rate of 1000 liters per hectare. After the application, the test plants were grown in the greenhouse for 25 days, and the herbicidal activity was examined. The growth of hemp sesbania, black nightshade, velvetleaf, pale smartweed, common lambsquarters and giant foxtail were completely controlled when the compound 1-12 was applied at the dosage of 250 g/ha.

Test Example 5

Test for Foliar Treatment of Field

A plastic pot having longer side of 27 cm, shorter side of 20 cm and depth of 7.5 cm was filled with soil and then seeded with ivyleaf morningglory (*Ipomoea hederacea*) and common cocklebur (*Xanthium pensylvanicum*). Three days after, barnyardgrass (*Echinochloa crus-galli*) was seeded therein and grown for 7 days in a greenhouse. Then, therein, transplanted were common lambsquarters (*Chenopodium album*), redroot pigweed and giant foxtail (*Setaria faberi*) which had been seeded and grown for 14 days in a green house in advance. The test plants were further grown in the greenhouse for 8 days. After then, present compound 7-7 was formulated into an emulsifiable concentrate according to Formulation Example 2 and then diluted to the prescribed amount with water containing a spreading agent and the dilution was uniformly sprayed over the foliage of the test plants with a sprayer at a rate of 1000 liters per hectare. After the application, the test plants were grown in the greenhouse for 6 days, and the herbicidal activity was examined. As a result, the growth of ivyleaf morningglory, common cocklebur, barnyardgrass, common lambsquarters, redroot pigweed and giant foxtail were completely controlled when the compound 7-7 was applied at the dosage of 16 g/ha.

In the following test examples, the herbicidal activity was evaluated at 11 levels with indices of 0 to 10, i.e., designated by the numeral "0", "1", "2", "3", "4", "5", "6", "7", "8", "9" or "10" wherein "0" means that there was no or little difference in the degree of germination or growth between the treated and the untreated tested plants at the time of examination, and "10" means that the test plants died complete or their germination or growth was completely inhibited.

TABLE 11

| Compound No | Structure | Note |
|---|---|---|
| A | (structure with $F_3C$, $CH_3$, $H_3CO$, $OCH_3$, pyrimidine, NH, F, Cl) | WO 92/11244 |
| B | (structure with $F_3C$, $CH_3$, $H_3CO$, $OCH_3$, triazine, O, F, Cl) | USP 4859229 |
| C | (structure with $F_3C$, $NH_2$, pyridine, $NHCOCH_3$, O, F, Cl) | WO 98/41093 |

Test Example 6

A plastic pot having longer side of 27 cm, shorter side of 19 cm and depth of 7 cm was filled with soil and then seeded with large crabgrass (*Digitaria sanguinalis*) and giant foxtail (*Setaria faberi*). Nine days after, barnyardgrass (*Echinochloa crus-galli*) was seeded therein and grown for 15 days in a greenhouse. Further, a plastic pot having longer side of 16.5 cm, shorter side of 12 cm and depth of 7 cm was filled with soil and then seeded with wild oat (*Avena fatua*), and grown for 18 days in a greenhouse. Then, each of the present compound 1-67 and A was formulated into an emulsifiable concentrate according to Formulation Example 2 and then diluted to the prescribed amount with water containing a spreading agent and the dilution was uniformly sprayed over the foliage of the test plants with a sprayer at a rate of 1000liters per hectare. After the application, the test plants were grown in the greenhouse for 4 days, and the herbicidal activity was examined. The results are shown in the following Table 12. (In the Table 12, the test plants are shown as follows.
Barnyardgrass: B, Large crabgrass: LC, Giant foxtail: GF, Wild oat: W

TABLE 12

| Compound No. | Dosage (g/ha) | Herbicidal activity | | | |
|---|---|---|---|---|---|
| | | B | LC | GF | W |
| 1-67 | 125 | 10 | 9 | 10 | 9 |
| | 32 | 10 | 9 | 10 | 8 |

TABLE 12-continued

| Compound No. | Dosage (g/ha) | Herbicidal activity | | | |
|---|---|---|---|---|---|
| | | B | LC | GF | W |
| A | 125 | 4 | 8 | 5 | 3 |
| | 32 | 4 | 6 | 4 | 2 |

Test Example 7

A plastic pot having longer side of 27 cm, shorter side of 19 cm and depth of 7 cm was filled with soil and then seeded with large crabgrass (*Digitaria sanguinalis*) and giant foxtail (*Setaria faberi*). Nine days after, barnyardgrass (*Echinochloa crus-galli*) was seeded therein and grown for 15 days in a greenhouse. Further, a plastic pot having longer side of 16.5 cm, shorter side of 12 cm and depth of 7 cm was filled with soil and then seeded with wild oat (*Avena fatua*), and grown for 18 days in a greenhouse. Then, each of the present compound 1-45 and B was formulated into an emulsifiable concentrate according to Formulation Example 2 and then diluted to the prescribed amount with water containing a spreading agent and the dilution was uniformly sprayed over the foliage of the test plants with a sprayer at a rate of 1000 liters per hectare. After the application, the test plants were grown in the greenhouse for 4 days, and the herbicidal activity was examined. The results are shown in the following Table 13. (In the Table 13, the test plants are shown as follows.
Barnyardgrass: B, Large crabgrass: LC, Giant foxtail: GF, Wild oat: W

TABLE 13

| Compound No. | Dosage (g/ha) | Herbicidal activity | | | |
|---|---|---|---|---|---|
| | | B | LC | GF | W |
| 1-45 | 125 | 10 | 10 | 10 | 9 |
| | 32 | 10 | 10 | 10 | 9 |
| B | 125 | 8 | 8 | 8 | 9 |
| | 32 | 6 | 8 | 6 | 6 |

Test Example 8

A plastic pot having longer side of 16.5 cm, shorter side of 12 cm and depth of 7 cm was filled with soil and then seeded with large crabgrass (*Digitaria sanguinalis*), giant foxtail (*Setaria faberi*) and johnsongrass (*Sorghum halepense*). These test plants were grown in a greenhouse for 25 days. Then, each of the present compound 2-52 and C was formulated into an emulsifiable concentrate according to Formulation Example 2 and then diluted to the prescribed amount with water containing a spreading agent and the dilution was uniformly sprayed over the foliage of the test plants with a sprayer at a rate of 373 liters per hectare. After the application, the test plants were grown in the greenhouse for 4 days, and the herbicidal activity was examined. The results are shown in the following Table 14. (In the Table 14, the test plants are shown as follows.
Large crabgrass: LC, Giant foxtail: GF, Johnsongrass: J

TABLE 14

| Compound No. | Dosage (g/ha) | Herbicidal activity | | |
|---|---|---|---|---|
| | | LC | GF | J |
| 2-52 | 125 | 10 | 10 | 10 |
| | 32 | 9 | 9 | 10 |
| C | 125 | 9 | 9 | 10 |
| | 32 | 7 | 6 | 8 |

The excellent herbicidal effect can be obtained by using the present compound.

What is claimed is:

1. A uracil compound of formula [I]:

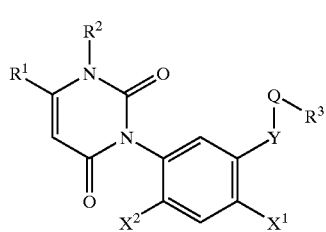

[wherein, Q—$R^3$ represents a $R^3$-substituted group of a 5-membered or 6-membered heterocyclic ring having at least one or two nitrogen selected from the group consisting of moieties represented by the following formulae

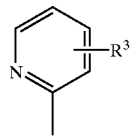
Q-1

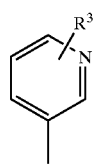
Q-2

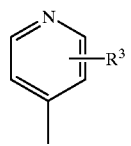
Q-3

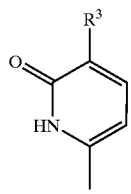
Q-4

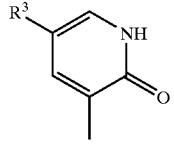
Q-5

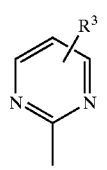
Q-6

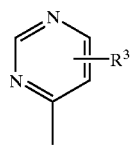
Q-7

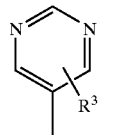
Q-8

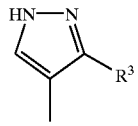
Q-9

-continued

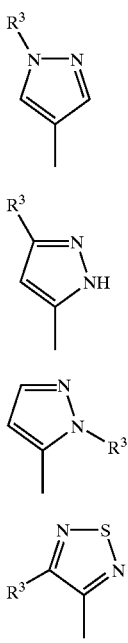

(wherein, this heterocyclic ring may be substituted with at least one kind of substituent selected from the group consisting of halogen, C1 to C6 alkyl, C1 to C6 haloalkyl, C2 to C6 alkenyl, C2 to C6 haloalkenyl, C2 to C6 alkynyl, C2 to C6 haloalkynyl, C1 to C6 alkoxy C1 to C6 alkyl, C1 to C6 alkoxy, C1 to C6 haloalkoxy, C1 to C6 alkoxycarbonyl C1 to C6 alkoxy, C1 to C6 alkoxycarbonyl C1 to C6 alkyl, cyano, hydroxy, mercapto), Y represents oxygen, sulfur, imino or C1 to C3 alkylimino, $R^1$ represents C1 to C3 alkyl or C1 to C3 haloalkyl, $R^2$ represents C1 to C3 alkyl, $R^3$ represents carboxy C1 to C6 alkyl, C1 to C6 alkoxycarbonyl C1 to C6 alkyl, C1 to C6 haloalkoxycarbonyl C1 to C6 alkyl, C3 to C6 alkenyloxycarbonyl C1 to C6 alkyl, C3 to C6 haloalkenyloxycarbonyl C1 to C6 alkyl, C3 to C6 alkynyloxycarbonyl C1 to C6 alkyl, C3 to C6 haloalkynyloxycarbonyl C1 to C6 alkyl, $OR^7$, $SR^8$ or $N(R^9)R^{10}$, $X^1$ represents halogen, cyano, thiocarbamoyl or nitro, $X^2$ represents hydrogen or halogen.
{wherein, each of $R^7$, $R^8$ and $R^{10}$ independently represents carboxy C1 to C6 alkyl, C1 to C6 alkoxycarbonyl C1 to C6 alkyl, C1 to C6 haloalkoxycarbonyl C1 to C6 alkyl, C3 to C6 alkenyloxycarbonyl C1 to C6 alkyl, C3 to C6 haloalkenyloxycarbonyl C1 to C6 alkyl, C3 to C6 alkynyloxycarbonyl C1 to C6 alkyl, C3 to C6 haloalkynyloxycarbonyl C1 to C6 alkyl, C3 to C8 cycloalkoxycarbonyl C1 to C6 alkyl, C3 to C8 halocycloalkoxycarbonyl C1 to C6 alkyl, C3 to C8 cycloalkenyloxycarbonyl C1 to C6 alkyl, C3 to C8 halocycloalkenyloxycarbonyl C1 to C6 alkyl, C1 to C6 alkoxycarbonyl C1 to C6 alkoxycarbonyl C1 to C6 alkyl, C1 to C8 alkylidenaminoxycarbonyl C1 to C6 alkyl, phenoxycarbonyl C1 to C6 alkyl which may be substituted, phenyl C1 to C4 alkoxycarbonyl C1 to C6 alkyl which may be substituted, C1 to C6 alkoxyaminocarbonyl C1 to C6 alkyl, (C1 to C6 alkoxy)(C1 to C3 alkyl) aminocarbonyl C1 to C6 alkyl, C1 to C6 alkylaminocarbonyl C1 to C6 alkyl, (C1 to C6 alkyl) C1 to C6 alkylaminocarbonyl C1 to C6 alkyl, phenylaminocarbonyl C1 to C6 alkyl which may be substituted, or phenyl C1 to C4 alkylaminocarbonyl C1 to C6 alkyl which may be substituted, and R9 represents hydrogen or C1 to C6 alkyl.}.].

2. The uracil compound according to claim 1, wherein the heterocyclic ring may be substituted with at least one kind of substituent selected from the group consisting of halogen, C1 to C6 alkyl, C1 to C6 haloalkyl, C3 to C6 alkenyl, C3 to C6 haloalkenyl, C3 to C6 alkynyl, C3 to C6 haloalkynyl, C1 to C6 alkoxy, C1 to C6 alkyl, C1 to C6 alkoxy, C1 to C6 haloalkoxy, C1 to C6 alkoxycarbonyl C1 to C6 alkoxy, C1 to C6 alkoxycarbonyl C1 to C6 alkyl, cyano, hydroxy, mercapto, $R^3$ represents carboxy C1 to C6 alkyl, C1 to C6 alkoxycarbonyl C1 to C6 alkyl, C1 to C6 haloalkoxycarbonyl C1 to C6 alkyl, C3 to C6 alkenyloxycarbonyl C1 to C6 alkyl, C3 to C6 haloalkenyloxycarbonyl C1 to C6 alkyl, C3 to C6 alkynyloxycarbonyl C1 to C6 alkyl, C3 to C6 haloalkynyloxycarbonyl C1 to C6 alkyl, $OR^7$, $S^8$ or $N(R^9)R^{10}$ {wherein, each of $R^7$, $R^8$ and $R^{10}$ independently represents carboxy C1 to C6 alkyl, C1 to C6 alkoxycarbonyl C1 to C4 alkyl, C1 to C6 haloalkoxycarbonyl C1 to C4 alkyl, C3 to C6 alkenyloxycarbonyl C1 to C4 alkyl, C3 to C6 alkynyloxycarbonyl C1 to C4 alkyl, phenoxycarbonyl C1 to C4 alkyl which may be substituted, phenyl C1 to C4 alkoxycarbonyl C1 to C4 alkyl which may be substituted, C1 to C6 alkoxyaminocarbonyl C1 to C4 alkyl, (C1 to C6 alkoxy)(C1 to C3 alkyl) aminocarbonyl C1 to C4 alkyl, C1 to C6 alkylaminocarbonyl C1 to C4 alkyl, (C1 to C6 alkyl) C1 to C6 alkylaminocarbonyl C1 to C4 alkyl, phenylaminocarbonyl C1 to C4 alkyl which may be substituted, or phenyl C1 to C4 alkylaminocarbonyl C1 to C4 alkyl which may be substituted, and $R^9$ represents hydrogen or C1 to C6 alkyl.}.

3. The uracil compound according to claim 1 or 2, wherein the group represented by Q—$R^3$ is any group selected from the group consisting of moieties represented by the following formulae:

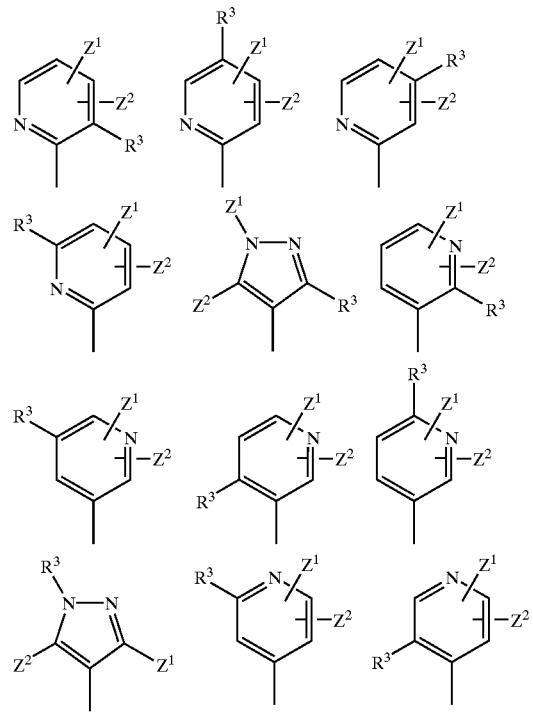

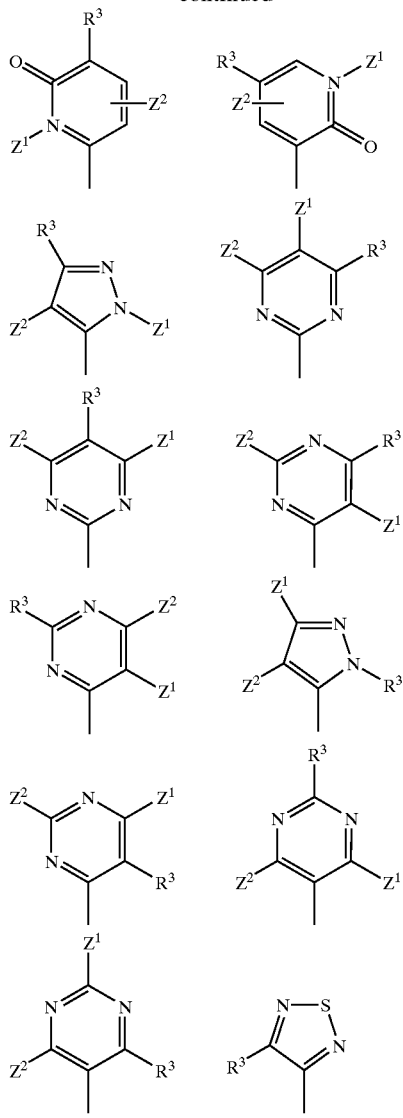

[wherein, R³ is the same as defined in claim 1 or 2, each of Z¹ and Z² independently represents hydrogen, halogen, C1 to C6 alkyl, C1 to C6 haloalkyl, C2 to C6 alkenyl, C2 to C6 haloalkenyl, C2 to C6 alkynyl, C2 to C6 haloalkynyl, C1 to C6 alkoxy C1 to C6 alkyl, C1 to C6 alkoxy, C1 to C6 haloalkoxy, C1 to C6 alkoxycarbonyl C1 to C6 alkoxy or cyano.].

4. The uracil compound according to claim 1 or 2, wherein X¹ is halogen.

5. The uracil compound according to claim 1 or 2, wherein X¹ is nitro.

6. The uracil compound according to claim 1 or 2, wherein X¹ is chlorine.

7. The uracil compound according to claim 1 or 2, wherein X² is hydrogen or fluorine.

8. The uracil compound according to claim 1 or 2, wherein X¹ is chlorine and x² is fluorine.

9. The uracil compound according to claim 1 or 2, wherein R¹ is CF₃.

10. The uracil compound according to claim 1 or 2, wherein R² is methyl.

11. The uracil compound according to claim 1 or 2, wherein Y is oxygen or sulfur.

12. The uracil compound according to claim 1 or 2, wherein Y is oxygen.

13. The uracil compound according to claim 1 or 2, wherein R³ is OR⁷, SR⁸ or N(R⁹)R¹⁰, and R⁷, R⁸ and R¹⁰ are C1 to C6 alkoxycarbonyl C1 to C6 alkyl, C1 to C6 haloalkoxycarbonyl C1 to C6 alkyl, C3 to C6 alkenyloxycarbonyl C1 to C6 alkyl, C3 to C6 alkynyloxycarbonyl C1 to C6 alkyl or C3 to C8 cycloalkoxycarbonyl C1 to C6 alkyl.

14. The uracil compound according to claim 1 or 2, wherein R³ is OR⁷, SR⁸ or N(R⁹)R¹⁰, and R⁷, R⁸ and R¹⁰ are C1 to C6 alkoxycarbonyl C1 to C3 alkyl, C1 to C6 haloalkoxycarbonyl C1 to C3 alkyl or C3 to C8 cycloalkoxycarbonyl C1 to C3 alkyl.

15. The uracil compound according to claim 1 or 2, wherein R³ is OR⁷ or SR⁸, and R⁷ and R⁸ are C1 to C6 alkoxycarbonylmethyl or 1-{(C1 to C6 alkoxy)carbonyl}ethyl.

16. The uracil compound according to claim 1 or 2, wherein R³ is OR⁷ or SR⁸, and R⁷ and R⁸ are methoxycarbonylmethyl, ethoxycarbonylmethyl, 1-(methoxycarbonyl)ethyl or 1-(ethoxycarbonyl)ethyl.

17. The uracil compound according to claim 3, wherein the group represented by Q—R³ is a group of the following formula:

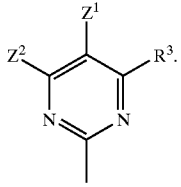

18. The uracil compound according to claim 3, wherein the group represented by Q—R³ is any group selected from the group consisting of moieties of the following formula:

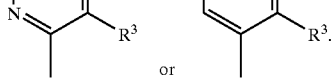

or

19. The uracil compound according to claim 3, the group represented by Q—R³ is a group of the following formula:

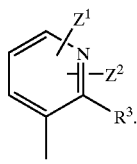

20. A herbicidal composition comprising as an active ingredient the uracil compound according to claim 1 or 2, and inert carrier or diluent.

21. A method for controlling weeds, which comprises applying an effective amount of the uracil compound according to claim 1 or 2 to weeds or a place where the weeds grow or will grow.

22. The uracil compound according to claim 1 or 2, wherein x¹ is halogen or nitro and X² is hydrogen or fluorine.

23. The uracil compound according to claim 22, wherein R¹ is CF₃.

24. The uracil compound according to claim 22, wherein $R^2$ is methyl.

25. The uracil compound according to claim 22, wherein Y is oxygen or sulfur.

26. The uracil compound according to claim 22, wherein $X^1$ is halogen, $X^2$ is hydrogen or fluorine, $R^1$ is $CF_3$, $R^2$ is methyl, Y is oxygen or sulfur and $R^3$ is $OR^7$, $SR^8$ or $N(R^9)R^{10}$, and $R^7$, $R^8$ and $R^{10}$ are C1 to C6 alkoxycarbonyl C1 to C6 alkyl, C1 to C6 haloalkoxycarbonyl C1 to C6 alkyl, C3 to C6 alkenyloxycarbonyl C1 to C6 alkyl, C3 to C6 alkynyloxycarbonyl C1 to C6 alkyl or C3 to C8 cycloalkoxycarbonyl C1 to C6 alkyl.

27. The uracil compound according to claim 8, wherein $R^1$ is $CF_3$, $R^2$ is methyl, Y is oxygen and $R^3$ is $OR^7$, $SR^8$ or $N(R^9)R^{10}$, and $R^7$, $R^8$ and $R^{10}$ are C1 to C6 alkoxycarbonyl C1 to C3 alkyl, C1 to C6 haloalkoxycarbonyl C1 to C3 alkyl or C3 to C8 cycloalkoxycarbonyl C1 to C3 alkyl.

28. The uracil compound according to claim 27, wherein the group represented by Q—$R^3$ is any group selected from the group consisting of moieties of the following formula:

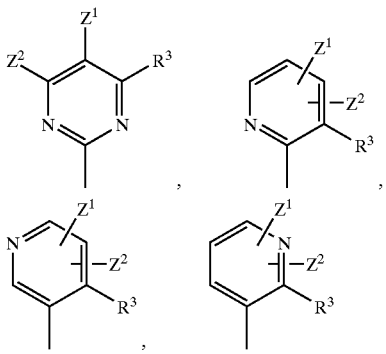

and $R^3$ is $OR^7$ or $SR^8$, and $R^7$ and $R^8$ are C1 to C6 alkoxycarbonylmethyl or 1-{(C1 to C6 alkoxy)carbonyl}ethyl.

29. The uracil compound according to claim 28,

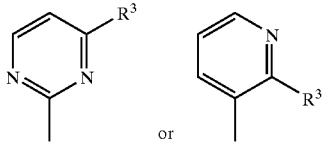

wherein $R^3$ is $OR^7$ or $SR^8$ and $R^7$ and $R^8$ are methoxycarbonylmethyl, ethoxycarbonylmethyl, 1-(methoxycarbonyl)ethyl or 1-(ethoxycarbonyl)ethyl.

30. A compound according to claim 1, which is one selected from the group consisting of
3-{2-chloro-4-fluoro-5-[3-methyl-2,6-dioxo-4-(trifluoromethyl)-1,2,3,6-tetrahydropyrimidin-1-yl]phenoxy}-2-(methoxycarbonyl)methoxypyridine,
3-{2-chloro-4-fluoro-5-[3-methyl-2,6-dioxo-4-(trifluoromethyl)-1,2,3,6-tetrahydropyrimidin-1-yl]phenoxy}-2-(ethoxycarbonyl)methoxypyridine,
3-{2-chloro-4-fluoro-5-[3-methyl-2,6-dioxo-4-(trifluoromethyl)-1,2,3,6-tetrahydropyrimidin-1-yl]phenoxy}-2-{1-(methoxycarbonyl)ethoxy}pyridine,
3-{2-chloro-4-fluoro-5-[3-methyl-2,6-dioxo-4-(trifluoromethyl)-1,2,3,6-tetrahydropyrimidin-1-yl]phenoxy}-2-{1-(ethoxycarbonyl)ethoxy}pyridine,
2-{2-chloro-4-fluoro-5-[3-methyl-2,6-dioxo-4-(trifluoromethyl)-1,2,3,6-tetrahydropyrimidin-1-yl]phenoxy}-4-(methoxycarbonyl)methoxypyrimidine,
2-{2-chloro-4-fluoro-5-[3-methyl-2,6-dioxo-4-(trifluoromethyl)-1,2,3,6-tetrahydropyrimidin-1-yl]phenoxy}-4-(ethoxycarbonyl)methoxypyrimidine,
2-{2-chloro-4-fluoro-5-[3-methyl-2,6-dioxo-4-(trifluoromethyl)-1,2,3,6-tetrahydropyrimidin-1-yl]phenoxy}-4-{1-(methoxycarbonyl)ethoxy}pyrimidine, and
2-{2-chloro-4-fluoro-5-[3-methyl-2,6-dioxo-4-(trifluoromethyl)-1,2,3,6-tetrahydropyrimidin-1-yl]phenoxy}-4-{1-(ethoxycarbonyl)ethoxy}pyrimidine.

31. A compound of the formula [XXXI]:

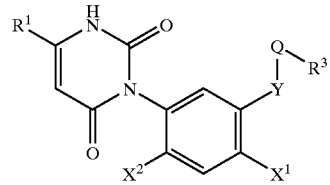

[XXXI]

wherein $X^1$ represents halogen, cyano, thiocarbamoyl or nitro, $X^2$ represents hydrogen or halogen; $R^1$ represents C1 to C3 alkyl or C1 to C3 haloalkyl; Q—$R^3$ represents a $R^3$-substituted group of a 5-membered or 6-membered heterocyclic ring having at least one or two nitrogen selected from the group consisting of moieties represented by the following formulae:

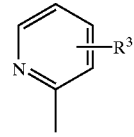

Q-1

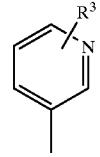

Q-2

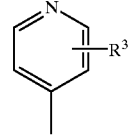

Q-3

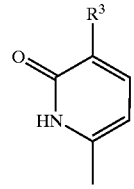

Q-4

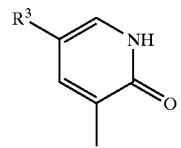

Q-5

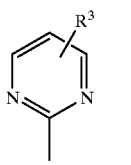 Q-6

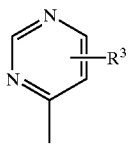 Q-7

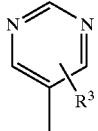 Q-8

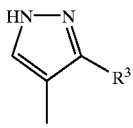 Q-9

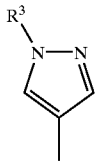 Q-10

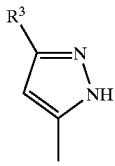 Q-11

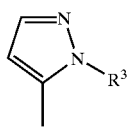 Q-12

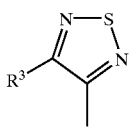 Q-13

(wherein, this heterocyclic ring may be substituted with at least one kind of substituent selected from the group consisting of halogen, C1 to C6 alkyl, C1 to C6 haloalkyl, C2 to C6 alkenyl, C2 to C6 haloalkenyl, C2 to C6 alkynyl, C2 to C6 haloalkynyl, C1 to C6 alkoxy C1 to C6 alkyl, C1 to C6 alkoxy, C1 to C6 haloalkoxy, C1 to C6 alkoxycarbonyl C1 to C6 alkoxy, C1 to C6 alkoxycarbonyl C1 to C6 alkyl, cyano, hydroxy, mercapto and Y represents oxygen, sulfur, imino or C1 to C3 alkylimino.

32. The compound according to claim 31, wherein the group represented by Q—$R^3$ is any group selected from the group consisting of moieties of the following formula:

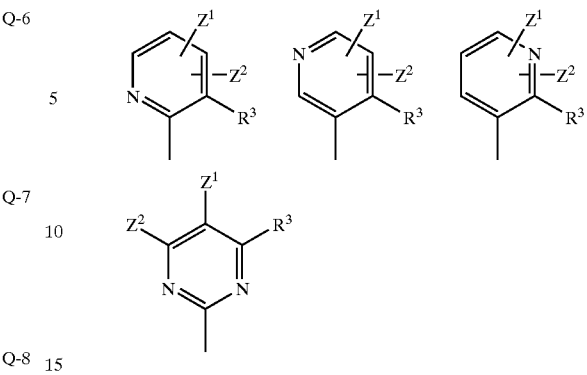

wherein, $X^1$ is halogen, cyano or nitro, $X^2$ is halogen, Y is oxygen or sulfur, $R^1$ is C1 to C3 haloalkyl, R3 is $OR^7$, $SR^8$ or $N(R^9)R^{10}$, $R^7$, $R^8$ and $R^{10}$ are C1 to C6 alkoxycarbonyl C1 to C6 alkyl, C1 to C6 haloalkoxycarbonyl C1 to C6 alkyl, C3 to C6 alkenyloxycarbonyl C1 to C6 alkyl, C3 to C6 alkynyloxycarbonyl C1 to C6 alkyl or C3 to C8 cycloalkoxycarbonyl C1 to C6 alkyl, and $Z^1$ and $Z^2$ independently represents hydrogen, halogen, C1 to C6 alkyl, C1 to C6 haloalkyl, C2 to C6 alkenyl, C2 to C6 haloalkenyl, C2 to C6 alkynyl, C2 to C6 haloalkynyl, C1 to C6 alkoxy C1 to C6 alkyl, C1 to C6 alkoxy, C1 to C6 haloalkoxy, C1 to C6 alkoxycarbonyl C1 to C6 alkoxy or cyano.

33. The compound according to claim 31, wherein $X^1$ is chlorine, $X^2$ is fluorine, Y is oxygen, Q—$R^3$ is the same as defined in claim 3, $Z^1$ and $Z^2$ are hydrogen, $R^1$ is trifluoromethyl, $R^3$ is $OR^7$ or $SR^8$, and $R^7$ and $R^8$ are methoxycarbonylmethyl, ethoxycarbonylmethyl, 1-(methoxycarbonyl)ethyl or 1-(ethoxycarbonyl)ethyl.

34. The compound according to claim 32, wherein $X^1$ is chlorine, $X^2$ is fluorine, Y is oxygen, $Z^1$ and $Z^2$ are hydrogen, $R^1$ is trifluoromethyl, $R^3$ is $OR^7$ or $SR^8$, and $R^7$ and $R^8$ are methoxycarbonylmethyl, ethoxycarbonylmethyl, 1-(methoxycarbonyl)ethyl or 1-(ethoxycarbonyl)ethyl.

35. A compound of the formula [XXXXXI]:

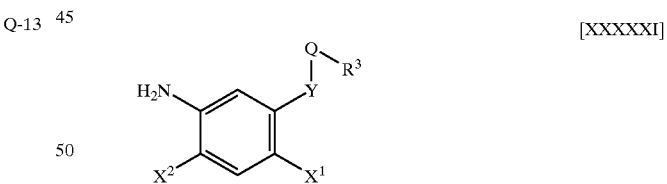 [XXXXXI]

wherein $X^1$ represents halogen, cyano, thiocarbamoyl or nitro, $X^2$ represents hydrogen or halogen; Q—$R^3$ represents a $R^3$-substituted group of a 5-membered or 6-membered heterocyclic ring having at least one or two nitrogen selected from the group consisting of moieties represented by the following formulae

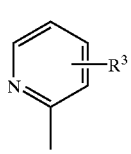 Q-1

-continued

Q-2 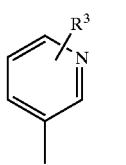

Q-3 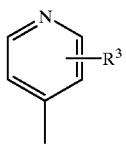

Q-4 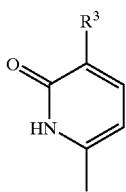

Q-5 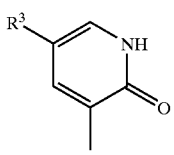

Q-6 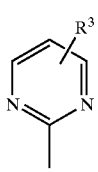

Q-7 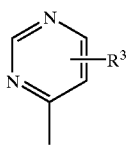

Q-8 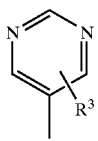

Q-9 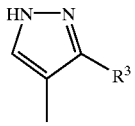

Q-10 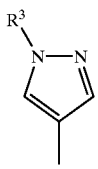

Q-11 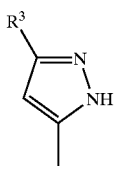

-continued

Q-12 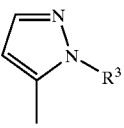

Q-13 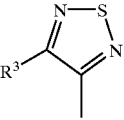

(wherein, this heterocyclic ring may be substituted with at least one kind of substituent selected from the group consisting of halogen, C1 to C6 alkyl, C1 to C6 haloalkyl, C2 to C6 alkenyl, C2 to C6 haloalkenyl, C2 to C6 alkynyl, C2 to C6 haloalkynyl, C1 to C6 alkoxy, C1 to C6 alkyl, C1 to C6 alkoxy, C1 to C6 haloalkoxy, C1 to C6 alkoxycarbonyl C1 to C6 alkoxy, C1 to C6 alkoxycarbonyl C1 to C6 alkyl, cyano, hydroxy, mercapto) and Y represents oxygen, sulfur, imino or C1 to C3 alkylimino.

36. The compound according to claim 35, wherein the group represented by Q—$R^3$ is any group selected from the group consisting of moieties of the following formula:

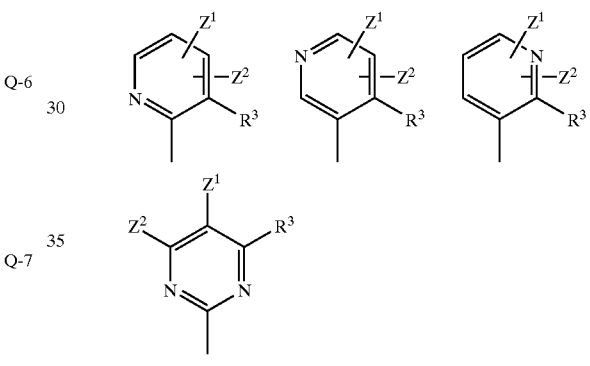

wherein, $X^1$ is halogen, cyano or nitro, $X^2$ is halogen, Y is oxygen or sulfur, $R^3$ is $OR^7$, $SR^8$ or $N(R^9)R^{10}$, $R^7$, $R^8$ and $R^{10}$ are C1 to C6 alkoxycarbonyl C1 to C6 alkyl, C1 to C6 haloalkoxycarbonyl C1 to C6 alkyl, C3 to C6 alkenyloxycarbonyl C1 to C6 alkyl, C3 to C6 alkynyloxycarbonyl C1 to C6 alkyl or C3 to C8 cycloalkoxycarbonyl C1 to C6 alkyl, and $Z^1$ and $Z^2$ independently represents hydrogen, halogen, C1 to C6 alkyl, C1 to C6 haloalkyl, C2 to C6 alkenyl, C2 to C6 haloalkenyl, C2 to C6 alkynyl, C2 to C6 haloalkynyl, C1 to C6 alkoxy C1 to C6 alkyl, C1 to C6 alkoxy, C1 to C6 haloalkoxy, C1 to C6 alkoxycarbonyl C1 to C6 alkoxy or cyano.

37. The compound according to claim 35, wherein $X^1$ is chlorine, $X^2$ is fluorine, Y is oxygen, Q—$R^3$ is the same as defined in claim 3, $Z^1$ and $Z^2$ are hydrogen, $R^3$ is $OR^7$ or $SR^8$, and $R^7$ and $R^8$ are methoxycarbonylmethyl, ethoxycarbonylmethyl, 1-(methoxycarbonyl)ethyl or 1-(ethoxycarbonyl)ethyl.

38. The compound according to claim 36, wherein $X^1$ is chlorine, $X^2$ is fluorine, Y is oxygen, $Z^1$ and $Z^2$ are hydrogen, $R^3$ is $OR^7$ or $SR^8$, and $R^7$ and $R^8$ are methoxycarbonylmethyl, ethoxycarbonylmethyl, 1-(methoxycarbonyl)ethyl or 1-(ethoxycarbonyl)ethyl.

39. A compound according to claim 35, which is one selected from the group consisting of
4-chloro-2-fluoro-5-{2-(methoxycarbonyl)methoxy-3-pyridyloxy}aniline, 4-chloro-2-fluoro-5-{2-(ethoxycarbonyl)methoxy-3-pyridyloxy}aniline,
4-chloro-2-fluoro-5-[2-{1-(methoxycarbonyl)ethoxy}-3-pyridyloxy]aniline,
4-chloro-2-fluoro-5-[2-{1-(ethoxycarbonyl)ethoxy}-3-pyridyloxy]aniline,
4-chloro-2-fluoro-5-[4-(methoxycarbonyl)methoxy-2-pyrimidyloxy]aniline,
4-chloro-2-fluoro-5-[4-(ethoxycarbonyl)methoxy-2-pyrimidyloxy]aniline,
4-chloro-2-fluoro-5-[4-{1-(methoxycarbonyl)ethoxy}-2-pyrimidyloxy]aniline, and
4-chloro-2-fluoro-5-[4-{1-(ethoxycarbonyl)ethoxy}-2-pyrimidyloxy]aniline.

40. A compound of the formula [XXXXXI]:

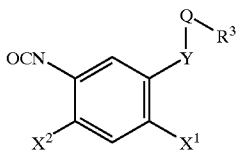

[XXXXXIII]

wherein $X^1$ represents halogen, cyano, thiocarbamoyl or nitro, $X^2$ represents hydrogen or halogen; Q—$R^3$ represents a $R^3$-substituted group of a 5-membered or 6-membered heterocyclic ring having at least one or two nitrogen selected from the group consisting of moieties represented by the following formulae

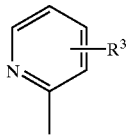

Q-1

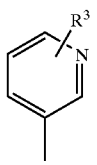

Q-2

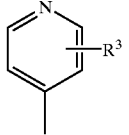

Q-3

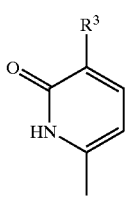

Q-4

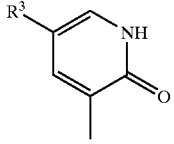

Q-5

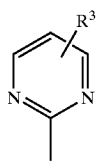

Q-6

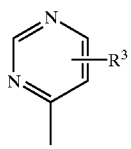

Q-7

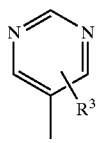

Q-8

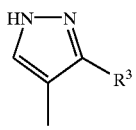

Q-9

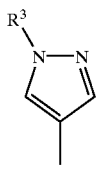

Q-10

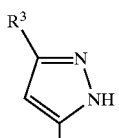

Q-11

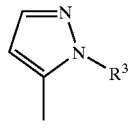

Q-12

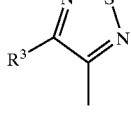

Q-13

(wherein, this heterocyclic ring may be substituted with at least one kind of substituent selected from the group consisting of halogen, C1 to C6 alkyl, C1 to C6 haloalkyl, C2 to C6 alkenyl, C2 to C6 haloalkenyl, C2 to C6 alkynyl, C2 to C6 haloalkynyl, C1 to C6 alkoxy, C1 to C6 alkyl, C1 to C6 alkoxy, C1 to C6 haloalkoxy, C1 to C6 alkoxycarbonyl C1 to C6 alkoxy, C1 to C6 alkoxycarbonyl C1 to C6 alkyl, cyano, hydroxy, mercapto) and Y represents oxygen, sulfur, imino or C1 to C3 alkylimino.

41. The compound according to claim 40, wherein the group represented by Q—$R^3$ is any group selected from the group consisting of moieties of the following formula:

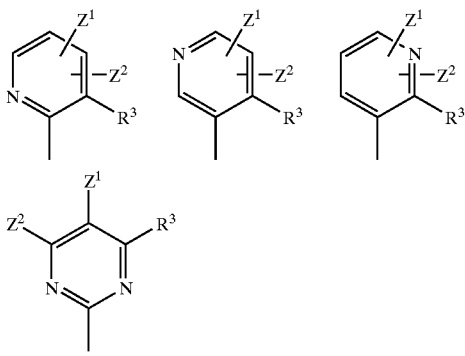

wherein, $X^1$ is halogen, cyano or nitro, $X^2$ is halogen, Y is oxygen or sulfur, $R^3$ is $OR^7$, $SR^8$ or $N(R^9)R^{10}$, $R^7$, $R^8$ and $R^{10}$ are C1 to C6 alkoxycarbonyl C1 to C6 alkyl, C1 to C6 haloalkoxycarbonyl C1 to C6 alkyl, C3 to C6 alkenyloxycarbonyl C1 to C6 alkyl, C3 to C6 alkynyloxycarbonyl C1 to C6 alkyl or C3 to C8 cycloalkoxycarbonyl C1 to C6 alkyl, and Z1 and $Z^2$ independently represents hydrogen, halogen, C1 to C6 alkyl, C1 to C6 haloalkyl, C2 to C6 alkenyl, C2 to C6 haloalkenyl, C2 to C6 alkynyl, C2 to C6 haloalkynyl, C1 to C6 alkoxy C1 to C6 alkyl, C1 to C6 alkoxy, C1 to C6 haloalkoxy, C1 to C6 alkoxycarbonyl C1 to C6 alkoxy or cyano.

42. The compound according to claim 40, wherein $X^1$ is chlorine, $X^2$ is fluorine, Y is oxygen, Q—$R^3$ is the same as defined in claim 3, $Z^1$ and $Z^2$ are hydrogen, $R^3$ is $OR^7$ or $SR^8$, and $R^7$ and $R^8$ are methoxycarbonylmethyl, ethoxycarbonylmethyl, 1-(methoxycarbonyl)ethyl or 1-(ethoxycarbonyl)ethyl.

43. The compound according to claim 41, wherein $X^1$ is chlorine, $X^2$ is fluorine, Y is oxygen, $Z^1$ and $Z^2$ are hydrogen, $R^3$ is $OR^7$ or $SR^8$, and $R^7$ and $R^8$ are methoxycarbonylmethyl, ethoxycarbonylmethyl, 1-(methoxycarbonyl)ethyl or 1-(ethoxycarbonyl)ethyl.

44. A compound according to claim 40, which is one selected from the group consisting of
4-chloro-2-fluoro-5-{2-(methoxycarbonyl)methoxy-3-pyridyloxy{phenyl isocyanate,
4-chloro-2-fluoro-5-{2-(ethoxycarbonyl)methoxy-3-pyridyloxy}phenyl isocyanate,
4-chloro-2-fluoro-5-[2-{1-(methoxycarbonyl)ethoxy)-3-pyridyloxy]phenyl isocyanate,
4-chloro-2-fluoro-5-[2-{1-(ethoxycarbonyl)ethoxy}-3-pyridyloxy]phenyl isocyanate,
4-chloro-2-fluoro-5-[4-(methoxycarbonyl)methoxy-2-pyrimidyloxy]phenyl isocyanate,
4-chloro-2-fluoro-5-[4-(ethoxycarbonyl)methoxy-2-pyrimidyloxy]phenyl isocyanate,
4-chloro-2-fluoro-5-[4-{1-(methoxycarbonyl)ethoxy}-2-pyrimidyloxy]phenyl isocyanate, and
4-chloro-2-fluoro-5-[4-{1-(ethoxycarbonyl)ethoxy)-2-pyrimidyloxy]phenyl isocyanate.

45. A compound according to claim 31, which is one selected from the group consisting of
3-{2-chloro-4-fluoro-5-[2,6-dioxo-4-(trifluoromethyl)-1,2,3,6-tetrahydropyrimidin-1-yl]phenoxy}-2-(methoxycarbonyl)methoxypyridine,
3-{2-chloro-4-fluoro-5-[2,6-dioxo-4-(trifluoromethyl)-1,2,3,6-tetrahydropyrimidin-1-yl]phenoxy}-2-(ethoxycarbonyl)methoxypyridine,
3-(2-chloro-4-fluoro-5-[2,6-dioxo-4-(trifluoromethyl)-1,2,3,6-tetrahydropyrimidin-1-yl]phenoxy}-2-(1-(methoxycarbonyl)ethoxy}pyridine,
3-{2-chloro-4-fluoro-5-[2,6-dioxo-4-(trifluoromethyl)-1,2,3,6-tetrahydropyrimidin-1-yl]phenoxy}-2-{1-(ethoxycarbonyl)ethoxy}pyridine,
2-{2-chloro-4-fluoro-5-[2,6-dioxo-4-(trifluoromethyl)-1,2,3,6-tetrahydropyrimidin-1-yl]phenoxy}-4-(methoxycarbonyl)methoxypyrimidine,
2-(2-chloro-4-fluoro-5-[2,6-dioxo-4-(trifluoromethyl)-1,2,3,6-tetrahydropyrimidin-1-yl]phenoxy}-4-(ethoxycarbonyl)methoxypyrimidine,
2-(2-chloro-4-fluoro-5-[2,6-dioxo-4-(trifluoromethyl)-1,2,3,6-tetrahydropyrimidin-1-yl]phenoxy}-4-{1-(methoxycarbonyl)ethoxy}pyrimidine, and
2-{2-chloro-4-fluoro-5-[2,6-dioxo-4-(trifluoromethyl)-1,2,3,6-tetrahydropyrimidin-1-yl]phenoxy}-4-{1-(ethoxycarbonyl)ethoxy}pyrimidine.

46. A compound of the formula:

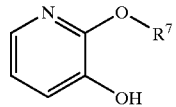

wherein $R^7$ represents carboxy C1 to C6 alkyl, C1 to C6 alkoxycarbonyl C1 to C6 alkyl, C1 to C6 haloalkoxycarbonyl C1 to C6 alkyl, C3 to C6 alkenyloxycarbonyl C1 to C6 alkyl, C3 to C6 haloalkenyloxycarbonyl C1 to C6 alkyl, C3 to C6 alkynyloxycarbonyl C1 to C6 alkyl, C3 to C6 haloalkynyloxycarbonyl C1 to C6 alkyl, C3 to C8 cycloalkoxycarbonyl C1 to C6 alkyl, C3 to C8 halocycloalkoxycarbonyl C1 to C6 alkyl, C3 to C8 cycloalkenyloxycarbonyl C1 to C6 alkyl, C3 to C8 halocycloalkenyloxycarbonyl C1 to C6 alkyl, C1 to C6 alkoxycarbonyl C1 to C6 alkoxycarbonyl C1 to C6 alkyl, C1 to C8 alkylidenaminoxycarbonyl C1 to C6 alkyl, phenoxycarbonyl C1 to C6 alkyl which may be substituted, phenyl C1 to C4 alkoxycarbonyl C1 to C6 alkyl which may be substituted, C1 to C6 alkoxyaminocarbonyl C1 to C6 alkyl, (C1 to C6 alkoxy)(C1 to C3 alkyl) aminocarbonyl C1 to C6 alkyl, C1 to C6 alkylaminocarbonyl C1 to C6 alkyl, (C1 to C6 alkyl) C1 to C6 alkylaminocarbonyl C1 to C6 alkyl, phenylaminocarbonyl C1 to C6 alkyl which may be substituted, or phenyl C1 to C4 alkylaminocarbonyl C1 to C6 alkyl which may be substituted.

47. A compound according to claim 46, which is one selected from the group consisting of
2-(methoxycarbonyl)methoxy-3-hydroxypyridine,
2-(ethoxycarbonyl)methoxy-3-hydroxypyridine,
2-{1-(methoxycarbonyl)ethoxy}-3-hydroxypyridine, and
2-{1-(ethoxycarbonyl)ethoxy}-3-hydroxypyridine.

48. A compound of the formula:

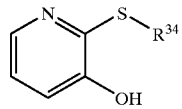

[wherein, $R^{34}$ is C1 to C6 alkoxycarbonyl methyl, 1-(C1 to C6 alkoxycarbonyl)ethyl, C1 to C6 haloalkoxycarbonyl methyl, 1-(C1 to C6 haloalkoxycarbonyl)ethyl, C3 to C8 cycloalkoxycarbonyl methyl, 1-(C3 to C8 cycloalkoxycarbonyl)ethyl.].

* * * * *

UNITED STATES PATENT AND TRADEMARK OFFICE
CERTIFICATE OF CORRECTION

PATENT NO.     : 6,537,948 B1
DATED          : March 25, 2003
INVENTOR(S)    : Yoshitomo Tohyama and Yuzuru Sanemitsu It is certified that error appears in the above-identified patent and that said Letters Patent is hereby corrected as shown below:

Column 114,
Lines 5-6, delete the "," (comma) in the recitation, "C1 to C6 alkoxy, C1 to C6 alkyl".
Line 15, the recitation "$S^8$" should read -- $SR^8$ --.

Column 115,
Lines 1-8, delete the formulae

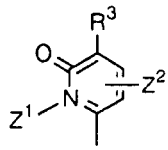 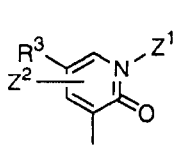

and and insert the following formulae:

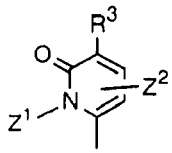 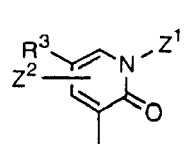

and

Column 122,
Line 18, delete the "," (comma) in the recitation, "C1 to C6 alkoxy, C1 to C6 alkyl".
Line 19, delete "to C6" in the recitation, "C6 to C6 alkoxy".

Column 124,
Line 58, delete the "," (comma) in the recitation "C1 to C6 alkoxy, C1 to C6 alkyl".

UNITED STATES PATENT AND TRADEMARK OFFICE
CERTIFICATE OF CORRECTION

PATENT NO. : 6,537,948 B1
DATED : March 25, 2003
INVENTOR(S) : Yoshitomo Tohyama and Yuzuru Sanemitsu It is certified that error appears in the above-identified patent and that said Letters Patent is hereby corrected as shown below:

Column 125,
Line 42, the "{" in the recitation, "pyridyloxyl {phenyl isocyanate" should read as -- } --.

Signed and Sealed this

Eighteenth Day of October, 2005

JON W. DUDAS
*Director of the United States Patent and Trademark Office*